United States Patent
Garske et al.

(10) Patent No.: US 9,353,116 B2
(45) Date of Patent: May 31, 2016

(54) METHODS AND COMPOSITIONS FOR KINASE INHIBITION

(71) Applicant: THE REGENTS OF THE UNIVERSITY OF CALIFORNIA, Oakland, CA (US)

(72) Inventors: Adam L. Garske, San Francisco, CA (US); Kevan M. Shokat, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/690,785

(22) Filed: Nov. 30, 2012

(65) Prior Publication Data

US 2013/0137708 A1    May 30, 2013

Related U.S. Application Data

(63) Continuation of application No. PCT/US2011/039347, filed on Jun. 6, 2011.

(60) Provisional application No. 61/351,663, filed on Jun. 4, 2010.

(51) Int. Cl.

| C12N 9/12 | (2006.01) |
|---|---|
| C12N 9/99 | (2006.01) |
| C07D 487/04 | (2006.01) |
| C07D 239/94 | (2006.01) |
| C07D 403/12 | (2006.01) |
| C07D 409/12 | (2006.01) |
| A01N 43/90 | (2006.01) |
| A61K 31/519 | (2006.01) |

(52) U.S. Cl.
CPC ............ *C07D 487/04* (2013.01); *C07D 239/94* (2013.01); *C07D 403/12* (2013.01); *C07D 409/12* (2013.01); *C12N 9/12* (2013.01)

(58) Field of Classification Search
None
See application file for complete search history.

(56) References Cited

U.S. PATENT DOCUMENTS

| 5,643,734 | A | 7/1997 | Henderson |
|---|---|---|---|
| 6,589,950 | B1 | 7/2003 | Hayler et al. |
| 7,271,262 | B2 | 9/2007 | La Greca et al. |
| 7,332,497 | B2 | 2/2008 | Hirst et al. |
| 7,585,868 | B2 | 9/2009 | Knight et al. |
| 8,642,604 | B2 | 2/2014 | Knight et al. |
| 2003/0187001 | A1 | 10/2003 | Calderwood et al. |
| 2005/0085472 | A1 | 4/2005 | Tanaka et al. |
| 2006/0035912 | A1 | 2/2006 | Marx et al. |
| 2007/0293489 | A1 | 12/2007 | Adams et al. |
| 2009/0029989 | A1 | 1/2009 | Adams et al. |
| 2009/0124638 | A1 | 5/2009 | Shokat et al. |
| 2009/0181988 | A1 | 7/2009 | Tanaka et al. |
| 2009/0221614 | A1 | 9/2009 | Taunton et al. |
| 2011/0144134 | A1 | 6/2011 | Shokat et al. |
| 2011/0224223 | A1 | 9/2011 | Shokat et al. |
| 2011/0275611 | A1* | 11/2011 | Axten et al. ............. 514/210.21 |
| 2011/0275651 | A1 | 11/2011 | Dar et al. |
| 2012/0065154 | A1 | 3/2012 | Tanaka et al. |
| 2014/0243357 | A1 | 8/2014 | Dar et al. |
| 2015/0031881 | A1 | 1/2015 | Tanaka et al. |
| 2016/0000789 | A1 | 1/2016 | Shokat et al. |

OTHER PUBLICATIONS

Chapman et al. (Bioorganic & Medicinal Chemistry Letters, Dec. 7, 2008, 19, 811-813).*
Chapman et al. Supplemental content.*
Ito et al. (Cancer Science, 2003, 94, 3-8).*
Aspel et al. (Nature Chemical Biology, 6, 2008, 691-699).*
Aspel et al. (Nature Chemical Biology, 6, 2008, Supplemental content).*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Azam et al., "Activation of tyrosine kinases by mutation of the gatekeeper threonine," Nat Struct Mol Biol, 15(10): 1109-18 (2008).
Cameron et al., "PKC Maturation is promoted by nucleotide pocket occupation independently of intrinsic kinase activity," Nat Struct Mol Biol, 16(6): 624-31 (2009).
Chapman et al., "A small molecule inhibitor selective for a variant ATP-binding site of the chaperonin GroEL," Bioorganic & Medicinal Chemistry Letters, 19: 811-813 (2009).
Elphick et al, "Using chemical genetics and ATP analogues to dissect protein kinase function," ACS Chemical Biology, 2: 299-314 (2007).
Hatzivassiliou et al., "RAF inhibitors prime wild-type RAF to activate the MAPK pathway and enhance growth," Nature, 464(7287): 431-5 (2010).
Hindie et al., "Structure and allosteric effects of low-molecular-weight activators on the protein kinase PDK1," Nat Chem Biol, 5(10): 758-64 (2009).
Liu et al., "Structural basis for selective inhibition of Src family kinases by PP1," Chemistry & Biology, 6:671-678 (1999).
No Author, Upstate KinaseProfiler Assay Protocols, Jun. 2003 publication.
Okuzumi et al., "Inhibitor Hijacking of Akt Activation," Nat Chem Biol, 5(7): 484-93 (2009).
Zunder et al., "Discovery of drug-resistant and drug-sensitizing mutations in the oncogenic PI3K isoform p110 alpha," Cancer Cell, 14(2): 180-92 (2008).
International Search Report and Written Opinion mailed Feb. 3, 2012 in related International Patent Application No. PCT/US2011/039347, filed Jun. 6, 2011, 11 pages.

* cited by examiner

*Primary Examiner* — Dennis Heyer
*Assistant Examiner* — Daniel M Podgorski
(74) *Attorney, Agent, or Firm* — Mintz Levin Cohn Ferris Glovsky and Popeo, P.C.

(57) ABSTRACT

The present invention sets forth a new chemical genetic approach for engineering kinase enzymes with a cysteine gatekeeper residue as well as for developing electrophilic inhibitors thereto. The present invention also provides a Src proto-oncogenic tyrosine kinase with a cysteine gatekeeper that recapitulates wild type activity and can be irreversibly inhibited both in vitro and in cells. The present invention also provides methods and compositions for modulating kinases and for treating kinase-associate diseases.

12 Claims, 22 Drawing Sheets

FIG. 8

```
Thu May 26, 2011 14:21 PDT
AG_144492-2_cSRCf-T338C-A_t7promoterB06.seq
/Users/algarske/Documents/Sequencing/cSRC/AG_144492-2_cSRCf-T338C-A_t7promoterB06.seq
From 1 to 918.
Translation 305 a.a. MW=35116.20999999997

H   H   H   H   H   H   D   Y   D   I   P   T   T   E   N   L   Y   F   Q   G
CATCATCATCATCATCACGATTACGATATCCCAACGACCGAAAACCTTTACTTCCAGGGC

H   M   Q   T   Q   G   L   A   K   D   A   W   E   I   P   R   E   S   L   R
CATATGCAGACCCAGGGACTCGCCAAGGACGCGTGGGAAATCCCCCGGGAGTCGCTGCGG

L   E   V   K   L   G   Q   G   C   F   G   E   V   W   M   G   T   W   N   G
CTGGAGGTGAAGCTGGGGCAGGGCTGCTTTGGAGAGGTCTGGATGGGGACCTGGAACGGC

T   T   R   V   A   I   K   T   L   K   P   G   T   M   S   P   E   A   F   L
ACCACCAGAGTGGCCATAAAGACTCTGAAGCCCGGCACCATGTCCCCGGAGGCCTTCCTG

Q   E   A   Q   V   M   K   K   L   R   H   E   K   L   V   Q   L   Y   A   V
CAGGAAGCCCAAGTGATGAAGAAGCTCCGGCATGAGAAGCTGGTTCAGCTGTACGCAGTG

V   S   E   E   P   I   Y   I   V   C   E   Y   M   S   K   G   S   L   L   D
GTGTCGGAAGAGCCCATCTACATCGTCTGTGAGTACATGAGCAAGGGGAGCCTCCTGGAT

F   L   K   G   E   M   G   K   Y   L   R   L   P   Q   L   V   D   M   A   A
TTCCTGAAGGGAGAGATGGGCAAGTACCTGCGGCTGCCACAGCTCGTCGATATGGCTGCT

Q   I   A   S   G   M   A   Y   V   E   R   M   N   Y   V   H   R   D   L   R
CAGATTGCATCCGGCATGGCCTATGTGGAGAGGATGAACTACGTGCACCGAGACCTGCGG

A   A   N   I   L   V   G   E   N   L   V   C   K   V   A   D   F   G   L   A
GCGGCCAACATCCTGGTGGGGGAGAACCTGGTGTGCAAGGTGGCTGACTTTGGGCTGGCA

R   L   I   E   D   N   E   Y   T   A   R   Q   G   A   K   F   P   I   K   W
CGCCTCATCGAGGACAACGAGTACACAGCACGGCAAGGTGCCAAGTTCCCCATCAAGTGG

T   A   P   E   A   A   L   Y   G   R   F   T   I   K   S   D   V   W   S   F
ACAGCCCCCGAGGCAGCCCTCTATGGCCGGTTCACCATCAAGTCGGATGTCTGGTCCTTC

G   I   L   L   T   E   L   T   T   K   G   R   V   P   Y   P   G   M   V   N
GGCATCCTGCTGACTGAGCTGACCACCAAGGGCCGGGTGCCATACCCAGGGATGGTCAAC

R   E   V   L   D   Q   V   E   R   G   Y   R   M   P   C   P   P   E   C   P
AGGGAGGTGCTGGACCAGGTGGAGAGGGGCTACCGCATGCCCTGCCCGCCCGAGTGCCCC

E   S   L   H   D   L   M   C   Q   C   W   R   K   D   P   E   E   R   P   T
GAGTCGCTGCATGACCTCATGTGCCAGTGCTGGCGGAAGGACCCTGAGGAGCGGCCCACT

F   E   Y   L   Q   A   F   L   E   D   Y   F   T   S   T   E   P   Q   Y   Q
TTTGAGTACCTGCAGGCCTTCCTGGAGGACTACTTCACCTCGACAGAGCCCCAGTACCAG

P   G   E   N   L   *
CCTGGAGAGAACCTATAG
```

FIG. 11

|  | 3-vs-Q |
|---|---|
| BTK | 59 |
| CHEK2 (CHK2) | 53 |
| EGFR (ErbB1) | 84 |
| EGFR (ErbB1) L858R | 69 |
| EGFR (ErbB1) L861Q | 76 |
| EGFR (ErbB1) T790M L858R | 41 |
| ERBB2 (HER2) | 66 |
| ERBB4 (HER4) | 80 |
| FLT3 D835Y | 99 |
| GRK5 | 49 |
| LRRK2 | 75 |
| LRRK2 G2019S | 91 |
| PDGFRA V561D | 45 |
| PIK3C2B (PI3K-C2 beta) | 65 |
| RPS6KA6 (RSK4) | 49 |
| SRMS (Srm) | 71 |
| TXK | 78 |

FIG. 12

| WT LRRK2 | G2019S LRRK2 |
|---|---|
| 156 nM | 33 nM |
| >1000 nM | >1000 nM |
| >1000 nM | >1000 nM |
| >1000 nM | >1000 nM |

LRRK2 GS

FIG. 16
| R= | WT LRRK2 IC$_{50}$ | G2019SLRRK2 IC$_{50}$ |
|---|---|---|
|  (3-vs-Q) | 213 nM | 45.5 nM |
|  Me | 353 nM | 100 nM |
|  | 334 nM | 121 nM |
|  | 241 nM | 90.1 nM |
|  | 186 nM | 46.9 nM |
| 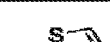 | 329 nM | 57.7 nM |
|  F F F | 380 nM | 274 nM |
|  | 334 nM | 121 nM |

FIG. 20
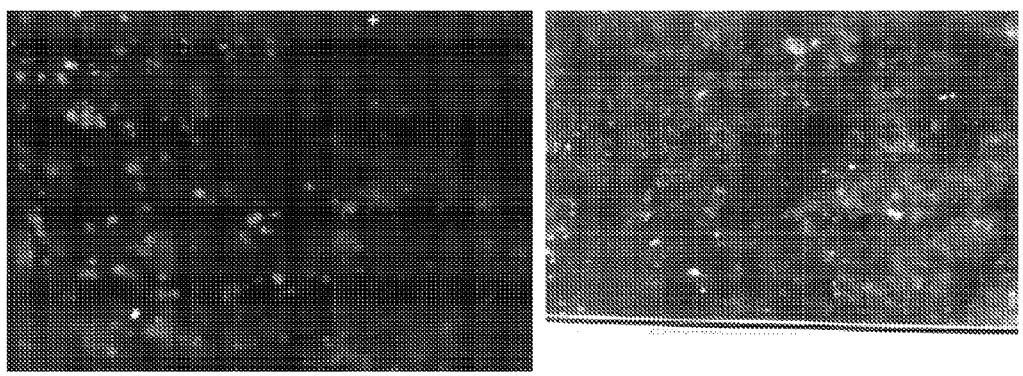
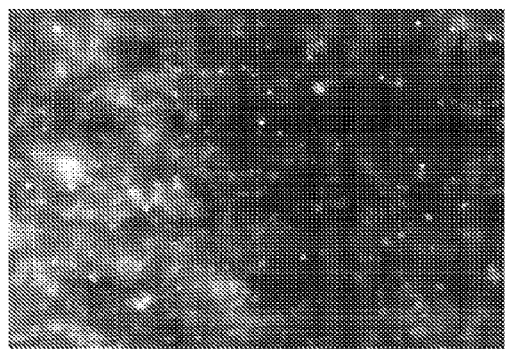

LRRK2 G2019S in-vitro Kinase Assay

SEQUENCE LISTING

```
<160> NUMBER OF SEQ ID NOS: 80

<210> SEQ ID NO 1
<211> LENGTH: 918
<212> TYPE: DNA
<213> ORGANISM: Artificial sequence
<220> FEATURE:
<223> OTHER INFORMATION: synthetic DNA construct for T338C c-src
      (251-533)

<400> SEQUENCE: 1
catcatcatc atcatcacga ttacgatatc ccaacgaccg aaaacctttta cttccagggc    60 catatgcaga cccagggact cgccaaggac gcgtgggaaa tcccccggga gtcgctgcgg   120
ctggaggtga agctggggca gggctgcttt ggagaggtct ggatggggac ctggaacggc   180
accaccagag tggccataaa gactctgaag cccggcacca tgtccccgga ggccttcctg   240
caggaagccc aagtgatgaa gaagctccgg catgagaagc tggttcagct gtacgcagtg   300
gtgtcggaag agcccatcta catcgtctgt gagtacatga gcaaggggag cctcctggat   360
ttcctgaagg gagagatggg caagtacctg cggctgccac agctcgtcga tatggctgct   420
cagattgcat ccggcatggc ctatgtggag aggatgaact acgtgcaccg agacctgcgg   480
gcggccaaca tcctggtggg ggagaacctg gtgtgcaagg tggctgactt tgggctggca   540
cgcctcatcg aggacaacga gtacacagca cggcaaggtg ccaagttccc catcaagtgg   600
acagcccccg aggcagccct ctatgccgg ttcaccatca gtcggatgt ctggtccttc   660 ggcatcctgc tgactgagct gaccaccaag ggccgggtgc catacccagg gatggtcaac   720
agggaggtgc tggaccaggt ggagaggggc taccgcatgc cctgcccgcc cgagtgcccc   780
gagtcgctgc atgacctcat gtgccagtgc tggcggaagg accctgagga gcggcccact   840
tttgagtacc tgcaggcctt cctggaggac tacttcacct cgacagagcc ccagtaccag   900
```
cctggagaga acctatag                                                     918

<210> SEQ ID NO 2
<211> LENGTH: 305
<212> TYPE: PRT
<213> ORGANISM: Artificial sequence
<220> FEATURE:
<223> OTHER INFORMATION: synthetic T338C c-src (251-533) protein

<400> SEQUENCE: 2

His His His His His His Asp Tyr Asp Ile Pro Thr Thr Glu Asn Leu
1               5                   10                  15

Tyr Phe Gln Gly His Met Gln Thr Gln Gly Leu Ala Lys Asp Ala Trp
            20                  25                  30

Glu Ile Pro Arg Glu Ser Leu Arg Leu Glu Val Lys Leu Gly Gln Gly
        35                  40                  45

Cys Phe Gly Glu Val Trp Met Gly Thr Trp Asn Gly Thr Thr Arg Val
    50                  55                  60

Ala Ile Lys Thr Leu Lys Pro Gly Thr Met Ser Pro Glu Ala Phe Leu
65                  70                  75                  80

Gln Glu Ala Gln Val Met Lys Lys Leu Arg His Glu Lys Leu Val Gln
                85                  90                  95

Leu Tyr Ala Val Val Ser Glu Glu Pro Ile Tyr Ile Val Cys Glu Tyr
            100                 105                 110

Met Ser Lys Gly Ser Leu Leu Asp Phe Leu Lys Gly Glu Met Gly Lys
        115                 120                 125

Tyr Leu Arg Leu Pro Gln Leu Val Asp Met Ala Ala Gln Ile Ala Ser
    130                 135                 140

Gly Met Ala Tyr Val Glu Arg Met Asn Tyr Val His Arg Asp Leu Arg
145                 150                 155                 160

Ala Ala Asn Ile Leu Val Gly Glu Asn Leu Val Cys Lys Val Ala Asp
                165                 170                 175

Phe Gly Leu Ala Arg Leu Ile Glu Asp Asn Glu Tyr Thr Ala Arg Gln
            180                 185                 190

Gly Ala Lys Phe Pro Ile Lys Trp Thr Ala Pro Glu Ala Ala Leu Tyr
        195                 200                 205

Gly Arg Phe Thr Ile Lys Ser Asp Val Trp Ser Phe Gly Ile Leu Leu
    210                 215                 220

Thr Glu Leu Thr Thr Lys Gly Arg Val Pro Tyr Pro Gly Met Val Asn
225                 230                 235                 240

Arg Glu Val Leu Asp Gln Val Glu Arg Gly Tyr Arg Met Pro Cys Pro
                245                 250                 255

Pro Glu Cys Pro Glu Ser Leu His Asp Leu Met Cys Gln Cys Trp Arg
            260                 265                 270

Lys Asp Pro Glu Glu Arg Pro Thr Phe Glu Tyr Leu Gln Ala Phe Leu
        275                 280                 285

Glu Asp Tyr Phe Thr Ser Thr Glu Pro Gln Tyr Gln Pro Gly Glu Asn
    290                 295                 300

Leu
305

<210> SEQ ID NO 3
<211> LENGTH: 533
<212> TYPE: PRT
<213> ORGANISM: Gallus gallus
<220> FEATURE:
<223> OTHER INFORMATION: proto-oncogene c-Src

<400> SEQUENCE: 3

```
Met Gly Ser Ser Lys Ser Lys Pro Lys Asp Pro Ser Gln Arg Arg Arg
1               5                   10                  15

Ser Leu Glu Pro Pro Asp Ser Thr His His Gly Gly Phe Pro Ala Ser
            20                  25                  30

Gln Thr Pro Asn Lys Thr Ala Ala Pro Asp Thr His Arg Thr Pro Ser
        35                  40                  45

Arg Ser Phe Gly Thr Val Ala Thr Glu Pro Lys Leu Phe Gly Gly Phe
    50                  55                  60

Asn Thr Ser Asp Thr Val Thr Ser Pro Gln Arg Ala Gly Ala Leu Ala
65                  70                  75                  80

Gly Gly Val Thr Thr Phe Val Ala Leu Tyr Asp Tyr Glu Ser Arg Thr
                85                  90                  95

Glu Thr Asp Leu Ser Phe Lys Lys Gly Glu Arg Leu Gln Ile Val Asn
            100                 105                 110

Asn Thr Glu Gly Asp Trp Trp Leu Ala His Ser Leu Thr Thr Gly Gln
        115                 120                 125

Thr Gly Tyr Ile Pro Ser Asn Tyr Val Ala Pro Ser Asp Ser Ile Gln
    130                 135                 140

Ala Glu Glu Trp Tyr Phe Gly Lys Ile Thr Arg Arg Glu Ser Glu Arg
145                 150                 155                 160

Leu Leu Leu Asn Pro Glu Asn Pro Arg Gly Thr Phe Leu Val Arg Glu
                165                 170                 175

Ser Glu Thr Thr Lys Gly Ala Tyr Cys Leu Ser Val Ser Asp Phe Asp
            180                 185                 190

Asn Ala Lys Gly Leu Asn Val Lys His Tyr Lys Ile Arg Lys Leu Asp
        195                 200                 205

Ser Gly Gly Phe Tyr Ile Thr Ser Arg Thr Gln Phe Ser Ser Leu Gln
    210                 215                 220

Gln Leu Val Ala Tyr Tyr Ser Lys His Ala Asp Gly Leu Cys His Arg
225                 230                 235                 240

Leu Thr Asn Val Cys Pro Thr Ser Lys Pro Gln Thr Gln Gly Leu Ala
                245                 250                 255

Lys Asp Ala Trp Glu Ile Pro Arg Glu Ser Leu Arg Leu Glu Val Lys
            260                 265                 270

Leu Gly Gln Gly Cys Phe Gly Glu Val Trp Met Gly Thr Trp Asn Gly
        275                 280                 285

Thr Thr Arg Val Ala Ile Lys Thr Leu Lys Pro Gly Thr Met Ser Pro
    290                 295                 300

Glu Ala Phe Leu Gln Glu Ala Gln Val Met Lys Lys Leu Arg His Glu
305                 310                 315                 320

Lys Leu Val Gln Leu Tyr Ala Val Val Ser Glu Pro Ile Tyr Ile
                325                 330                 335

Val Thr Glu Tyr Met Ser Lys Gly Ser Leu Leu Asp Phe Leu Lys Gly
            340                 345                 350

Glu Met Gly Lys Tyr Leu Arg Leu Pro Gln Leu Val Asp Met Ala Ala
        355                 360                 365

Gln Ile Ala Ser Gly Met Ala Tyr Val Glu Arg Met Asn Tyr Val His
    370                 375                 380

Arg Asp Leu Arg Ala Ala Asn Ile Leu Val Gly Glu Asn Leu Val Cys
385                 390                 395                 400

Lys Val Ala Asp Phe Gly Leu Ala Arg Leu Ile Glu Asp Asn Glu Tyr
```

```
                405                 410                 415
Thr Ala Arg Gln Gly Ala Lys Phe Pro Ile Lys Trp Thr Ala Pro Glu
            420                 425                 430

Ala Ala Leu Tyr Gly Arg Phe Thr Ile Lys Ser Asp Val Trp Ser Phe
            435                 440                 445

Gly Ile Leu Leu Thr Glu Leu Thr Thr Lys Gly Arg Val Pro Tyr Pro
            450                 455                 460

Gly Met Val Asn Arg Glu Val Leu Asp Gln Val Glu Arg Gly Tyr Arg
465                 470                 475                 480

Met Pro Cys Pro Pro Glu Cys Pro Glu Ser Leu His Asp Leu Met Cys
            485                 490                 495

Gln Cys Trp Arg Lys Asp Pro Glu Glu Arg Pro Thr Phe Glu Tyr Leu
            500                 505                 510

Gln Ala Phe Leu Glu Asp Tyr Phe Thr Ser Thr Glu Pro Gln Tyr Gln
            515                 520                 525

Pro Gly Glu Asn Leu
            530

<210> SEQ ID NO 4
<211> LENGTH: 283
<212> TYPE: PRT
<213> ORGANISM: Artificial sequence
<220> FEATURE:
<223> OTHER INFORMATION: synthetic Gallus gallus proto-oncogene c-Src
      (251-533)

<400> SEQUENCE: 4

Gln Thr Gln Gly Leu Ala Lys Asp Ala Trp Glu Ile Pro Arg Glu Ser
1               5                   10                  15

Leu Arg Leu Glu Val Lys Leu Gly Gln Gly Cys Phe Gly Glu Val Trp
            20                  25                  30

Met Gly Thr Trp Asn Gly Thr Thr Arg Val Ala Ile Lys Thr Leu Lys
        35                  40                  45

Pro Gly Thr Met Ser Pro Glu Ala Phe Leu Gln Glu Ala Gln Val Met
    50                  55                  60

Lys Lys Leu Arg His Glu Lys Leu Val Gln Leu Tyr Ala Val Val Ser
65                  70                  75                  80

Glu Glu Pro Ile Tyr Ile Val Thr Glu Tyr Met Ser Lys Gly Ser Leu
                85                  90                  95

Leu Asp Phe Leu Lys Gly Glu Met Gly Lys Tyr Leu Arg Leu Pro Gln
            100                 105                 110

Leu Val Asp Met Ala Ala Gln Ile Ala Ser Gly Met Ala Tyr Val Glu
        115                 120                 125

Arg Met Asn Tyr Val His Arg Asp Leu Arg Ala Ala Asn Ile Leu Val
130                 135                 140

Gly Glu Asn Leu Val Cys Lys Val Ala Asp Phe Gly Leu Ala Arg Leu
145                 150                 155                 160

Ile Glu Asp Asn Glu Tyr Thr Ala Arg Gln Gly Ala Lys Phe Pro Ile
                165                 170                 175

Lys Trp Thr Ala Pro Glu Ala Ala Leu Tyr Gly Arg Phe Thr Ile Lys
            180                 185                 190

Ser Asp Val Trp Ser Phe Gly Ile Leu Leu Thr Glu Leu Thr Thr Lys
        195                 200                 205

Gly Arg Val Pro Tyr Pro Gly Met Val Asn Arg Glu Val Leu Asp Gln
    210                 215                 220
```

-continued

```
Val Glu Arg Gly Tyr Arg Met Pro Cys Pro Pro Glu Cys Pro Glu Ser
225                 230                 235                 240

Leu His Asp Leu Met Cys Gln Cys Trp Arg Lys Asp Pro Glu Glu Arg
                245                 250                 255

Pro Thr Phe Glu Tyr Leu Gln Ala Phe Leu Glu Asp Tyr Phe Thr Ser
            260                 265                 270

Thr Glu Pro Gln Tyr Gln Pro Gly Glu Asn Leu
        275                 280
```

<210> SEQ ID NO 5
<211> LENGTH: 286
<212> TYPE: PRT
<213> ORGANISM: Artificial sequence
<220> FEATURE:
<223> OTHER INFORMATION: synthetic Gallus gallus proto-oncogene c-Src
      (251-533) with GHM at N-terminal

<400> SEQUENCE: 5

```
Gly His Met Gln Thr Gln Gly Leu Ala Lys Asp Ala Trp Glu Ile Pro
1               5                   10                  15

Arg Glu Ser Leu Arg Leu Glu Val Lys Leu Gly Gln Gly Cys Phe Gly
                20                  25                  30

Glu Val Trp Met Gly Thr Trp Asn Gly Thr Thr Arg Val Ala Ile Lys
            35                  40                  45

Thr Leu Lys Pro Gly Thr Met Ser Pro Glu Ala Phe Leu Gln Glu Ala
        50                  55                  60

Gln Val Met Lys Lys Leu Arg His Glu Lys Leu Val Gln Leu Tyr Ala
65                  70                  75                  80

Val Val Ser Glu Glu Pro Ile Tyr Ile Val Thr Glu Tyr Met Ser Lys
                85                  90                  95

Gly Ser Leu Leu Asp Phe Leu Lys Gly Glu Met Gly Lys Tyr Leu Arg
            100                 105                 110

Leu Pro Gln Leu Val Asp Met Ala Ala Gln Ile Ala Ser Gly Met Ala
        115                 120                 125

Tyr Val Glu Arg Met Asn Tyr Val His Arg Asp Leu Arg Ala Ala Asn
130                 135                 140

Ile Leu Val Gly Glu Asn Leu Val Cys Lys Val Ala Asp Phe Gly Leu
145                 150                 155                 160

Ala Arg Leu Ile Glu Asp Asn Glu Tyr Thr Ala Arg Gln Gly Ala Lys
                165                 170                 175

Phe Pro Ile Lys Trp Thr Ala Pro Glu Ala Ala Leu Tyr Gly Arg Phe
            180                 185                 190

Thr Ile Lys Ser Asp Val Trp Ser Phe Gly Ile Leu Leu Thr Glu Leu
        195                 200                 205

Thr Thr Lys Gly Arg Val Pro Tyr Pro Gly Met Val Asn Arg Glu Val
    210                 215                 220

Leu Asp Gln Val Glu Arg Gly Tyr Arg Met Pro Cys Pro Pro Glu Cys
225                 230                 235                 240

Pro Glu Ser Leu His Asp Leu Met Cys Gln Cys Trp Arg Lys Asp Pro
                245                 250                 255

Glu Glu Arg Pro Thr Phe Glu Tyr Leu Gln Ala Phe Leu Glu Asp Tyr
            260                 265                 270

Phe Thr Ser Thr Glu Pro Gln Tyr Gln Pro Gly Glu Asn Leu
        275                 280                 285
```

<210> SEQ ID NO 6

-continued

```
<211> LENGTH: 283
<212> TYPE: PRT
<213> ORGANISM: Artificial sequence
<220> FEATURE:
<223> OTHER INFORMATION: synthetic Gallus gallus proto-oncogene
      [T338X]c-Src (251-533)
<220> FEATURE:
<221> NAME/KEY: VARIANT
<222> LOCATION: (88)..(88)
<223> OTHER INFORMATION: Xaa = any naturally occurring amino acid

<400> SEQUENCE: 6

Gln Thr Gln Gly Leu Ala Lys Asp Ala Trp Glu Ile Pro Arg Glu Ser
1               5                   10                  15

Leu Arg Leu Glu Val Lys Leu Gly Gln Gly Cys Phe Gly Glu Val Trp
            20                  25                  30

Met Gly Thr Trp Asn Gly Thr Thr Arg Val Ala Ile Lys Thr Leu Lys
        35                  40                  45

Pro Gly Thr Met Ser Pro Glu Ala Phe Leu Gln Glu Ala Gln Val Met
    50                  55                  60

Lys Lys Leu Arg His Glu Lys Leu Val Gln Leu Tyr Ala Val Val Ser
65                  70                  75                  80

Glu Glu Pro Ile Tyr Ile Val Xaa Glu Tyr Met Ser Lys Gly Ser Leu
                85                  90                  95

Leu Asp Phe Leu Lys Gly Glu Met Gly Lys Tyr Leu Arg Leu Pro Gln
            100                 105                 110

Leu Val Asp Met Ala Ala Gln Ile Ala Ser Gly Met Ala Tyr Val Glu
        115                 120                 125

Arg Met Asn Tyr Val His Arg Asp Leu Arg Ala Ala Asn Ile Leu Val
130                 135                 140

Gly Glu Asn Leu Val Cys Lys Val Ala Asp Phe Gly Leu Ala Arg Leu
145                 150                 155                 160

Ile Glu Asp Asn Glu Tyr Thr Ala Arg Gln Gly Ala Lys Phe Pro Ile
                165                 170                 175

Lys Trp Thr Ala Pro Glu Ala Ala Leu Tyr Gly Arg Phe Thr Ile Lys
            180                 185                 190

Ser Asp Val Trp Ser Phe Gly Ile Leu Leu Thr Glu Leu Thr Thr Lys
        195                 200                 205

Gly Arg Val Pro Tyr Pro Gly Met Val Asn Arg Glu Val Leu Asp Gln
210                 215                 220

Val Glu Arg Gly Tyr Arg Met Pro Cys Pro Pro Glu Cys Pro Glu Ser
225                 230                 235                 240

Leu His Asp Leu Met Cys Gln Cys Trp Arg Lys Asp Pro Glu Glu Arg
                245                 250                 255

Pro Thr Phe Glu Tyr Leu Gln Ala Phe Leu Glu Asp Tyr Phe Thr Ser
            260                 265                 270

Thr Glu Pro Gln Tyr Gln Pro Gly Glu Asn Leu
        275                 280

<210> SEQ ID NO 7
<211> LENGTH: 286
<212> TYPE: PRT
<213> ORGANISM: Artificial sequence
<220> FEATURE:
<223> OTHER INFORMATION: synthetic Gallus gallus proto-oncogene
      GHM-[T338X]c-Src (251-533) (GHM at N-terminal)
<220> FEATURE:
<221> NAME/KEY: VARIANT
<222> LOCATION: (91)..(91)
<223> OTHER INFORMATION: Xaa can be any naturally occurring amino acid
```

<400> SEQUENCE: 7

```
Gly His Met Gln Thr Gln Gly Leu Ala Lys Asp Ala Trp Glu Ile Pro
1               5                   10                  15

Arg Glu Ser Leu Arg Leu Glu Val Lys Leu Gly Gln Gly Cys Phe Gly
            20                  25                  30

Glu Val Trp Met Gly Thr Trp Asn Gly Thr Thr Arg Val Ala Ile Lys
        35                  40                  45

Thr Leu Lys Pro Gly Thr Met Ser Pro Glu Ala Phe Leu Gln Glu Ala
50                  55                  60

Gln Val Met Lys Lys Leu Arg His Glu Lys Leu Val Gln Leu Tyr Ala
65                  70                  75                  80

Val Val Ser Glu Glu Pro Ile Tyr Ile Val Xaa Glu Tyr Met Ser Lys
                85                  90                  95

Gly Ser Leu Leu Asp Phe Leu Lys Gly Glu Met Gly Lys Tyr Leu Arg
            100                 105                 110

Leu Pro Gln Leu Val Asp Met Ala Ala Gln Ile Ala Ser Gly Met Ala
        115                 120                 125

Tyr Val Glu Arg Met Asn Tyr Val His Arg Asp Leu Arg Ala Ala Asn
130                 135                 140

Ile Leu Val Gly Glu Asn Leu Val Cys Lys Val Ala Asp Phe Gly Leu
145                 150                 155                 160

Ala Arg Leu Ile Glu Asp Asn Glu Tyr Thr Ala Arg Gln Gly Ala Lys
                165                 170                 175

Phe Pro Ile Lys Trp Thr Ala Pro Glu Ala Ala Leu Tyr Gly Arg Phe
            180                 185                 190

Thr Ile Lys Ser Asp Val Trp Ser Phe Gly Ile Leu Leu Thr Glu Leu
        195                 200                 205

Thr Thr Lys Gly Arg Val Pro Tyr Pro Gly Met Val Asn Arg Glu Val
210                 215                 220

Leu Asp Gln Val Glu Arg Gly Tyr Arg Met Pro Cys Pro Pro Glu Cys
225                 230                 235                 240

Pro Glu Ser Leu His Asp Leu Met Cys Gln Cys Trp Arg Lys Asp Pro
                245                 250                 255

Glu Glu Arg Pro Thr Phe Glu Tyr Leu Gln Ala Phe Leu Glu Asp Tyr
            260                 265                 270

Phe Thr Ser Thr Glu Pro Gln Tyr Gln Pro Gly Glu Asn Leu
        275                 280                 285
```

<210> SEQ ID NO 8
<211> LENGTH: 283
<212> TYPE: PRT
<213> ORGANISM: Artificial sequence
<220> FEATURE:
<223> OTHER INFORMATION: synthetic Gallus gallus proto-oncogene
    [T338C]c-Src (251-533) (c-Src "ES1")

<400> SEQUENCE: 8

```
Gln Thr Gln Gly Leu Ala Lys Asp Ala Trp Glu Ile Pro Arg Glu Ser
1               5                   10                  15

Leu Arg Leu Glu Val Lys Leu Gly Gln Gly Cys Phe Gly Glu Val Trp
            20                  25                  30

Met Gly Thr Trp Asn Gly Thr Thr Arg Val Ala Ile Lys Thr Leu Lys
        35                  40                  45

Pro Gly Thr Met Ser Pro Glu Ala Phe Leu Gln Glu Ala Gln Val Met
50                  55                  60
```

```
Lys Lys Leu Arg His Glu Lys Leu Val Gln Leu Tyr Ala Val Val Ser
 65                  70                  75                  80

Glu Glu Pro Ile Tyr Ile Val Cys Glu Tyr Met Ser Lys Gly Ser Leu
                 85                  90                  95

Leu Asp Phe Leu Lys Gly Glu Met Gly Lys Tyr Leu Arg Leu Pro Gln
            100                 105                 110

Leu Val Asp Met Ala Ala Gln Ile Ala Ser Gly Met Ala Tyr Val Glu
            115                 120                 125

Arg Met Asn Tyr Val His Arg Asp Leu Arg Ala Ala Asn Ile Leu Val
        130                 135                 140

Gly Glu Asn Leu Val Cys Lys Val Ala Asp Phe Gly Leu Ala Arg Leu
145                 150                 155                 160

Ile Glu Asp Asn Glu Tyr Thr Ala Arg Gln Gly Ala Lys Phe Pro Ile
                165                 170                 175

Lys Trp Thr Ala Pro Glu Ala Ala Leu Tyr Gly Arg Phe Thr Ile Lys
            180                 185                 190

Ser Asp Val Trp Ser Phe Gly Ile Leu Leu Thr Glu Leu Thr Thr Lys
        195                 200                 205

Gly Arg Val Pro Tyr Pro Gly Met Val Asn Arg Glu Val Leu Asp Gln
            210                 215                 220

Val Glu Arg Gly Tyr Arg Met Pro Cys Pro Pro Glu Cys Pro Glu Ser
225                 230                 235                 240

Leu His Asp Leu Met Cys Gln Cys Trp Arg Lys Asp Pro Glu Glu Arg
                245                 250                 255

Pro Thr Phe Glu Tyr Leu Gln Ala Phe Leu Glu Asp Tyr Phe Thr Ser
            260                 265                 270

Thr Glu Pro Gln Tyr Gln Pro Gly Glu Asn Leu
        275                 280

<210> SEQ ID NO 9
<211> LENGTH: 286
<212> TYPE: PRT
<213> ORGANISM: Artificial sequence
<220> FEATURE:
<223> OTHER INFORMATION: synthetic Gallus gallus proto-oncogene
      GHM-[T338C]c-Src (251-533) (GHM at N-terminal) (c-Src "ES1")

<400> SEQUENCE: 9

Gly His Met Gln Thr Gln Gly Leu Ala Lys Asp Ala Trp Glu Ile Pro
  1               5                  10                  15

Arg Glu Ser Leu Arg Leu Glu Val Lys Leu Gly Gln Gly Cys Phe Gly
             20                  25                  30

Glu Val Trp Met Gly Thr Trp Asn Gly Thr Thr Arg Val Ala Ile Lys
         35                  40                  45

Thr Leu Lys Pro Gly Thr Met Ser Pro Glu Ala Phe Leu Gln Glu Ala
 50                  55                  60

Gln Val Met Lys Lys Leu Arg His Glu Lys Leu Val Gln Leu Tyr Ala
 65                  70                  75                  80

Val Val Ser Glu Glu Pro Ile Tyr Ile Val Cys Glu Tyr Met Ser Lys
                 85                  90                  95

Gly Ser Leu Leu Asp Phe Leu Lys Gly Glu Met Gly Lys Tyr Leu Arg
            100                 105                 110

Leu Pro Gln Leu Val Asp Met Ala Ala Gln Ile Ala Ser Gly Met Ala
        115                 120                 125

Tyr Val Glu Arg Met Asn Tyr Val His Arg Asp Leu Arg Ala Ala Asn
```

```
                130                 135                 140
Ile Leu Val Gly Glu Asn Leu Val Cys Lys Val Ala Asp Phe Gly Leu
145                 150                 155                 160

Ala Arg Leu Ile Glu Asp Asn Glu Tyr Thr Ala Arg Gln Gly Ala Lys
                165                 170                 175

Phe Pro Ile Lys Trp Thr Ala Pro Glu Ala Ala Leu Tyr Gly Arg Phe
                180                 185                 190

Thr Ile Lys Ser Asp Val Trp Ser Phe Gly Ile Leu Leu Thr Glu Leu
                195                 200                 205

Thr Thr Lys Gly Arg Val Pro Tyr Pro Gly Met Val Asn Arg Glu Val
210                 215                 220

Leu Asp Gln Val Glu Arg Gly Tyr Arg Met Pro Cys Pro Pro Glu Cys
225                 230                 235                 240

Pro Glu Ser Leu His Asp Leu Met Cys Gln Cys Trp Arg Lys Asp Pro
                245                 250                 255

Glu Glu Arg Pro Thr Phe Glu Tyr Leu Gln Ala Phe Leu Glu Asp Tyr
                260                 265                 270

Phe Thr Ser Thr Glu Pro Gln Tyr Gln Pro Gly Glu Asn Leu
                275                 280                 285

<210> SEQ ID NO 10
<211> LENGTH: 283
<212> TYPE: PRT
<213> ORGANISM: Artificial sequence
<220> FEATURE:
<223> OTHER INFORMATION: synthetic Gallus gallus proto-oncogene [T338X,
      V323X]c-Src (251-533)
<220> FEATURE:
<221> NAME/KEY: VARIANT
<222> LOCATION: (73)..(88)
<223> OTHER INFORMATION: Xaa = any naturally occurring amino acid

<400> SEQUENCE: 10

Gln Thr Gln Gly Leu Ala Lys Asp Ala Trp Glu Ile Pro Arg Glu Ser
1               5                   10                  15

Leu Arg Leu Glu Val Lys Leu Gly Gln Gly Cys Phe Gly Glu Val Trp
                20                  25                  30

Met Gly Thr Trp Asn Gly Thr Thr Arg Val Ala Ile Lys Thr Leu Lys
            35                  40                  45

Pro Gly Thr Met Ser Pro Glu Ala Phe Leu Gln Glu Ala Gln Val Met
        50                  55                  60

Lys Lys Leu Arg His Glu Lys Leu Xaa Gln Leu Tyr Ala Val Val Ser
65                  70                  75                  80

Glu Glu Pro Ile Tyr Ile Val Xaa Glu Tyr Met Ser Lys Gly Ser Leu
                85                  90                  95

Leu Asp Phe Leu Lys Gly Glu Met Gly Lys Tyr Leu Arg Leu Pro Gln
                100                 105                 110

Leu Val Asp Met Ala Ala Gln Ile Ala Ser Gly Met Ala Tyr Val Glu
            115                 120                 125

Arg Met Asn Tyr Val His Arg Asp Leu Arg Ala Ala Asn Ile Leu Val
        130                 135                 140

Gly Glu Asn Leu Val Cys Lys Val Ala Asp Phe Gly Leu Ala Arg Leu
145                 150                 155                 160

Ile Glu Asp Asn Glu Tyr Thr Ala Arg Gln Gly Ala Lys Phe Pro Ile
                165                 170                 175

Lys Trp Thr Ala Pro Glu Ala Ala Leu Tyr Gly Arg Phe Thr Ile Lys
            180                 185                 190
```

```
Ser Asp Val Trp Ser Phe Gly Ile Leu Leu Thr Glu Leu Thr Thr Lys
        195                 200                 205

Gly Arg Val Pro Tyr Pro Gly Met Val Asn Arg Glu Val Leu Asp Gln
    210                 215                 220

Val Glu Arg Gly Tyr Arg Met Pro Cys Pro Pro Glu Cys Pro Glu Ser
225                 230                 235                 240

Leu His Asp Leu Met Cys Gln Cys Trp Arg Lys Asp Pro Glu Glu Arg
            245                 250                 255

Pro Thr Phe Glu Tyr Leu Gln Ala Phe Leu Glu Asp Tyr Phe Thr Ser
                260                 265                 270

Thr Glu Pro Gln Tyr Gln Pro Gly Glu Asn Leu
        275                 280

<210> SEQ ID NO 11
<211> LENGTH: 286
<212> TYPE: PRT
<213> ORGANISM: Artificial sequence
<220> FEATURE:
<223> OTHER INFORMATION: synthetic Gallus gallus proto-oncogene
      GHM-[T338X, V323X]c-Src (251-533) (GHM at N-terminal)
<220> FEATURE:
<221> NAME/KEY: VARIANT
<222> LOCATION: (76)..(91)
<223> OTHER INFORMATION: Xaa = any naturally occurring amino acid

<400> SEQUENCE: 11

Gly His Met Gln Thr Gln Gly Leu Ala Lys Asp Ala Trp Glu Ile Pro
1               5                   10                  15

Arg Glu Ser Leu Arg Leu Glu Val Lys Leu Gly Gln Gly Cys Phe Gly
            20                  25                  30

Glu Val Trp Met Gly Thr Trp Asn Gly Thr Thr Arg Val Ala Ile Lys
        35                  40                  45

Thr Leu Lys Pro Gly Thr Met Ser Pro Glu Ala Phe Leu Gln Glu Ala
    50                  55                  60

Gln Val Met Lys Lys Leu Arg His Glu Lys Leu Xaa Gln Leu Tyr Ala
65                  70                  75                  80

Val Val Ser Glu Glu Pro Ile Tyr Ile Val Xaa Glu Tyr Met Ser Lys
                85                  90                  95

Gly Ser Leu Leu Asp Phe Leu Lys Gly Glu Met Gly Lys Tyr Leu Arg
            100                 105                 110

Leu Pro Gln Leu Val Asp Met Ala Ala Gln Ile Ala Ser Gly Met Ala
        115                 120                 125

Tyr Val Glu Arg Met Asn Tyr Val His Arg Asp Leu Arg Ala Ala Asn
    130                 135                 140

Ile Leu Val Gly Glu Asn Leu Val Cys Lys Val Ala Asp Phe Gly Leu
145                 150                 155                 160

Ala Arg Leu Ile Glu Asp Asn Glu Tyr Thr Ala Arg Gln Gly Ala Lys
                165                 170                 175

Phe Pro Ile Lys Trp Thr Ala Pro Glu Ala Ala Leu Tyr Gly Arg Phe
            180                 185                 190

Thr Ile Lys Ser Asp Val Trp Ser Phe Gly Ile Leu Leu Thr Glu Leu
        195                 200                 205

Thr Thr Lys Gly Arg Val Pro Tyr Pro Gly Met Val Asn Arg Glu Val
    210                 215                 220

Leu Asp Gln Val Glu Arg Gly Tyr Arg Met Pro Cys Pro Pro Glu Cys
225                 230                 235                 240
```

```
Pro Glu Ser Leu His Asp Leu Met Cys Gln Cys Trp Arg Lys Asp Pro
            245                 250                 255

Glu Glu Arg Pro Thr Phe Glu Tyr Leu Gln Ala Phe Leu Glu Asp Tyr
        260                 265                 270

Phe Thr Ser Thr Glu Pro Gln Tyr Gln Pro Gly Glu Asn Leu
    275                 280                 285

<210> SEQ ID NO 12
<211> LENGTH: 283
<212> TYPE: PRT
<213> ORGANISM: Artificial sequence
<220> FEATURE:
<223> OTHER INFORMATION: synthetic Gallus gallus proto-oncogene [T338C,
      V323X]c-Src (251-533)
<220> FEATURE:
<221> NAME/KEY: VARIANT
<222> LOCATION: (73)..(73)
<223> OTHER INFORMATION: Xaa = any naturally occurring amino acid

<400> SEQUENCE: 12

Gln Thr Gln Gly Leu Ala Lys Asp Ala Trp Glu Ile Pro Arg Glu Ser
1               5                   10                  15

Leu Arg Leu Glu Val Lys Leu Gly Gln Gly Cys Phe Gly Glu Val Trp
            20                  25                  30

Met Gly Thr Trp Asn Gly Thr Thr Arg Val Ala Ile Lys Thr Leu Lys
        35                  40                  45

Pro Gly Thr Met Ser Pro Glu Ala Phe Leu Gln Glu Ala Gln Val Met
    50                  55                  60

Lys Lys Leu Arg His Glu Lys Leu Xaa Gln Leu Tyr Ala Val Val Ser
65                  70                  75                  80

Glu Glu Pro Ile Tyr Ile Val Cys Glu Tyr Met Ser Lys Gly Ser Leu
                85                  90                  95

Leu Asp Phe Leu Lys Gly Glu Met Gly Lys Tyr Leu Arg Leu Pro Gln
            100                 105                 110

Leu Val Asp Met Ala Ala Gln Ile Ala Ser Gly Met Ala Tyr Val Glu
        115                 120                 125

Arg Met Asn Tyr Val His Arg Asp Leu Arg Ala Ala Asn Ile Leu Val
    130                 135                 140

Gly Glu Asn Leu Val Cys Lys Val Ala Asp Phe Gly Leu Ala Arg Leu
145                 150                 155                 160

Ile Glu Asp Asn Glu Tyr Thr Ala Arg Gln Gly Ala Lys Phe Pro Ile
                165                 170                 175

Lys Trp Thr Ala Pro Glu Ala Ala Leu Tyr Gly Arg Phe Thr Ile Lys
            180                 185                 190

Ser Asp Val Trp Ser Phe Gly Ile Leu Leu Thr Glu Leu Thr Thr Lys
        195                 200                 205

Gly Arg Val Pro Tyr Pro Gly Met Val Asn Arg Glu Val Leu Asp Gln
    210                 215                 220

Val Glu Arg Gly Tyr Arg Met Pro Cys Pro Glu Cys Pro Glu Ser
225                 230                 235                 240

Leu His Asp Leu Met Cys Gln Cys Trp Arg Lys Asp Pro Glu Glu Arg
                245                 250                 255

Pro Thr Phe Glu Tyr Leu Gln Ala Phe Leu Glu Asp Tyr Phe Thr Ser
            260                 265                 270

Thr Glu Pro Gln Tyr Gln Pro Gly Glu Asn Leu
        275                 280
```

<210> SEQ ID NO 13
<211> LENGTH: 286
<212> TYPE: PRT
<213> ORGANISM: Artificial sequence
<220> FEATURE:
<223> OTHER INFORMATION: synthetic Gallus gallus proto-oncogene
    GHM-[T338C, V323X]c-Src (251-533) (GHM at N-terminal)
<220> FEATURE:
<221> NAME/KEY: VARIANT
<222> LOCATION: (76)..(76)
<223> OTHER INFORMATION: Xaa = any naturally occurring amino acid

<400> SEQUENCE: 13

```
Gly His Met Gln Thr Gln Gly Leu Ala Lys Asp Ala Trp Glu Ile Pro
1               5                   10                  15

Arg Glu Ser Leu Arg Leu Glu Val Lys Leu Gly Gln Gly Cys Phe Gly
            20                  25                  30

Glu Val Trp Met Gly Thr Trp Asn Gly Thr Thr Arg Val Ala Ile Lys
        35                  40                  45

Thr Leu Lys Pro Gly Thr Met Ser Pro Glu Ala Phe Leu Gln Glu Ala
    50                  55                  60

Gln Val Met Lys Lys Leu Arg His Glu Lys Leu Xaa Gln Leu Tyr Ala
65                  70                  75                  80

Val Val Ser Glu Glu Pro Ile Tyr Ile Val Cys Glu Tyr Met Ser Lys
                85                  90                  95

Gly Ser Leu Leu Asp Phe Leu Lys Gly Glu Met Gly Lys Tyr Leu Arg
            100                 105                 110

Leu Pro Gln Leu Val Asp Met Ala Ala Gln Ile Ala Ser Gly Met Ala
        115                 120                 125

Tyr Val Glu Arg Met Asn Tyr Val His Arg Asp Leu Arg Ala Ala Asn
    130                 135                 140

Ile Leu Val Gly Glu Asn Leu Val Cys Lys Val Ala Asp Phe Gly Leu
145                 150                 155                 160

Ala Arg Leu Ile Glu Asp Asn Glu Tyr Thr Ala Arg Gln Gly Ala Lys
                165                 170                 175

Phe Pro Ile Lys Trp Thr Ala Pro Glu Ala Ala Leu Tyr Gly Arg Phe
            180                 185                 190

Thr Ile Lys Ser Asp Val Trp Ser Phe Gly Ile Leu Leu Thr Glu Leu
        195                 200                 205

Thr Thr Lys Gly Arg Val Pro Tyr Pro Gly Met Val Asn Arg Glu Val
    210                 215                 220

Leu Asp Gln Val Glu Arg Gly Tyr Arg Met Pro Cys Pro Pro Glu Cys
225                 230                 235                 240

Pro Glu Ser Leu His Asp Leu Met Cys Gln Cys Trp Arg Lys Asp Pro
                245                 250                 255

Glu Glu Arg Pro Thr Phe Glu Tyr Leu Gln Ala Phe Leu Glu Asp Tyr
            260                 265                 270

Phe Thr Ser Thr Glu Pro Gln Tyr Gln Pro Gly Glu Asn Leu
        275                 280                 285
```

<210> SEQ ID NO 14
<211> LENGTH: 283
<212> TYPE: PRT
<213> ORGANISM: Artificial sequence
<220> FEATURE:
<223> OTHER INFORMATION: synthetic Gallus gallus proto-oncogene [T338C,
    V323A]c-Src (251-533) (c-Src "ES2")

<400> SEQUENCE: 14

```
Gln Thr Gln Gly Leu Ala Lys Asp Ala Trp Glu Ile Pro Arg Glu Ser
1               5                  10                  15

Leu Arg Leu Glu Val Lys Leu Gly Gln Gly Cys Phe Gly Glu Val Trp
            20                  25                  30

Met Gly Thr Trp Asn Gly Thr Thr Arg Val Ala Ile Lys Thr Leu Lys
        35                  40                  45

Pro Gly Thr Met Ser Pro Glu Ala Phe Leu Gln Glu Ala Gln Val Met
    50                  55                  60

Lys Lys Leu Arg His Glu Lys Leu Ala Gln Leu Tyr Ala Val Val Ser
65                  70                  75                  80

Glu Glu Pro Ile Tyr Ile Val Cys Glu Tyr Met Ser Lys Gly Ser Leu
                85                  90                  95

Leu Asp Phe Leu Lys Gly Glu Met Gly Lys Tyr Leu Arg Leu Pro Gln
            100                 105                 110

Leu Val Asp Met Ala Ala Gln Ile Ala Ser Gly Met Ala Tyr Val Glu
        115                 120                 125

Arg Met Asn Tyr Val His Arg Asp Leu Arg Ala Ala Asn Ile Leu Val
    130                 135                 140

Gly Glu Asn Leu Val Cys Lys Val Ala Asp Phe Gly Leu Ala Arg Leu
145                 150                 155                 160

Ile Glu Asp Asn Glu Tyr Thr Ala Arg Gln Gly Ala Lys Phe Pro Ile
                165                 170                 175

Lys Trp Thr Ala Pro Glu Ala Ala Leu Tyr Gly Arg Phe Thr Ile Lys
            180                 185                 190

Ser Asp Val Trp Ser Phe Gly Ile Leu Leu Thr Glu Leu Thr Thr Lys
        195                 200                 205

Gly Arg Val Pro Tyr Pro Gly Met Val Asn Arg Glu Val Leu Asp Gln
210                 215                 220

Val Glu Arg Gly Tyr Arg Met Pro Cys Pro Pro Glu Cys Pro Glu Ser
225                 230                 235                 240

Leu His Asp Leu Met Cys Gln Cys Trp Arg Lys Asp Pro Glu Glu Arg
                245                 250                 255

Pro Thr Phe Glu Tyr Leu Gln Ala Phe Leu Glu Asp Tyr Phe Thr Ser
            260                 265                 270

Thr Glu Pro Gln Tyr Gln Pro Gly Glu Asn Leu
        275                 280

<210> SEQ ID NO 15
<211> LENGTH: 286
<212> TYPE: PRT
<213> ORGANISM: Artificial sequence
<220> FEATURE:
<223> OTHER INFORMATION: synthetic Gallus gallus proto-oncogene
      GHM-[T338C, V323A]c-Src (251-533) (GHM at N-terminal) (c-Src
      "ES2")

<400> SEQUENCE: 15

Gly His Met Gln Thr Gln Gly Leu Ala Lys Asp Ala Trp Glu Ile Pro
1               5                  10                  15

Arg Glu Ser Leu Arg Leu Glu Val Lys Leu Gly Gln Gly Cys Phe Gly
            20                  25                  30

Glu Val Trp Met Gly Thr Trp Asn Gly Thr Thr Arg Val Ala Ile Lys
        35                  40                  45

Thr Leu Lys Pro Gly Thr Met Ser Pro Glu Ala Phe Leu Gln Glu Ala
    50                  55                  60

Gln Val Met Lys Lys Leu Arg His Glu Lys Leu Ala Gln Leu Tyr Ala
```

```
                      65                  70                  75                  80
            Val Val Ser Glu Glu Pro Ile Tyr Ile Val Cys Glu Tyr Met Ser Lys
                              85                  90                  95
            Gly Ser Leu Leu Asp Phe Leu Lys Gly Glu Met Gly Lys Tyr Leu Arg
                             100                 105                 110
            Leu Pro Gln Leu Val Asp Met Ala Ala Gln Ile Ala Ser Gly Met Ala
                             115                 120                 125
            Tyr Val Glu Arg Met Asn Tyr Val His Arg Asp Leu Arg Ala Ala Asn
                    130                 135                 140
            Ile Leu Val Gly Glu Asn Leu Val Cys Lys Val Ala Asp Phe Gly Leu
            145                 150                 155                 160
            Ala Arg Leu Ile Glu Asp Asn Glu Tyr Thr Ala Arg Gln Gly Ala Lys
                             165                 170                 175
            Phe Pro Ile Lys Trp Thr Ala Pro Glu Ala Ala Leu Tyr Gly Arg Phe
                             180                 185                 190
            Thr Ile Lys Ser Asp Val Trp Ser Phe Gly Ile Leu Leu Thr Glu Leu
                             195                 200                 205
            Thr Thr Lys Gly Arg Val Pro Tyr Pro Gly Met Val Asn Arg Glu Val
                    210                 215                 220
            Leu Asp Gln Val Glu Arg Gly Tyr Arg Met Pro Cys Pro Pro Glu Cys
            225                 230                 235                 240
            Pro Glu Ser Leu His Asp Leu Met Cys Gln Cys Trp Arg Lys Asp Pro
                             245                 250                 255
            Glu Glu Arg Pro Thr Phe Glu Tyr Leu Gln Ala Phe Leu Glu Asp Tyr
                             260                 265                 270
            Phe Thr Ser Thr Glu Pro Gln Tyr Gln Pro Gly Glu Asn Leu
                    275                 280                 285

<210> SEQ ID NO 16
<211> LENGTH: 283
<212> TYPE: PRT
<213> ORGANISM: Artificial sequence
<220> FEATURE:
<223> OTHER INFORMATION: synthetic Gallus gallus proto-oncogene [T338C,
      V323S]c-Src (251-533) (c-Src "ES3")

<400> SEQUENCE: 16

Gln Thr Gln Gly Leu Ala Lys Asp Ala Trp Glu Ile Pro Arg Glu Ser
            1               5                   10                  15
            Leu Arg Leu Glu Val Lys Leu Gly Gln Gly Cys Phe Gly Glu Val Trp
                             20                  25                  30
            Met Gly Thr Trp Asn Gly Thr Thr Arg Val Ala Ile Lys Thr Leu Lys
                             35                  40                  45
            Pro Gly Thr Met Ser Pro Glu Ala Phe Leu Gln Glu Ala Gln Val Met
                    50                  55                  60
            Lys Lys Leu Arg His Glu Lys Leu Ser Gln Leu Tyr Ala Val Val Ser
            65                  70                  75                  80
            Glu Glu Pro Ile Tyr Ile Val Cys Glu Tyr Met Ser Lys Gly Ser Leu
                             85                  90                  95
            Leu Asp Phe Leu Lys Gly Glu Met Gly Lys Tyr Leu Arg Leu Pro Gln
                             100                 105                 110
            Leu Val Asp Met Ala Ala Gln Ile Ala Ser Gly Met Ala Tyr Val Glu
                             115                 120                 125
            Arg Met Asn Tyr Val His Arg Asp Leu Arg Ala Ala Asn Ile Leu Val
                    130                 135                 140
```

Gly Glu Asn Leu Val Cys Lys Val Ala Asp Phe Gly Leu Ala Arg Leu
145                 150                 155                 160

Ile Glu Asp Asn Glu Tyr Thr Ala Arg Gln Gly Ala Lys Phe Pro Ile
                165                 170                 175

Lys Trp Thr Ala Pro Glu Ala Ala Leu Tyr Gly Arg Phe Thr Ile Lys
            180                 185                 190

Ser Asp Val Trp Ser Phe Gly Ile Leu Leu Thr Glu Leu Thr Thr Lys
        195                 200                 205

Gly Arg Val Pro Tyr Pro Gly Met Val Asn Arg Glu Val Leu Asp Gln
    210                 215                 220

Val Glu Arg Gly Tyr Arg Met Pro Cys Pro Pro Glu Cys Pro Glu Ser
225                 230                 235                 240

Leu His Asp Leu Met Cys Gln Cys Trp Arg Lys Asp Pro Glu Glu Arg
                245                 250                 255

Pro Thr Phe Glu Tyr Leu Gln Ala Phe Leu Glu Asp Tyr Phe Thr Ser
            260                 265                 270

Thr Glu Pro Gln Tyr Gln Pro Gly Glu Asn Leu
        275                 280

<210> SEQ ID NO 17
<211> LENGTH: 286
<212> TYPE: PRT
<213> ORGANISM: Artificial sequence
<220> FEATURE:
<223> OTHER INFORMATION: synthetic Gallus gallus proto-oncogene
      GHM-[T338C, V323S]c-Src (251-533) (GHM at N-terminal) (c-Src
      "ES3")

<400> SEQUENCE: 17

Gly His Met Gln Thr Gln Gly Leu Ala Lys Asp Ala Trp Glu Ile Pro
1               5                   10                  15

Arg Glu Ser Leu Arg Leu Glu Val Lys Leu Gly Gln Gly Cys Phe Gly
            20                  25                  30

Glu Val Trp Met Gly Thr Trp Asn Gly Thr Thr Arg Val Ala Ile Lys
        35                  40                  45

Thr Leu Lys Pro Gly Thr Met Ser Pro Glu Ala Phe Leu Gln Glu Ala
50                  55                  60

Gln Val Met Lys Lys Leu Arg His Glu Lys Leu Ser Gln Leu Tyr Ala
65                  70                  75                  80

Val Val Ser Glu Glu Pro Ile Tyr Ile Val Cys Glu Tyr Met Ser Lys
                85                  90                  95

Gly Ser Leu Leu Asp Phe Leu Lys Gly Glu Met Gly Lys Tyr Leu Arg
            100                 105                 110

Leu Pro Gln Leu Val Asp Met Ala Ala Gln Ile Ala Ser Gly Met Ala
        115                 120                 125

Tyr Val Glu Arg Met Asn Tyr Val His Arg Asp Leu Arg Ala Ala Asn
    130                 135                 140

Ile Leu Val Gly Glu Asn Leu Val Cys Lys Val Ala Asp Phe Gly Leu
145                 150                 155                 160

Ala Arg Leu Ile Glu Asp Asn Glu Tyr Thr Ala Arg Gln Gly Ala Lys
                165                 170                 175

Phe Pro Ile Lys Trp Thr Ala Pro Glu Ala Ala Leu Tyr Gly Arg Phe
            180                 185                 190

Thr Ile Lys Ser Asp Val Trp Ser Phe Gly Ile Leu Leu Thr Glu Leu
        195                 200                 205

Thr Thr Lys Gly Arg Val Pro Tyr Pro Gly Met Val Asn Arg Glu Val

-continued

```
                210                 215                 220
Leu Asp Gln Val Glu Arg Gly Tyr Arg Met Pro Cys Pro Glu Cys
225                 230                 235                 240

Pro Glu Ser Leu His Asp Leu Met Cys Gln Cys Trp Arg Lys Asp Pro
                245                 250                 255

Glu Glu Arg Pro Thr Phe Glu Tyr Leu Gln Ala Phe Leu Glu Asp Tyr
                260                 265                 270

Phe Thr Ser Thr Glu Pro Gln Tyr Gln Pro Gly Glu Asn Leu
                275                 280                 285

<210> SEQ ID NO 18
<211> LENGTH: 283
<212> TYPE: PRT
<213> ORGANISM: Artificial sequence
<220> FEATURE:
<223> OTHER INFORMATION: synthetic Gallus gallus proto-oncogene [T338C,
      V323D]c-Src (251-533) (c-Src "ES4")

<400> SEQUENCE: 18

Gln Thr Gln Gly Leu Ala Lys Asp Ala Trp Glu Ile Pro Arg Glu Ser
1               5                   10                  15

Leu Arg Leu Glu Val Lys Leu Gly Gln Gly Cys Phe Gly Glu Val Trp
                20                  25                  30

Met Gly Thr Trp Asn Gly Thr Thr Arg Val Ala Ile Lys Thr Leu Lys
            35                  40                  45

Pro Gly Thr Met Ser Pro Glu Ala Phe Leu Gln Glu Ala Gln Val Met
    50                  55                  60

Lys Lys Leu Arg His Glu Lys Leu Asp Gln Leu Tyr Ala Val Val Ser
65                  70                  75                  80

Glu Glu Pro Ile Tyr Ile Val Cys Glu Tyr Met Ser Lys Gly Ser Leu
                85                  90                  95

Leu Asp Phe Leu Lys Gly Glu Met Gly Lys Tyr Leu Arg Leu Pro Gln
                100                 105                 110

Leu Val Asp Met Ala Ala Gln Ile Ala Ser Gly Met Ala Tyr Val Glu
            115                 120                 125

Arg Met Asn Tyr Val His Arg Asp Leu Arg Ala Ala Asn Ile Leu Val
    130                 135                 140

Gly Glu Asn Leu Val Cys Lys Val Ala Asp Phe Gly Leu Ala Arg Leu
145                 150                 155                 160

Ile Glu Asp Asn Glu Tyr Thr Ala Arg Gln Gly Ala Lys Phe Pro Ile
                165                 170                 175

Lys Trp Thr Ala Pro Glu Ala Ala Leu Tyr Gly Arg Phe Thr Ile Lys
                180                 185                 190

Ser Asp Val Trp Ser Phe Gly Ile Leu Leu Thr Glu Leu Thr Thr Lys
            195                 200                 205

Gly Arg Val Pro Tyr Pro Gly Met Val Asn Arg Glu Val Leu Asp Gln
    210                 215                 220

Val Glu Arg Gly Tyr Arg Met Pro Cys Pro Glu Cys Pro Glu Ser
225                 230                 235                 240

Leu His Asp Leu Met Cys Gln Cys Trp Arg Lys Asp Pro Glu Glu Arg
                245                 250                 255

Pro Thr Phe Glu Tyr Leu Gln Ala Phe Leu Glu Asp Tyr Phe Thr Ser
                260                 265                 270

Thr Glu Pro Gln Tyr Gln Pro Gly Glu Asn Leu
            275                 280
```

<210> SEQ ID NO 19
<211> LENGTH: 286
<212> TYPE: PRT
<213> ORGANISM: Artificial sequence
<220> FEATURE:
<223> OTHER INFORMATION: synthetic Gallus gallus proto-oncogene
      GHM-[T338C, V323D]c-Src (251-533) (GHM at N-terminal) (c-Src
      "ES4")

<400> SEQUENCE: 19

Gly His Met Gln Thr Gln Gly Leu Ala Lys Asp Ala Trp Glu Ile Pro
1               5                   10                  15

Arg Glu Ser Leu Arg Leu Glu Val Lys Leu Gly Gln Gly Cys Phe Gly
            20                  25                  30

Glu Val Trp Met Gly Thr Trp Asn Gly Thr Thr Arg Val Ala Ile Lys
        35                  40                  45

Thr Leu Lys Pro Gly Thr Met Ser Pro Glu Ala Phe Leu Gln Glu Ala
    50                  55                  60

Gln Val Met Lys Lys Leu Arg His Glu Lys Leu Asp Gln Leu Tyr Ala
65                  70                  75                  80

Val Val Ser Glu Glu Pro Ile Tyr Ile Val Cys Glu Tyr Met Ser Lys
                85                  90                  95

Gly Ser Leu Leu Asp Phe Leu Lys Gly Glu Met Gly Lys Tyr Leu Arg
            100                 105                 110

Leu Pro Gln Leu Val Asp Met Ala Ala Gln Ile Ala Ser Gly Met Ala
        115                 120                 125

Tyr Val Glu Arg Met Asn Tyr Val His Arg Asp Leu Arg Ala Ala Asn
    130                 135                 140

Ile Leu Val Gly Glu Asn Leu Val Cys Lys Val Ala Asp Phe Gly Leu
145                 150                 155                 160

Ala Arg Leu Ile Glu Asp Asn Glu Tyr Thr Ala Arg Gln Gly Ala Lys
                165                 170                 175

Phe Pro Ile Lys Trp Thr Ala Pro Glu Ala Leu Tyr Gly Arg Phe
            180                 185                 190

Thr Ile Lys Ser Asp Val Trp Ser Phe Gly Ile Leu Leu Thr Glu Leu
        195                 200                 205

Thr Thr Lys Gly Arg Val Pro Tyr Pro Gly Met Val Asn Arg Glu Val
    210                 215                 220

Leu Asp Gln Val Glu Arg Gly Tyr Arg Met Pro Cys Pro Pro Glu Cys
225                 230                 235                 240

Pro Glu Ser Leu His Asp Leu Met Cys Gln Cys Trp Arg Lys Asp Pro
                245                 250                 255

Glu Glu Arg Pro Thr Phe Glu Tyr Leu Gln Ala Phe Leu Glu Asp Tyr
            260                 265                 270

Phe Thr Ser Thr Glu Pro Gln Tyr Gln Pro Gly Glu Asn Leu
        275                 280                 285

<210> SEQ ID NO 20
<211> LENGTH: 283
<212> TYPE: PRT
<213> ORGANISM: Artificial sequence
<220> FEATURE:
<223> OTHER INFORMATION: synthetic Gallus gallus proto-oncogene [T338C,
      V323E]c-Src (251-533) (c-Src "ES5")

<400> SEQUENCE: 20

Gln Thr Gln Gly Leu Ala Lys Asp Ala Trp Glu Ile Pro Arg Glu Ser
1               5                   10                  15

Leu Arg Leu Glu Val Lys Leu Gly Gln Gly Cys Phe Gly Glu Val Trp
            20                  25                  30

Met Gly Thr Trp Asn Gly Thr Thr Arg Val Ala Ile Lys Thr Leu Lys
        35                  40                  45

Pro Gly Thr Met Ser Pro Glu Ala Phe Leu Gln Glu Ala Gln Val Met
    50                  55                  60

Lys Lys Leu Arg His Glu Lys Leu Glu Gln Leu Tyr Ala Val Val Ser
65                  70                  75                  80

Glu Glu Pro Ile Tyr Ile Val Cys Glu Tyr Met Ser Lys Gly Ser Leu
                85                  90                  95

Leu Asp Phe Leu Lys Gly Glu Met Gly Lys Tyr Leu Arg Leu Pro Gln
            100                 105                 110

Leu Val Asp Met Ala Ala Gln Ile Ala Ser Gly Met Ala Tyr Val Glu
        115                 120                 125

Arg Met Asn Tyr Val His Arg Asp Leu Arg Ala Ala Asn Ile Leu Val
130                 135                 140

Gly Glu Asn Leu Val Cys Lys Val Ala Asp Phe Gly Leu Ala Arg Leu
145                 150                 155                 160

Ile Glu Asp Asn Glu Tyr Thr Ala Arg Gln Gly Ala Lys Phe Pro Ile
                165                 170                 175

Lys Trp Thr Ala Pro Glu Ala Ala Leu Tyr Gly Arg Phe Thr Ile Lys
            180                 185                 190

Ser Asp Val Trp Ser Phe Gly Ile Leu Leu Thr Glu Leu Thr Thr Lys
        195                 200                 205

Gly Arg Val Pro Tyr Pro Gly Met Val Asn Arg Glu Val Leu Asp Gln
    210                 215                 220

Val Glu Arg Gly Tyr Arg Met Pro Cys Pro Pro Glu Cys Pro Glu Ser
225                 230                 235                 240

Leu His Asp Leu Met Cys Gln Cys Trp Arg Lys Asp Pro Glu Glu Arg
                245                 250                 255

Pro Thr Phe Glu Tyr Leu Gln Ala Phe Leu Glu Asp Tyr Phe Thr Ser
            260                 265                 270

Thr Glu Pro Gln Tyr Gln Pro Gly Glu Asn Leu
        275                 280

<210> SEQ ID NO 21
<211> LENGTH: 286
<212> TYPE: PRT
<213> ORGANISM: Artificial sequence
<220> FEATURE:
<223> OTHER INFORMATION: synthetic Gallus gallus proto-oncogene
      GHM-[T338C, V323E]c-Src (251-533) (GHM at N-terminal) (c-Src
      "ES5")

<400> SEQUENCE: 21

Gly His Met Gln Thr Gln Gly Leu Ala Lys Asp Ala Trp Glu Ile Pro
1               5                   10                  15

Arg Glu Ser Leu Arg Leu Glu Val Lys Leu Gly Gln Gly Cys Phe Gly
            20                  25                  30

Glu Val Trp Met Gly Thr Trp Asn Gly Thr Thr Arg Val Ala Ile Lys
        35                  40                  45

Thr Leu Lys Pro Gly Thr Met Ser Pro Glu Ala Phe Leu Gln Glu Ala
    50                  55                  60

Gln Val Met Lys Lys Leu Arg His Glu Lys Leu Glu Gln Leu Tyr Ala
65                  70                  75                  80

```
Val Val Ser Glu Glu Pro Ile Tyr Ile Val Cys Glu Tyr Met Ser Lys
                 85                  90                  95
Gly Ser Leu Leu Asp Phe Leu Lys Gly Glu Met Gly Lys Tyr Leu Arg
            100                 105                 110
Leu Pro Gln Leu Val Asp Met Ala Ala Gln Ile Ala Ser Gly Met Ala
            115                 120                 125
Tyr Val Glu Arg Met Asn Tyr Val His Arg Asp Leu Arg Ala Ala Asn
        130                 135                 140
Ile Leu Val Gly Glu Asn Leu Val Cys Lys Val Ala Asp Phe Gly Leu
145                 150                 155                 160
Ala Arg Leu Ile Glu Asp Asn Glu Tyr Thr Ala Arg Gln Gly Ala Lys
            165                 170                 175
Phe Pro Ile Lys Trp Thr Ala Pro Glu Ala Ala Leu Tyr Gly Arg Phe
            180                 185                 190
Thr Ile Lys Ser Asp Val Trp Ser Phe Gly Ile Leu Leu Thr Glu Leu
        195                 200                 205
Thr Thr Lys Gly Arg Val Pro Tyr Pro Gly Met Val Asn Arg Glu Val
    210                 215                 220
Leu Asp Gln Val Glu Arg Gly Tyr Arg Met Pro Cys Pro Pro Glu Cys
225                 230                 235                 240
Pro Glu Ser Leu His Asp Leu Met Cys Gln Cys Trp Arg Lys Asp Pro
            245                 250                 255
Glu Glu Arg Pro Thr Phe Glu Tyr Leu Gln Ala Phe Leu Glu Asp Tyr
            260                 265                 270
Phe Thr Ser Thr Glu Pro Gln Tyr Gln Pro Gly Glu Asn Leu
        275                 280                 285

<210> SEQ ID NO 22
<211> LENGTH: 283
<212> TYPE: PRT
<213> ORGANISM: Artificial sequence
<220> FEATURE:
<223> OTHER INFORMATION: synthetic Gallus gallus proto-oncogene [T338C,
      V323H]c-Src (251-533) (c-Src "ES6")

<400> SEQUENCE: 22

Gln Thr Gln Gly Leu Ala Lys Asp Ala Trp Glu Ile Pro Arg Glu Ser
1               5                   10                  15
Leu Arg Leu Glu Val Lys Leu Gly Gln Gly Cys Phe Gly Glu Val Trp
            20                  25                  30
Met Gly Thr Trp Asn Gly Thr Thr Arg Val Ala Ile Lys Thr Leu Lys
        35                  40                  45
Pro Gly Thr Met Ser Pro Glu Ala Phe Leu Gln Glu Ala Gln Val Met
    50                  55                  60
Lys Lys Leu Arg His Glu Lys Leu His Gln Leu Tyr Ala Val Val Ser
65                  70                  75                  80
Glu Glu Pro Ile Tyr Ile Val Cys Glu Tyr Met Ser Lys Gly Ser Leu
                85                  90                  95
Leu Asp Phe Leu Lys Gly Glu Met Gly Lys Tyr Leu Arg Leu Pro Gln
            100                 105                 110
Leu Val Asp Met Ala Ala Gln Ile Ala Ser Gly Met Ala Tyr Val Glu
            115                 120                 125
Arg Met Asn Tyr Val His Arg Asp Leu Arg Ala Ala Asn Ile Leu Val
        130                 135                 140
Gly Glu Asn Leu Val Cys Lys Val Ala Asp Phe Gly Leu Ala Arg Leu
145                 150                 155                 160
```

```
Ile Glu Asp Asn Glu Tyr Thr Ala Arg Gln Gly Ala Lys Phe Pro Ile
            165                 170                 175

Lys Trp Thr Ala Pro Glu Ala Ala Leu Tyr Gly Arg Phe Thr Ile Lys
            180                 185                 190

Ser Asp Val Trp Ser Phe Gly Ile Leu Leu Thr Glu Leu Thr Thr Lys
            195                 200                 205

Gly Arg Val Pro Tyr Pro Gly Met Val Asn Arg Glu Val Leu Asp Gln
            210                 215                 220

Val Glu Arg Gly Tyr Arg Met Pro Cys Pro Pro Glu Cys Pro Glu Ser
225                 230                 235                 240

Leu His Asp Leu Met Cys Gln Cys Trp Arg Lys Asp Pro Glu Glu Arg
            245                 250                 255

Pro Thr Phe Glu Tyr Leu Gln Ala Phe Leu Glu Asp Tyr Phe Thr Ser
            260                 265                 270

Thr Glu Pro Gln Tyr Gln Pro Gly Glu Asn Leu
            275                 280

<210> SEQ ID NO 23
<211> LENGTH: 286
<212> TYPE: PRT
<213> ORGANISM: Artificial sequence
<220> FEATURE:
<223> OTHER INFORMATION: synthetic Gallus gallus proto-oncogene
      GHM-[T338C, V323H]c-Src (251-533) (GHM at N-terminal) (c-Src
      "ES6")

<400> SEQUENCE: 23

Gly His Met Gln Thr Gln Gly Leu Ala Lys Asp Ala Trp Glu Ile Pro
1               5                   10                  15

Arg Glu Ser Leu Arg Leu Glu Val Lys Leu Gly Gln Gly Cys Phe Gly
            20                  25                  30

Glu Val Trp Met Gly Thr Trp Asn Gly Thr Thr Arg Val Ala Ile Lys
        35                  40                  45

Thr Leu Lys Pro Gly Thr Met Ser Pro Glu Ala Phe Leu Gln Glu Ala
    50                  55                  60

Gln Val Met Lys Lys Leu Arg His Glu Lys Leu His Gln Leu Tyr Ala
65                  70                  75                  80

Val Val Ser Glu Glu Pro Ile Tyr Ile Val Cys Glu Tyr Met Ser Lys
                85                  90                  95

Gly Ser Leu Leu Asp Phe Leu Lys Gly Glu Met Gly Lys Tyr Leu Arg
            100                 105                 110

Leu Pro Gln Leu Val Asp Met Ala Ala Gln Ile Ala Ser Gly Met Ala
        115                 120                 125

Tyr Val Glu Arg Met Asn Tyr Val His Arg Asp Leu Arg Ala Ala Asn
130                 135                 140

Ile Leu Val Gly Glu Asn Leu Val Cys Lys Val Ala Asp Phe Gly Leu
145                 150                 155                 160

Ala Arg Leu Ile Glu Asp Asn Glu Tyr Thr Ala Arg Gln Gly Ala Lys
                165                 170                 175

Phe Pro Ile Lys Trp Thr Ala Pro Glu Ala Ala Leu Tyr Gly Arg Phe
            180                 185                 190

Thr Ile Lys Ser Asp Val Trp Ser Phe Gly Ile Leu Leu Thr Glu Leu
        195                 200                 205

Thr Thr Lys Gly Arg Val Pro Tyr Pro Gly Met Val Asn Arg Glu Val
    210                 215                 220
```

```
Leu Asp Gln Val Glu Arg Gly Tyr Arg Met Pro Cys Pro Glu Cys
225                 230                 235                 240

Pro Glu Ser Leu His Asp Leu Met Cys Gln Cys Trp Arg Lys Asp Pro
            245                 250                 255

Glu Glu Arg Pro Thr Phe Glu Tyr Leu Gln Ala Phe Leu Glu Asp Tyr
        260                 265                 270

Phe Thr Ser Thr Glu Pro Gln Tyr Gln Pro Gly Glu Asn Leu
        275                 280                 285

<210> SEQ ID NO 24
<211> LENGTH: 570
<212> TYPE: PRT
<213> ORGANISM: Arabidopsis thaliana
<220> FEATURE:
<223> OTHER INFORMATION: hypothetical Ser-Thr protein kinase, kinase
      with gatekeeper Cys

<400> SEQUENCE: 24

Met Ala Val Asp Val Lys Ser Val Leu Glu Phe Leu Arg Arg Asn Gly
1               5                   10                  15

Leu Thr Glu Ala Glu Ser Ala Leu Arg Asp Asp Ile Asn Glu Lys Asn
            20                  25                  30

Lys Leu Ala Ser Phe Asp Phe Glu Lys Phe Leu Phe Pro Ile Pro Thr
        35                  40                  45

Pro Ile Lys Ile Thr Ala Ser Ser Arg Pro Ser Asp Ser Gly Gly Asp
    50                  55                  60

Gly Ser Asn Ser Lys Ser Ser Ser Asp Asp Glu Phe Val Ser Leu
65                  70                  75                  80

Asp Ser Ser Thr Ser Gly Phe Cys Ser Ser Ser Gly Phe Val Asn Pro
                85                  90                  95

Tyr Gly Asp Ser Ser Ser Ser Asp Gly Gln Ser Gln Phe Gly Thr
            100                 105                 110

Ala Arg Thr Tyr Pro Glu Trp Ser Glu Phe Tyr Leu His Asn Glu Thr
        115                 120                 125

Glu Asp Glu Asp Glu Phe Met Ser Pro Ala Phe Arg Glu Ser Asp Cys
    130                 135                 140

Phe Ile Leu Pro Glu Asn Ala Glu Asp Lys Phe Ile Thr Asp Asn Gln
145                 150                 155                 160

Phe Glu Asn Ser Leu Gly Val Tyr Asp Arg Ser Ser Ser Gln Gly Ser
                165                 170                 175

Leu Thr Glu Ala Ser Leu Asp Tyr Leu Asp Lys Pro Phe Leu Leu Asp
            180                 185                 190

Ile Gly Leu Glu Asp Lys Thr Asp Glu Leu Asp Leu Lys Thr Gly Asp
        195                 200                 205

Gln Leu Asn Val Thr Asp Glu Val Asp Val Val His Glu Val Glu
    210                 215                 220

Asp Glu Tyr Glu Val Phe Asn Leu Arg Ile Ile His Trp Lys Asn Arg
225                 230                 235                 240

Thr Gly Phe Glu Glu Asn Lys Asp Leu Pro Ile Val Ile Asn Thr Val
                245                 250                 255

Ile Gly Gly Arg Tyr Tyr Ile Thr Glu Tyr Ile Gly Ser Ala Ala Phe
            260                 265                 270

Ser Lys Val Val Gln Ala Gln Asp Leu His Asn Gly Val Asp Val Cys
        275                 280                 285

Leu Lys Ile Ile Lys Asn Asp Lys Asp Phe Phe Asp Gln Ser Leu Asp
    290                 295                 300
```

Glu Ile Lys Leu Leu Lys His Val Asn Lys His Asp Pro Ala Asp Glu
305                 310                 315                 320

His His Ile Leu Arg Leu Tyr Asp Tyr Phe Tyr His Gln Glu His Leu
                325                 330                 335

Phe Ile Val Cys Glu Leu Leu Arg Ala Asn Leu Tyr Glu Phe Gln Lys
            340                 345                 350

Phe Asn Gln Glu Ser Gly Gly Glu Pro Tyr Phe Asn Leu Ser Arg Leu
        355                 360                 365

Gln Val Ile Thr Arg Gln Cys Leu Asp Ala Leu Val Phe Leu His Gly
    370                 375                 380

Leu Gly Ile Ile His Cys Asp Leu Lys Pro Glu Asn Ile Leu Ile Lys
385                 390                 395                 400

Ser Tyr Lys Arg Cys Ala Val Lys Ile Ile Asp Leu Gly Ser Ser Cys
                405                 410                 415

Phe Arg Ser Asp Asn Leu Cys Leu Tyr Val Gln Ser Arg Ser Tyr Arg
            420                 425                 430

Ala Pro Glu Val Ile Leu Gly Leu Pro Tyr Asp Glu Lys Ile Asp Leu
        435                 440                 445

Trp Ser Leu Gly Cys Ile Leu Ala Glu Leu Cys Ser Gly Glu Val Leu
    450                 455                 460

Phe Pro Asn Glu Ala Val Ala Met Ile Leu Ala Arg Ile Val Ala Val
465                 470                 475                 480

Leu Gly Pro Ile Glu Thr Glu Met Leu Glu Lys Gly Gln Glu Thr His
                485                 490                 495

Lys Tyr Phe Thr Lys Glu Tyr Asp Leu Tyr His Leu Asn Glu Glu Ser
            500                 505                 510

Asn Glu Ile Glu Tyr Ile Ile Thr Glu Glu Ser Ser Leu Glu Glu Gln
        515                 520                 525

Leu Gln Val Ser Asp Glu Leu Phe Leu Asp Phe Val Arg Thr Leu Leu
    530                 535                 540

Asp Ile Asn Pro Leu Arg Arg Pro Thr Ala Leu Glu Ala Leu Asn His
545                 550                 555                 560

Pro Trp Leu Ser Ser Ser Ser Tyr Asn
                565                 570

<210> SEQ ID NO 25
<211> LENGTH: 276
<212> TYPE: PRT
<213> ORGANISM: Arabidopsis thaliana
<220> FEATURE:
<223> OTHER INFORMATION: hypothetical Ser-Thr protein kinase, kinase
      with gatekeeper Cys

<400> SEQUENCE: 25

Asp Phe Phe Asp Gln Ser Leu Asp Glu Ile Lys Leu Leu Lys Tyr Val
1               5                   10                  15

Asn Lys His Asp Pro Ala Asp Lys Tyr His Leu Leu Arg Leu Tyr Asp
            20                  25                  30

Tyr Phe Tyr Tyr Arg Glu His Leu Leu Ile Val Cys Glu Leu Leu Lys
        35                  40                  45

Ala Asn Leu Tyr Glu Phe His Lys Phe Asn Arg Glu Ser Gly Gly Glu
    50                  55                  60

Val Tyr Phe Thr Met Pro Arg Leu Gln Ser Ile Thr Ile Gln Cys Leu
65                  70                  75                  80

Glu Ser Leu Gln Phe Leu His Gly Leu Gly Leu Ile His Cys Asp Leu

```
                     85                  90                  95
Lys Pro Glu Asn Ile Leu Val Lys Ser Tyr Ser Arg Cys Glu Ile Lys
                100                 105                 110

Val Ile Asp Leu Gly Ser Ser Cys Phe Glu Thr Asp His Leu Cys Ser
                115                 120                 125

Tyr Val Gln Ser Arg Ser Tyr Arg Ala Pro Glu Val Ile Leu Gly Leu
            130                 135                 140

Pro Tyr Asp Lys Lys Ile Asp Val Trp Ser Leu Gly Cys Ile Leu Ala
145                 150                 155                 160

Glu Leu Cys Thr Gly Asn Val Leu Phe Arg Asn Asp Ser Pro Ala Ser
                165                 170                 175

Leu Leu Ala Arg Val Met Gly Ile Val Gly Ser Phe Asp Asn Glu Met
                180                 185                 190

Leu Thr Lys Gly Arg Asp Ser His Lys Tyr Phe Thr Lys Asn Arg Met
                195                 200                 205

Leu Tyr Glu Arg Asn Gln Glu Ser Asn Arg Leu Glu Tyr Leu Ile Pro
            210                 215                 220

Lys Arg Thr Ser Leu Arg His Arg Leu Pro Met Gly Asp Gln Gly Phe
225                 230                 235                 240

Thr Asp Phe Val Ala His Leu Leu Glu Ile Asn Pro Lys Lys Arg Pro
                245                 250                 255

Ser Ala Glu Ala Leu Lys His Pro Trp Leu Ser Tyr Pro Tyr Glu
                260                 265                 270

Pro Ile Ser Ala
            275

<210> SEQ ID NO 26
<211> LENGTH: 617
<212> TYPE: PRT
<213> ORGANISM: Arabidopsis thaliana
<220> FEATURE:
<223> OTHER INFORMATION: putative serine/threonine protein kinase,
      kinase with gatekeeper Cys

<400> SEQUENCE: 26

Met Leu Phe Leu Arg Arg Ile Ala Val Val Phe Phe Val Phe Thr Ser
1               5                   10                  15

Phe Ser Ala Ala Gln Asn Ser Thr Cys Pro Leu Asp Phe Ser Val Leu
                20                  25                  30

Glu Pro Phe Arg Arg Pro Lys Pro Asp Gly Ala Thr Thr Cys Gln Tyr
            35                  40                  45

Leu Leu Gln Gly Leu Arg Leu Leu Tyr Ser His His Leu Arg Gln Thr
        50                  55                  60

Gly Ser Phe Leu Pro Pro Pro Glu Ser Ala Ala Ser Cys Trp Ala Ala
65                  70                  75                  80

Leu Gln Ser Ser Val Ala Gly Phe Leu Pro Arg Phe Asp Val Arg Ser
                85                  90                  95

Thr Cys Gly Phe Gln Thr Pro Trp Ile Ser Gln Gly Cys Met Asp Ile
                100                 105                 110

Thr Thr Arg Ser Gln Phe Glu Ser Leu Ile Pro Asn Ser Ser Leu Ala
            115                 120                 125

Thr Thr Ala Met Arg Cys Asn Thr Ser Leu Glu Ser Asn Thr Pro Cys
        130                 135                 140

Ala Ser Cys Thr Gln Ser Leu Ser Ala Phe Gln Pro Tyr Leu Ser Gly
145                 150                 155                 160
```

```
Pro Ser Leu Gly Asn Val Ser Asp Cys Ala Ser Phe Pro Ser Ile Tyr
            165                 170                 175
Ala Ala Ala Phe Ala Asn Ser Leu Gly Pro Thr Asp Lys Gly Thr Ala
            180                 185                 190
Lys Cys Leu Phe Gln Leu Asp Leu Ala Ser Pro Thr Ser Ser Gly Ala
            195                 200                 205
Asn Lys Val Lys Val Leu Val Ser Ser Phe Ser Val Leu Leu Val Ala
            210                 215                 220
Ser Val Leu Val Ile Thr Ala Trp Phe Trp Tyr Cys Arg Arg Lys Lys
225                 230                 235                 240
Ser Lys Leu Leu Lys Pro Arg Asp Thr Ser Leu Glu Ala Gly Thr Gln
            245                 250                 255
Ser Arg Leu Asp Ser Met Ser Glu Ser Thr Thr Leu Val Lys Phe Ser
            260                 265                 270
Phe Asp Glu Ile Lys Lys Ala Thr Asn Asn Phe Ser Arg His Asn Ile
            275                 280                 285
Ile Gly Arg Gly Gly Tyr Gly Asn Val Phe Lys Gly Ala Leu Pro Asp
            290                 295                 300
Gly Thr Gln Val Ala Phe Lys Arg Phe Lys Asn Cys Ser Ala Gly Gly
305                 310                 315                 320
Asp Ala Asn Phe Ala His Glu Val Glu Val Ile Ala Ser Ile Arg His
            325                 330                 335
Val Asn Leu Leu Ala Leu Arg Gly Tyr Cys Thr Ala Thr Thr Pro Tyr
            340                 345                 350
Glu Gly His Gln Arg Ile Ile Val Cys Asp Leu Val Ser Asn Gly Ser
            355                 360                 365
Leu His Asp His Leu Phe Gly Asp Leu Glu Ala Gln Leu Ala Trp Pro
            370                 375                 380
Leu Arg Gln Arg Ile Ala Leu Gly Met Ala Arg Gly Leu Ala Tyr Leu
385                 390                 395                 400
His Tyr Gly Ala Gln Pro Ser Ile Ile His Arg Asp Ile Lys Ala Ser
            405                 410                 415
Asn Ile Leu Leu Asp Glu Arg Phe Glu Ala Lys Val Ala Asp Phe Gly
            420                 425                 430
Leu Ala Lys Phe Asn Pro Glu Gly Met Thr His Met Ser Thr Arg Val
            435                 440                 445
Ala Gly Thr Met Gly Tyr Val Ala Pro Glu Tyr Ala Leu Tyr Gly Gln
            450                 455                 460
Leu Thr Glu Lys Ser Asp Val Tyr Ser Phe Gly Val Val Leu Leu Glu
465                 470                 475                 480
Leu Leu Ser Arg Arg Lys Ala Ile Val Thr Asp Glu Glu Gly Gln Pro
            485                 490                 495
Val Ser Val Ala Asp Trp Ala Trp Ser Leu Val Arg Glu Gly Gln Thr
            500                 505                 510
Leu Asp Val Val Glu Asp Gly Met Pro Glu Lys Gly Pro Pro Glu Val
            515                 520                 525
Leu Glu Lys Tyr Val Leu Ile Ala Val Leu Cys Ser His Pro Gln Leu
            530                 535                 540
His Ala Arg Pro Thr Met Asp Gln Val Val Lys Met Leu Glu Ser Asn
545                 550                 555                 560
Glu Phe Thr Val Ile Ala Ile Pro Gln Arg Pro Ile Pro Leu Val Ala
            565                 570                 575
Cys Arg Glu Glu Ile Asp Arg Ser Val Ser Ser Ser Gly Ser Gly
```

```
                          580                 585                 590
Lys Leu Thr Ser Pro Thr Gly Tyr Gln Ala Phe Ser Phe Gly Gly Asp
                595                 600                 605
Gly Pro Ser Gly Asn Thr Asn Thr Thr
        610                 615

<210> SEQ ID NO 27
<211> LENGTH: 369
<212> TYPE: PRT
<213> ORGANISM: Arabidopsis thaliana
<220> FEATURE:
<223> OTHER INFORMATION: protein kinase-like protein, kinase with
      gatekeeper Cys

<400> SEQUENCE: 27

Met Ala His Ile Ser Asp Ile Lys Leu Ile Arg Thr Asp Thr Thr Leu
1               5                   10                  15
Asp Leu Ser Gln Lys Ala Glu Lys Gly Met Ile Trp Thr Met Gly Gly
            20                  25                  30
Ala Ser Tyr Leu Tyr Tyr Asn Ala Tyr Asp His Gly Ser Leu Thr Cys
        35                  40                  45
Arg Cys Gly Thr Leu Leu Ile Ala Ser Ser Gly Gly Lys Tyr Asn Pro
    50                  55                  60
Ile Arg Thr Phe Ser Ser His Gln Ile Leu Glu Ala Thr Asn Asn Phe
65                  70                  75                  80
Asp Trp Ser Tyr Ala Ile Gly Val Asp Arg Phe Val Trp Tyr Lys Gly
                85                  90                  95
Thr Ile Glu Asn Arg Ala Val Leu Ile Lys Tyr Tyr Lys Gly Glu Pro
            100                 105                 110
Phe Asn Phe Asp Pro Asp Asn Phe Tyr Arg Asp Ile Ala Val Ser Ser
        115                 120                 125
Met Met Ser Ser His Lys Asn Val Leu Lys Leu Leu Gly Cys Cys Leu
    130                 135                 140
Glu Phe Pro Arg Pro Val Leu Val Cys Glu Tyr Pro Glu Lys Gly Ala
145                 150                 155                 160
Leu Ala Tyr Ile Gly Gly Ala Gly Glu Val Ile Lys Pro Leu Ala Trp
                165                 170                 175
Ser Val Arg Leu Lys Ile Ala Lys Glu Ile Ala Asp Ala Val Thr Tyr
            180                 185                 190
Leu His Thr Glu Phe Pro Arg Thr Ile Ile His Arg Asp Leu Lys Leu
        195                 200                 205
Thr Asn Ile Phe Leu Asp Glu Asn Trp Thr Ala Lys Leu Ser Ser Phe
    210                 215                 220
Ser Leu Ser Ile Pro Ile Pro Glu Gly Glu Leu Gly Val Glu Asp Ile
225                 230                 235                 240
Val Cys Gly Thr Gln Gly Phe Gly Glu Pro His Tyr Met Val Thr Gly
                245                 250                 255
Phe Val Thr Glu Asn Val Asp Ile Tyr Ser Phe Gly Phe Ile Met Leu
            260                 265                 270
Ser Leu Leu Thr Gly Lys His Gly Phe Tyr Gln Glu Pro Ala Asn Gly
        275                 280                 285
Asp Ser Tyr Asn Met Ile Leu Leu Pro Asp Tyr Val Glu Lys Cys Leu
    290                 295                 300
Gly Arg Gly Pro Leu Ala Lys Leu Ile Asp Pro Ser Met Leu Asn Ser
305                 310                 315                 320
```

```
Thr Asp Asp Asp Ile Pro Asp His Ser Lys Leu Gln Met Glu Ala Phe
            325                 330                 335

Val Asn Leu Ala Leu Arg Cys Val Gly Phe Arg Ser Gly Glu Thr Lys
        340                 345                 350

Leu His Met Ile Asp Val Ala Lys Glu Leu Lys Arg Ile Gln Lys Gln
        355                 360                 365

Thr

<210> SEQ ID NO 28
<211> LENGTH: 372
<212> TYPE: PRT
<213> ORGANISM: Arabidopsis thaliana
<220> FEATURE:
<223> OTHER INFORMATION: putative kinase-like protein, kinase with
      gatekeeper Cys

<400> SEQUENCE: 28

Met Asp Lys Ile Ile Ile Ser Asn Leu Ser Glu Phe Asp His Ser Val
1               5                   10                  15

Val Asp Tyr His Lys Ser Ser Leu Leu Cys Lys Ser Gln Ser Phe
            20                  25                  30

Glu Leu Ser Pro Ile Glu Met Ser Lys Asn Asn Lys Lys Lys Arg Arg
        35                  40                  45

Trp Asp Leu Lys Asn Gly Gly Ile Leu Glu Glu Leu Ile Ala Ser
50                  55                  60

Phe Asp Gly Lys Thr Asn Pro Ile Arg Cys Phe Ser Ser Asp Gln Ile
65                  70                  75                  80

Leu Lys Ala Thr Asp Asn Phe Ser Glu Ser Arg Ile Ile Ser Ser Trp
                85                  90                  95

Gly Tyr Phe Ile Trp Tyr Lys Gly Val Ile Glu Glu Arg Gln Val Ser
            100                 105                 110

Ile Lys Lys Trp Ser Ser Gln Asn Leu Ser Ser Phe Thr Glu Ala Tyr
        115                 120                 125

Arg Asp Ile Ser Val Ser Ser Gln Met Ser Gly His Lys Asn Ala Leu
    130                 135                 140

Lys Leu Ile Gly Cys Cys Leu Glu Phe Asp Leu Pro Ala Leu Val Cys
145                 150                 155                 160

Glu Tyr Thr Glu His Gly Pro Leu Asn Arg Asp Gly Gly Leu Ser Ser
                165                 170                 175

Gly Val Val Leu Pro Trp Lys Val Arg Leu Lys Ile Ala Lys Glu Ile
            180                 185                 190

Ala Ser Ser Val Thr Tyr Leu His Thr Ala Phe Pro Glu Thr Ile Val
        195                 200                 205

His Arg Asn Ile Asn Pro Thr Asn Ile Phe Ile Asp Glu Asn Trp Thr
    210                 215                 220

Ala Lys Leu Ser Asp Phe Trp Phe Cys Val Ala Ile Pro Glu Gly Glu
225                 230                 235                 240

Leu Tyr Val Glu Asp Val Lys Gly Val Ile Gly Phe Val Asp Pro
                245                 250                 255

Asp Tyr Tyr Trp Thr Met Lys Val Thr Glu Lys Val Asp Ile Tyr Ser
            260                 265                 270

Phe Gly Val Val Met Leu Val Leu Ser Gly Arg Ala Ala Val Phe
        275                 280                 285

Asn Gly Pro Asp Glu Ala Pro Met Ser Leu Asn Asp His Val Ser Glu
    290                 295                 300
```

```
Val Met Glu Lys Gly Glu Phe Asp Glu Ile Val Asp Lys Glu Ile Trp
305                 310                 315                 320

Asn Asp Leu Gly Gly Asp Asp Leu Val Leu Arg Arg Ser Gln Val
                325                 330                 335

Lys Ala Phe Leu Arg Leu Ala Leu Arg Cys Val Arg Tyr Lys Lys Glu
            340                 345                 350

Asp Pro Val Ser Gly Met Leu Glu Val Ala Lys Glu Leu Lys Leu Ile
            355                 360                 365

Glu Lys Leu Ser
    370
```

<210> SEQ ID NO 29
<211> LENGTH: 357
<212> TYPE: PRT
<213> ORGANISM: Arabidopsis thaliana
<220> FEATURE:
<223> OTHER INFORMATION: putative kinase-like protein, kinase with gatekeeper Cys

<400> SEQUENCE: 29

```
Met Ser Cys Trp Arg Lys Lys Ser Lys Lys Lys Asn Ser Glu Ala Asn
1               5                   10                  15

Gln Arg Gln Arg Trp Phe Gln Glu Asn Gly Lys Val Leu Leu Glu Asp
                20                  25                  30

Leu Ile Glu Leu Cys Asn Gly Lys Ser Asn Pro Ile Lys Thr Phe Ser
            35                  40                  45

Ala Glu Glu Ile Leu Gln Ala Thr Asp Asn Phe Ser Glu Ser Asn Leu
        50                  55                  60

Val Ile Arg Phe Asn Phe Met Tyr Arg Gly Ile Leu Gln Asn Arg Pro
65                  70                  75                  80

Val Leu Ile Lys Arg Ala Thr Trp Asn Tyr Tyr Lys Ser Asp Thr Leu
                85                  90                  95

Glu Lys Ile Cys Arg Asp Ile Ala Val Ser Ser Met Val Ser Gly His
            100                 105                 110

Lys Asn Phe Leu Lys Leu Leu Gly Cys Cys Leu Glu Phe Glu His Pro
        115                 120                 125

Val Leu Val Cys Glu Tyr Ala Glu Arg Ile Pro Phe Asn Thr Pro Asn
130                 135                 140

Pro Glu Met Leu Leu Pro Trp Arg Met Arg Ile Lys Ile Ala Lys Glu
145                 150                 155                 160

Ile Ala Ile Ala Val Ser Tyr Leu His Thr Ala Leu Ser Arg Thr Met
                165                 170                 175

Ile His Thr Asp Ile Gln Pro Phe Asn Ile Phe Val Asp Ser Asn Gly
            180                 185                 190

Thr Ala Lys Leu Ser Asp Phe Cys Leu Cys Ile Ala Ile Pro Glu Gly
        195                 200                 205

Glu Thr Phe Val Lys Val His Ala Asp Arg Val Glu Gly Thr Leu Asp
    210                 215                 220

Tyr Leu Glu Tyr Asn Tyr Ala Ala Thr Gly Leu Ile Thr Glu Tyr Thr
225                 230                 235                 240

Asp Val Phe Ser Phe Gly Val Leu Leu Gln Asn Phe Thr Arg Thr
                245                 250                 255

Tyr Gly Val Val Asp Cys Cys Ser Glu Asp Glu Ser Leu Phe Glu
            260                 265                 270

Glu Phe Glu Asp Lys Gln Asn Val Met Asn Leu Arg Ile Ser Asp Arg
        275                 280                 285
```

Ile Ser Lys Phe Val Glu Gly Arg Ile Phe Asp Met Leu Asp Pro
    290                 295                 300

Lys Met Leu Glu Ser Met Gly Asp Asp Glu Thr Glu Glu His Lys Ile
305                 310                 315                 320

Arg Arg Met Lys Ala Val Leu Met Leu Ser Leu Arg Cys Thr Gly His
                325                 330                 335

Arg Gly Asp Val Pro Lys Met Met Glu Val Ala Lys Glu Leu Lys Arg
            340                 345                 350

Ile Glu Arg Trp Thr
            355

<210> SEQ ID NO 30
<211> LENGTH: 340
<212> TYPE: PRT
<213> ORGANISM: Arabidopsis thaliana
<220> FEATURE:
<223> OTHER INFORMATION: protein kinase-like protein, kinase with
      gatekeeper Cys

<400> SEQUENCE: 30

Met Leu Arg Leu Phe Arg Lys Lys Lys Gln Lys Lys Glu Glu Glu
1               5                   10                  15

Ile Asn Leu Gln Lys Asn Gly Ser Leu Leu Glu Glu Leu Ile Ala
                20                  25                  30

Thr Ser Gly Gly Ile Tyr Asn Pro Ile Arg Thr Phe Ser Ser Asp Gln
        35                  40                  45

Ile Leu Gln Ala Thr Asn His Phe Asp Trp Asn Tyr Val Ile Ser Glu
50                  55                  60

Asp Arg Phe Val Trp Tyr Lys Gly Met Ile Glu Asn Arg Pro Val Leu
65                  70                  75                  80

Ile Lys Lys Phe Gln Asp Cys Ser Val Phe Asp Ala Asp Asn Phe Tyr
                85                  90                  95

Arg Asp Ile Ala Val Ser Ser Leu Met Ser Ser His Lys Asn Val Leu
            100                 105                 110

Lys Leu Leu Gly Cys Cys Leu Glu Phe Pro Arg Pro Val Leu Val Cys
        115                 120                 125

Glu Tyr Pro Glu His Gly Ala Leu Asn Cys Ile Arg Cys Gly Lys Glu
    130                 135                 140

Gly Val Arg Ser Phe Pro Trp Asn Val Arg Leu Arg Ile Ala Lys Glu
145                 150                 155                 160

Ile Ala Asp Ala Val Ala Tyr Leu His Thr Glu Phe Pro Arg Thr Ile
                165                 170                 175

Ile His Arg Asp Leu Lys Leu Ala Asn Ile Phe Leu Asp Glu Asn Trp
            180                 185                 190

Ser Ala Lys Leu Ser Ser Phe Ser Leu Ser Ile Val Leu Pro Glu Gly
        195                 200                 205

Glu Thr Gly Val Asn Asp Met Val Cys Arg Thr Ser Ser Tyr Ile Glu
    210                 215                 220

Pro Asp Tyr Phe Asn Thr Gly Leu Val Thr Glu Asn Val Asp Ile Tyr
225                 230                 235                 240

Ser Leu Gly Ile Ile Met Leu Ile Ile Leu Thr Gly Lys Ser Glu Tyr
                245                 250                 255

Asn Ser Glu Val Ala Val Tyr Leu Pro Val Leu Pro Tyr Val Gly
            260                 265                 270

Lys Phe Leu Glu Arg Gly Leu Leu Thr Glu Leu Ile Asp Pro Ser Ile

```
                    275                 280                 285
Leu Asp Ser Thr Ser Asp Asp Ile Pro Lys His Ser Arg Leu Gln Met
    290                 295                 300

Glu Ala Phe Ile Glu Leu Ala Phe Arg Cys Val Arg Phe Arg Pro Gly
305                 310                 315                 320

Glu Asn Val Pro Arg Met Ile Asp Val Ala Lys Glu Leu Lys Lys Ile
                325                 330                 335

Glu Lys His Ile
            340

<210> SEQ ID NO 31
<211> LENGTH: 351
<212> TYPE: PRT
<213> ORGANISM: Arabidopsis thaliana
<220> FEATURE:
<223> OTHER INFORMATION: putative kinase-like protein, kinase with
      gatekeeper Cys

<400> SEQUENCE: 31

Met Lys Gly Phe Phe Lys Thr Glu Ser Glu Thr Arg Lys His Ser Asp
1               5                   10                  15

Lys Asn Gly Ser Leu Leu His Glu Glu Leu Ile Ala Cys Ser Asp Gly
                20                  25                  30

Lys Tyr Asn Pro Ile Arg Met Phe Ser Ser Asp Gln Ile Leu Lys Ala
            35                  40                  45

Thr Asn Asn Phe Asp Ala Asp His Ile Ile Ala Lys Asp Arg Phe Ile
        50                  55                  60

Trp Tyr Lys Gly Thr Ile Glu Arg Arg Val Leu Ile Lys Lys Trp
65                  70                  75                  80

Glu Gly Asp Tyr Val Leu Phe Ser Ser Pro Glu Asn Val Tyr Arg Asp
                85                  90                  95

Ile Ala Val Leu Ser Met Met Ser Ser His Lys Asn Val Leu Lys Leu
            100                 105                 110

Leu Gly Cys Cys Val Glu Phe Tyr Lys Pro Val Leu Val Cys Glu Leu
        115                 120                 125

Ala Glu Lys Gly Pro Leu Lys Leu Glu Asp Met Asp Gly Thr Pro Leu
    130                 135                 140

Pro Trp Ser Ala Arg Leu Lys Ile Gly Lys Asp Ile Ala Asn Ala Val
145                 150                 155                 160

Ala Tyr Leu His Thr Ala Phe Pro Arg Val Ile Ile Asn Arg Asp Val
                165                 170                 175

Arg Pro Gln Asn Ile Phe Leu Asp Glu Asp Gly Thr Ala Lys Leu Ser
            180                 185                 190

Ser Phe Cys Leu Arg Ile Ser Ile Pro Glu Gly Glu Ser Ser Val Tyr
        195                 200                 205

Asp Asp Lys Val Val Tyr Gly Val Ser Val Asp Pro Glu Tyr Asn Gly
    210                 215                 220

Thr Gly Leu Val Ser Glu Lys Phe Asp Val Tyr Ser Phe Gly Val Thr
225                 230                 235                 240

Met Leu Phe Leu Leu Gly Gly Glu Leu Gly Leu Thr Trp Leu Ser Ala
                245                 250                 255

Ile Ile Gly Glu Phe Gly Phe Pro Phe Pro Gly Cys Gly Glu Glu Leu
            260                 265                 270

Ala Asp Gln Phe Met Tyr Val Ile Asp Ser Asn Ile Trp Asn Gly Glu
        275                 280                 285
```

```
Ser Glu Ala Ser Ala Val Gln Val Glu Thr Phe Phe Gly Leu Ala Leu
    290                 295                 300
Arg Cys Ile Arg Phe Trp Pro Gly Gln Asp Val Leu Thr Met Ile Asp
305                 310                 315                 320
Val Ala Lys Glu Leu Lys Gly Ile Glu Glu Leu Phe Lys Ala Ser Ser
                325                 330                 335
Ser Glu Gln Asp Lys Glu Gln Ile Asp Gln Val Asn Tyr Ser Val
                340                 345                 350

<210> SEQ ID NO 32
<211> LENGTH: 690
<212> TYPE: PRT
<213> ORGANISM: Arabidopsis thaliana
<220> FEATURE:
<223> OTHER INFORMATION: similar to eukaryotic protein kinase domains,
      kinase with gatekeeper Cys

<400> SEQUENCE: 32

Met Leu Met Gln Ser Leu Leu Phe Thr Ile His Leu Ser Phe Leu
1               5                   10                  15
Phe Ser Leu Leu Cys Gln Ser Asn Cys Ser Cys Lys His His Ile Val
                20                  25                  30
Pro Phe Ser Lys Val Ser Gln Glu Asp Ala Pro His Ala Ser His Ala
                35                  40                  45
Gly Ala Tyr Pro Gln Arg Ile Gln Arg His Gly Thr Thr Asn Ser Glu
    50                  55                  60
Ala Ile Leu Lys Phe Lys Glu Ser Leu Val Val Gly Gln Glu Asn Ala
65                  70                  75                  80
Leu Ala Ser Trp Asn Ala Lys Ser Pro Pro Cys Thr Trp Ser Gly Val
                85                  90                  95
Leu Cys Asn Gly Gly Ser Val Trp Arg Leu Gln Met Glu Asn Leu Glu
                100                 105                 110
Leu Ser Gly Ser Ile Asp Ile Glu Ala Leu Ser Gly Leu Thr Ser Leu
                115                 120                 125
Arg Thr Leu Ser Phe Met Asn Asn Lys Phe Glu Gly Pro Phe Pro Asp
130                 135                 140
Phe Lys Lys Leu Ala Ala Leu Lys Ser Leu Tyr Leu Ser Asn Asn Gln
145                 150                 155                 160
Phe Gly Gly Asp Ile Pro Gly Asp Ala Phe Glu Gly Met Gly Trp Leu
                165                 170                 175
Lys Lys Val His Leu Ala Gln Asn Lys Phe Thr Gly Gln Ile Pro Ser
                180                 185                 190
Ser Val Ala Lys Leu Pro Lys Leu Leu Glu Leu Arg Leu Asp Gly Asn
                195                 200                 205
Gln Phe Thr Gly Glu Ile Pro Glu Phe Glu His Gln Leu His Leu Leu
    210                 215                 220
Asn Leu Ser Asn Asn Ala Leu Thr Gly Pro Ile Pro Glu Ser Leu Ser
225                 230                 235                 240
Met Thr Asp Pro Lys Val Phe Glu Gly Asn Lys Gly Leu Tyr Gly Lys
                245                 250                 255
Pro Leu Glu Thr Glu Cys Asp Ser Pro Tyr Ile Glu His Pro Pro Gln
                260                 265                 270
Ser Glu Ala Arg Pro Lys Ser Ser Arg Gly Pro Leu Val Ile Thr
                275                 280                 285
Ala Ile Val Ala Ala Leu Thr Ile Leu Ile Ile Leu Gly Val Ile Phe
    290                 295                 300
```

```
Leu Leu Asn Arg Ser Tyr Lys Asn Lys Lys Pro Arg Leu Ala Val Glu
305                 310                 315                 320

Thr Gly Pro Ser Ser Leu Gln Lys Lys Thr Gly Ile Arg Glu Ala Asp
                325                 330                 335

Gln Ser Arg Arg Asp Arg Lys Lys Ala Asp His Arg Lys Gly Ser Gly
            340                 345                 350

Thr Thr Lys Arg Met Gly Ala Ala Gly Val Glu Asn Thr Lys Leu
355                 360                 365

Ser Phe Leu Arg Glu Asp Arg Glu Lys Phe Asp Leu Gln Asp Leu Leu
370                 375                 380

Lys Ala Ser Ala Glu Ile Leu Gly Ser Gly Cys Phe Gly Ala Ser Tyr
385                 390                 395                 400

Lys Ala Val Leu Ser Ser Gly Gln Met Met Val Val Lys Arg Phe Lys
                405                 410                 415

Gln Met Asn Asn Ala Gly Arg Asp Glu Phe Gln Glu His Met Lys Arg
                420                 425                 430

Leu Gly Arg Leu Met His His Asn Leu Leu Ser Ile Val Ala Tyr Tyr
            435                 440                 445

Tyr Arg Lys Glu Glu Lys Leu Leu Val Cys Asp Phe Ala Glu Arg Gly
450                 455                 460

Ser Leu Ala Ile Asn Leu His Ser Asn Gln Ser Leu Gly Lys Pro Ser
465                 470                 475                 480

Leu Asp Trp Pro Thr Arg Leu Lys Ile Val Lys Gly Val Ala Lys Gly
                485                 490                 495

Leu Phe Tyr Leu His Gln Asp Leu Pro Ser Leu Met Ala Pro His Gly
            500                 505                 510

His Leu Lys Ser Ser Asn Val Leu Leu Thr Lys Thr Phe Glu Pro Leu
            515                 520                 525

Leu Thr Asp Tyr Gly Leu Ile Pro Leu Ile Asn Gln Glu Lys Ala Gln
530                 535                 540

Met His Met Ala Ala Tyr Arg Ser Pro Glu Tyr Leu Gln His Arg Arg
545                 550                 555                 560

Ile Thr Lys Lys Thr Asp Val Trp Gly Leu Gly Ile Leu Ile Leu Glu
                565                 570                 575

Ile Leu Thr Gly Lys Phe Pro Ala Asn Phe Ser Gln Ser Ser Glu Glu
            580                 585                 590

Asp Leu Ala Ser Trp Val Asn Ser Gly Phe His Gly Val Trp Ala Pro
            595                 600                 605

Ser Leu Phe Asp Lys Gly Met Gly Lys Thr Ser His Cys Glu Gly Gln
610                 615                 620

Ile Leu Lys Leu Leu Thr Ile Gly Leu Asn Cys Cys Glu Pro Asp Val
625                 630                 635                 640

Glu Lys Arg Leu Asp Ile Gly Gln Ala Val Glu Lys Ile Glu Glu Leu
                645                 650                 655

Lys Glu Arg Glu Gly Asp Asp Asp Phe Tyr Ser Thr Tyr Val Ser
            660                 665                 670

Glu Thr Asp Gly Arg Ser Ser Lys Gly Glu Ser Cys Glu Ser Ile Ser
            675                 680                 685

Phe Ala
690

<210> SEQ ID NO 33
<211> LENGTH: 662
```

```
<212> TYPE: PRT
<213> ORGANISM: Arabidopsis thaliana
<220> FEATURE:
<223> OTHER INFORMATION: leucine-rich repeat protein kinase-like
      protein, leucine-rich repeat transmembrane protein kinase-like
      protein, kinase with gatekeeper Cys

<400> SEQUENCE: 33

Met Pro Pro Met Gln Ala Arg Thr Leu Ser Val Tyr Asn Val Met Val
1               5                   10                  15

Pro Leu Val Cys Leu Leu Leu Phe Phe Ser Thr Pro Thr His Gly Leu
                20                  25                  30

Ser Asp Ser Glu Ala Ile Leu Lys Phe Lys Glu Ser Leu Val Val Gly
            35                  40                  45

Gln Glu Asn Ala Leu Ala Ser Trp Asn Ala Lys Ser Pro Pro Cys Thr
    50                  55                  60

Trp Ser Gly Val Leu Cys Asn Gly Gly Ser Val Trp Arg Leu Gln Met
65                  70                  75                  80

Glu Asn Leu Glu Leu Ser Gly Ser Ile Asp Ile Glu Ala Leu Ser Gly
                85                  90                  95

Leu Thr Ser Leu Arg Thr Leu Ser Phe Met Asn Asn Lys Phe Glu Gly
            100                 105                 110

Pro Phe Pro Asp Phe Lys Lys Leu Ala Ala Leu Lys Ser Leu Tyr Leu
        115                 120                 125

Ser Asn Asn Gln Phe Gly Gly Asp Ile Pro Gly Asp Ala Phe Glu Gly
    130                 135                 140

Met Gly Trp Leu Lys Lys Val His Leu Ala Gln Asn Lys Phe Thr Gly
145                 150                 155                 160

Gln Ile Pro Ser Ser Val Ala Lys Leu Pro Lys Leu Leu Glu Leu Arg
                165                 170                 175

Leu Asp Gly Asn Gln Phe Thr Gly Glu Ile Pro Glu Phe Glu His Gln
            180                 185                 190

Leu His Leu Leu Asn Leu Ser Asn Asn Ala Leu Thr Gly Pro Ile Pro
        195                 200                 205

Glu Ser Leu Ser Met Thr Asp Pro Lys Val Phe Glu Gly Asn Lys Gly
    210                 215                 220

Leu Tyr Gly Lys Pro Leu Glu Thr Glu Cys Asp Ser Pro Tyr Ile Glu
225                 230                 235                 240

His Pro Pro Gln Ser Glu Ala Arg Pro Lys Ser Ser Arg Gly Pro
                245                 250                 255

Leu Val Ile Thr Ala Ile Val Ala Ala Leu Thr Ile Leu Ile Ile Leu
            260                 265                 270

Gly Val Ile Phe Leu Leu Asn Arg Ser Tyr Lys Asn Lys Lys Pro Arg
        275                 280                 285

Leu Ala Val Glu Thr Gly Pro Ser Ser Leu Gln Lys Lys Thr Gly Ile
    290                 295                 300

Arg Glu Ala Asp Gln Ser Arg Arg Asp Arg Lys Lys Ala Asp His Arg
305                 310                 315                 320

Lys Gly Ser Gly Thr Thr Lys Arg Met Gly Ala Ala Gly Val Glu
                325                 330                 335

Asn Thr Lys Leu Ser Phe Leu Arg Glu Asp Arg Glu Lys Phe Asp Leu
            340                 345                 350

Gln Asp Leu Leu Lys Ala Ser Ala Glu Ile Leu Gly Ser Gly Cys Phe
        355                 360                 365

Gly Ala Ser Tyr Lys Ala Val Leu Ser Ser Gly Gln Met Met Val Val
```

```
                370             375             380
Lys Arg Phe Lys Gln Met Asn Asn Ala Gly Arg Asp Glu Phe Gln Glu
385                 390                 395                 400

His Met Lys Arg Leu Gly Arg Leu Met His His Asn Leu Leu Ser Ile
                405                 410                 415

Val Ala Tyr Tyr Tyr Arg Lys Glu Glu Lys Leu Leu Val Cys Asp Phe
                420                 425                 430

Ala Glu Arg Gly Ser Leu Ala Ile Asn Leu His Ser Asn Gln Ser Leu
                435                 440                 445

Gly Lys Pro Ser Leu Asp Trp Pro Thr Arg Leu Lys Ile Val Lys Gly
                450                 455                 460

Val Ala Lys Gly Leu Phe Tyr Leu His Gln Asp Leu Pro Ser Leu Met
465                 470                 475                 480

Ala Pro His Gly His Leu Lys Ser Ser Asn Val Leu Leu Thr Lys Thr
                485                 490                 495

Phe Glu Pro Leu Leu Thr Asp Tyr Gly Leu Ile Pro Leu Ile Asn Gln
                500                 505                 510

Glu Lys Ala Gln Met His Met Ala Ala Tyr Arg Ser Pro Glu Tyr Leu
                515                 520                 525

Gln His Arg Arg Ile Thr Lys Lys Thr Asp Val Trp Gly Leu Gly Ile
                530                 535                 540

Leu Ile Leu Glu Ile Leu Thr Gly Lys Phe Pro Ala Asn Phe Ser Gln
545                 550                 555                 560

Ser Ser Glu Glu Asp Leu Ala Ser Trp Val Asn Ser Gly Phe His Gly
                565                 570                 575

Val Trp Ala Pro Ser Leu Phe Asp Lys Gly Met Gly Lys Thr Ser His
                580                 585                 590

Cys Glu Gly Gln Ile Leu Lys Leu Leu Thr Ile Gly Leu Asn Cys Cys
                595                 600                 605

Glu Pro Asp Val Glu Lys Arg Leu Asp Ile Gly Gln Ala Val Glu Lys
                610                 615                 620

Ile Glu Glu Leu Lys Glu Arg Glu Gly Asp Asp Asp Phe Tyr Ser
625                 630                 635                 640

Thr Tyr Val Ser Glu Thr Asp Gly Arg Ser Ser Lys Gly Glu Ser Cys
                645                 650                 655

Glu Ser Ile Ser Phe Ala
                660

<210> SEQ ID NO 34
<211> LENGTH: 1266
<212> TYPE: PRT
<213> ORGANISM: Arabidopsis thaliana
<220> FEATURE:
<223> OTHER INFORMATION: Ser-Thr protein kinase-like protein, kinase
      with gatekeeper Cys

<400> SEQUENCE: 34

Met Ile Phe His Gly Ser Lys Ala Val Lys Glu Ala Gln Ser Trp Gln
1               5                   10                  15

Glu Ala Gln Phe Glu Leu His Ser Glu Ser His Gly Ser Leu Ser Ile
                20                  25                  30

Asp Asn Arg Ile Arg Val Arg Asp Val Ser Gln Asp Thr Thr Phe Ser
                35                  40                  45

Gly Tyr Arg Cys Phe Ile Asp Gly Ser Trp Lys Ala Ser Asp Gln Phe
                50                  55                  60
```

-continued

```
Ser Gly Thr Gly Trp Phe Cys Leu Ser Ser Leu Gly Glu Ser Pro Thr
 65                  70                  75                  80

Met Gly Ala Val Asn Val Arg Arg Ser Leu Ser Pro Leu His Thr Glu
                 85                  90                  95

Met Glu Ala Leu Leu Trp Ala Met Lys Cys Met Ile Gly Ala Asp Asn
            100                 105                 110

Gln Asn Val Ala Phe Phe Thr Asp Cys Ser Cys His Arg Phe Gly Glu
        115                 120                 125

Met Glu Asp Ser Ser Ser Ile Asp Ser Ile Leu Glu Phe Leu Arg Lys
    130                 135                 140

Asn His Phe Met Arg Ala Glu Ala Ala Leu Ile Ser Glu Leu Ser Lys
145                 150                 155                 160

Lys Pro Ser Ser Asn Gly Ser Leu Gln Lys Leu Asn Phe Glu Asp Asn
                165                 170                 175

Cys Val Ser Lys Leu Leu Asp Lys Lys Lys Gln Gly Gly Ser Ser Gln
            180                 185                 190

Ala Leu Gly Leu His Asn Asp Ser His Ile Ser Asp Glu Leu Val Val
        195                 200                 205

Lys Glu Ile Gln Cys Gly Ala Ala Asn Asn Leu His Glu Ser Asn Leu
    210                 215                 220

Met Asn Asp Val Ser Val Gln Thr Gln Ser Gly Asn Ala Asp Phe Trp
225                 230                 235                 240

Glu Glu Arg Phe Thr Phe Ala Glu Gly Phe Glu Asp Thr Glu Leu Asp
                245                 250                 255

Leu Pro Pro Trp Asn His Thr Ser Thr Asp Ile Val Ala Asp Ser Glu
            260                 265                 270

Glu Tyr Ser Ile Asn Pro Ser Lys Arg Gly Phe Val Asn Pro Arg Ser
        275                 280                 285

Ser Lys Gln Ser Ser His Glu Lys Val Pro Glu Pro Gly Lys Ser Asn
    290                 295                 300

Lys Val Val Val Glu Asp Val Phe Ser Ser Phe Glu Lys Ile Arg Thr
305                 310                 315                 320

Gly Ser Ser Ser Gln Val Ser Gln Tyr Asp His Gly Lys Ala Cys Gln
                325                 330                 335

Ser Leu Glu Val Asp Asn Lys Val Gly Asn Ser Ala Ile Gln Glu Gly
            340                 345                 350

Phe Val Thr Thr Ser Trp Ser Arg Ser Glu Glu Asn Ile Gly Ala Ser
        355                 360                 365

Pro Asp His Trp Lys Asp Cys Ser Val Thr Thr Val Phe Pro Leu Ser
    370                 375                 380

Lys Gly Ser Thr Ser Thr Lys Asp Asn Gly Val Ala Ile Leu Asp Lys
385                 390                 395                 400

Trp Gln Gly Lys Lys Leu Val Gly Ala Ser Asp Ser Arg Ile Leu Ile
                405                 410                 415

Lys Glu Gln Glu Asp Asp Val Ala Thr Ala Leu Tyr Leu Gly Lys Ser
            420                 425                 430

Gln Ser Gly Tyr Glu His Lys Ile Pro Ser Ser Leu Ala Phe Ser Leu
        435                 440                 445

Ala His Asp Ala Pro Arg Glu Asp Leu Pro Arg Leu Pro His Val Lys
    450                 455                 460

Ile Lys Ser Glu Asp Lys Leu Met Asn Phe Thr Trp Glu Glu Lys His
465                 470                 475                 480

Glu Arg Asp Ile Leu Asp Glu Lys Leu Ile Asn Thr Asp Asn Ala Phe
```

```
                485                 490                 495
Leu Leu Gly Ser Tyr Leu Asp Val Pro Ile Gly Gln Glu Ile Asn Ser
            500                 505                 510
Ser Gly Gly Lys Met Ala Gly Gly Asn Trp Leu Ser Val Ser His
        515                 520                 525
Gly Ile Ala Asp Asp Ala Ser Asp Leu Ile Phe Gly Phe Gly Asp Gly
        530                 535                 540
Leu Gly Ala Leu Asn Glu His Ser Asn Glu Tyr Trp Asp Ser Asp Glu
545                 550                 555                 560
Tyr Asp Asp Asp Asp Val Gly Tyr Ile Arg Gln Pro Ile Glu Asp
                565                 570                 575
Glu Ala Trp Phe Leu Gly His Glu Val Asp Tyr Pro Ser Asp Asn Glu
            580                 585                 590
Lys Gly Thr Glu His Gly Ser Val Pro Asp Thr Gln Asp Lys Ser Gln
            595                 600                 605
Thr Lys Asn Asp Asp Asp His Ser Phe Ala Glu Glu Asp Ser Tyr Phe
            610                 615                 620
Ser Gly Glu Gln Tyr Val Leu Ala Lys Gly Ile Glu Pro Val Thr Ala
625                 630                 635                 640
Ser Asn Asp Pro Met Gly Leu Ser Met Thr Glu Thr Tyr Ser Thr Thr
                645                 650                 655
Lys Gln Ala Asp Leu Val Ala Arg Tyr Asp Gly Gln Leu Met Asp Ala
            660                 665                 670
Glu Glu Leu Ser Leu Met Asp Thr Glu Pro Val Trp Lys Gly Phe Val
            675                 680                 685
Ser His Glu Asn Asp Val Ile Leu Leu Lys Lys Gly Lys Val Glu Asp
            690                 695                 700
Asn Ser Gly Arg Ile Cys Arg Lys Asp Ile Arg Ala Glu Asp Asp Arg
705                 710                 715                 720
Asn Ala Ala Val Arg Ser Ile Gly Val Gly Met Ser Asp Asp Val Asp
                725                 730                 735
Asp Asn Gly Ser Ile Ile Pro Glu Tyr Phe Pro Gly Glu Gly Ser Glu
            740                 745                 750
Trp Asp Leu Glu Leu Pro Tyr Arg Gly Val Gly Val Ala Gly Val
            755                 760                 765
Lys Pro Pro Gly Lys Gly Ala Ser Met Leu Leu Lys Asn Phe Ala
        770                 775                 780
Asp Gly Gly Phe Ser Phe Pro Ser Pro Val Ala Asp Arg Gln Lys Ser
785                 790                 795                 800
Gln Asp Asp Ser Ala Asn Pro Glu Trp Ser Asn His Cys Asp Ala Val
                805                 810                 815
Val Arg Asn Glu Ser Asp Glu Pro Lys Gly Leu Ile Gln Ser Asp Ser
            820                 825                 830
Met Ile Val Ser Ser Thr Lys Arg Cys Ser Gly Ser Ser Glu Arg
        835                 840                 845
Asn Leu Arg Asp Met Asp Asp Glu Lys Val Ala Ser Ser Arg Asn Ser
        850                 855                 860
Ser Pro Ser Ala Leu Ser His Ser Asp Thr Gly Arg Glu His Lys
865                 870                 875                 880
Glu Glu Asp Glu Glu Glu Thr Ser His Gly Pro Glu Glu Asp Pro Gly
                885                 890                 895
Thr Ser Phe Glu Asp Glu Asp Ala Ile Val Val Gln Glu Gln Val Arg
            900                 905                 910
```

Gln Ile Gln Ala Gln Glu Gln Asp Phe Glu Thr Phe Asn Leu Lys Ile
            915                 920                 925

Val His Arg Lys Asn Arg Thr Gly Phe Glu Glu Asp Lys Asn Phe His
    930                 935                 940

Val Val Leu Asn Ser Val Ile Ala Gly Arg Tyr His Val Thr Glu His
945                 950                 955                 960

Leu Gly Ser Ala Ala Phe Ser Lys Ala Ile Gln Ala His Asp Leu His
            965                 970                 975

Thr Gly Ile Asp Val Cys Val Lys Ile Ile Lys Asn Asn Lys Asp Phe
            980                 985                 990

Phe Asp Gln Ser Leu Asp Glu Ile Lys Leu Leu Lys Tyr Val Asn Gln
            995                 1000                1005

His Asp Pro Ala Asp Lys Tyr His Leu Leu Arg Leu Tyr Asp Tyr
    1010                1015                1020

Phe Tyr Phe Arg Glu His Leu Leu Ile Val Cys Glu Leu Leu Lys
    1025                1030                1035

Ala Asn Leu Tyr Glu Phe Gln Lys Phe Asn Arg Glu Ser Gly Gly
    1040                1045                1050

Glu Val Tyr Phe Thr Met Pro Arg Leu Gln Ser Ile Thr Ile Gln
    1055                1060                1065

Cys Leu Glu Ala Leu Asn Phe Leu His Gly Leu Gly Leu Ile His
    1070                1075                1080

Cys Asp Leu Lys Pro Glu Asn Ile Leu Ile Lys Ser Tyr Ser Arg
    1085                1090                1095

Cys Glu Ile Lys Val Ile Asp Leu Gly Ser Ser Cys Phe Glu Thr
    1100                1105                1110

Asp His Leu Cys Ser Tyr Val Gln Ser Arg Ser Tyr Arg Ala Pro
    1115                1120                1125

Glu Val Ile Leu Gly Leu Pro Tyr Asp Lys Lys Ile Asp Ile Trp
    1130                1135                1140

Ser Leu Gly Cys Ile Leu Ala Glu Leu Cys Thr Gly Asn Val Leu
    1145                1150                1155

Phe Gln Asn Asp Ser Pro Ala Thr Leu Leu Ala Arg Val Ile Gly
    1160                1165                1170

Ile Ile Gly Ser Ile Asp Gln Glu Met Leu Ala Lys Gly Arg Asp
    1175                1180                1185

Thr Cys Lys Tyr Phe Thr Lys Asn His Leu Leu Tyr Glu Arg Asn
    1190                1195                1200

Gln Glu Ser Asn Asn Leu Glu Tyr Leu Ile Pro Lys Lys Ser Ser
    1205                1210                1215

Leu Arg Arg Arg Leu Pro Met Gly Asp Gln Gly Phe Ile Asp Phe
    1220                1225                1230

Val Ala Tyr Leu Leu Gln Val Asp Pro Lys Lys Arg Pro Ser Ala
    1235                1240                1245

Phe Glu Ala Leu Lys His Pro Trp Leu Thr Tyr Pro Tyr Glu Pro
    1250                1255                1260

Ile Ser Ala
    1265

<210> SEQ ID NO 35
<211> LENGTH: 1157
<212> TYPE: PRT
<213> ORGANISM: Arabidopsis thaliana
<220> FEATURE:

<223> OTHER INFORMATION: hypothetical kinase-like protein, kinase with gatekeeper Cys

<400> SEQUENCE: 35

```
Met Thr Asp Gln Ser Ser Val Asp Gly Ile Leu Glu Phe Leu Arg Asn
1               5                   10                  15

Asn Arg Phe Ser Gln Ala Glu Glu Ala Leu Arg Asn Glu Leu Asn Asn
            20                  25                  30

Arg Ser Asp Ile Asn Gly Phe Leu Gln Lys Leu Lys Leu Glu Asp Lys
        35                  40                  45

Asp Ser Asn Glu Lys Ala Ala Gly Asn Glu Leu Arg Arg Ser Gly Ser
    50                  55                  60

Arg Asp Ser Glu Val Ser Lys Glu Leu Ile Val Lys Glu Val Asp Cys
65                  70                  75                  80

Gly Thr Ser Thr Asn Gly Ser Val Ile Lys Trp Glu Asn Gly Ala Thr
                85                  90                  95

Ala Asp Asn Pro Ser Lys Lys Glu Pro Val Val Ser Ser Glu Met Ser
            100                 105                 110

Phe Thr Phe Ser Lys Asn Ser Gly Asp Ala Ala Ala Pro Pro Asp Ala
        115                 120                 125

His Ser Tyr Lys Phe Thr Ser Arg Asn Gly Thr Val Glu Pro Ser Arg
    130                 135                 140

Asn Ile Asp Asp Ser Ser Ser Ser Ser Leu Val Asp Leu Tyr Ala Phe
145                 150                 155                 160

Glu Gln Ser Arg His Gly Asn Phe Ala Asp Ile Asp Lys Lys Ile Val
                165                 170                 175

Glu Thr Gly Glu Asp Ile Val Phe Phe Gly Asn Lys Ser Thr Ser Trp
            180                 185                 190

Ser Gly Asn Ser Ser Lys Gly Asn Ser Gly Ser Lys Ile Lys Glu Pro
        195                 200                 205

Asn Glu Ile His Arg Leu Val Glu Asn Ser Gly Lys His Asp Ser Tyr
    210                 215                 220

Lys Gly Ser Ile Leu Leu Arg Ser Glu Asp Val Val Asp Thr Ser Ala
225                 230                 235                 240

Asn Trp Arg Glu Cys Ser Val Lys Thr Leu Phe Gln Ser Ser Arg Gly
                245                 250                 255

Asp Ala Ser Asn Ser Tyr Asn Leu Val Ser Ser Ser Asp Lys Arg Glu
            260                 265                 270

Gly Lys Lys Lys Ala Asp Ile Ser Asp Val Arg Val Ala Ile Lys Glu
        275                 280                 285

Gln Glu Ser Glu Val Ala Arg Ala Leu Phe Phe Gly Lys Ser Gln Ser
    290                 295                 300

Thr Phe Asp Asp Lys Asn Ile Ser Ser Leu Gly Phe Pro Leu Val Tyr
305                 310                 315                 320

Asp Thr Arg Lys Glu Glu Phe Pro Arg Leu Pro Val Lys Leu Lys
                325                 330                 335

Ser Glu Asp Asn Pro Leu Ser Leu His Cys Glu Glu Lys Phe Glu Arg
            340                 345                 350

Asp Gly Ser Gly Pro Arg Leu Ile Asn Asp Glu Asp Ala Leu Leu Ile
        355                 360                 365

Gly Ser Tyr Leu Asp Val Pro Ile Gly Gln Glu Ile Ser Ser Ser Val
    370                 375                 380

Ser Gln Gly Ile Ala Glu Asp Ala Ser Asp Leu Val Ser Gly Phe Ala
385                 390                 395                 400
```

```
Thr Ile Gly Asp Gly Leu Ser Glu Ser Val Asp Tyr Arg Asn Glu Tyr
            405                 410                 415

Trp Asp Ser Asp Glu Tyr Glu Asp Asp Asp Ile Gly Tyr Val Arg
        420                 425                 430

Gln Pro Ile Glu Asp Glu Pro Trp Phe Leu Ala His Gly Ile Asp Tyr
            435                 440                 445

Pro Ser Asp His Glu Lys Gly Thr Thr Arg Gly Ser Pro Asp His His
        450                 455                 460

Glu Arg Asp Ala Asn Lys Asp Ala Asp Gln Ser Tyr Ala Glu Glu
465                 470                 475                 480

Ala Ser Tyr Ile Ser Gly Glu Gln Tyr Leu Gln Ser Lys Asp Ala Glu
            485                 490                 495

Pro Ile Ser Ser Glu Asn Asp Arg Arg Leu Thr Val Ser Glu Ile Tyr
        500                 505                 510

Pro Ala Ser Lys Lys Asn Asp Leu Leu Ala Gln Tyr Asp Gly His Leu
        515                 520                 525

Met Asp Glu Glu Leu Leu Ser Ser Met Arg Asp Glu Pro Val Trp Gln
        530                 535                 540

Gly Phe Val Ala Gln Ser Asn Glu Leu Leu Met Leu Gly Asp Lys Lys
545                 550                 555                 560

Gly Ile Asn Val His Arg Lys Ser His Arg Asp Asp Val Tyr Val Glu
            565                 570                 575

Asp Asp Gln His Asp Ser Val Arg Ser Ile Gly Val Gly Ile Asn Ser
            580                 585                 590

Asp Ala Ala Asp Phe Gly Ser Glu Val Arg Asp Ser Leu Ala Gly Gly
        595                 600                 605

Ser Ser Glu Gly Asp Phe Glu Tyr Ser Arg Asp His Asp Pro Val Ala
        610                 615                 620

Ser Arg Phe Lys Gln Leu Tyr Ser Glu Ser Asp Lys Lys His Ile Asp
625                 630                 635                 640

Ala Pro Asn Lys Asn Lys Gln Gln Ala Ser Lys Asn Asp Gly Pro Asp
            645                 650                 655

Tyr Ile Ala Asp Asn Asp Ser Ser Gly Ser Phe His Val Lys Ile Gln
            660                 665                 670

Thr Asp Gly Gly Phe Ser Phe Gly Ser Ser Gln Lys Asp Gly Gln Ser
        675                 680                 685

Met His Ala Glu Ser Ser Lys Ser Leu Trp Ser Gly Asn His Glu Thr
        690                 695                 700

Val Thr Arg Asp Arg Asn Thr Glu Arg Leu Ser Ala Ser Thr Ala Met
705                 710                 715                 720

Asp Asp Met Val Ala Thr Trp Arg Arg Lys Ser Ser Asp Ser Ser Ser
                725                 730                 735

Ser His Ser Ser Val Lys Asp Asn Asn Ala Thr Ser Ile Lys Ser Leu
            740                 745                 750

Asn Ser Ser Pro Ser Ser Leu Ser Asn Tyr Ala Cys Glu Glu Arg Lys
        755                 760                 765

His Ala Asp Lys Glu Asp Asp Arg Asn Asp Ser Ser Glu Ile Glu Asp
        770                 775                 780

Asp Asn Ala Thr Ala Leu Asp Asp Glu Glu Ala Val Ala Val Gln Glu
785                 790                 795                 800

Gln Val Arg Gln Ile Lys Ala Gln Glu Glu Phe Glu Thr Phe Asp
            805                 810                 815
```

Leu Lys Ile Val His Arg Lys Asn Arg Thr Gly Phe Glu Glu Lys
                820                 825                 830

Asn Phe Asn Val Val Leu Asn Ser Val Ile Ala Gly Arg Tyr His Val
            835                 840                 845

Thr Glu Tyr Leu Gly Ser Ala Ala Phe Ser Lys Ala Ile Gln Ala His
        850                 855                 860

Asp Leu Gln Thr Gly Met Asp Val Cys Ile Lys Ile Lys Asn Asn
865                 870                 875                 880

Lys Asp Phe Phe Asp Gln Ser Leu Asp Glu Ile Lys Leu Leu Lys Tyr
                885                 890                 895

Val Asn Lys His Asp Pro Ala Asp Lys Tyr His Leu Leu Arg Leu Tyr
            900                 905                 910

Asp Tyr Phe Tyr Tyr Arg Glu His Leu Leu Ile Val Cys Glu Leu Leu
        915                 920                 925

Lys Ala Asn Leu Tyr Glu Phe His Lys Phe Asn Arg Glu Ser Gly Gly
    930                 935                 940

Glu Val Tyr Phe Thr Met Pro Arg Leu Gln Ser Ile Thr Ile Gln Cys
945                 950                 955                 960

Leu Glu Ser Leu Gln Phe Leu His Gly Leu Gly Leu Ile His Cys Asp
                965                 970                 975

Leu Lys Pro Glu Asn Ile Leu Val Lys Ser Tyr Ser Arg Cys Glu Ile
            980                 985                 990

Lys Val Ile Asp Leu Gly Ser Ser Cys Phe Glu Thr Asp His Leu Cys
        995                1000                1005

Ser Tyr Val Gln Ser Arg Ser Tyr Arg Ala Pro Glu Val Ile Leu
    1010                1015                1020

Gly Leu Pro Tyr Asp Lys Lys Ile Asp Val Trp Ser Leu Gly Cys
    1025                1030                1035

Ile Leu Ala Glu Leu Cys Thr Gly Asn Val Leu Phe Gln Asn Asp
    1040                1045                1050

Ser Pro Ala Ser Leu Leu Ala Arg Val Met Gly Ile Val Gly Ser
    1055                1060                1065

Phe Asp Asn Glu Met Leu Thr Lys Gly Arg Asp Ser His Lys Tyr
    1070                1075                1080

Phe Thr Lys Asn Arg Met Leu Tyr Glu Arg Asn Gln Glu Ser Asn
    1085                1090                1095

Arg Leu Glu Tyr Leu Ile Pro Lys Arg Thr Ser Leu Arg His Arg
    1100                1105                1110

Leu Pro Met Gly Asp Gln Gly Phe Thr Asp Phe Val Ala His Leu
    1115                1120                1125

Leu Glu Ile Asn Pro Lys Lys Arg Pro Ser Ala Ala Glu Ala Leu
    1130                1135                1140

Lys His Pro Trp Leu Ser Tyr Pro Tyr Glu Pro Ile Ser Ala
    1145                1150                1155

<210> SEQ ID NO 36
<211> LENGTH: 1155
<212> TYPE: PRT
<213> ORGANISM: Arabidopsis thaliana
<220> FEATURE:
<223> OTHER INFORMATION: putative protein kinase-like protein, kinase
      with gatekeeper Cys

<400> SEQUENCE: 36

Met Ala Asp Gln Ser Ser Val Asp Gly Ile Leu Glu Phe Leu Arg Asn
1               5                   10                  15

```
Asn Arg Phe Ser Asn Ala Glu Glu Ala Leu Arg Asn Glu Leu Ser Asn
            20                  25                  30

Arg Ser Asp Ile Asn Gly Phe Leu Gln Lys Leu Met Leu Glu Glu Lys
        35                  40                  45

Asp Ser Ser Lys Asp Ser Asn Glu Arg Ala Asn Gly Lys Glu Leu Arg
50                  55                  60

Arg Ser Gly Ser Arg Asp Ser Glu Val Ser Lys Glu Leu Val Val Lys
65                  70                  75                  80

Glu Val Asp Cys Gly Thr Ser Thr Thr Gly Ser Val Ile Lys Trp Glu
                85                  90                  95

Asn Gly Ala Ala Ala Glu Asn Pro Ser Lys Lys Glu Thr Phe Val Pro
            100                 105                 110

Ser Glu Met Ser Phe Thr Phe Ser Lys Asn Ser Gly Asp Ala Ala Ala
            115                 120                 125

Pro Pro Asp Ala His Ser Tyr Glu Phe Thr Ser Gly Asn Gly Thr Leu
130                 135                 140

Glu Pro Tyr Gly Asn Ile Asp Asp Asn Ser Ser Ser Ser Leu Val Asp
145                 150                 155                 160

Ser Tyr Ala Ile Glu Gln Leu Ala Asp Ile Asp Lys Lys Ile Val Glu
                165                 170                 175

Thr Gly Glu Asp Ile Val Phe Phe Gly Asn Lys Ser Thr Leu Leu Ser
            180                 185                 190

Gly Asn Ser Ser Lys Gly Asn Ser Gly Ser Lys Ile Lys Lys Pro Asn
            195                 200                 205

Glu Ile Asp Gln Leu Gly Glu Ile Phe Gly Lys His Asp Ser Tyr Lys
        210                 215                 220

Gly Ser Val Leu Leu Arg Thr Glu Asp Val Ile Asp Thr Ser Glu Asn
225                 230                 235                 240

Trp Lys Glu Arg Ser Val Lys Thr Leu Phe Gln Ser Ser Arg Gly Asp
                245                 250                 255

Ala Ser Asn Ser Tyr Asn Leu Val Ser Ser Ser Asp Lys Arg Glu Gly
            260                 265                 270

Lys Lys Lys Ala Glu Ile Ser Asp Val Arg Val Ala Ile Lys Glu Gln
        275                 280                 285

Glu Ser Glu Val Ala Arg Ala Leu Phe Phe Gly Lys Ser Gln Ser Thr
        290                 295                 300

Phe Asp Asp Lys Asn Ile Ser Ser Leu Gly Phe Pro Leu Val Phe Asp
305                 310                 315                 320

Thr Arg Lys Glu Glu Phe Pro Arg Leu Pro Pro Val Lys Leu Lys Ser
                325                 330                 335

Glu Asp Asn Pro Leu Ser Leu His Cys Glu Glu Lys Phe Glu Arg Asp
            340                 345                 350

Gly Ser Gly Pro Arg Leu Ile Asn Asp Asp Glu Ala Leu Leu Ile Gly
        355                 360                 365

Ser Tyr Leu Asp Val Pro Ile Gly Gln Glu Ile Ser Ser Val Ser
            370                 375                 380

Gln Gly Ile Ala Asp Leu Val Ser Gly Phe Ala Thr Ile Gly Asp Gly
385                 390                 395                 400

Leu Ser Glu Ser Val Asp Tyr Arg Asn Glu Tyr Trp Asp Ser Asp Glu
                405                 410                 415

Tyr Glu Asp Asp Gly Asp Ile Gly Tyr Val Arg Gln Pro Ile Glu Asp
            420                 425                 430
```

```
Glu Thr Trp Phe Leu Ala His Glu Ile Asp Tyr Pro Ser Asp His Glu
        435                 440                 445

Lys Gly Thr Thr Arg Gly Ser Pro Asp His Asp Arg Asp Ala Asn
450                 455                 460

Lys Asp Glu Asp Asp Gln Ser Tyr Ala Glu Asp Glu Ser Tyr Leu Ser
465                 470                 475                 480

Gly Glu Arg Tyr Leu Gln Ser Lys Asp Ala Glu Pro Ile Ser Ser Glu
                485                 490                 495

Asn Asp Arg Arg Leu Thr Val Ser Glu Ile Tyr Pro Ala Cys Lys Lys
            500                 505                 510

Asn Asp Leu Leu Ala Gln Tyr Asp Gly Gln Leu Met Asp Glu Asp Leu
            515                 520                 525

Leu Asn Ser Met Arg Thr Glu Pro Val Trp Gln Gly Phe Val Ala Gln
            530                 535                 540

Ser Asn Glu Leu Val Met Leu Gly Asp Lys Lys Gly Ile Asn Val His
545                 550                 555                 560

Arg Lys Ser His Leu Asp Asp Val Tyr Val Glu Asp Gln His Asp
                565                 570                 575

Ser Val Arg Ser Ile Gly Val Gly Ile Asn Ser Asp Ala Ala Asp Phe
            580                 585                 590

Gly Ser Glu Val Arg Asp Ser Leu Ala Gly Gly Ser Ser Glu Gly Asp
            595                 600                 605

Phe Glu Tyr Ser Arg Asp His Asp Pro Val Ala Ser Arg Phe Lys Gln
            610                 615                 620

Leu Tyr Ser Glu Ser Asp Lys Lys His Ile Asp Gly Gln Asn Lys Asn
625                 630                 635                 640

Lys Gln Lys Ala Ser Lys Asn Asp Ser Gly Gly Ser Phe His Val Lys
                645                 650                 655

Ile Gln Thr Asp Gly Asp Phe Ser Phe Gly Ser Ser Gln Lys Asp Gly
            660                 665                 670

Gln Leu Met His Ala Glu Ser Ser Lys Ser Leu Trp Ser Gly Asn Arg
            675                 680                 685

Glu Thr Val Thr Arg Asp Arg Asn Thr Glu Leu Leu Ser Ala Ser Thr
690                 695                 700

Ala Thr Asp Asp Met Val Ala Thr Trp Arg Gln Lys Ser Ser Asp Ser
705                 710                 715                 720

Ser Ser Ser Arg Ser Ser Val Lys Glu Asn Asn Ala Thr Ser Ile Lys
                725                 730                 735

Ser Val Asn Ser Ser Pro Ser Ser Leu Ser Asn Tyr Ala Arg Gly Glu
            740                 745                 750

Arg Lys His Ala Glu Lys Glu Asn Asp Ser Ser Glu Arg Glu Asp Gly
            755                 760                 765

His Ala Thr Ala Leu Asp Asp Glu Glu Ala Val Ala Val Gln Glu Gln
            770                 775                 780

Val Arg Gln Ile Lys Ala Gln Glu Glu Phe Glu Thr Phe Asp Leu
785                 790                 795                 800

Lys Ile Val His Arg Lys Asn Arg Thr Gly Phe Glu Glu Lys Asn
                805                 810                 815

Phe Asn Val Val Leu Asn Ser Val Ile Ala Gly Arg Tyr His Val Thr
            820                 825                 830

Glu Tyr Leu Gly Ser Ala Ala Phe Ser Lys Ala Ile Gln Ala His Asp
            835                 840                 845

Leu Gln Thr Gly Met Asp Val Cys Ile Lys Ile Ile Lys Asn Asn Lys
```

```
                  850                 855                 860

Asp Phe Phe Asp Gln Ser Leu Asp Glu Ile Lys Leu Lys Tyr Val
865                 870                 875                 880

Asn Lys His Asp Pro Ala Asp Lys Tyr His Leu Leu Arg Leu Tyr Asp
                885                 890                 895

Tyr Phe Tyr Tyr Arg Glu His Leu Leu Ile Val Cys Glu Leu Leu Lys
            900                 905                 910

Ala Asn Leu Tyr Glu Phe His Lys Phe Asn Arg Glu Ser Gly Gly Glu
        915                 920                 925

Val Tyr Phe Thr Met Pro Arg Leu Gln Ser Ile Thr Ile Gln Cys Leu
    930                 935                 940

Glu Ser Leu Gln Phe Leu His Gly Leu Gly Leu Ile His Cys Asp Leu
945                 950                 955                 960

Lys Pro Glu Asn Ile Leu Val Lys Ser Tyr Ser Arg Cys Glu Ile Lys
                965                 970                 975

Val Ile Asp Leu Gly Ser Ser Cys Phe Glu Thr Asp His Leu Cys Ser
            980                 985                 990

Tyr Val Gln Ser Arg Ser Tyr Arg Ala Pro Glu Val Ile Leu Gly Leu
        995                 1000                1005

Pro Tyr Asp Lys Lys Ile Asp Val Trp Ser Leu Gly Cys Ile Leu
    1010                1015                1020

Ala Glu Leu Cys Thr Gly Asn Asp Lys Val Asn Pro Cys Leu
    1025                1030                1035

Asn Ile Glu Leu Leu Leu Gln Val Leu Phe Gln Asn Asp Ser Pro
    1040                1045                1050

Ala Ser Leu Leu Ala Arg Val Met Gly Ile Val Gly Ser Phe Asp
    1055                1060                1065

Asn Glu Met Leu Thr Lys Gly Arg Asp Ser His Lys Tyr Phe Thr
    1070                1075                1080

Lys Asn Arg Met Leu Tyr Glu Arg Asn Gln Glu Ser Asn Arg Leu
    1085                1090                1095

Glu Tyr Leu Ile Pro Lys Arg Thr Ser Leu Arg His Arg Leu Pro
    1100                1105                1110

Met Gly Asp Gln Gly Phe Thr Asp Phe Val Ala His Leu Leu Glu
    1115                1120                1125

Ile Asn Pro Lys Lys Arg Pro Ser Ala Ala Glu Ala Leu Lys His
    1130                1135                1140

Pro Trp Leu Ser Tyr Pro Tyr Glu Pro Ile Ser Ala
    1145                1150                1155

<210> SEQ ID NO 37
<211> LENGTH: 654
<212> TYPE: PRT
<213> ORGANISM: Arabidopsis thaliana
<220> FEATURE:
<223> OTHER INFORMATION: receptor-like protein kinase, kinase with
      gatekeeper Cys

<400> SEQUENCE: 37

Met Met Gln Phe His Phe Gln Phe Tyr Val Gly Pro Val Phe Thr Leu
1               5                   10                  15

Arg Pro Ser Lys Gly Phe Leu Ser Thr Cys Leu Val Ser Phe Leu Phe
            20                  25                  30

Val Thr Thr Thr Phe Cys Ser Tyr Ala Ile Ala Asp Leu Asn Ser Asp
        35                  40                  45
```

-continued

Arg Gln Ala Leu Leu Ala Phe Ala Ala Ser Val Pro His Leu Arg Arg
    50                  55                  60

Leu Asn Trp Asn Ser Thr Asn His Ile Cys Lys Ser Trp Val Gly Val
65                  70                  75                  80

Thr Cys Thr Ser Asp Gly Thr Ser Val His Ala Leu Arg Leu Pro Gly
                85                  90                  95

Ile Gly Leu Leu Gly Pro Ile Pro Pro Asn Thr Leu Gly Lys Leu Glu
            100                 105                 110

Ser Leu Arg Ile Leu Ser Leu Arg Ser Asn Leu Leu Ser Gly Asn Leu
            115                 120                 125

Pro Pro Asp Ile His Ser Leu Pro Ser Leu Asp Tyr Ile Tyr Leu Gln
            130                 135                 140

His Asn Asn Phe Ser Gly Glu Val Pro Ser Phe Val Ser Arg Gln Leu
145                 150                 155                 160

Asn Ile Leu Asp Leu Ser Phe Asn Ser Phe Thr Gly Lys Ile Pro Ala
                165                 170                 175

Thr Phe Gln Asn Leu Lys Gln Leu Thr Gly Leu Ser Leu Gln Asn Asn
            180                 185                 190

Lys Leu Ser Gly Pro Val Pro Asn Leu Asp Thr Val Ser Leu Arg Arg
            195                 200                 205

Leu Asn Leu Ser Asn Asn His Leu Asn Gly Ser Ile Pro Ser Ala Leu
            210                 215                 220

Gly Gly Phe Pro Ser Ser Phe Ser Gly Asn Thr Leu Leu Cys Gly
225                 230                 235                 240

Leu Pro Leu Gln Pro Cys Ala Thr Ser Ser Pro Pro Pro Ser Leu Thr
                245                 250                 255

Pro His Ile Ser Thr Pro Pro Leu Pro Pro Phe Pro His Lys Glu Gly
                260                 265                 270

Ser Lys Arg Lys Leu His Val Ser Thr Ile Ile Pro Ile Ala Ala Gly
            275                 280                 285

Gly Ala Ala Leu Leu Leu Ile Thr Val Ile Leu Cys Cys Cys
            290                 295                 300

Ile Lys Lys Lys Asp Lys Arg Glu Asp Ser Ile Val Lys Val Lys Thr
305                 310                 315                 320

Leu Thr Glu Lys Ala Lys Gln Glu Phe Gly Ser Gly Val Gln Glu Pro
                325                 330                 335

Glu Lys Asn Lys Leu Val Phe Phe Asn Gly Cys Ser Tyr Asn Phe Asp
            340                 345                 350

Leu Glu Asp Leu Leu Arg Ala Ser Ala Glu Val Leu Gly Lys Gly Ser
            355                 360                 365

Tyr Gly Thr Ala Tyr Lys Ala Val Leu Glu Glu Ser Thr Thr Val Val
            370                 375                 380

Val Lys Arg Leu Lys Glu Val Ala Ala Gly Lys Arg Glu Phe Glu Gln
385                 390                 395                 400

Gln Met Glu Ile Ile Ser Arg Val Gly Asn His Pro Ser Val Val Pro
                405                 410                 415

Leu Arg Ala Tyr Tyr Tyr Ser Lys Asp Glu Lys Leu Met Val Cys Asp
            420                 425                 430

Tyr Tyr Pro Ala Gly Asn Leu Ser Leu Leu His Gly Asn Arg Gly
            435                 440                 445

Ser Glu Lys Thr Pro Leu Asp Trp Asp Ser Arg Val Lys Ile Thr Leu
450                 455                 460

Ser Ala Ala Lys Gly Ile Ala His Leu His Ala Ala Gly Gly Pro Lys

```
                465                 470                 475                 480
        Phe Ser His Gly Asn Ile Lys Ser Ser Asn Val Ile Met Lys Gln Glu
                            485                 490                 495

Ser Asp Ala Cys Ile Ser Asp Phe Gly Leu Thr Pro Leu Met Ala Val
                        500                 505                 510

Pro Ile Ala Pro Met Arg Gly Ala Gly Tyr Arg Ala Pro Glu Val Met
                        515                 520                 525

Glu Thr Arg Lys His Thr His Lys Ser Asp Val Tyr Ser Phe Gly Val
                    530                 535                 540

Leu Ile Leu Glu Met Leu Thr Gly Lys Ser Pro Val Gln Ser Pro Ser
        545                 550                 555                 560

Arg Asp Asp Met Val Asp Leu Pro Arg Trp Val Gln Ser Val Val Arg
                            565                 570                 575

Glu Glu Trp Thr Ser Glu Val Phe Asp Ile Leu Met Arg Phe Gln
                        580                 585                 590

Asn Ile Glu Glu Glu Met Val Gln Met Leu Gln Ile Ala Met Ala Cys
                        595                 600                 605

Val Ala Gln Val Pro Glu Val Arg Pro Thr Met Asp Asp Val Val Arg
                    610                 615                 620

Met Ile Glu Glu Ile Arg Val Ser Asp Ser Glu Thr Thr Arg Pro Ser
        625                 630                 635                 640

Ser Asp Asp Asn Ser Lys Pro Lys Asp Ser Asn Val Gln Val
                            645                 650

<210> SEQ ID NO 38
<211> LENGTH: 420
<212> TYPE: PRT
<213> ORGANISM: Mus musculus
<220> FEATURE:
<223> OTHER INFORMATION: MAPK/MAK/MRK overlapping kinase, MOK protein
      kinase, T/STK 30, renal tumor antigen, RAGE1, kinase with
      gatekeeper Cys

<400> SEQUENCE: 38

Met Lys Asn Tyr Lys Ala Ile Gly Lys Ile Gly Glu Gly Thr Phe Ser
1               5                   10                  15

Glu Val Met Lys Met Gln Ser Leu Arg Asp Gly Asn Tyr Tyr Ala Cys
                20                  25                  30

Lys Gln Met Lys Gln His Phe Glu Ser Ile Glu Gln Val Asn Ser Leu
            35                  40                  45

Arg Glu Ile Gln Ala Leu Arg Arg Leu Asn Pro His Pro Asn Ile Leu
        50                  55                  60

Ala Leu His Glu Val Val Phe Asp Arg Lys Ser Gly Ser Leu Ala Leu
65                  70                  75                  80

Ile Cys Glu Leu Met Asp Met Asn Ile Tyr Glu Leu Ile Arg Gly Arg
                85                  90                  95

Arg His Pro Leu Ser Glu Lys Lys Ile Met Leu Tyr Met Tyr Gln Leu
            100                 105                 110

Cys Lys Ser Leu Asp His Met His Arg Asn Gly Ile Phe His Arg Asp
        115                 120                 125

Val Lys Pro Glu Asn Ile Leu Val Lys Gln Asp Val Leu Lys Leu Gly
    130                 135                 140

Asp Phe Gly Ser Cys Arg Ser Val Tyr Ser Lys Gln Pro Tyr Thr Glu
145                 150                 155                 160

Tyr Ile Ser Thr Arg Trp Tyr Arg Ala Pro Glu Cys Leu Leu Thr Asp
                165                 170                 175
```

```
Gly Phe Tyr Thr Tyr Lys Met Asp Leu Trp Ser Ala Gly Cys Val Phe
            180                 185                 190

Tyr Glu Ile Ala Ser Leu Gln Pro Leu Phe Pro Gly Val Asn Glu Leu
            195                 200                 205

Asp Gln Ile Ser Lys Ile His Asp Val Ile Gly Thr Pro Cys Gln Lys
    210                 215                 220

Thr Leu Thr Lys Phe Lys Gln Ser Arg Ala Met Ser Phe Asp Phe Pro
225                 230                 235                 240

Phe Lys Lys Gly Ser Gly Ile Pro Leu Leu Thr Ala Asn Leu Ser Pro
                245                 250                 255

Gln Cys Leu Ser Leu Leu His Ala Met Val Ala Tyr Asp Pro Asp Glu
        260                 265                 270

Arg Ile Ala Ala His Gln Ala Leu Gln His Pro Tyr Phe Gln Val Gln
            275                 280                 285

Arg Ala Ala Glu Thr Gln Thr Leu Ala Lys His Arg Arg Ala Phe Cys
        290                 295                 300

Pro Lys Phe Ser Met Val Pro Glu Ser Ser Ser His Asn Trp Ser Phe
305                 310                 315                 320

Ser Gln Glu Gly Arg Lys Gln Lys Gln Ser Leu Arg His Glu Glu Gly
                325                 330                 335

His Ala Arg Arg Gln Gly Pro Thr Ser Leu Met Glu Leu Pro Lys Leu
            340                 345                 350

Arg Leu Ser Gly Met Thr Lys Leu Ser Ser Cys Ser Ser Pro Ala Leu
        355                 360                 365

Arg Ser Val Leu Gly Thr Gly Ala Asn Gly Lys Val Pro Val Leu Arg
    370                 375                 380

Pro Leu Lys Cys Ala Ala Val Asn Lys Lys Thr Asp Thr Gln Lys Asp
385                 390                 395                 400

Ile Lys Pro His Leu Lys His Tyr His Leu Pro Thr Ile Asn Arg Lys
                405                 410                 415

Gly Gly Glu Tyr
            420

<210> SEQ ID NO 39
<211> LENGTH: 344
<212> TYPE: PRT
<213> ORGANISM: Carassius auratus
<220> FEATURE:
<223> OTHER INFORMATION: cyclin-dependent kinase 7 (CDK7), 40kDa protein
      kinase, CDC2/CDK2, 4-activating kinase, cell division protein
      kinase 7, P40 MO15, kinase with gatekeeper Cys

<400> SEQUENCE: 39

Met Ala Leu Asp Val Lys Ser Arg Ala Lys Leu Tyr Glu Lys Leu Asp
1               5                   10                  15

Phe Leu Gly Glu Gly Gln Phe Ala Thr Val Tyr Lys Ala Arg Asp Lys
            20                  25                  30

Thr Thr Asn Thr Ile Val Ala Ile Lys Lys Ile Lys Val Gly His Arg
        35                  40                  45

Thr Glu Ala Lys Asp Gly Ile Asn Arg Thr Ala Leu Arg Glu Ile Lys
    50                  55                  60

Leu Leu Gln Glu Leu Ser His Pro Asn Ile Ile Gly Leu Leu Asp Ala
65                  70                  75                  80

Phe Gly His Lys Ser Asn Ile Ser Leu Leu Cys Phe Met Glu Thr Asp
                85                  90                  95
```

Leu Glu Val Ile Ile Lys Asp Thr Ser Leu Val Leu Thr Pro Ala Asn
            100                 105                 110

Ile Lys Ala Tyr Ile Leu Met Ser Leu Gln Gly Leu Glu Tyr Met His
        115                 120                 125

Asn His Trp Ile Leu His Arg Asp Leu Lys Pro Asn Asn Leu Leu Leu
    130                 135                 140

Asp Glu Asn Gly Val Leu Lys Leu Ala Asp Phe Gly Leu Ala Lys Ala
145                 150                 155                 160

Phe Gly Ser Pro Asn Arg Val Tyr Thr His Gln Val Val Thr Arg Trp
                165                 170                 175

Tyr Arg Ala Pro Glu Leu Leu Phe Gly Ala Arg Met Tyr Gly Val Gly
            180                 185                 190

Val Asp Met Trp Ala Val Gly Ser Ile Leu Ala Glu Leu Leu Leu Arg
        195                 200                 205

Val Pro Phe Leu Ala Gly Asp Ser Asp Leu Asp Gln Leu Thr Gly Ile
    210                 215                 220

Phe Glu Ala Leu Gly Thr Pro Thr Glu Glu Thr Trp Pro Gly Met Ser
225                 230                 235                 240

Asn Leu Pro Asp Tyr Val Ser Phe Lys Leu Phe Pro Gly Thr Pro Leu
                245                 250                 255

Glu His Ile Phe Ser Ala Ala Gly Asp Asp Leu Leu Glu Leu Leu Lys
            260                 265                 270

Gly Leu Phe Thr Phe Asn Pro Cys Thr Arg Thr Thr Ala Ser Gln Ala
        275                 280                 285

Leu Lys Met Arg Tyr Phe Ser Ile Arg Pro Gly Pro Thr Pro Gly Pro
    290                 295                 300

Gln Leu Pro Arg Pro Asn Ser Ser Thr Glu Ala Leu Lys Glu Lys Glu
305                 310                 315                 320

Asn Leu Leu Ile Gly Ile Lys Arg Lys Arg Asp Ser Ile Glu Gln Gly
                325                 330                 335

Thr Leu Lys Lys Lys Leu Val Phe
            340

<210> SEQ ID NO 40
<211> LENGTH: 134
<212> TYPE: PRT
<213> ORGANISM: Capsicum annuum
<220> FEATURE:
<223> OTHER INFORMATION: protein kinase homolog D3, kinase with
      gatekeeper Cys

<400> SEQUENCE: 40

Thr Ser Gly Cys Glu Val Ala Leu Lys Arg Phe Lys Asn Cys Ser Ala
1               5                   10                  15

Gly Gly Asp Ser Ser Phe Ile His Glu Leu Glu Val Ile Ala Ser Val
            20                  25                  30

Arg His Val Asn Leu Leu Gly Leu Arg Gly Tyr Cys Thr Ala Thr Phe
        35                  40                  45

Pro Leu Glu Gly His Gln Arg Ile Ile Val Cys Asp Leu Val Lys His
    50                  55                  60

Gly Ser Leu Tyr Asp His Leu Phe Gly Leu Arg Cys Asn Lys Leu Ser
65                  70                  75                  80

Trp Pro Ile Arg Gln Arg Ile Ala Ile Gly Thr Ala Arg Gly Leu Ala
                85                  90                  95

Tyr Leu His Tyr Gly Ala Gln Pro Ala Ile Ile His Arg Asp Ile Lys
            100                 105                 110

-continued

```
Ser Ser Asn Ile Leu Leu Asp Glu Asn Phe Glu Pro Lys Val Ala Asp
        115                 120                 125

Phe Gly Leu Ala Lys Leu
    130

<210> SEQ ID NO 41
<211> LENGTH: 983
<212> TYPE: PRT
<213> ORGANISM: Leishmania major
<220> FEATURE:
<223> OTHER INFORMATION: possible serine/threonine kinase, kinase with
      gatekeeper Cys

<400> SEQUENCE: 41

Met Glu Glu Tyr Thr Ile Lys Arg Lys Ile Gly Asp Gly Ala Gln Gly
1               5                   10                  15

Val Val Tyr Glu Val Glu His Arg Thr Ser Lys Thr Ser Tyr Ala Met
                20                  25                  30

Lys Val Ile Cys Cys Thr Asp Gln Glu Gln Val Asn Met Ala Leu Lys
            35                  40                  45

Glu Ile Lys Val Leu Leu Gln Leu Arg His Pro Ser Ile Val Ser Tyr
    50                  55                  60

Val Asp Phe Phe Leu Val Phe Asn Ser Val Lys Leu Arg Arg Glu Phe
65                  70                  75                  80

Ala Ala Gln Ser Glu Gly Ala Cys Gly Ser Gly Gly Cys Gly Asn Gly
                85                  90                  95

Gln Gln Arg Glu Gln Asp Ser Leu Phe Leu Cys Ser Leu Ser Asn Ser
            100                 105                 110

Glu Leu Asp His Gly Cys Ala Ala Asp Ser Gly Trp Lys Pro Ala Ala
    115                 120                 125

Ala Glu Ala Ser Ser Asn Ala Pro Thr Gly Lys Pro Gln Ser Gly Ala
    130                 135                 140

Thr Arg Val Val Pro Thr Ser Leu Leu Ser Lys His Arg Gln Gln Ala
145                 150                 155                 160

Gly Ala His Trp Leu Gly Glu Glu Ile Ala Val Cys Leu Val Met
                165                 170                 175

Glu Leu Cys Ser Asn Gly Asp Met Gln Gly Leu Val Arg Glu Thr Arg
            180                 185                 190

Gln Glu Phe Met Lys Thr Gly Ser His Ser Ile Ala Glu Ala Gln Ala
    195                 200                 205

Val Ser Trp Leu Glu Gln Ala Ala Ala Leu Gln Phe Ile His Asn
    210                 215                 220

Lys Gly Phe Leu His Arg Asp Leu Lys Pro Thr Asn Ile Phe Phe Asp
225                 230                 235                 240

Glu Tyr Lys Asn Ile Lys Val Gly Asp Phe Gly Leu Ala Ala Thr Val
                245                 250                 255

Gly Leu Gly Arg Asn Ser Ala Val Gly Thr Pro Tyr Tyr Leu Ala Pro
            260                 265                 270

Glu Arg Met Leu Gln Gln Arg Tyr Asp Gly Lys Val Asp Ile Trp Gly
    275                 280                 285

Leu Gly Val Val Leu Leu Glu Leu Leu Thr Leu Arg Glu Gln Pro Ile
    290                 295                 300

Asn Ser Met Leu Leu Glu Asn Pro Lys Val Val Asp Thr Val Ile Pro
305                 310                 315                 320

Gln Ile Thr Lys Met Gly Tyr Ser Thr Lys Leu Ala Thr Leu Leu Arg
```

```
                    325                 330                 335
Asp Met Leu Gln Arg Gln Pro Gln Asp Arg Pro Thr Pro Ser Ser Ile
                340                 345                 350

Leu His Arg Leu Ala Ser Ile Thr Ala Thr Ser Pro His Pro Gly Met
                355                 360                 365

Ser Ala Thr Leu Phe Ala Gly Met Ser Cys Pro Lys Leu Thr Glu Ala
                370                 375                 380

Leu Cys Asp Val Cys Glu Val Glu Val Ala Gly Val Met Cys Ser Ser
385                 390                 395                 400

Cys Lys Ala Ala Phe Ala Gly Cys Asp Arg Ala Arg His Arg His
                    405                 410                 415

His Ser Arg Gln Ser His Asp Arg Thr Asn Met Ser Ser Ile Val Asn
                420                 425                 430

Ser Met Asn Gly Ala Ser Ser Leu Pro Leu Ser Ala Thr Pro Met Gln
                435                 440                 445

Gln Gln Gln Gln Gln Lys Thr Leu Ser Phe Ser Arg Gly Pro Ser
                450                 455                 460

Pro Ala Asn Thr Ser Asp Gln Thr Arg Ala Ser Met Gln Asn Ile Val
465                 470                 475                 480

Val Phe Pro Ser Ser Asn Ser Ser His Ser Arg Thr Leu Pro Arg Glu
                    485                 490                 495

Arg Glu Met Asn Ser Arg Thr Phe Thr Arg Phe Gln Leu Ala Leu Pro
                500                 505                 510

Gly Arg Ser Val Ser Met Ser Asp Phe Ser Met Thr Gln Gly Leu Gln
                515                 520                 525

Gly Pro Arg Asp Gly Ser Gly Ile Asn Ala Ala Val Ala Glu Thr Val
                530                 535                 540

Leu Arg Val Pro Asp Asp Val Pro Ser Leu Ala Gln Ala Leu Arg Val
545                 550                 555                 560

Val Glu Ser Met Pro His Ile Arg Lys Ile Leu Val Ala Gly Asn Thr
                    565                 570                 575

Thr His Thr Val Pro Leu Val Leu Thr Ser Arg Leu Pro Asp Ser Ile
                580                 585                 590

Lys Leu Val Gly Glu Ser Pro Pro Met Leu Glu Val Ala Asp Ser
                595                 600                 605

Pro Phe Ala Leu His Cys His Ser Gly Arg Gly Ser Val Glu Asn Phe
                610                 615                 620

Ile Leu Arg His Val Gly Arg Phe Cys Phe Lys Leu Leu Lys Leu Asp
625                 630                 635                 640

Thr Asn Leu His Gln Thr Asp Ala Asn Ala Met Thr Ser Ala Pro Ala
                    645                 650                 655

Lys Lys Pro Ser Arg Pro Thr Ala Val Ser Ile Thr Gly Gly Glu Trp
                660                 665                 670

Arg Leu His Lys Cys Arg Ile Ser Cys Val Glu Gly Ser Gly Val Thr
                675                 680                 685

Val Gly Gly Ser Lys His Thr Pro Ser Ser Ala Thr Asn Gly Gln Asn
                690                 695                 700

Pro Ser Ala Thr Gly Ala Arg Ser Arg Pro Pro Gln Ser Pro Ser
705                 710                 715                 720

Leu Val Ala Arg Ser Ser Leu Val Asn Gly Ala Asp Glu Gly Ala Glu
                    725                 730                 735

Asp Ala Asp Val Met Ser Met Glu Pro Ile Ile Thr Lys Cys Ser Phe
                740                 745                 750
```

```
Ile Asp Val Thr Ala Ala Gly Ile Val Val Met Glu Lys Ser Arg Gly
            755                 760                 765

Leu Tyr Glu Gly Asn Thr Phe Ser Gly Cys Gly Phe Ala Ala Phe Leu
    770                 775                 780

Leu Arg Lys Asp Ala Thr Pro Arg Ile Arg Ala Asn His Ile Thr Asp
785                 790                 795                 800

Gly Ala Glu Ala Gly Ile Phe Cys Gln Asp Ala Ser Gly Leu Met Glu
                805                 810                 815

Tyr Asn Val Ile Ala Gln Asn Ala Gly Cys Gly Ile Val Val Lys Gly
            820                 825                 830

Ala Ser Ala Val Pro Val Ile Arg Lys Asn Arg Val Leu Ser Asn Val
        835                 840                 845

Gln Ala Gly Val Phe Cys Cys Asp Lys Ala Ala Pro Phe Val Ser Asp
    850                 855                 860

Asn Glu Ile Arg Gln Asn Gly Lys Ala Gly Val Leu Val Lys Thr Thr
865                 870                 875                 880

Ala Ala Pro Lys Ile Thr Arg Asn Val Ile Glu Ser Gly Lys Glu Ala
                885                 890                 895

Gly Ile Tyr Ile Phe Glu Lys Gly Ala Gly Ile Glu Glu Asn Arg
            900                 905                 910

Ile Arg Gly Asn Gln Asn Ala Gly Leu Leu Val Thr Thr Gly Gly Asn
        915                 920                 925

Pro His Val Ile His Asn Thr Ile Thr Lys Asn Ala Tyr Glu Gly Ile
    930                 935                 940

Trp Val Cys Lys His Gly Gly Thr Phe Cys Asp Asn Asp Leu Arg
945                 950                 955                 960

Gly Asn Thr Lys Gly Ala Lys Asp Ile Glu Ala Asp Ser Arg Val Thr
                965                 970                 975

Trp Val Gly Asn Val Glu Gln
            980

<210> SEQ ID NO 42
<211> LENGTH: 419
<212> TYPE: PRT
<213> ORGANISM: Homo sapiens
<220> FEATURE:
<223> OTHER INFORMATION: MOK protein kinase, kinase with gatekeeper Cys

<400> SEQUENCE: 42

Met Lys Asn Tyr Lys Ala Ile Gly Lys Ile Gly Glu Gly Thr Phe Ser
1               5                   10                  15

Glu Val Met Lys Met Gln Ser Leu Arg Asp Gly Asn Tyr Tyr Ala Cys
            20                  25                  30

Lys Gln Met Lys Gln Arg Phe Glu Ser Ile Glu Gln Val Asn Asn Leu
        35                  40                  45

Arg Glu Ile Gln Ala Leu Arg Arg Leu Asn Pro His Pro Asn Ile Leu
    50                  55                  60

Met Leu His Glu Val Val Phe Asp Arg Lys Ser Gly Ser Leu Ala Leu
65                  70                  75                  80

Ile Cys Glu Leu Met Asp Met Asn Ile Tyr Glu Leu Ile Arg Gly Arg
                85                  90                  95

Arg Tyr Pro Leu Ser Glu Lys Lys Ile Met His Tyr Met Tyr Gln Leu
            100                 105                 110

Cys Lys Ser Leu Asp His Ile His Arg Asn Gly Ile Phe His Arg Asp
        115                 120                 125
```

```
Val Lys Pro Glu Asn Ile Leu Ile Lys Gln Asp Val Leu Lys Leu Gly
    130                 135                 140

Asp Phe Gly Ser Cys Arg Ser Val Tyr Ser Lys Gln Pro Tyr Thr Glu
145                 150                 155                 160

Tyr Ile Ser Thr Arg Trp Tyr Arg Ala Pro Glu Cys Leu Leu Thr Asp
                165                 170                 175

Gly Phe Tyr Thr Tyr Lys Met Asp Leu Trp Ser Ala Gly Cys Val Phe
            180                 185                 190

Tyr Glu Ile Ala Ser Leu Gln Pro Leu Phe Pro Gly Val Asn Glu Leu
        195                 200                 205

Asp Gln Ile Ser Lys Ile His Asp Val Ile Gly Thr Pro Ala Gln Lys
    210                 215                 220

Ile Leu Thr Lys Phe Lys Gln Ser Arg Ala Met Asn Phe Asp Phe Pro
225                 230                 235                 240

Phe Lys Lys Gly Ser Gly Ile Pro Leu Leu Thr Thr Asn Leu Ser Pro
                245                 250                 255

Gln Cys Leu Ser Leu Leu His Ala Met Val Ala Tyr Asp Pro Asp Glu
            260                 265                 270

Arg Ile Ala Ala His Gln Ala Leu Gln His Pro Tyr Phe Gln Glu Gln
        275                 280                 285

Arg Lys Thr Glu Lys Arg Ala Leu Gly Ser His Arg Lys Ala Gly Phe
    290                 295                 300

Pro Glu His Pro Val Ala Pro Glu Pro Leu Ser Asn Ser Cys Gln Ile
305                 310                 315                 320

Ser Lys Glu Gly Arg Lys Gln Lys Gln Ser Leu Lys Gln Glu Glu Asp
                325                 330                 335

Arg Pro Lys Arg Arg Gly Pro Ala Tyr Val Met Glu Leu Pro Lys Leu
            340                 345                 350

Lys Leu Ser Gly Val Val Arg Leu Ser Ser Tyr Ser Ser Pro Thr Leu
        355                 360                 365

Gln Ser Val Leu Gly Ser Gly Thr Asn Gly Arg Val Pro Val Leu Arg
    370                 375                 380

Pro Leu Lys Cys Ile Pro Ala Ser Lys Lys Thr Asp Pro Gln Lys Asp
385                 390                 395                 400

Leu Lys Pro Ala Pro Gln Gln Cys Arg Leu Pro Thr Ile Val Arg Lys
                405                 410                 415

Gly Gly Arg

<210> SEQ ID NO 43
<211> LENGTH: 278
<212> TYPE: PRT
<213> ORGANISM: Trichomonas vaginalis
<220> FEATURE:
<223> OTHER INFORMATION: probable protein kinase cdc2/cdc28-related,
      kinase with gatekeeper Cys

<400> SEQUENCE: 43

Met Asp Leu Ser Ala Tyr His Lys Asp Met Lys Leu Gly Glu Gly Thr
1               5                   10                  15

Tyr Gly Ser Val Phe Arg Ala Thr His Ile Pro Thr Asp Gln Pro Val
                20                  25                  30

Val Leu Lys Leu Val Arg Met Asp Leu Glu Glu Asp Gly Ile Pro Pro
            35                  40                  45

Ser Ser Val Arg Glu Val Cys Ile Leu Lys Ser Leu Asn His Pro Asn
        50                  55                  60
```

Ile Leu His Phe Arg Glu Val Ile Cys Lys Asp Ser Lys Ile Ile Met
65                  70                  75                  80

Val Cys Glu Phe Met Asp Met Asp Leu Lys Asn Phe Leu Ser Lys Arg
                85                  90                  95

Arg Met Asn Pro Asp Leu Leu Arg Ser Tyr Ala Phe Gln Leu Leu Cys
            100                 105                 110

Gly Thr Tyr Tyr Leu His Arg Ile Gly Ile Val His Arg Asp Ile Lys
        115                 120                 125

Pro Glu Asn Ile Leu Ile Asp Arg Asn Gly Leu Leu Lys Leu Gly Asp
    130                 135                 140

Phe Gly Thr Ala Ala Tyr Cys Phe His Pro Ile Pro Tyr Asp Ile Glu
145                 150                 155                 160

Glu Ile Lys Thr Pro Trp Tyr Leu Ala Pro Glu Ile Leu Ile Asn Ala
                165                 170                 175

Pro Ala His Gly Thr Glu Ile Asp Ile Trp Ser Ile Gly Cys Val Ile
            180                 185                 190

Ala Glu Met Ala Arg Gly Asn Leu Phe Met Gly Asp Ser Gln Val Asp
        195                 200                 205

Gln Leu Ile Lys Ile Thr Glu Val Leu Gly Ile Pro Ser Glu Glu Asp
    210                 215                 220

Tyr Pro Asp Phe Tyr Lys Tyr Lys Ile Asn Asn Met Pro Cys Met Lys
225                 230                 235                 240

Lys Glu Lys Pro Asp Phe Asn Ser Phe Phe Pro Gly Val Asp Pro Glu
                245                 250                 255

Leu Val Asp Leu Ile Ser Lys Met Leu Gln Met Asn Pro Glu His Arg
            260                 265                 270

Ile Asn Ala Gln Thr His
        275

<210> SEQ ID NO 44
<211> LENGTH: 2485
<212> TYPE: PRT
<213> ORGANISM: Plasmodium falciparum
<220> FEATURE:
<223> OTHER INFORMATION: putative protein kinase, Ser/Thr protein
      kinase, kinase with gatekeeper Cys

<400> SEQUENCE: 44

Met Phe Ser Val Glu Leu Glu Asn Arg Ser Gly Tyr Lys Lys Arg Lys
1               5                   10                  15

Lys Lys Lys Trp Asn Asn Lys Ser Thr Gly Gln Asp Lys Phe Thr Asn
            20                  25                  30

Lys Asp Ile Ile Ser Glu Glu Lys Glu Glu Gly Leu Asp Ile Glu Cys
        35                  40                  45

Gly His Asn Ile Leu Gly Asp Val Gln Tyr Asp Gly Thr Tyr Asn Ile
    50                  55                  60

Asn Glu Gln Val Lys Lys Asn Ser Leu Phe Tyr Phe Lys Cys Lys Glu
65                  70                  75                  80

Glu Ile Asn Leu Lys Asp Gly Asn Ile Ile Leu Asp Asp Lys Asn Arg
                85                  90                  95

Lys Val Asp Asp Ile Asn Ile Thr Gly Asp Asp Lys Asn Ile Lys Val
            100                 105                 110

Asp Asp Lys Asn Ile Lys Val Asp Asp Lys Asn Ile Thr Gly Glu Asp
        115                 120                 125

Lys Asn Ile Thr Gly Glu Asp Lys Asn Ile Thr Gly Asp Asp Lys Asn

```
              130                 135                 140
Ile Ile Phe Asp Val Asp Glu Ile Leu Ile His Gln His Asn Thr Ser
145                 150                 155                 160
Asn Ser Asn Ile Tyr Ile Asn Cys Asn Asp Asn Asn Asp Ile Arg
                165                 170                 175
Asn Ser Ser Asn Val Gln His Tyr Tyr Asn Asp Lys Ile Lys Glu Asn
            180                 185                 190
Ile Asn Lys Gln Asn Lys Lys Tyr Val Leu Ile Asn Asp Tyr Ile Asn
        195                 200                 205
Asn Lys Tyr Ile Leu Ser Lys Asn Lys Thr Cys Lys Ile Asn Lys Gly
    210                 215                 220
Lys Lys Leu Ile Lys Lys Lys Val Asn Asn Ile Ser Arg Arg Arg
225                 230                 235                 240
Asn His Ile Leu Tyr Lys Cys Arg Asn Lys Leu Tyr Asn Gly Asn Val
                245                 250                 255
Phe Ser Asp Asp Ile Ile Lys Ser Glu Val Asn Val Cys Asn Ser Leu
            260                 265                 270
Thr Val Leu His Lys Asn Tyr Asn Ile Asn Met Asp Asn Tyr Leu Asp
        275                 280                 285
Asp Asn Ile His Thr Asn Asn Ser Asn Ile Tyr Asp Ile Asn Tyr Thr
    290                 295                 300
Asn Glu Asn Val Ile Asn Ser Thr Cys Arg Tyr Tyr Pro Ile Gly Asn
305                 310                 315                 320
Asn Asn Thr Leu Ser Lys Asp Glu Val Thr Lys Ser Ser Ser Lys Ile
                325                 330                 335
Asn Ser Leu Ser Tyr Phe Asp Asp Ile Ile Asn Val Asn Lys Asn Asp
            340                 345                 350
Ile Pro Ile Leu His Asp Lys Glu Asn Ile Asn Ile Ile Ser Asn Lys
        355                 360                 365
Glu Ser Cys His Lys Asp Glu Lys Glu Glu Lys Tyr Ile Met Tyr
    370                 375                 380
Asn Ser Asn Leu Val Glu Glu Lys Lys Gln Lys Lys Met Ile Trp Asn
385                 390                 395                 400
Ser Leu Asn Val Leu Pro Ile Asp Ile Leu Leu Lys Asn Gly His Asp
                405                 410                 415
Glu Ile Asn Lys Glu Ile Cys Lys Lys Lys Lys Ser Phe Phe Ser
            420                 425                 430
Gln Asn Asp Ile Lys Ser Lys Met Leu Tyr Asn Asn Lys Ser Tyr Ser
        435                 440                 445
Lys Ser Glu Lys Val Leu Tyr Thr Asn Asn Lys Asn Ser Asn Thr Phe
    450                 455                 460
Ile Pro Ile Phe Phe Leu Asn Lys Val Gly Asp Lys Phe Lys Asn Ser
465                 470                 475                 480
Glu Asn Ile Tyr Asp Met Tyr Asn Asn Lys Asn Val Tyr Ile His
                485                 490                 495
Asp Lys Lys Ile Tyr Thr Asn Met Tyr Ser Asn Lys Leu Lys Gln Lys
            500                 505                 510
His Tyr Tyr Ser Thr Ser Asn Ile Asn Leu Leu Tyr Asn Asn Ile Gly
        515                 520                 525
Lys Val Leu Asp Asn Gly Leu His Leu Ser Asn Met Tyr Cys Arg
    530                 535                 540
Leu Asn Ser Asn Pro Pro Tyr Lys Ser Ile Ser Leu Ile Asn Asn Asn
545                 550                 555                 560
```

```
Val Phe Phe Tyr Lys Lys Arg Lys Ser Asn Ser Asn Asn Asn Asn
                565                 570                 575

Asn Asn Asn Ile Ser Ser Ser Ser Ser Ser Lys Lys Asn His
            580                 585                 590

Val Ile Ile Asn Lys Lys Ile Ser Ser Tyr Asn Ile His Tyr Lys Glu
                595                 600                 605

Arg Lys Asp Ser Phe Lys Glu Asn Phe Leu Phe Phe Lys Glu Lys Ile
            610                 615                 620

Leu Pro Ser Lys Lys Asp Thr Cys Val Phe Asn Glu Arg Gln Lys Asp
625                 630                 635                 640

Leu Phe Glu Lys Ser Asn Glu His Ile Lys Cys Val Ser Ser Phe Asn
                645                 650                 655

Asn Thr Ser Asp Asp Ile Ser Ser His Ser Ser Val Asn Lys Lys Glu
                660                 665                 670

Pro Phe Phe Ala Leu Lys Asn Asn Ser Ile Arg His Ile Pro Lys Glu
                675                 680                 685

Asn Asn Ile Ile Tyr Thr Ser Gly Lys Ser Phe Asn His Val Gln Asp
            690                 695                 700

Lys Glu Lys Thr Val Leu Leu Lys Lys Lys Glu Ile Asn Asp Lys
705                 710                 715                 720

Asn Thr Phe Ser Ser Cys Leu Ile Asn His Asn Ile Thr Thr Tyr Thr
                725                 730                 735

Leu Gln Asn Gly Val Asn Lys Asn Leu Asn Met Leu Gly Ile Arg Asp
            740                 745                 750

Ser Ile Tyr Lys Ile Asp Glu Lys Asn Met Leu Lys Glu Cys Tyr
            755                 760                 765

Asn Gly Asn Asn Asp Ser Asn Asn Lys Lys Lys Lys Lys Lys Lys
770                 775                 780

Leu Ser Phe Ser Cys Asp Ile Ile Asn Asp Asn Ile Thr Pro Tyr Glu
785                 790                 795                 800

Ser Asp Lys Glu Lys Asn Asn Ser Asn Asn Ile Lys Ser Met Asp Ile
            805                 810                 815

Phe Asn Tyr Val Lys Arg Lys Ser Asn Leu Tyr Asn Asn Leu Ser Ser
                820                 825                 830

Asn Arg Asp Ser Thr Val Asp Met His Asn Lys Tyr Asn Ser Glu Glu
            835                 840                 845

Tyr Ile Asn Ile Gln Arg Thr Asn Lys Ile Tyr Glu Leu Ser Asn Lys
            850                 855                 860

Arg Ile Arg Asn Tyr Lys Leu Tyr Ser Met Asp Glu Ile Phe Lys Val
865                 870                 875                 880

Ser Leu Lys Glu Lys Lys Tyr Ile Asp Asn Ile Ser Asn Asn Met Glu
                885                 890                 895

Arg Val Thr Tyr Lys Asn Glu Met Ile Asn Glu Lys Ile Ser Lys Met
                900                 905                 910

Asp Asp Ile Leu Tyr Pro Cys Asp Lys Asn Lys Ser Leu Asn Met Ser
            915                 920                 925

Cys Pro Val Ile Ile Glu Asn Asn Ile Ser Arg Glu Glu Asn Glu Lys
            930                 935                 940

Asn Ser Ser Val Ile Leu Asn Lys Lys Asn Glu Asn Met Phe Asn
945                 950                 955                 960

Cys Val Gly Arg Leu His Cys His Met Gly Lys Met Asn Asn Gln Asp
                965                 970                 975
```

-continued

Asn Ile Tyr Asp Gln Gly Asn Ile Lys Lys Asn Glu Glu Glu Ile Thr
                    980                 985                 990

Lys His Asp Glu Tyr Ile Ser Arg Glu Glu Lys Asn Lys Tyr Asn Ser
        995                1000                1005

Lys Cys Ile Arg Asn Phe Asp Asp Tyr Lys Tyr Glu Gln Val Leu
        1010                1015                1020

Ser Tyr His Thr Leu Asp Glu Asp Lys Lys Asn Asp Met Asn
        1025                1030                1035

Asn Leu Ile Asp Met Asn Asn Glu Ala Ile Ile Glu Thr Val Asn
        1040                1045                1050

Gly Val Ile Asn Asn Ile Ile Leu Asp Arg Lys Asp Asn Asn Ser
        1055                1060                1065

Arg Lys Asp Met Glu Lys Glu Met Glu Lys Glu Met Glu Lys Lys
        1070                1075                1080

Met Glu Lys Glu Met Glu Lys Val Met Glu Lys Glu Met Glu Lys
        1085                1090                1095

Val Met Glu Lys Glu Val Glu Lys Glu Leu Lys Asn Glu Met Asn
        1100                1105                1110

Asn Arg Met Asn Asn Arg Met Asn Asn Glu Met Lys Asn Glu Ile
        1115                1120                1125

Asn Ile Tyr Lys Asn Asn Glu Ile Tyr Val Asp Asn Asp Lys Glu
        1130                1135                1140

Leu Glu Ile Val Asn Glu Glu Lys Lys Leu Ile Tyr Pro Phe Asn
        1145                1150                1155

Tyr Glu Ser Asp Val His Lys Asn Met Asn Met Ser Ile Asn Ile
        1160                1165                1170

Asn Asn Cys Lys Asp Asp Tyr Asn Asn Ile Leu Lys Glu Tyr Val
        1175                1180                1185

Asp Asn Ser Cys Leu Ala Gln Lys Glu Glu Asn Ile Phe Arg Pro
        1190                1195                1200

Leu Phe Asn Leu Asn Lys Lys Asp Lys Val Trp Lys Arg Phe Asn
        1205                1210                1215

Ile Lys Asn Asn Ile Lys Thr Ile Ile His Asn Glu Glu Met Lys
        1220                1225                1230

Arg Ile Tyr Gln Thr Ile Asn Lys Asn Val Phe Pro Ile Tyr Asn
        1235                1240                1245

Phe Asn Arg Tyr Glu Asn Phe Leu Ile Asn His Leu Thr Tyr Asn
        1250                1255                1260

Phe Pro Lys Asn Asp Leu Phe Lys Leu Ser Tyr Lys Val Ser Met
        1265                1270                1275

Asn Asn Ile Arg Asn Leu Tyr Ile Ala Asn Lys His Ile Asn Asn
        1280                1285                1290

Asn Tyr Asp Tyr Met Asn Lys Leu Tyr Asn Gln Asn Ile Tyr Thr
        1295                1300                1305

Leu Lys Tyr Gln Val Ala Asn Ile Asp Asn Asp His His Ile Cys
        1310                1315                1320

Lys Lys Gly Gly Gly Leu Asp Tyr Ile Asn Met Asn Ile Ser Lys
        1325                1330                1335

Glu Cys Lys Asn Arg Lys Asp Lys Thr Tyr Leu Asn Lys Ile Phe
        1340                1345                1350

His Tyr Lys Lys Lys Lys Asp Ala Arg Phe Phe Ile Asn Asp Glu
        1355                1360                1365

Ile Gly Ser Asn Asp Tyr Met Tyr Asp Ile Lys Lys Lys Tyr Ser

-continued

```
                    1370               1375               1380

Asn Asp Glu Asn Asn Tyr Lys Leu Asn Glu Lys Met Asn Ile Ser
        1385               1390               1395

Met Ser Asn Asp Glu Asp Met Ile Pro Thr Leu Asn Ser Glu His
1400               1405               1410

Gly Asn Asn Phe Pro Ser Cys Gln Pro Asn Leu Leu Glu Lys Lys
1415               1420               1425

Ser Thr Tyr Ile Asp Leu Asn Leu Tyr Asp Ser Asn Ser Met Asp
1430               1435               1440

Asp Phe Thr Glu Glu Lys Tyr Asn Phe Val Asn Asn Glu Asn Asp
1445               1450               1455

Leu Phe Asn Thr Lys Arg Trp Lys Phe Asn Phe Ser Lys Gly Lys
1460               1465               1470

Asn Leu Phe Asn Asn Lys Phe Phe Asn Val Ser Asn Glu Asp Gly
    1475               1480               1485

Val Phe Ser Phe Phe Lys Asn Met Asn Leu Phe Arg Glu Leu Asn
1490               1495               1500

Lys Ser Asn Asn Ser Leu Lys Leu Glu Ser Val Lys Asn Ser Asn
1505               1510               1515

Asn Asn Cys Ser Asn Asn Lys Gly Asp Asp Asn Ile Gly Asn Met
1520               1525               1530

Glu Asn Met Asn Thr Thr Asn Val Thr Ile Ala Ser Asp Glu His
1535               1540               1545

Ile Ser Thr Lys Gly Asp Ile His Asp Glu Ser Phe Ser Arg Asp
1550               1555               1560

Asp Asn Asp Cys Ile Leu Leu Lys Ile Glu Gly Arg Ser Lys Lys
1565               1570               1575

Tyr Ser Asp Ile Thr Leu Tyr Asn Glu Asp Lys Ser Asn Leu Glu
1580               1585               1590

Asn Asp Asn Glu Thr Ile Asn Glu Tyr Glu Asn Val Cys Ser Asn
1595               1600               1605

Ile Asp Val Asn Glu Trp Glu Asp Lys Val Asn Gly Thr Cys Asn
1610               1615               1620

Ser Val Gly Asp Lys Glu Thr Glu Lys Asn Asn Glu Lys Asn Asn
1625               1630               1635

Glu Lys Asn Asn Glu Lys Asn Asn Glu Lys Asn Asn Glu Lys Asn
1640               1645               1650

Asn Glu Lys Asn Asn Glu Lys Asn Asn Glu Lys Asn Asn Glu Glu
1655               1660               1665

Asn Asn Glu Gly Asn Asn Glu Glu Asn Asn Glu Glu Asn Asn Glu
1670               1675               1680

Glu Asn Asn Glu Glu Asn Asn Asp Ile Glu Lys Asn Asp Ile Lys
1685               1690               1695

Asp Asn Asn Ser Gly Gln Val Lys Glu Asn Ile Ile Val Met Asn
1700               1705               1710

Asn Thr Asn Asn Met Asp Val Asp Asn Asp Asp Asn Asn Asn Asn
1715               1720               1725

Tyr Asn Asn Val Ser Thr Asp Glu Gly Ile Asp Ile Ile Lys Asn
1730               1735               1740

Ile Lys Ser Glu Met Asn Asp Tyr Ile Tyr Asn Asp Asn Ile Met
1745               1750               1755

Ile Lys Ile Asn Asn Lys Ser Ile Asp Leu Met Asn Ile Lys Asn
1760               1765               1770
```

```
Gln Lys Asn Glu Pro Phe Leu Asn Tyr Thr Asn Glu Lys Asp Ile
1775                1780                1785

His Met Lys Ser Asn Ser Ser Tyr Asn Val Asn Asp Lys Met Asn
1790                1795                1800

Leu Phe Asn Asn Asn Glu Lys Thr Glu Lys Asn Asn Thr Ser Leu
1805                1810                1815

Asn Asp Leu Leu Tyr Lys Arg Lys Glu Glu Leu Asp Asp Glu Lys
1820                1825                1830

Ile Ser Glu Tyr Lys Asp Thr Asn Leu Thr Asn Asn Thr Phe Glu
1835                1840                1845

His Ile Ala Lys Arg Ile Asn Leu Ile Leu Asn Asp Thr Ile Glu
1850                1855                1860

Phe Phe Gln Lys His Thr Tyr Leu His Asn Gly Tyr Gly Asn Val
1865                1870                1875

Gln Val Cys Lys Lys Asn Lys Arg Lys Leu Glu Lys Lys Lys Leu
1880                1885                1890

Lys Lys Trp Ser Cys Ile Tyr Lys Ile Asn Lys Ile Val Arg Lys
1895                1900                1905

Gly Ala His Gly Val Val Phe Ser Ala Trp Arg Ser Glu Asn Val
1910                1915                1920

Asp Phe Phe Asn His Ser Phe Phe Glu Asn Leu Asn Leu Glu Asn
1925                1930                1935

Lys Lys Lys Gly Tyr Ile Asp Glu Thr Asn Val Asn Glu Asn Tyr
1940                1945                1950

Glu Ser Asp Asn Glu Tyr Asp Ser Asp Glu Asp Thr Glu Ser
1955                1960                1965

Asp Asn Asp Asp Glu Gln Asn Lys Glu Asn Glu Arg Gly Asp Glu
1970                1975                1980

Lys Asp Gly Tyr Glu Glu Met Asn Gly Gly Asp Lys Asn Glu Glu
1985                1990                1995

Met Asn Gly Gly Asp Lys Asn Glu Glu Met Asn Val Gly Asp Lys
2000                2005                2010

Asn Gly Gly Ile Asn Glu Glu His Lys Asn Glu Gly Ile Asn Glu
2015                2020                2025

Glu His Lys Asp Glu Leu Ile Asn Lys Glu His Lys Asn Glu Arg
2030                2035                2040

Ile Asn Glu Glu His Lys Asn Glu Arg Ile Asn Glu Glu His Lys
2045                2050                2055

Asn Glu Gly Ile Asn Glu Glu His Lys Asn Glu Gly Ile Asn Glu
2060                2065                2070

Glu His Lys Asn Glu Arg Ile Asn Glu Glu His Lys Asn Glu Gly
2075                2080                2085

Ile Asn Lys Leu Thr Tyr His Asn Met Asn Lys Asn Asn Ile Ser
2090                2095                2100

Asn Glu Asn Asn Tyr Asn Asp Asp Ser Tyr Asp Glu Asp Asn
2105                2110                2115

Leu Val Ser Leu Lys Ile Ile Asn Leu Lys Tyr Leu Ser Lys Lys
2120                2125                2130

Asn Ser Leu Lys Asn Ile Leu Arg Glu Val Asn Phe Leu Lys Met
2135                2140                2145

Cys Glu His Pro Asn Val Val Lys Tyr Phe Glu Ser Phe Phe Trp
2150                2155                2160
```

| | | | | | | | | | | | | |
|---|---|---|---|---|---|---|---|---|---|---|---|---|
| Pro | Pro<br>2165 | Cys | Tyr | Leu | Val<br>2170 | Ile | Val | Cys | Glu<br>2175 | Tyr | Leu | Ser | Gly | Gly |

Thr Leu Tyr Asp Leu Tyr Lys Asn Tyr Gly Arg Ile Ser Glu Asp
    2180                2185                2190

Leu Leu Val Tyr Ile Leu Asp Asp Val Leu Asn Gly Leu Asn Tyr
    2195                2200                2205

Leu His Asn Glu Cys Ser Ser Pro Leu Ile His Arg Asp Ile Lys
    2210                2215                2220

Pro Thr Asn Ile Val Leu Ser Lys Asp Gly Ile Ala Lys Ile Ile
    2225                2230                2235

Asp Phe Gly Ser Cys Glu Glu Leu Lys Asn Ser Asp Gln Ser Lys
    2240                2245                2250

Glu Leu Val Gly Thr Ile Tyr Tyr Ile Ser Pro Glu Ile Leu Met
    2255                2260                2265

Arg Thr Asn Tyr Asp Cys Ser Ser Asp Ile Trp Ser Leu Gly Ile
    2270                2275                2280

Thr Ile Tyr Glu Ile Val Leu Cys Thr Leu Pro Trp Lys Arg Asn
    2285                2290                2295

Gln Ser Phe Glu Asn Tyr Ile Lys Thr Ile Ile Asn Ser Ser Pro
    2300                2305                2310

Lys Ile Asn Ile Thr Glu Gly Tyr Ser Lys His Leu Cys Tyr Phe
    2315                2320                2325

Val Glu Lys Cys Leu Gln Lys Lys Pro Glu Asn Arg Gly Asn Val
    2330                2335                2340

Lys Asp Leu Leu Asn His Lys Phe Leu Ile Lys Lys Arg Tyr Ile
    2345                2350                2355

Lys Lys Lys Pro Ser Ser Ile Tyr Glu Ile Arg Asp Ile Leu Lys
    2360                2365                2370

Ile Tyr Asn Gly Lys Gly Lys Thr Asn Ile Phe Arg Asn Phe Phe
    2375                2380                2385

Lys Asn Leu Phe Phe Phe Asn Asp Lys Asn Lys Lys Lys Lys Pro
    2390                2395                2400

Asn Lys Met Ile Ser Ser Lys Ser Cys Asp Ala Glu Met Phe Phe
    2405                2410                2415

Glu Gln Leu Lys Arg Glu Asn Phe Asp Phe Phe Glu Ile Lys Leu
    2420                2425                2430

Lys Asp Asp Glu Asn Ser Arg Ser Leu Asn Thr Phe Asn Ile Asn
    2435                2440                2445

Ile Ser Lys Glu Arg Asp Asp Ile Ser Tyr Ser Ser Leu Asn Leu
    2450                2455                2460

Glu Lys Ile Lys Glu His Ser Leu Asn Met Val Ala Ser Val Val
    2465                2470                2475

Gly Thr Glu Gln Ser Gln Lys
    2480                2485

<210> SEQ ID NO 45
<211> LENGTH: 527
<212> TYPE: PRT
<213> ORGANISM: Dictyostelium discoideum
<220> FEATURE:
<223> OTHER INFORMATION: SHK1 protein, kinase with gatekeeper Cys

<400> SEQUENCE: 45

Met Ala Thr Gln Gln Gln Gln Gln Gln Gln Gln Gln Gln Gln Gln Gln
1               5                   10                  15

```
Ile Lys Ala Arg Lys Asp Ile Gln Ile Gln Ala Gln Ser Ala Ser
            20                  25                  30

Asp Ile Leu Gly Pro Pro Glu Ile Ser Glu Thr Glu Ile Thr Thr Glu
        35                  40                  45

Ser Ile Leu Gly Asp Gly Ser Phe Gly Thr Val Tyr Lys Gly Arg Cys
    50                  55                  60

Lys Leu Lys Asp Val Pro Val Lys Val Met Leu Lys Gln Val Asp Gln
65                  70                  75                  80

Lys Thr Leu Thr Asp Phe Arg Lys Glu Val Ala Ile Met Ser Lys Ile
                85                  90                  95

Phe His Pro Asn Ile Val Leu Phe Leu Gly Ala Cys Thr Ser Thr Pro
            100                 105                 110

Gly Lys Leu Met Ile Cys Thr Glu Leu Met Lys Gly Asn Leu Glu Ser
        115                 120                 125

Leu Leu Leu Asp Pro Met Val Lys Leu Pro Leu Ile Thr Arg Met Arg
    130                 135                 140

Met Ala Lys Asp Ala Ala Leu Gly Val Leu Trp Leu His Ser Ser Asn
145                 150                 155                 160

Pro Val Phe Ile His Arg Asp Leu Lys Thr Ser Asn Leu Leu Val Asp
                165                 170                 175

Ala Asn Leu Thr Val Lys Val Cys Asp Phe Gly Leu Ser Gln Ile Lys
            180                 185                 190

Gln Arg Gly Glu Asn Leu Lys Asp Gly Gln Asp Gly Ala Lys Gly Thr
        195                 200                 205

Pro Leu Trp Met Ala Pro Glu Val Leu Gln Gly Arg Leu Phe Asn Glu
    210                 215                 220

Lys Ala Asp Val Tyr Ser Phe Gly Leu Val Leu Trp Gln Ile Phe Thr
225                 230                 235                 240

Arg Gln Glu Leu Phe Pro Glu Phe Asp Asn Phe Lys Phe Val Ala
                245                 250                 255

Ala Ile Cys Glu Lys Gln Leu Arg Pro Ser Ile Pro Asp Asp Cys Pro
            260                 265                 270

Lys Ser Leu Lys Glu Leu Ile Gln Lys Cys Trp Asp Pro Asn Pro Glu
        275                 280                 285

Val Arg Pro Ser Phe Glu Gly Ile Val Ser Glu Leu Glu Glu Ile Ile
    290                 295                 300

Ile Asp Cys Cys Ile Pro Asp Glu Tyr Gly Ala Ile Leu Trp Lys Asn
305                 310                 315                 320

His Phe Lys His Glu Asn Glu Ala Asn Trp Lys Asp Phe Ile Asn Val
                325                 330                 335

Phe Ser Asn Phe Val Gly Leu Thr Asn Ala Asn Thr Pro Ser Met Ser
            340                 345                 350

Asp Leu Leu Gln Phe Ser Pro Asn Leu Asn Gly Ser Thr Ile Glu Leu
        355                 360                 365

Asn Phe Lys Cys Leu Lys Ser Ile Ile Val Ser Pro Lys Gly Pro
    370                 375                 380

His Glu Glu Glu Val Val Leu Met Glu Gln Phe Gly Lys Val Leu Ala
385                 390                 395                 400

Trp Phe Gly Asn Leu Lys Glu Asp Gly Ser Gln Ile Leu Asp Lys Ile
                405                 410                 415

Arg Gln Leu Met Glu Cys Ala Trp Phe His Gly Asp Ile Ser Thr Ser
            420                 425                 430

Glu Ser Glu Asn Arg Leu Arg Gln Lys Pro Glu Gly Thr Phe Leu Val
```

```
                435                 440                 445
Arg Phe Ser Thr Ser Glu Tyr Gly Ala Tyr Thr Ile Ser Lys Val Ser
        450                 455                 460

Lys Asn Gly Gly Ile Ser His Gln Arg Ile His Arg Pro Gln Gly Lys
465                 470                 475                 480

Phe Gln Val Asn Asn Ser Lys Tyr Leu Ser Val Lys Glu Leu Ile Thr
                485                 490                 495

Gly Glu Ala Gln Ala Leu Gly Ile Asn Thr Pro Cys Leu Gly Ser Arg
                500                 505                 510

Phe Leu Phe Leu Ile Tyr Lys Ala Gln Leu Ser Gly Tyr Ile Asn
            515                 520                 525

<210> SEQ ID NO 46
<211> LENGTH: 523
<212> TYPE: PRT
<213> ORGANISM: Rous sarcoma virus
<220> FEATURE:
<223> OTHER INFORMATION: v-Src

<400> SEQUENCE: 46

Met Gly Ser Ser Lys Ser Lys Pro Lys Asp Pro Ser Gln Arg Arg Arg
1               5                   10                  15

Ser Leu Glu Pro Pro Asp Ser Thr His His Gly Gly Phe Pro Ala Ser
            20                  25                  30

Gln Thr Pro Asn Lys Thr Ala Ala Pro Asp Thr His Arg Thr Pro Ser
        35                  40                  45

Arg Ser Phe Gly Thr Val Ala Thr Glu Pro Lys Leu Phe Gly Asp Phe
    50                  55                  60

Asn Thr Ser Asp Thr Val Thr Ser Pro Gln Arg Ala Gly Ala Leu Ala
65                  70                  75                  80

Gly Gly Val Thr Thr Phe Val Ala Leu Tyr Asp Tyr Glu Ser Trp Ile
                85                  90                  95

Glu Thr Asp Leu Ser Phe Lys Lys Gly Glu Arg Leu Gln Ile Val Asn
            100                 105                 110

Asn Thr Glu Gly Asn Trp Trp Leu Ala His Ser Val Thr Thr Gly Gln
        115                 120                 125

Thr Gly Tyr Ile Pro Ser Asn Tyr Val Ala Pro Ser Asp Ser Ile Gln
    130                 135                 140

Ala Glu Glu Trp Tyr Phe Gly Lys Ile Thr Arg Arg Glu Ser Glu Arg
145                 150                 155                 160

Leu Leu Leu Asn Pro Glu Asn Pro Arg Gly Thr Phe Leu Val Arg Glu
                165                 170                 175

Ser Glu Thr Thr Lys Gly Ala Tyr Cys Leu Ser Val Ser Asp Phe Asp
            180                 185                 190

Asn Ala Lys Gly Leu Asn Val Lys His Tyr Lys Ile Arg Lys Leu Asp
        195                 200                 205

Ser Gly Gly Phe Tyr Ile Thr Ser Arg Thr Gln Phe Ser Ser Leu Gln
    210                 215                 220

Gln Leu Val Ala Tyr Tyr Ser Lys His Ala Asp Gly Leu Cys His Arg
225                 230                 235                 240

Leu Thr Asn Val Cys Pro Thr Ser Lys Pro Gln Thr Gln Gly Leu Ala
                245                 250                 255

Lys Asp Ala Trp Glu Ile Pro Arg Glu Ser Leu Arg Leu Glu Val Lys
            260                 265                 270

Leu Gly Gln Gly Cys Phe Gly Glu Val Trp Met Gly Thr Trp Asn Gly
```

-continued

```
                275                 280                 285
Thr Thr Arg Val Ala Ile Lys Thr Leu Lys Pro Gly Thr Met Ser Pro
    290                 295                 300
Glu Ala Phe Leu Gln Glu Ala Gln Val Met Lys Lys Leu Arg His Glu
305                 310                 315                 320
Lys Leu Val Gln Leu Tyr Ala Val Val Ser Glu Glu Pro Ile Tyr Ile
                325                 330                 335
Val Ile Glu Tyr Met Ser Lys Gly Ser Leu Leu Asp Phe Leu Lys Gly
            340                 345                 350
Lys Tyr Leu Arg Leu Pro Gln Leu Val Asp Met Ala Ala Gln Ile Ala
        355                 360                 365
Ser Gly Met Ala Tyr Val Glu Arg Met Asn Tyr Val His Arg Asp Leu
    370                 375                 380
Arg Ala Ala Asn Ile Leu Val Gly Glu Asn Leu Val Cys Lys Val Ala
385                 390                 395                 400
Asp Phe Gly Leu Ala Arg Leu Ile Glu Asp Asn Glu Tyr Thr Ala Arg
                405                 410                 415
Gln Gly Ala Lys Phe Pro Ile Lys Trp Thr Ala Pro Glu Ala Ala Leu
            420                 425                 430
Tyr Gly Arg Phe Thr Ile Lys Ser Asp Val Trp Ser Phe Gly Ile Leu
        435                 440                 445
Leu Thr Glu Leu Thr Thr Lys Gly Arg Met Pro Tyr Pro Gly Met Gly
    450                 455                 460
Asn Gly Glu Val Leu Asp Arg Val Glu Arg Gly Tyr Arg Met Pro Cys
465                 470                 475                 480
Pro Pro Glu Cys Pro Glu Ser Leu His Asp Leu Met Cys Gln Cys Trp
                485                 490                 495
Arg Arg Asp Pro Glu Glu Arg Pro Thr Phe Glu Tyr Leu Gln Ala Gln
            500                 505                 510
Leu Leu Pro Ala Cys Val Leu Glu Val Ala Glu
        515                 520

<210> SEQ ID NO 47
<211> LENGTH: 523
<212> TYPE: PRT
<213> ORGANISM: Artificial Sequence
<220> FEATURE:
<223> OTHER INFORMATION: synthetic [I338X]v-Src
<220> FEATURE:
<221> NAME/KEY: VARIANT
<222> LOCATION: (338)..(338)
<223> OTHER INFORMATION: Xaa = any naturally occurring amino acid

<400> SEQUENCE: 47

Met Gly Ser Ser Lys Ser Lys Pro Lys Asp Pro Ser Gln Arg Arg Arg
1               5                   10                  15
Ser Leu Glu Pro Pro Asp Ser Thr His His Gly Gly Phe Pro Ala Ser
            20                  25                  30
Gln Thr Pro Asn Lys Thr Ala Ala Pro Asp Thr His Arg Thr Pro Ser
        35                  40                  45
Arg Ser Phe Gly Thr Val Ala Thr Glu Pro Lys Leu Phe Gly Asp Phe
    50                  55                  60
Asn Thr Ser Asp Thr Val Thr Ser Pro Gln Arg Ala Gly Ala Leu Ala
65                  70                  75                  80
Gly Gly Val Thr Thr Phe Val Ala Leu Tyr Asp Tyr Glu Ser Trp Ile
                85                  90                  95
```

```
Glu Thr Asp Leu Ser Phe Lys Lys Gly Glu Arg Leu Gln Ile Val Asn
            100                 105                 110

Asn Thr Glu Gly Asn Trp Trp Leu Ala His Ser Val Thr Gly Gln
        115                 120                 125

Thr Gly Tyr Ile Pro Ser Asn Tyr Val Ala Pro Ser Asp Ser Ile Gln
            130                 135                 140

Ala Glu Glu Trp Tyr Phe Gly Lys Ile Thr Arg Arg Glu Ser Glu Arg
145                 150                 155                 160

Leu Leu Leu Asn Pro Glu Asn Pro Arg Gly Thr Phe Leu Val Arg Glu
                165                 170                 175

Ser Glu Thr Thr Lys Gly Ala Tyr Cys Leu Ser Val Ser Asp Phe Asp
            180                 185                 190

Asn Ala Lys Gly Leu Asn Val Lys His Tyr Lys Ile Arg Lys Leu Asp
            195                 200                 205

Ser Gly Gly Phe Tyr Ile Thr Ser Arg Thr Gln Phe Ser Ser Leu Gln
            210                 215                 220

Gln Leu Val Ala Tyr Tyr Ser Lys His Ala Asp Gly Leu Cys His Arg
225                 230                 235                 240

Leu Thr Asn Val Cys Pro Thr Ser Lys Pro Gln Thr Gln Gly Leu Ala
                245                 250                 255

Lys Asp Ala Trp Glu Ile Pro Arg Glu Ser Leu Arg Leu Glu Val Lys
            260                 265                 270

Leu Gly Gln Gly Cys Phe Gly Glu Val Trp Met Gly Thr Trp Asn Gly
            275                 280                 285

Thr Thr Arg Val Ala Ile Lys Thr Leu Lys Pro Gly Thr Met Ser Pro
            290                 295                 300

Glu Ala Phe Leu Gln Glu Ala Gln Val Met Lys Lys Leu Arg His Glu
305                 310                 315                 320

Lys Leu Val Gln Leu Tyr Ala Val Val Ser Glu Pro Ile Tyr Ile
            325                 330                 335

Val Xaa Glu Tyr Met Ser Lys Gly Ser Leu Leu Asp Phe Leu Lys Gly
            340                 345                 350

Lys Tyr Leu Arg Leu Pro Gln Leu Val Asp Met Ala Ala Gln Ile Ala
            355                 360                 365

Ser Gly Met Ala Tyr Val Glu Arg Met Asn Tyr Val His Arg Asp Leu
            370                 375                 380

Arg Ala Ala Asn Ile Leu Val Gly Glu Asn Leu Val Cys Lys Val Ala
385                 390                 395                 400

Asp Phe Gly Leu Ala Arg Leu Ile Glu Asp Asn Glu Tyr Thr Ala Arg
                405                 410                 415

Gln Gly Ala Lys Phe Pro Ile Lys Trp Thr Ala Pro Glu Ala Ala Leu
            420                 425                 430

Tyr Gly Arg Phe Thr Ile Lys Ser Asp Val Trp Ser Phe Gly Ile Leu
            435                 440                 445

Leu Thr Glu Leu Thr Thr Lys Gly Arg Met Pro Tyr Pro Gly Met Gly
            450                 455                 460

Asn Gly Glu Val Leu Asp Arg Val Glu Arg Gly Tyr Arg Met Pro Cys
465                 470                 475                 480

Pro Pro Glu Cys Pro Glu Ser Leu His Asp Leu Met Cys Gln Cys Trp
                485                 490                 495

Arg Arg Asp Pro Glu Glu Arg Pro Thr Phe Glu Tyr Leu Gln Ala Gln
                500                 505                 510

Leu Leu Pro Ala Cys Val Leu Glu Val Ala Glu
```

<210> SEQ ID NO 48
<211> LENGTH: 523
<212> TYPE: PRT
<213> ORGANISM: Artificial sequence
<220> FEATURE:
<223> OTHER INFORMATION: synthetic [I338C]v-Src

<400> SEQUENCE: 48

| | | | | | | | | | | | | | | | |
|---|---|---|---|---|---|---|---|---|---|---|---|---|---|---|---|
| Met | Gly | Ser | Ser | Lys | Ser | Lys | Pro | Lys | Asp | Pro | Ser | Gln | Arg | Arg | Arg |
| 1 | | | | 5 | | | | | 10 | | | | | 15 | |
| Ser | Leu | Glu | Pro | Pro | Asp | Ser | Thr | His | His | Gly | Gly | Phe | Pro | Ala | Ser |
| | | | 20 | | | | | 25 | | | | | 30 | | |
| Gln | Thr | Pro | Asn | Lys | Thr | Ala | Ala | Pro | Asp | Thr | His | Arg | Thr | Pro | Ser |
| | | 35 | | | | | 40 | | | | | 45 | | | |
| Arg | Ser | Phe | Gly | Thr | Val | Ala | Thr | Glu | Pro | Lys | Leu | Phe | Gly | Asp | Phe |
| | 50 | | | | | 55 | | | | | 60 | | | | |
| Asn | Thr | Ser | Asp | Thr | Val | Thr | Ser | Pro | Gln | Arg | Ala | Gly | Ala | Leu | Ala |
| 65 | | | | | 70 | | | | | 75 | | | | | 80 |
| Gly | Gly | Val | Thr | Thr | Phe | Val | Ala | Leu | Tyr | Asp | Tyr | Glu | Ser | Trp | Ile |
| | | | | 85 | | | | | 90 | | | | | 95 | |
| Glu | Thr | Asp | Leu | Ser | Phe | Lys | Lys | Gly | Glu | Arg | Leu | Gln | Ile | Val | Asn |
| | | | 100 | | | | | 105 | | | | | 110 | | |
| Asn | Thr | Glu | Gly | Asn | Trp | Trp | Leu | Ala | His | Ser | Val | Thr | Thr | Gly | Gln |
| | | 115 | | | | | 120 | | | | | 125 | | | |
| Thr | Gly | Tyr | Ile | Pro | Ser | Asn | Tyr | Val | Ala | Pro | Ser | Asp | Ser | Ile | Gln |
| | 130 | | | | | 135 | | | | | 140 | | | | |
| Ala | Glu | Glu | Trp | Tyr | Phe | Gly | Lys | Ile | Thr | Arg | Arg | Glu | Ser | Glu | Arg |
| 145 | | | | | 150 | | | | | 155 | | | | | 160 |
| Leu | Leu | Leu | Asn | Pro | Glu | Asn | Pro | Arg | Gly | Thr | Phe | Leu | Val | Arg | Glu |
| | | | | 165 | | | | | 170 | | | | | 175 | |
| Ser | Glu | Thr | Thr | Lys | Gly | Ala | Tyr | Cys | Leu | Ser | Val | Ser | Asp | Phe | Asp |
| | | | 180 | | | | | 185 | | | | | 190 | | |
| Asn | Ala | Lys | Gly | Leu | Asn | Val | Lys | His | Tyr | Lys | Ile | Arg | Lys | Leu | Asp |
| | | 195 | | | | | 200 | | | | | 205 | | | |
| Ser | Gly | Gly | Phe | Tyr | Ile | Thr | Ser | Arg | Thr | Gln | Phe | Ser | Ser | Leu | Gln |
| | 210 | | | | | 215 | | | | | 220 | | | | |
| Gln | Leu | Val | Ala | Tyr | Tyr | Ser | Lys | His | Ala | Asp | Gly | Leu | Cys | His | Arg |
| 225 | | | | | 230 | | | | | 235 | | | | | 240 |
| Leu | Thr | Asn | Val | Cys | Pro | Thr | Ser | Lys | Pro | Gln | Thr | Gln | Gly | Leu | Ala |
| | | | | 245 | | | | | 250 | | | | | 255 | |
| Lys | Asp | Ala | Trp | Glu | Ile | Pro | Arg | Glu | Ser | Leu | Arg | Leu | Glu | Val | Lys |
| | | | 260 | | | | | 265 | | | | | 270 | | |
| Leu | Gly | Gln | Gly | Cys | Phe | Gly | Glu | Val | Trp | Met | Gly | Thr | Trp | Asn | Gly |
| | | 275 | | | | | 280 | | | | | 285 | | | |
| Thr | Thr | Arg | Val | Ala | Ile | Lys | Thr | Leu | Lys | Pro | Gly | Thr | Met | Ser | Pro |
| | 290 | | | | | 295 | | | | | 300 | | | | |
| Glu | Ala | Phe | Leu | Gln | Glu | Ala | Gln | Val | Met | Lys | Lys | Leu | Arg | His | Glu |
| 305 | | | | | 310 | | | | | 315 | | | | | 320 |
| Lys | Leu | Val | Gln | Leu | Tyr | Ala | Val | Val | Ser | Glu | Glu | Pro | Ile | Tyr | Ile |
| | | | | 325 | | | | | 330 | | | | | 335 | |
| Val | Cys | Glu | Tyr | Met | Ser | Lys | Gly | Ser | Leu | Leu | Asp | Phe | Leu | Lys | Gly |
| | | | 340 | | | | | 345 | | | | | 350 | | |
| Lys | Tyr | Leu | Arg | Leu | Pro | Gln | Leu | Val | Asp | Met | Ala | Ala | Gln | Ile | Ala |

```
                355                 360                 365
Ser Gly Met Ala Tyr Val Glu Arg Met Asn Tyr Val His Arg Asp Leu
    370                 375                 380

Arg Ala Ala Asn Ile Leu Val Gly Glu Asn Leu Val Cys Lys Val Ala
385                 390                 395                 400

Asp Phe Gly Leu Ala Arg Leu Ile Glu Asp Asn Glu Tyr Thr Ala Arg
                405                 410                 415

Gln Gly Ala Lys Phe Pro Ile Lys Trp Thr Ala Pro Glu Ala Ala Leu
            420                 425                 430

Tyr Gly Arg Phe Thr Ile Lys Ser Asp Val Trp Ser Phe Gly Ile Leu
        435                 440                 445

Leu Thr Glu Leu Thr Thr Lys Gly Arg Met Pro Tyr Pro Gly Met Gly
    450                 455                 460

Asn Gly Glu Val Leu Asp Arg Val Glu Arg Gly Tyr Arg Met Pro Cys
465                 470                 475                 480

Pro Pro Glu Cys Pro Glu Ser Leu His Asp Leu Met Cys Gln Cys Trp
                485                 490                 495

Arg Arg Asp Pro Glu Glu Arg Pro Thr Phe Glu Tyr Leu Gln Ala Gln
            500                 505                 510

Leu Leu Pro Ala Cys Val Leu Glu Val Ala Glu
        515                 520

<210> SEQ ID NO 49
<211> LENGTH: 523
<212> TYPE: PRT
<213> ORGANISM: Artificial sequence
<220> FEATURE:
<223> OTHER INFORMATION: synthetic [I338T]v-Src

<400> SEQUENCE: 49

Met Gly Ser Ser Lys Ser Lys Pro Lys Asp Pro Ser Gln Arg Arg Arg
1               5                   10                  15

Ser Leu Glu Pro Pro Asp Ser Thr His His Gly Gly Phe Pro Ala Ser
            20                  25                  30

Gln Thr Pro Asn Lys Thr Ala Ala Pro Asp Thr His Arg Thr Pro Ser
        35                  40                  45

Arg Ser Phe Gly Thr Val Ala Thr Glu Pro Lys Leu Phe Gly Asp Phe
    50                  55                  60

Asn Thr Ser Asp Thr Val Thr Ser Pro Gln Arg Ala Gly Ala Leu Ala
65                  70                  75                  80

Gly Gly Val Thr Thr Phe Val Ala Leu Tyr Asp Tyr Glu Ser Trp Ile
                85                  90                  95

Glu Thr Asp Leu Ser Phe Lys Lys Gly Glu Arg Leu Gln Ile Val Asn
            100                 105                 110

Asn Thr Glu Gly Asn Trp Trp Leu Ala His Ser Val Thr Thr Gly Gln
        115                 120                 125

Thr Gly Tyr Ile Pro Ser Asn Tyr Val Ala Pro Ser Asp Ser Ile Gln
    130                 135                 140

Ala Glu Glu Trp Tyr Phe Gly Lys Ile Thr Arg Arg Glu Ser Glu Arg
145                 150                 155                 160

Leu Leu Leu Asn Pro Glu Asn Pro Arg Gly Thr Phe Leu Val Arg Glu
                165                 170                 175

Ser Glu Thr Thr Lys Gly Ala Tyr Cys Leu Ser Val Ser Asp Phe Asp
            180                 185                 190

Asn Ala Lys Gly Leu Asn Val Lys His Tyr Lys Ile Arg Lys Leu Asp
```

```
            195                 200                 205
Ser Gly Gly Phe Tyr Ile Thr Ser Arg Thr Gln Phe Ser Ser Leu Gln
    210                 215                 220

Gln Leu Val Ala Tyr Tyr Ser Lys His Ala Asp Gly Leu Cys His Arg
225                 230                 235                 240

Leu Thr Asn Val Cys Pro Thr Ser Lys Pro Gln Thr Gln Gly Leu Ala
                245                 250                 255

Lys Asp Ala Trp Glu Ile Pro Arg Glu Ser Leu Arg Leu Glu Val Lys
            260                 265                 270

Leu Gly Gln Gly Cys Phe Gly Glu Val Trp Met Gly Thr Trp Asn Gly
        275                 280                 285

Thr Thr Arg Val Ala Ile Lys Thr Leu Lys Pro Gly Thr Met Ser Pro
290                 295                 300

Glu Ala Phe Leu Gln Glu Ala Gln Val Met Lys Lys Leu Arg His Glu
305                 310                 315                 320

Lys Leu Val Gln Leu Tyr Ala Val Val Ser Glu Glu Pro Ile Tyr Ile
                325                 330                 335

Val Thr Glu Tyr Met Ser Lys Gly Ser Leu Leu Asp Phe Leu Lys Gly
            340                 345                 350

Lys Tyr Leu Arg Leu Pro Gln Leu Val Asp Met Ala Ala Gln Ile Ala
        355                 360                 365

Ser Gly Met Ala Tyr Val Glu Arg Met Asn Tyr Val His Arg Asp Leu
    370                 375                 380

Arg Ala Ala Asn Ile Leu Val Gly Glu Asn Leu Val Cys Lys Val Ala
385                 390                 395                 400

Asp Phe Gly Leu Ala Arg Leu Ile Glu Asp Asn Glu Tyr Thr Ala Arg
                405                 410                 415

Gln Gly Ala Lys Phe Pro Ile Lys Trp Thr Ala Pro Glu Ala Ala Leu
            420                 425                 430

Tyr Gly Arg Phe Thr Ile Lys Ser Asp Val Trp Ser Phe Gly Ile Leu
        435                 440                 445

Leu Thr Glu Leu Thr Thr Lys Gly Arg Met Pro Tyr Pro Gly Met Gly
    450                 455                 460

Asn Gly Glu Val Leu Asp Arg Val Glu Arg Gly Tyr Arg Met Pro Cys
465                 470                 475                 480

Pro Pro Glu Cys Pro Glu Ser Leu His Asp Leu Met Cys Gln Cys Trp
                485                 490                 495

Arg Arg Asp Pro Glu Glu Arg Pro Thr Phe Glu Tyr Leu Gln Ala Gln
            500                 505                 510

Leu Leu Pro Ala Cys Val Leu Glu Val Ala Glu
        515                 520

<210> SEQ ID NO 50
<211> LENGTH: 523
<212> TYPE: PRT
<213> ORGANISM: Artificial sequence
<220> FEATURE:
<223> OTHER INFORMATION: synthetic [I338G]v-Src

<400> SEQUENCE: 50

Met Gly Ser Ser Lys Ser Lys Pro Lys Asp Pro Ser Gln Arg Arg Arg
1               5                   10                  15

Ser Leu Glu Pro Pro Asp Ser Thr His His Gly Gly Phe Pro Ala Ser
            20                  25                  30

Gln Thr Pro Asn Lys Thr Ala Ala Pro Asp Thr His Arg Thr Pro Ser
```

```
            35                  40                  45
Arg Ser Phe Gly Thr Val Ala Thr Glu Pro Lys Leu Phe Gly Asp Phe
 50                  55                  60

Asn Thr Ser Asp Thr Val Thr Ser Pro Gln Arg Ala Gly Ala Leu Ala
 65                  70                  75                  80

Gly Gly Val Thr Thr Phe Val Ala Leu Tyr Asp Tyr Glu Ser Trp Ile
                 85                  90                  95

Glu Thr Asp Leu Ser Phe Lys Lys Gly Glu Arg Leu Gln Ile Val Asn
            100                 105                 110

Asn Thr Glu Gly Asn Trp Trp Leu Ala His Ser Val Thr Thr Gly Gln
        115                 120                 125

Thr Gly Tyr Ile Pro Ser Asn Tyr Val Ala Pro Ser Asp Ser Ile Gln
    130                 135                 140

Ala Glu Glu Trp Tyr Phe Gly Lys Ile Thr Arg Arg Glu Ser Glu Arg
145                 150                 155                 160

Leu Leu Leu Asn Pro Glu Asn Pro Arg Gly Thr Phe Leu Val Arg Glu
                165                 170                 175

Ser Glu Thr Thr Lys Gly Ala Tyr Cys Leu Ser Val Ser Asp Phe Asp
            180                 185                 190

Asn Ala Lys Gly Leu Asn Val Lys His Tyr Lys Ile Arg Lys Leu Asp
        195                 200                 205

Ser Gly Gly Phe Tyr Ile Thr Ser Arg Thr Gln Phe Ser Ser Leu Gln
    210                 215                 220

Gln Leu Val Ala Tyr Tyr Ser Lys His Ala Asp Gly Leu Cys His Arg
225                 230                 235                 240

Leu Thr Asn Val Cys Pro Thr Ser Lys Pro Gln Thr Gln Gly Leu Ala
                245                 250                 255

Lys Asp Ala Trp Glu Ile Pro Arg Glu Ser Leu Arg Leu Glu Val Lys
            260                 265                 270

Leu Gly Gln Gly Cys Phe Gly Glu Val Trp Met Gly Thr Trp Asn Gly
        275                 280                 285

Thr Thr Arg Val Ala Ile Lys Thr Leu Lys Pro Gly Thr Met Ser Pro
    290                 295                 300

Glu Ala Phe Leu Gln Glu Ala Gln Val Met Lys Lys Leu Arg His Glu
305                 310                 315                 320

Lys Leu Val Gln Leu Tyr Ala Val Val Ser Glu Glu Pro Ile Tyr Ile
                325                 330                 335

Val Gly Glu Tyr Met Ser Lys Gly Ser Leu Leu Asp Phe Leu Lys Gly
            340                 345                 350

Lys Tyr Leu Arg Leu Pro Gln Leu Val Asp Met Ala Ala Gln Ile Ala
        355                 360                 365

Ser Gly Met Ala Tyr Val Glu Arg Met Asn Tyr Val His Arg Asp Leu
    370                 375                 380

Arg Ala Ala Asn Ile Leu Val Gly Glu Asn Leu Val Cys Lys Val Ala
385                 390                 395                 400

Asp Phe Gly Leu Ala Arg Leu Ile Glu Asp Asn Glu Tyr Thr Ala Arg
                405                 410                 415

Gln Gly Ala Lys Phe Pro Ile Lys Trp Thr Ala Pro Glu Ala Ala Leu
            420                 425                 430

Tyr Gly Arg Phe Thr Ile Lys Ser Asp Val Trp Ser Phe Gly Ile Leu
        435                 440                 445

Leu Thr Glu Leu Thr Thr Lys Gly Arg Met Pro Tyr Pro Gly Met Gly
    450                 455                 460
```

```
Asn Gly Glu Val Leu Asp Arg Val Glu Arg Gly Tyr Arg Met Pro Cys
465                 470                 475                 480

Pro Pro Glu Cys Pro Glu Ser Leu His Asp Leu Met Cys Gln Cys Trp
                485                 490                 495

Arg Arg Asp Pro Glu Glu Arg Pro Thr Phe Glu Tyr Leu Gln Ala Gln
            500                 505                 510

Leu Leu Pro Ala Cys Val Leu Glu Val Ala Glu
        515                 520
```

<210> SEQ ID NO 51
<211> LENGTH: 8
<212> TYPE: PRT
<213> ORGANISM: Artificial sequence
<220> FEATURE:
<223> OTHER INFORMATION: synthetic kinase peptide substrate

<400> SEQUENCE: 51

```
Ile Tyr Gly Glu Phe Lys Lys Lys
1               5
```

<210> SEQ ID NO 52
<211> LENGTH: 38
<212> TYPE: PRT
<213> ORGANISM: Artificial sequence
<220> FEATURE:
<223> OTHER INFORMATION: synthetic ATP binding site region of src kinase
      domain

<400> SEQUENCE: 52

```
Pro Glu Ala Phe Leu Gln Glu Ala Gln Val Met Lys Lys Leu Arg His
1               5                   10                  15

Glu Lys Leu Val Gln Leu Tyr Ala Val Val Ser Glu Glu Pro Ile Tyr
            20                  25                  30

Ile Val Thr Glu Tyr Met
        35
```

<210> SEQ ID NO 53
<211> LENGTH: 40
<212> TYPE: PRT
<213> ORGANISM: Artificial sequence
<220> FEATURE:
<223> OTHER INFORMATION: synthetic ATP binding site region of rsk2
      kinase domain

<400> SEQUENCE: 53

```
Lys Arg Asp Pro Thr Glu Glu Ile Glu Ile Leu Leu Arg Tyr Gly Gln
1               5                   10                  15

His Pro Asn Ile Ile Thr Leu Lys Asp Val Tyr Asp Asp Gly Lys Tyr
            20                  25                  30

Val Tyr Val Val Thr Glu Leu Met
        35                  40
```

<210> SEQ ID NO 54
<211> LENGTH: 44
<212> TYPE: PRT
<213> ORGANISM: Artificial sequence
<220> FEATURE:
<223> OTHER INFORMATION: synthetic ATP binding site region of nek2
      kinase domain

<400> SEQUENCE: 54

```
Glu Val Glu Lys Gln Met Leu Val Ser Glu Val Asn Leu Leu Arg Glu
1               5                   10                  15
```

```
Leu Lys His Pro Asn Ile Val Arg Tyr Tyr Asp Arg Ile Ile Asp Arg
            20                  25                  30

Thr Asn Thr Thr Leu Tyr Ile Val Met Glu Tyr Cys
            35                  40

<210> SEQ ID NO 55
<211> LENGTH: 43
<212> TYPE: PRT
<213> ORGANISM: Artificial sequence
<220> FEATURE:
<223> OTHER INFORMATION: synthetic ATP binding site region of mekk1
      kinase domain

<400> SEQUENCE: 55

Gln Glu Glu Val Val Glu Ala Leu Arg Glu Ile Arg Met Met Ser
1               5                   10                  15

His Leu Asn His Pro Asn Ile Ile Arg Met Leu Gly Ala Thr Cys Glu
            20                  25                  30

Lys Ser Asn Tyr Asn Leu Phe Ile Glu Trp Met
            35                  40

<210> SEQ ID NO 56
<211> LENGTH: 41
<212> TYPE: PRT
<213> ORGANISM: Artificial sequence
<220> FEATURE:
<223> OTHER INFORMATION: synthetic ATP binding site region of msk1
      kinase domain

<400> SEQUENCE: 56

Met Glu Ala Asn Thr Gln Lys Glu Ile Thr Ala Leu Lys Leu Cys Glu
1               5                   10                  15

Gly His Pro Asn Ile Val Lys Leu His Glu Val Phe His Asp Gln Leu
            20                  25                  30

His Thr Phe Leu Val Met Glu Leu Leu
            35                  40

<210> SEQ ID NO 57
<211> LENGTH: 42
<212> TYPE: PRT
<213> ORGANISM: Artificial sequence
<220> FEATURE:
<223> OTHER INFORMATION: synthetic ATP binding site region of plk1
      kinase domain

<400> SEQUENCE: 57

Pro His Gln Arg Glu Lys Met Ser Met Glu Ile Ser Ile His Arg Ser
1               5                   10                  15

Leu Ala His Gln His Val Val Gly Phe His Gly Phe Phe Glu Asp Asn
            20                  25                  30

Asp Phe Val Phe Val Val Leu Glu Leu Cys
            35                  40

<210> SEQ ID NO 58
<211> LENGTH: 40
<212> TYPE: PRT
<213> ORGANISM: Artificial sequence
<220> FEATURE:
<223> OTHER INFORMATION: synthetic region of v-Src kinase domain

<400> SEQUENCE: 58

Arg His Glu Lys Leu Val Gln Leu Tyr Ala Met Val Ser Glu Glu Pro
1               5                   10                  15
```

```
Ile Tyr Ile Val Ile Glu Tyr Met Ser Lys Gly Ser Leu Leu Asp Phe
            20                  25                  30

Leu Lys Gly Glu Met Gly Lys Tyr
        35                  40

<210> SEQ ID NO 59
<211> LENGTH: 40
<212> TYPE: PRT
<213> ORGANISM: Artificial sequence
<220> FEATURE:
<223> OTHER INFORMATION: synthetic region of c-Src kinase domain

<400> SEQUENCE: 59

Arg His Glu Lys Leu Val Gln Leu Tyr Ala Val Val Ser Glu Glu Pro
1               5                   10                  15

Ile Tyr Ile Val Thr Glu Tyr Met Ser Lys Gly Ser Leu Leu Asp Phe
            20                  25                  30

Leu Lys Gly Glu Thr Gly Lys Tyr
        35                  40

<210> SEQ ID NO 60
<211> LENGTH: 40
<212> TYPE: PRT
<213> ORGANISM: Artificial sequence
<220> FEATURE:
<223> OTHER INFORMATION: synthetic region of Lck kinase domain

<400> SEQUENCE: 60

Gln His Gln Arg Leu Val Arg Leu Tyr Ala Val Val Thr Gln Glu Pro
1               5                   10                  15

Ile Tyr Ile Ile Thr Glu Tyr Met Glu Asn Gly Ser Leu Val Asp Phe
            20                  25                  30

Leu Lys Thr Pro Ser Gly Ile Lys
        35                  40

<210> SEQ ID NO 61
<211> LENGTH: 40
<212> TYPE: PRT
<213> ORGANISM: Artificial sequence
<220> FEATURE:
<223> OTHER INFORMATION: synthetic region of Fyn kinase domain

<400> SEQUENCE: 61

Lys His Asp Lys Leu Val Gln Leu Tyr Ala Val Val Ser Glu Glu Pro
1               5                   10                  15

Ile Tyr Ile Val Thr Glu Tyr Met Asn Lys Gly Ser Leu Leu Asp Phe
            20                  25                  30

Leu Lys Asp Gly Glu Gly Arg Ala
        35                  40

<210> SEQ ID NO 62
<211> LENGTH: 40
<212> TYPE: PRT
<213> ORGANISM: Artificial sequence
<220> FEATURE:
<223> OTHER INFORMATION: synthetic region of c-Yes kinase domain

<400> SEQUENCE: 62

Arg His Asp Lys Leu Val Pro Leu Tyr Ala Val Val Ser Glu Glu Pro
1               5                   10                  15

Ile Tyr Ile Val Thr Glu Phe Met Ser Lys Gly Ser Leu Leu Asp Phe
            20                  25                  30
```

```
Leu Lys Glu Gly Asp Gly Lys Tyr
        35              40

<210> SEQ ID NO 63
<211> LENGTH: 40
<212> TYPE: PRT
<213> ORGANISM: Artificial sequence
<220> FEATURE:
<223> OTHER INFORMATION: synthetic region of Yrk kinase domain

<400> SEQUENCE: 63

Arg His Asp Lys Leu Val Gln Leu Tyr Ala Val Val Ser Glu Glu Pro
1               5                   10                  15

Ile Tyr Ile Val Thr Glu Phe Met Ser Gln Gly Ser Leu Leu Asp Phe
            20                  25                  30

Leu Lys Asp Gly Asp Gly Arg Tyr
        35              40

<210> SEQ ID NO 64
<211> LENGTH: 40
<212> TYPE: PRT
<213> ORGANISM: Artificial sequence
<220> FEATURE:
<223> OTHER INFORMATION: synthetic region of c-Fgr kinase domain

<400> SEQUENCE: 64

Arg His Asp Lys Leu Val Gln Leu Tyr Ala Val Val Ser Glu Glu Pro
1               5                   10                  15

Ile Tyr Ile Val Thr Glu Phe Met Cys His Gly Ser Leu Leu Asp Phe
            20                  25                  30

Leu Lys Asn Pro Glu Gly Gln Asp
        35              40

<210> SEQ ID NO 65
<211> LENGTH: 41
<212> TYPE: PRT
<213> ORGANISM: Artificial sequence
<220> FEATURE:
<223> OTHER INFORMATION: synthetic region of Lyn kinase domain

<400> SEQUENCE: 65

Gln His Asp Lys Leu Val Arg Leu Tyr Ala Val Val Thr Arg Glu Glu
1               5                   10                  15

Pro Ile Tyr Ile Ile Thr Glu Tyr Met Ala Lys Gly Ser Leu Leu Asp
            20                  25                  30

Phe Leu Lys Ser Asp Glu Gly Gly Lys
        35              40

<210> SEQ ID NO 66
<211> LENGTH: 40
<212> TYPE: PRT
<213> ORGANISM: Artificial sequence
<220> FEATURE:
<223> OTHER INFORMATION: synthetic region of Hck kinase domain

<400> SEQUENCE: 66

Gln His Asp Lys Leu Val Lys Leu His Ala Val Val Thr Lys Glu Pro
1               5                   10                  15

Ile Tyr Ile Ile Thr Glu Phe Met Ala Lys Gly Ser Leu Leu Asp Phe
            20                  25                  30

Leu Lys Ser Asp Glu Gly Ser Lys
        35              40
```

```
<210> SEQ ID NO 67
<211> LENGTH: 40
<212> TYPE: PRT
<213> ORGANISM: Artificial sequence
<220> FEATURE:
<223> OTHER INFORMATION: synthetic region of Blk kinase domain

<400> SEQUENCE: 67

Gln His Glu Arg Leu Val Arg Leu Tyr Ala Val Val Thr Arg Glu Pro
1               5                   10                  15

Ile Tyr Ile Val Thr Glu Tyr Met Ala Arg Gly Cys Leu Leu Asp Phe
            20                  25                  30

Leu Lys Thr Asp Glu Gly Ser Arg
        35                  40

<210> SEQ ID NO 68
<211> LENGTH: 41
<212> TYPE: PRT
<213> ORGANISM: Artificial sequence
<220> FEATURE:
<223> OTHER INFORMATION: synthetic region of Abl kinase domain

<400> SEQUENCE: 68

Lys His Pro Asn Leu Val Gln Leu Leu Gly Val Cys Thr Arg Glu Pro
1               5                   10                  15

Pro Phe Tyr Ile Ile Thr Glu Phe Met Thr Tyr Gly Asn Leu Leu Asp
            20                  25                  30

Tyr Leu Arg Glu Cys Asn Arg Gln Glu
        35                  40

<210> SEQ ID NO 69
<211> LENGTH: 40
<212> TYPE: PRT
<213> ORGANISM: Artificial sequence
<220> FEATURE:
<223> OTHER INFORMATION: synthetic region of Btk kinase domain

<400> SEQUENCE: 69

Ser His Glu Lys Leu Val Gln Leu Tyr Gly Val Cys Thr Lys Gln Arg
1               5                   10                  15

Pro Ile Phe Ile Ile Thr Glu Tyr Met Ala Asn Gly Cys Leu Leu Asn
            20                  25                  30

Tyr Leu Arg Glu Met Arg His Arg
        35                  40

<210> SEQ ID NO 70
<211> LENGTH: 42
<212> TYPE: PRT
<213> ORGANISM: Artificial sequence
<220> FEATURE:
<223> OTHER INFORMATION: synthetic region of Csk kinase domain

<400> SEQUENCE: 70

Arg His Ser Asn Leu Val Gln Leu Leu Gly Val Ile Val Glu Glu Lys
1               5                   10                  15

Gly Gly Leu Tyr Ile Val Thr Glu Tyr Met Ala Lys Gly Ser Leu Val
            20                  25                  30

Asp Tyr Leu Arg Ser Arg Gly Arg Ser Val
        35                  40

<210> SEQ ID NO 71
```

```
<211> LENGTH: 41
<212> TYPE: PRT
<213> ORGANISM: Artificial sequence
<220> FEATURE:
<223> OTHER INFORMATION: synthetic region of PDGFR kinase domain

<400> SEQUENCE: 71

Pro His Leu Asn Val Val Asn Leu Leu Gly Ala Cys Thr Lys Gly Gly
1               5                   10                  15

Pro Ile Tyr Ile Ile Thr Glu Tyr Cys Arg Tyr Gly Asp Leu Val Asp
            20                  25                  30

Tyr Leu His Arg Asn Lys His Thr Phe
        35                  40

<210> SEQ ID NO 72
<211> LENGTH: 41
<212> TYPE: PRT
<213> ORGANISM: Artificial sequence
<220> FEATURE:
<223> OTHER INFORMATION: synthetic region of p38 kinase domain

<400> SEQUENCE: 72

Gly Leu Leu Asp Val Phe Thr Pro Ala Arg Ser Leu Glu Glu Phe Asn
1               5                   10                  15

Asp Val Val Leu Val Thr His Leu Met Gly Ala Asp Leu Asn Asn Ile
            20                  25                  30

Val Lys Cys Gln Lys Leu Thr Asp Asp
        35                  40

<210> SEQ ID NO 73
<211> LENGTH: 39
<212> TYPE: PRT
<213> ORGANISM: Artificial sequence
<220> FEATURE:
<223> OTHER INFORMATION: synthetic region of ZAP-70 kinase domain

<400> SEQUENCE: 73

Asp Asn Pro Tyr Ile Val Arg Leu Ile Gly Val Cys Gln Ala Glu Ala
1               5                   10                  15

Leu Met Leu Val Met Glu Met Ala Gly Gly Pro Leu His Lys Phe
            20                  25                  30

Leu Val Gly Lys Arg Glu Glu
        35

<210> SEQ ID NO 74
<211> LENGTH: 42
<212> TYPE: PRT
<213> ORGANISM: Artificial sequence
<220> FEATURE:
<223> OTHER INFORMATION: synthetic region of JAK2 kinase domain

<400> SEQUENCE: 74

Gln His Asp Asn Ile Val Lys Tyr Lys Gly Val Cys Tyr Ser Ala Gly
1               5                   10                  15

Arg Arg Asn Leu Arg Leu Ile Met Glu Tyr Leu Pro Tyr Gly Ser Leu
            20                  25                  30

Arg Asp Tyr Leu Gln Lys His Lys Glu Arg
        35                  40

<210> SEQ ID NO 75
<211> LENGTH: 39
<212> TYPE: PRT
<213> ORGANISM: Artificial sequence
```

```
<220> FEATURE:
<223> OTHER INFORMATION: synthetic region of PKA kinase domain

<400> SEQUENCE: 75

Asn Phe Pro Phe Leu Val Lys Leu Glu Phe Ser Phe Lys Asp Asn Ser
1               5                   10                  15

Asn Leu Tyr Met Val Met Glu Tyr Val Pro Gly Gly Glu Met Phe Ser
            20                  25                  30

His Leu Arg Arg Ile Gly Arg
            35

<210> SEQ ID NO 76
<211> LENGTH: 39
<212> TYPE: PRT
<213> ORGANISM: Artificial sequence
<220> FEATURE:
<223> OTHER INFORMATION: synthetic region of CamK II kinase domain

<400> SEQUENCE: 76

Lys His Pro Asn Ile Val Arg Leu His Asp Ser Ile Ser Glu Glu Gly
1               5                   10                  15

His His Tyr Leu Ile Phe Asp Leu Val Thr Gly Gly Glu Leu Phe Glu
            20                  25                  30

Asp Ile Val Ala Arg Glu Tyr
            35

<210> SEQ ID NO 77
<211> LENGTH: 40
<212> TYPE: PRT
<213> ORGANISM: Artificial sequence
<220> FEATURE:
<223> OTHER INFORMATION: synthetic region of Cdk2 kinase domain

<400> SEQUENCE: 77

Asn His Pro Asn Ile Val Lys Leu Leu Asp Val Ile His Thr Glu Asn
1               5                   10                  15

Lys Leu Tyr Leu Val Phe Glu Phe Leu His Gln Asp Leu Lys Lys Phe
            20                  25                  30

Met Asp Ala Ser Ala Leu Thr Gly
            35                  40

<210> SEQ ID NO 78
<211> LENGTH: 6
<212> TYPE: PRT
<213> ORGANISM: Artificial sequence
<220> FEATURE:
<223> OTHER INFORMATION: synthetic N-terminal His-6 tag

<400> SEQUENCE: 78

His His His His His His
1               5

<210> SEQ ID NO 79
<211> LENGTH: 7
<212> TYPE: PRT
<213> ORGANISM: Artificial sequence
<220> FEATURE:
<223> OTHER INFORMATION: synthetic spacer sequence
```

```
<400> SEQUENCE: 79

Asp Tyr Asp Ile Pro Thr Thr
1               5

<210> SEQ ID NO 80
<211> LENGTH: 7
<212> TYPE: PRT
<213> ORGANISM: Artificial sequence
<220> FEATURE:
<223> OTHER INFORMATION: synthetic tobacco etch virus (TEV) protease
      site

<400> SEQUENCE: 80

Glu Asn Leu Tyr Phe Gln Gly
1               5
```

METHODS AND COMPOSITIONS FOR KINASE INHIBITION

CROSS-REFERENCES TO RELATED APPLICATIONS

This application claims the benefit of U.S. Provisional Patent Application 61/351,663, filed Jun. 4, 2010, and International Patent Application PCT/US2011/039347, filed Jun. 6, 2011, which are hereby incorporated by reference in their entirety for all purposes.

STATEMENT AS TO RIGHTS TO INVENTIONS MADE UNDER FEDERALLY SPONSORED RESEARCH OR DEVELOPMENT REFERENCE TO A "SEQUENCE LISTING," A TABLE, OR A COMPUTER PROGRAM LISTING APPENDIX SUBMITTED AS AN ASCII TEXT FILE

The Sequence Listing written in file -122-1.TXT, created on Jan. 23, 2013, 229,376 bytes, machine format IBM-PC, MS-Windows operating system, is hereby incorporated by reference in its entirety for all purposes.

This invention was made with Government support under Grant Nos. 5F32CA138103-2 and 1R01EB001987-16, awarded by the National Institutes of Health. The Government has certain rights in this invention.

BACKGROUND OF THE INVENTION

Kinases, which constitute a large family of enzymes (>500 in humans), catalyze the transfer of the γ-phosphate of ATP to protein substrates. Reversible phosphorylation plays a paramount role in cell signaling processes and is regulated by kinases and phosphatases. Accordingly, kinases are critical mediators of a myriad of signal transduction processes. Aberrant kinase activity is linked to cancer as well as metabolic, immunological, and nervous system disorders. As a result, kinases have emerged as an important class of drug targets for human disease. However, due to the conserved nature of the active sites of the protein kinase family, it is difficult to obtain selective inhibitors for any one kinase.

There are at least 518 kinases, such as those which catalyze the transfer of the gamma phosphate of ATP to protein and small molecule substrates and are involved in cell signaling processes. Small molecules provide a means for delineating kinase signaling because they are fast acting and dosable. However, because all kinase active sites recognize ATP, it is difficult to develop selective ATP-competitive inhibitors. Several years ago, a chemical genetic strategy for selective kinase inhibition was developed with reversible inhibitors (U.S. Patent Publication No. 2009/0221614). The chemical genetic strategy involves the engineered mutation of a conserved bulky residue in the kinase active site known as "the gatekeeper" to a small residue such as glycine or alanine (See Bishop A C, et al. (1998) Design of allele-specific inhibitors to probe protein kinase signaling. *Curr Biol* 8(5):257-266; and Bishop A C, et al. (2000) A chemical switch for inhibitor-sensitive alleles of any protein kinase. *Nature* 407(6802):395-401). The engineered active site can then accommodate an inhibitor capable of occupying the newly formed binding pocket. While this strategy has utility, mutation of the gatekeeper residue to a small amino acid may impair the activity of the kinase and the selective inhibition can only be applied to one kinase at a time. In addition, it is sometimes not possible to achieve the desired potency.

It is known in the field that mutations in Leucine-Rich Repeat Kinase 2 (Lrrk-2) can lead to Parkinsons Disease. Also, it is thought that Parkinson's Disease (PD) is caused by uncontrolled apoptosis of dopaminergic neurons. Because inhibition of Lrrk-2 kinase activity can inhibit the apoptotic effects, there is a need to develop inhibitors for Lrrk-2 to provide treatments for Parkinson's Disease.

As such, there is a need in the field to develop kinase gatekeeper residue mutations which do not diminish kinase activity or ATP affinity as well as small molecules which inhibit these kinases. There is also a need to develop effective Lrrk-2 inhig. Surprisingly, the present invention solves these as well as other problems in the field.

BRIEF SUMMARY OF THE INVENTION

In one aspect, the present invention provides a compound having the formula:

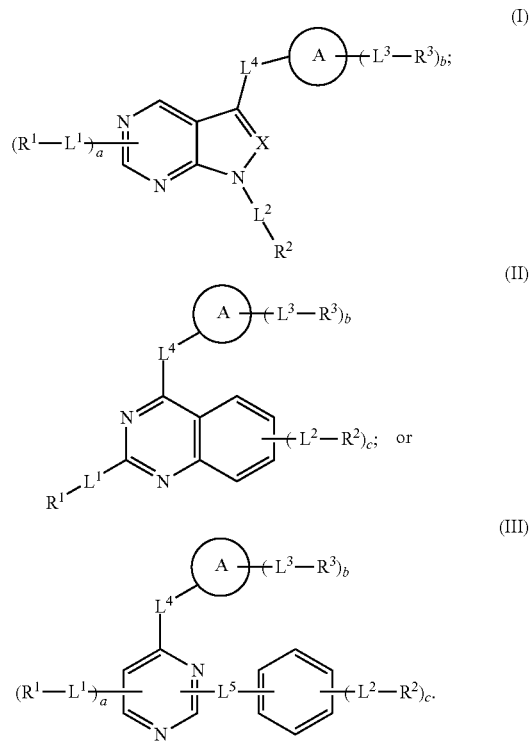

$X$ is $=N-$ or $=C(L^6\text{-}R^6)-$. Ring A is, in each instance, independently selected from cycloalkyl, heterocycloalkyl, aryl, or heteroaryl; $L^1$, $L^2$, $L^3$, $L^4$, $L^5$, and $L^6$ are, in each instance, independently selected from a bond, —C(O)—, —C(O)N($R^7$)—, —C(O)O—, —S(O)$_g$—, —S(O)$_2$N($R^7$)—, —O—, —N($R^7$)—, —N($R^7$)C(O)N($R^8$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, wherein g is an integer from 0 to 2; $R^1$, $R^2$, $R^3$, $R^4$, $R^5$, $R^6$, $R^7$, and $R^8$ are, in each instance, independently selected from hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; a is an integer from 0 to 2; b is an integer from 0 to 5; and c is an integer from 0 to 4.

In a second aspect, the present invention provides a recombinant kinase comprising a cysteine substitution at a gatekeeper amino acid position.

In a third aspect, the present invention provides a co-crystal comprising a recombinant kinase and a compound of provided herein (e.g. formula I, II, or III).

In a fourth aspect, the present invention provides an isolated nucleic acid comprising a polynucleotide sequence encoding a recombinant kinase provided herein.

In a fifth aspect, the present invention provides a method of inhibiting a recombinant kinase provided herein, comprising contacting the recombinant kinase with an effective amount of an inhibitor provided herein, thereby inhibiting the recombinant kinase.

In a sixth aspect, the present invention provides a compound having the formula:

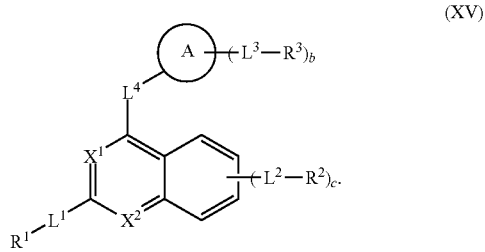

(XV)

$X^1$ and $X^2$ are, in each instance, independently =N— or =C(-$L^6$-$R^6$)—. Ring A is as defined above. $R^1$, $R^2$, and $R^3$ are as defined above. $L^1$, $L^2$, and $L^3$ are as defined above. The variables b and c are as defined above.

In a seventh aspect, the present invention provides a method of inhibiting a Lrrk-2 kinase, the method comprising contacting the Lrrk-2 kinase with an effective amount of a Lrrk-2 inhibitor, thereby inhibiting the Lrrk-2 kinase.

In an eighth aspect, the present invention provides a method of forming a recombinant kinase, comprising transforming a cell with a nucleic acid as set forth herein, thereby forming a recombinant kinase as set forth herein.

In a ninth aspect, the present invention provides a method of treating a kinase-associated disease or condition, in a patient in need thereof, said method comprising administering to said patient a therapeutically effective amount of a compound of the present invention, thereby treating a kinase-associated disease or condition.

In a tenth aspect, the present invention provides a method of treating a Lrrk-2-associated disease or condition, in a patient in need thereof, said method comprising administering to said patient a therapeutically effective amount of a compound of the present invention, thereby treating a Lrrk-2-associated disease or condition.

In an eleventh aspect, the present invention provides a kit comprising, a recombinant kinase or a nucleic acid provided herein; and instructions for using the kit.

BRIEF DESCRIPTION OF THE DRAWINGS

FIG. 8 shows the amino acid sequence (SEQ ID NO: 2) of Src and also the nucleic acid sequence (SEQ ID NO: 1) encoding therefor.

FIG. 11 shows selectivity of compound 19 (3-vs-Q) in the Invitrogen SelectScreen Kinase Assay.

FIG. 12 shows SAR analysis and inhibition as dependent on a vinylsulfonamide in the 3 position.

FIG. 16 shows in vitro kinase assay data for wild type and G2019S Lrrk-2.

FIG. 20 shows immunocytochemistry. Top left: Staruasporine, TUNEL stain; Top Right: G2019S mutant, −drug; Bottom: G2019S mutant, +Th.

DETAILED DESCRIPTION OF THE INVENTION

I. General

Figure 1:
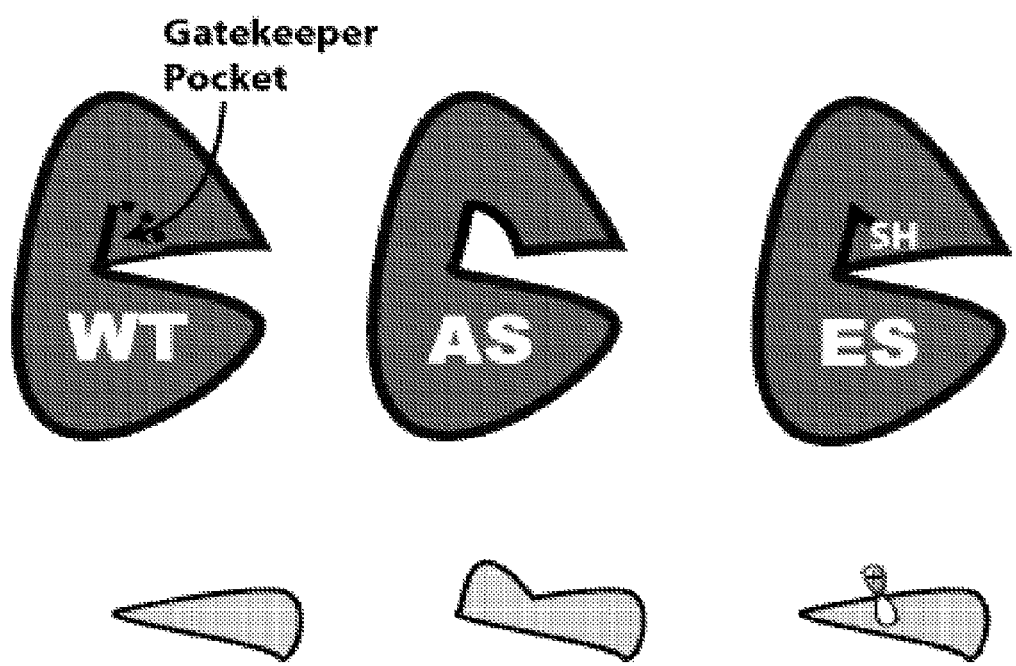
FIG. 1 shows a schematic of the chemical genetic strategies for inhibiting protein kinases. Kinases are depicted on top, e.g. WT, AS, and ES, and inhibitors types are represented on the bottom. Wild type (WT) kinases generally harbor hydrophobic gatekeeper residues and may not be inhibited selectively. An analog-sensitive (AS) protein kinase has an engineered glycine or alanine gatekeeper and may be selectively inhibited by a bulky inhibitor. An electrophile-sensitive (ES) protein kinase contains an engineered cysteine gatekeeper and may be selectively inhibited by an electrophilic inhibitor.

Provided herein, inter alia, are methods and compositions for imparting to a kinase the capability of being inhibited by a heterocyclic compound e.g., a cysteine substituted kinase having a gatekeeper amino acid residue within an ATP binding site of a kinase replaced with a cysteine residue. Also provided are methods and compositions for inhibiting a kinase with a heterocyclic compound. Furthermore, methods and compositions are provided for determining a biological activity of a kinase and treating kinase-associate diseases. In addition, methods and compositions are provided for inhibiting a Lrrk-2 kinase.

II. Definitions

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —CH₂CH₂CH₂CH₂—, —CH₂CH=CH—CH₂—, —CH₂C≡CCH₂—, —CH₂CH₂CH(CH₂CH₂CH₃)CH₂—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH₂—CH₂—O—CH₃, —CH₂—CH₂—NH—CH₃, —CH₂—CH₂—N(CH₃)—CH₃, —CH₂—S—CH₂—CH₃, —CH₂—CH₂—, —S(O)—CH₃, —CH₂—CH₂—S(O)₂—CH₃, —CH=CH—O—CH₃, —Si(CH₃)₃, —CH₂—CH=N—OCH₃, —CH=CH—N(CH₃)—CH₃, O—CH₃, —O—CH₂—CH₃, and —CN. Up to two or three heteroatoms may be consecutive, such as, for example, —CH₂—NH—OCH₃ and —CH₂—O—Si(CH₃)₃. Similarly, the term "heteroalkylene" by itself or as part of another substituent means a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "aryl" means, unless otherwise stated, a polyunsaturated, aromatic, hydrocarbon substituent which can be a single ring or multiple rings (preferably from 1 to 3 rings) which are fused together (e.g. naphthyl) or linked covalently. The term "heteroaryl" refers to aryl groups (or rings) that contain heteroatoms (in at least one ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 6-isoquinolyl, 2-quinoxalinyl, 5-quinoxalinyl, 3-quinolyl, and 6-quinolyl. Thus, the term "heteroaryl" include fused ring structures in which at least one ring includes at least two double bonds. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" referrers to a carbon or heteroatom.

The term "oxo" as used herein means an oxygen that is double bonded to a carbon atom.

Each of above terms (e.g., "alkyl," "heteroalkyl," "cycloalkyl", and "heterocycloalkyl", "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R''' and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen radical. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR"", —NR—C(NR'R")=NR''', —S(O)R', —S(O)$_2$R', —S(O)$_2$NR'R", —NRSO$_2$R', —CN and —NO$_2$, —R', —CH(Ph)$_2$, fluoro(C$_1$-C$_4$)alkoxo, and fluoro(C$_1$-C$_4$) alkyl, in a number ranging from zero to the total number of open valences on aromatic ring system; and where R', R", R''' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R''' and R"" groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. Alternatively, at least one or all of these groups are substituted with at least one lower substituent group.

In other embodiments of the compounds herein, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and/or each substituted or unsubstituted heterocycloalkyl is a substituted or unsubstituted 5 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_5$-$C_7$ cycloalkylene, and/or each substituted or unsubstituted heterocycloalkylene is a substituted or unsubstituted 5 to 7 membered heterocycloalkylene. In some embodiments, the compound is a chemical species set forth in the Examples section below.

A "bulky residue" in an amino acid residue having a side chain group that is larger (i.e. having more atoms and tending to fill more space) than glycine and alanine, and optionally larger than cysteine. A bulky residue may be methionine, leucine, phenylalanine and threonine In some embodiments, the bulky reside may be larger than leucine, isoleucine and threonine. In some embodiments, the bulky reside includes a cyclic moiety.

"Electrophilic" is used herein in accordance with its plain ordinary meaning and refers to a chemical group having a tendency to attract, acquire or accept electrons or react at electron-rich sites.

"Nucleophilic" is used herein in accordance with its plain ordinary meaning and refers to a chemical group having a tendency to donate electrons (e.g. lower electron density) or react at electron poor sites.

"Electrophilic moiety" as used herein refers to a functional group or chemical substituent that is electrophilic. Example electrophilic moieties include, but are not limited to vinylsulfonamides, acrylamides, epoxides, and fluoromethylketones.

As defined herein, the term "electrophilic substituent" is a substituent that is electrophilic. An electrophilic substituent, electrophilic moieties and electrophilic chemical groups are typically electron-poor functional groups and can react with an electron-donating group, such as a nucleophile, by accepting an electron pair. In some embodiments, the electrophilic substituent, moiety or chemical group of a compound is capable of reacting with a cysteine residue. In some embodiments, the electrophilic substituent, moiety or chemical group is capable of forming a covalent bond with a cysteine residue within the ATP binding site of the kinase. The covalent bond is usually formed between the electrophilic substituent, moiety or chemical group and the sulfhydryl group of the cysteine and may be a reversible or irreversible bond. In some embodiments, the covalent bond is irreversible.

As used herein, the terms "protein kinase" or "kinase" are used in accordance with its plain ordinary meaning and referst to an enzyme that is capable of phosphorylating an amino acid residue, e.g. an amino acid residue on a protein. Typically specific serine, threonine, or tyrosine residues are phosphorylated. Thus, protein kinase encompasses serine protein kinases, threonine protein kinases, and tyrosine protein kinases. An "inhibitor of a protein kinase" is a compound or agent that reduces the activity of a protein kinase. In some embodiments, a "protein kinase inhibitor" is a compound that reduces the activity of the protein kinase by binding to the protein kinase. Thus, a "protein kinase inhibitor" can inhibit activity of the enzyme in a competitive, or a noncompetitive manner.

As defined herein, the term "cysteine substituted kinase" refers to a recombinant kinase where a gatekeeper amino acid residue (e.g. within an ATP binding site of the kinase) is replaced with a cysteine residue. Similarly, a "glycine substituted kinase" refers to a recombinant kinase where a gatekeeper amino acid residue (e.g. within an ATP binding site of the kinase) is replaced with a glycine residue, and a "alanine substituted kinase" refers to a kinase where a gatekeeper amino acid residue (e.g. within an ATP binding site of the kinase) is replaced with a alanine residue.

As defined herein, the term "fused rings" refers to a ring system with two or more rings having at least one bond and two atoms in common.

The terms "nucleic acid," "oligonucleotide," "polynucleotide," and like terms typically refer to polymers of deoxyribonucleotides or ribonucleotides in either single—or double-stranded form, and complements thereof. The term "nucleotide" typically refers to a monomer. The terms encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, N.Y.), which is incorporated herein by reference.

The terms "peptide," "polypeptide," and "protein" are used interchangeably herein to refer to a polymer of amino acid residues.

The term "amino acid" refers to naturally occurring and synthetic amino acids, as well as amino acid analogs. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

A "conservative substitution" as used with respect to amino acids, refers to the substitution of an amino acid with a chemically similar amino acid. Amino acid substitutions which often preserve the structural and/or functional properties of the polypeptide in which the substitution is made are known in the art and are described, for example, by H. Neurath and R. L. Hill, 1979, in "The Proteins," Academic Press, New York. The most commonly occurring exchanges are isoleucine/valine, tyrosine/phenylalanine, aspartic acid/glutamic acid, lysine/arginine, methionine/leucine, aspartic acid/asparagine, glutamic acid/glutamine, leucine/isoleucine, methionine/isoleucine, threonine/serine, tryptophan/phenylalanine, tyrosine/histidine, tyrosine/tryptophan, glutamine/arginine, histidine/asparagine, histidine/glutamine, lysine/asparagine, lysine/glutamine, lysine/glutamic acid, phenylalanine/leucine, phenylalanine/methionine, serine/alanine, serine/asparagine, valine/leucine, and valine/methionine. In some embodiments, there may be at least 1, at least 2, at least 3, at least 4, at least 5, at least 6, at least 7, at least 8, at least 9, at least 10, at least 15, at least 20, at least 25, at least 30, at least 35, or at least 40 conservative substitutions.

The term "amino acid substitution set" or "substitution set" refers to a group of amino acid substitutions. A substitution set can have 1, 2, 3, 4, 5, 6, 7, 8, 9, 10, 11, 12, 13, 14, 15, or more amino acid substitutions.

The term "isolated" refers to a nucleic acid, polynucleotide, polypeptide, protein, or other component that is partially or completely separated from components with which it is normally associated (other proteins, nucleic acids, cells, etc.). In some embodiments, an isolated polypeptide or protein is a recombinant polypeptide or protein.

A nucleic acid (such as a polynucleotide), a polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Identity" or "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

Optimal alignment of sequences for comparison and determination of sequence identity can be determined by a sequence comparison algorithm or by visual inspection (see, generally, Ausubel et al., infra). When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters as known in the art, for example BLAST or BLAST 2.0. For example, comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, or by computerized implementations of these algorithms (GAP, BESTFIT, FASTA, and TFASTA in the Wisconsin Genetics Software Package, Genetics Computer Group, 575 Science Dr., Madison, Wis.). Thus alignment can be carried out for sequences that have deletions and/or additions, as well as those that have substitutions, as well as naturally occurring, e.g., polymorphic or allelic variants, and man-made variants.

The phrase "substantial sequence identity" or "substantial identity," in the context of two nucleic acid or polypeptide sequences, refers to a sequence that has at least 70% identity to a reference sequence. Percent identity can be any integer from 70% to 100%. Two nucleic acid or polypeptide sequences that have 100% sequence identity are said to be "identical." A nucleic acid or polypeptide sequence are said to have "substantial sequence identity" to a reference sequence when the sequences have at least about 70%, at least about 75%, at least 80%, at least 85%, at least 90%, at least 91%, at least 92%, at least 93%, at least 94%, at least 95%, at least 96%, at least 97%, at least 98%, at least 99% or greater sequence identity as determined using the methods described herein, such as BLAST using standard parameters as described above.

The term "pre-protein" refers to a protein including an amino-terminal signal peptide (or leader sequence) region attached. The signal peptide is cleaved from the pre-protein by a signal peptidase prior to secretion to result in the "mature" or "secreted" protein.

A "vector" is a DNA construct for introducing a DNA sequence into a cell. A vector may be an expression vector that is operably linked to a suitable control sequence capable of effecting the expression in a suitable host of the polypeptide encoded in the DNA sequence. An "expression vector" has a promoter sequence operably linked to the DNA sequence (e.g., transgene) to drive expression in a host cell, and in some embodiments a transcription terminator sequence.

The term "expression" includes any step involved in the production of the polypeptide including, but not limited to, transcription, post-transcriptional modification, translation, post-translational modification, and secretion.

The term "operably linked" refers to a configuration in which a control sequence is appropriately placed at a position relative to the coding sequence of the DNA sequence such that the control sequence influences the expression of a polypeptide.

An amino acid or nucleotide sequence (e.g., a promoter sequence, signal peptide, terminator sequence, etc.) is "heterologous" to another sequence with which it is operably linked if the two sequences are not associated in nature.

The terms "transform" or "transformation," as used in reference to a cell, means a cell has a non-native nucleic acid sequence integrated into its genome or as an episome (e.g., plasmid) that is maintained through multiple generations.

The term "culturing" refers to growing a population of microbial cells under suitable conditions in a liquid or solid medium.

The term "introduced," as used in the context of inserting a nucleic acid sequence into a cell, means conjugated, transfected, transduced or transformed (collectively "transformed") or otherwise incorporated into the genome of, or maintained as an episome in, the cell.

As defined herein, the term "gatekeeper amino acid residue" or "gatekeeper residue" refers to a residue (e.g. within the ATP binding site of a kinase) that is capable of controlling or modulating the ability of a kinase substrate to bind to the kinase. For example, in some embodiments, the accessibility of a protein kinase substrate to the ATP binding site is controlled by the gatekeeper residue. In certain embodiments, the gatekeeper residue controls the ability of the substrate to access or bind a hydrophobic pocket adjacent to the ATP binding site. (Elphick et al. *ACS Chemical Biology*, 2:299-314, 2007). As defined herein, a natural gatekeeper residue refers to a gatekeeper residue identified in a wild-type kinase. Examples of gatekeeper residues include, e.g., Thr338 of c-Src (v-Src numbering, see Liu et al., Chemistry & Biology, 6:671-678, 1999), and Thr 493 of rsk2 (see US Application No. 2009/0221614). Gatekeeper residues in other kinases, e.g., gatekeeper residues corresponding to Thr338 of c-Src can be readily identified by structure-based sequence alignment of kinase domain of various src or non-src kinases. The following is a structure-based sequence alignment of several kinase domains (see U.S. Patent Publication No. 2009/0221614). The gatekeeper residues referred to herein are highlighted in bold italics:

| Name | Sequence | SEQ ID NO: |
|---|---|---|
| src | ----PEAFLQEAQVMK--KLRHEKLVQLYAVVSEEP---IYIV*T*EYM | 52 |
| rsk2 | ----KRDPTEEIEILLR-YGQHPNIITLKDVYDDGKY--VYVV*T*ELM | 53 |
| nek2 | -EVEKQMLVSEVNLLR--ELKHPNIVRYYDRIIDRTNTTLYIV*M*EYC | 54 |
| mekk1 | QEEVVEALREEIRMMS--HLNHPNIIRMLGATCEKSN--YNLF*I*EWM | 55 |

| Name | Sequence | SEQ ID NO: |
|---|---|---|
| msk1 | ---MEANTQKEITALK-LCEGHPNIVKLHEVFHDQLH--TFLVMELL | 56 |
| plk1 | -PHQREKMSMEISIHR--SLAHQHVVGFHGFFEDNDF--VFVVLELC | 57 |

Additional gatekeeper residues in various kinases can be identified by sequence alignment (see Liu et al., Chemistry & Biology, 6:671-678, 1999). For example, gatekeeper residues in various kinases corresponding to Thr338 of v-Src are highlighted in bold underlined in the sequence alignment below:

| Name | Start | Sequence (338) | SEQ ID NO: |
|---|---|---|---|
| v-Src | (318) | RHEKLVQLYAMVSE-------------EPIYIVTEYMSK--GSLLDFLKGEMGKY | 58 |
| c-Src | (318) | RHEKLVQLYAVVSE-------------EPIYIVTEYMSK--GSLLDFLKGETGKY | 59 |
| Lck | (296) | QHQRLVRLYAVVTQ-------------EPIYIITEYMEN--GSLVDFLKTPSGIK | 60 |
| Fyn | (319) | KHDKLVQLYAVVSE-------------EPIYIVTEYMNK--GSLLDFLKDGEGRA | 61 |
| c-Yes | (325) | RHDKLVPLYAVVSE-------------EPIYIVTEFMSK--GSLLDFLKEGDGKY | 62 |
| Yrk | (318) | RHDKLVQLYAVVSE-------------EPIYIVTEFMSQ--GSLLDFLKDGDGRY | 63 |
| c-Fgr | (311) | RHDKLVQLYAVVSE-------------EPIYIVTEFMCH--GSLLDFLKNPEGQD | 64 |
| Lyn | (295) | QHDKLVRLYAVVTRE------------EPIYIITEYMAK--GSLLDFLKSDEGGK | 65 |
| Hck | (318) | QHDKLVKLHAVVTK-------------EPIYIITEFMAK--GSLLDFLKSDEGSK | 66 |
| Blk | (287) | QHERLVRLYAVVTR-------------EPIYIVTEYMAR--GCLLDFLKTDEGSR | 67 |
| Abl | (313) | KHPNLVQLLGVCTRE------------PPFYIITEFMTY--GNLLDYLRECNRQE | 68 |
| Btk | (473) | SHEKLVQLYGVCTKQ------------RPIFIITEYMAN--GCLLNYLREMRHR | 69 |
| Csk | (244) | RHSNLVQLLGVIVEEK-----------GGLYIVTEYMAK--GSLVDYLRSRGRSV | 70 |
| PDGFR | (660) | PHLNVVNLLGACTKG------------GPIYIITEYCRY--GDLVDYLHRNKHTF | 71 |
| p38 | (85) | GLLDVFTPARSLEEF------------NDVVLVTHLMGA---DLNNIVKCQKLTDD | 72 |
| ZAP-70 | (394) | DNPYIVRLIGVCQA-------------EALMLVMEMAGG--GPLHKFL-VGKREE | 73 |
| JAK2 | (906) | QHDNIVKYKGVCYSAGR----------RNLRLIMEYLPY--GSLRDYLQKHKER | 74 |
| PKA | (99) | NFPFLVKLEFSFKDN------------SNLYMVMEYVPG--GEMFSHLRRIGR | 75 |
| CamK II | (68) | KHPNIVRLHDSISEE------------GHHYLIFDLVTG--GELFEDIVAREY | 76 |
| Cdk2 | (59) | NHPNIVKLLDVIHTE------------NKLYLVFEFLHQ---DLKKFMDASALTG | 77 |

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, the resulting reaction product can be produced directly from a reaction between the added reagents or from an intermediate from one or more of the added reagents which can be produced in the reaction mixture. The term "contacting" includes incubating an inhibitor with the kinase.

As defined herein, the term "inhibition", "inhibit", "inhibiting" and the like in reference to a kinase-inhibitor interaraction means negatively affecting (e.g. decreasing) the activity of the kinase relative to the activity of the kinase in the absence of the inhibitor. Thus, inhibition includes, at least in part, partially or totally blocking stimulation, decreasing, preventing, or delaying activation, or inactivating, desensitizing, or down-regulating signal transduction. Similarly an "inhibitor" is a compound that inhibits kinase activity, e.g., by binding, partially or totally block stimulation, decrease, prevent, or delay activation, or inactivate, desensitize, or down-regulate signal transduction.

"Disease" or "condition" refer a state of being or health status of a patient or subject capable of being treated with the compounds provided herein. Examples of disorders or conditions include, but are not limited to, cancer, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, and migraine headaches. In some instances, "disease" or "condition" refer to cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), and multiple myeloma.

"Patient" or "subject in need thereof" refers to a living organism suffering from or prone to a condition that can be treated by administration of a pharmaceutical composition as provided herein. Non-limiting examples include humans, other mammals and other non-mammalian animals.

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

As used herein, the symbol,

indicates the point of attachment of a substituents to the remainder of a molecule.

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer.

An "effective amount" is an amount sufficient to contribute to the treatment, prevention, or reduction of a symptom or symptoms of a disease. An "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) a disease, or reducing the likelihood of the onset (or reoccurrence) of a disease or its symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an osteoclast or leukocyte relative to the absence of the antagonist.

As used herein, the phrase "ATP-binding pocket" refers to the active site of a kinase that binds ATP. The active site of the kinase where ATP binds is the set of amino acid residues that are able to interact with and or bind to an ATP molecule or an ATP competitive inhibitor.

As used herein, the term "mutated" refers to a kinase with a non-natural (e.g. non-wild type) amino acid sequence. A mutated kinase is typically recombinant (e.g. engineered). In some embodiments as described below, the mutated kinase has a cysteine residue substitution at the gatekeeper amino acid position. As used herein, the term "unmutated" refers to the corresponding kinase wherein the mutation (e.g. a cysteine residue is substituted for a gatekeeper amino acid position) is not present (e.g. the natural or wild-type sequence). Thus, in some instances, unmutated refers to the wild-type or natural kinase. In some other instances, the corresponding kinase is another recombinant kinase having similar but distinct substitutions.

As used herein the term "not substantially lower" when referring to $k_{cat}$ means that the $k_{cat}$ is not less than a thousandth, i.e. 1/1000, of the corresponding $k_{cat}$ used for comparison. In some embodiments, the $k_{cat}$ is not less than a hundredth, i.e. 1/100, of the corresponding $k_{cat}$ used for comparison. In some instances, the $k_{cat}$ is not less than a tenth, i.e. 1/10, of the corresponding $k_{cat}$ used for comparison. In some instances, the $k_{cat}$ is not less than a quarter, i.e. 1/4, of the corresponding $k_{cat}$ used for comparison. In some instances, the $k_{cat}$ is not less than half, i.e. 1/2, of the corresponding $k_{cat}$ used for comparison. For example, an engineered or mutated kinase may have a $k_{cat}$ that is not substantially lower than the corresponding $k_{cat}$ of the corresponding wild-type or natural or unmutated kinase.

As used herein the terms "not substantially lower" when referring to $K_m$ means that the $K_m$ is not less than a thousandth, i.e. 1/1000, of the corresponding $K_m$ used for comparison. In some embodiments, the $K_m$ is not less than a hundredth, i.e. 1/100, of the corresponding $K_m$ used for comparison. In some instances, the $K_m$ is not less than a tenth, i.e. 1/10, of the corresponding $K_m$ used for comparison. In some instances, the $K_m$ is not less than a quarter, i.e. 1/4, of the corresponding $K_m$ used for comparison. In some instances, the $K_m$ is not less than half, i.e. 1/2, of the corresponding $K_m$ used for comparison. For example, an engineered or mutated kinase may have a $K_m$ that is not substantially lower than the corresponding $K_m$ of the corresponding wild-type or natural or unmutated kinase.

"Disease" or "condition" refer a state of being or health status of a patient or subject capable of being treated with the compounds provided herein. Examples of disorders or conditions include, but are not limited to, cancer, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, and migraine headaches. In some instances, "disease" or "condition" refer to cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), and multiple myeloma.

As used herein, the term "kinase-associated disease" refers to a disease or condition that is mediated, at least in part, by a kinase.

As used herein, the term "Lrrk-2-associated disease" refers to a disease or condition that is mediated, at least in part, by a Lrrk-2 kinase.

As used herein, the term "cancer" refers to all types of cancer, neoplasm or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Mcdulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The $P_{388}$ leukemia model is widely accepted as being predictive of in vivo anti-leukemic activity. It is believed that a compound that tests positive in the $P_{388}$ assay will generally exhibit some level of anti-leukemic activity in vivo regardless of the type of leukemia being treated. Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniformi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

As used herein, the term "isomers" refers to compounds having the same number and kind of atoms, and hence the same molecular weight, but differing in respect to the structural arrangement or configuration of the atoms.

As used herein, the term "tautomer," refers to one of two or more structural isomers which exist in equilibrium and which are readily converted from one isomeric form to another.

III. Introduction

Provided herein are, inter alia, novel methods and compositions for inhibiting a protein kinase, e.g., a cysteine substituted kinase, determining the function of a protein kinase in a cell, and treating kinase-associated diseases and conditions. Certain heterocyclic compounds having an electrophilic substituent provided herein that specifically, and optionally irreversibly, inhibit cysteine substituted kinases. In some embodiments, the heterocyclic compound comprises two or more fused rings and an electrophilic substituent. In some embodiments, at least one of the two or more fused rings comprises a nitrogen atom. In some embodiments, the heterocyclic compounds inhibit a cysteine substituted kinase, i.e., a kinase having a cysteine residue in the gatekeeper position of the ATP binding site. In some embodiments, the heterocyclic compounds also inhibit a kinase not having a cysteine residue in the gatekeeper position (e.g. of the ATP binding site).

IV. Compounds

The present invention provides compounds suitable for use with the methods and assays described herein.

In some other embodiments, the heterocyclic compounds useful for inhibiting a kinase include two or more fused rings which include at least one heteroatom selected from N, O, or S. In some embodiments, the fused rings are substituted with a ring selected from substituted or unsubstituted cycloalkyl, substituted or unsubstituted aryl, or substituted or unsubstituted heteroaryl. In some other embodiments, the cycloalkyl, heterocycloalkyl, aryl, or heteroaryl is substituted with a substituent selected from substituted or unsubstituted alkyl, substituted or unsubstituted heteroalkyl, substituted or unsubstituted aryl, substituted or unsubstituted heteroaryl. In other embodiments, the ring which substitutes the fused rings is an aryl or heteroaryl. In some embodiments, the ring which substitutes the fused rings is an aryl. In some other embodiments, the ring which substitutes the fused rings is an aryl which is substituted with an electrophilic substituent that is capable of accepting electron density from a cysteine gatekeeper residue of a protein kinase. In some embodiments, the electrophilic substituent is capable of forming a covalent bond to the sulfhydryl group of the cysteine gate keeper residue.

In some embodiments, the compound is a substituted or unsubstituted phenyl-derivatized pyrazolopyrimidine, e.g. 3-phenyl-substituted pyrazolopyrimidines, having an electrophilic substituent. In some other embodiments, the present invention provides 3-phenyl-substituted pyrazolopyrimidines which are synthesized with an electrophilic groups at positions expected to be in close proximity to the gatekeeper residue. In some embodiments, compound is a substituted or unsubstituted quinazoline having an electrophilic substituent. In some embodiments, compound is a substituted or unsubstituted 4-anilinoquinazoline, e.g. Michael acceptor-derivatized 4-anilinoquinazolines, having an electrophilic substituent. In some embodiments, the compound is a substituted or unsubstituted benzyl-derivatized pyrazolopyrimidine having an electrophilic substituent. In some embodiments, the compound is a substituted or unsubstituted pyrazolopyrimidine having an electrophilic substituent pyrazolopyrimidine.

In some other embodiments, the electrophilic substituent is an electrophilic ATP-binding pocket moiety (i.e. a chemical moiety that interacts with amino acids that form part of the ATP-binding pocket). In other embodiments, the electrophilic substituent is a vinylsulfonamide, a vinylsulfone, an acrylamide, a chloroacetamide, an α-chloroacetamide, an epoxide, or a fluoromethylketones.

In some embodiments the compounds described herein are inhibitors of kinases ("kinase inhibitors") such as an inhibitor of a recombinant cysteine gatekeeper kinase ("cysteine gatekeeper kinase inhibitor"). In some other embodiments, the cysteine gatekeeper kinase inhibitor includes an ATP-binding pocket moiety (e.g. an ATP-binding pocket moiety including a heterocyclic moiety) covalently bound to an electrophilic moiety capable of binding the thiol of the gatekeeper cysteine residue of the cysteine gatekeeper kinase. In some embodiments, the inhibitor is one or more of the compounds set forth in Table 1 of Formulas (I) to (XXIX) (e.g. Formula (I) to (XIV)).

In some embodiments, the compounds has the formula:

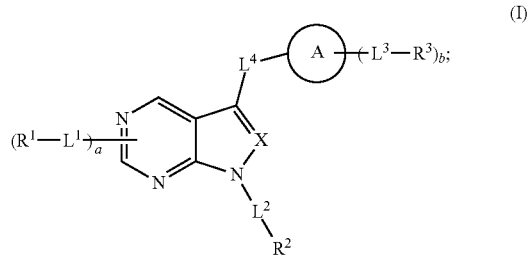

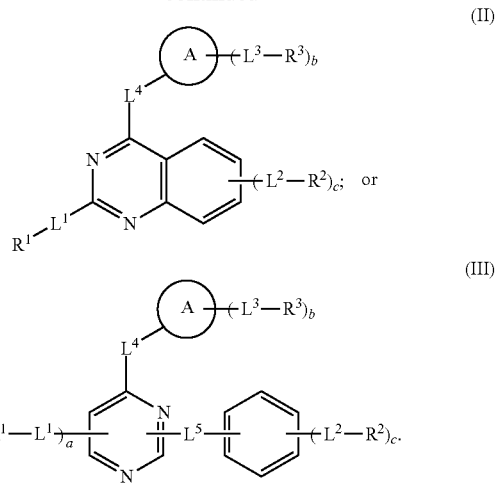

In these formula, X is =N— or =C(-L$^6$-R$^6$)—; Ring A is, in each instance, independently cycloalkyl, heterocycloalkyl, aryl, or heteroaryl; L$^1$, L$^2$, L$^3$, L$^4$, L$^5$, and L$^6$ are, in each instance, independently selected from a bond, —C(O)—, —C(O)N(R$^7$)—, —C(O)O—, —S(O)$_g$— (i.e. —S—, —S(O)— or —S(O)$_2$—), —S(O)$_2$N(R$^7$)—, —O—, —N(R$^7$)—, —N(R$^7$)C(O)N(R$^8$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, wherein g is independently an integer from 0 to 2; R$^1$, R$^2$, R$^3$, R$^4$, R$^5$, R$^6$, R$^7$, and R$^8$ are, in each instance, independently selected from hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; a is an integer from 0 to 2; b is an integer from 0 to 5; and c is an integer from 0 to 4. In some embodiments, A is aryl (e.g. phenyl). In some embodiments, R$^7$ is hydrogen. In some embodiments, R$^7$ and R$^8$ are hydrogen. R$^1$, R$^2$, R$^3$, R$^4$, R$^5$, R$^6$, R$^7$, and R$^8$ may also independently be hydrogen, halogen (e.g. —Cl or —F), —CN, —OH, —NH$_2$, —COOH, —CONH$_2$, —NO$_2$, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, R$^1$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, R$^9$-substituted or unsubstituted alkyl, R$^9$-substituted or unsubstituted heteroalkyl, R$^9$-substituted or unsubstituted cycloalkyl, R$^9$-substituted or unsubstituted heterocycloalkyl, R$^9$-substituted or unsubstituted aryl, or R$^9$-substituted or unsubstituted heteroaryl.

R$^9$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, R$^{10}$-substituted or unsubstituted alkyl, R$^{10}$-substituted or unsubstituted heteroalkyl, R$^{10}$-substituted or unsubstituted cycloalkyl, R$^{10}$-substituted or unsubstituted heterocycloalkyl, R$^{10}$-substituted or unsubstituted aryl, or R$^{10}$-substituted or unsubstituted heteroaryl.

$R^{10}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl.

In some embodiments, $R^2$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl.

$R^{12}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{13}$-substituted or unsubstituted alkyl, $R^H$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl.

$R^{13}$ independently is halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{14}$-substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$-substituted or unsubstituted heteroaryl.

In some embodiments, $R^3$ hydrogen, is halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl.

$R^{15}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl.

$R^{16}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl.

In some embodiments, $R^4$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl.

$R^{18}$ independently is halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

$R^{19}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In some embodiments, $R^5$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

$R^{21}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

$R^{22}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

In some embodiments, $R^6$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

$R^{24}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

$R^{25}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

In some embodiments, $R^7$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl.

$R^{27}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

$R^{28}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl.

In some embodiments, $R^8$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

$R^{30}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

$R^{31}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl.

In some embodiments, $R^{11}$, $R^{14}$, $R^{17}$, $R^{20}$, $R^{23}$, $R^{26}$, $R^{29}$, and $R^{32}$ are independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $L^1$ is in each instance, independently selected from a bond, —C(O)—, —C(O)N($R^7$)—, —C(O)O—, —S(O)$_g$—, —S(O)$_2$N($R^7$)—, —O—, —N($R^7$)—, —N($R^7$)C(O)N($R^8$)—, $R^{33}$-substituted or unsubstituted alkylene, $R^{33}$-substituted or unsubstituted heteroalkylene, $R^{33}$-substituted or unsubstituted cycloalkylene, $R^{33}$-substituted or unsubstituted heterocycloalkylene, $R^{33}$-substituted or unsubstituted arylene, or $R^{33}$-substituted or unsubstituted heteroarylene.

$R^{33}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

$R^{34}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl.

In some embodiments, $L^2$ is in each instance, independently selected from a bond, —C(O)—, —C(O)N($R^7$)—, —C(O)O—, —S(O)$_g$— (i.e. —S—, —S(O)— or —S(O)$_2$), —S(O)$_2$N($R^7$)—, —O—, —N($R^7$)—, —N($R^7$)C(O)N($R^8$)—, $R^{36}$-substituted or unsubstituted alkylene, $R^{36}$-substituted or unsubstituted heteroalkylene, $R^{36}$-substituted or unsubstituted cycloalkylene, $R^{36}$-substituted or unsubstituted heterocycloalkylene, $R^{36}$-substituted or unsubstituted arylene, or $R^{36}$-substituted or unsubstituted heteroarylene.

$R^{36}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

$R^{37}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl.

In some embodiments, $L^3$ is in each instance, independently selected from a bond, —C(O)—, —C(O)N($R^7$)—, —C(O)O—, —S(O)$_g$— (i.e. —S—, —S(O)— or —S(O)$_2$), —S(O)$_2$N($R^7$)—, —O—, —N($R^7$)—, —N($R^7$)C(O)N($R^8$)—, $R^{39}$-substituted or unsubstituted alkylene, $R^{39}$-substituted or unsubstituted heteroalkylene, $R^{39}$-substituted or unsubstituted cyclo alkylene, $R^{39}$-substituted or unsubstituted heterocycloalkylene, $R^{39}$-substituted or unsubstituted arylene, or $R^{39}$-substituted or unsubstituted heteroarylene.

$R^{39}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

$R^{40}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

In some embodiments, $L^4$ is in each instance, independently selected from a bond, —C(O)—, —C(O)N($R^7$)—, —C(O)O—, —S(O)$_g$— (i.e. —S—, —S(O)— or —S(O)$_2$), —S(O)$_2$N($R^7$)—, —O—, —N($R^7$)—, —N($R^7$)C(O)N($R^8$)—, $R^{39}$-substituted or unsubstituted alkylene, $R^{42}$-substituted or unsubstituted heteroalkylene, $R^{42}$-substituted or unsubstituted cycloalkylene, $R^{42}$-substituted or unsubstituted heterocycloalkylene, $R^{42}$-substituted or unsubstituted arylene, or $R^{42}$-substituted or unsubstituted heteroarylene.

$R^{42}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl.

$R^{43}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl.

In some embodiments, $L^5$ is in each instance, independently selected from a bond, —C(O)—, —C(O)N($R^7$)—, —C(O)O—, —S(O)$_g$— (i.e. —S—, —S(O)— or —S(O)$_2$), —S(O)$_2$N($R^7$)—, —O—, —N($R^7$)—, —N($R^7$)C(O)N ($R^8$)—, $R^{45}$-substituted or unsubstituted alkylene, $R^{45}$-substituted or unsubstituted heteroalkylene, $R^{45}$-substituted or unsubstituted cyclo alkylene, $R^{45}$-substituted or unsubstituted heterocycloalkylene, $R^{45}$-substituted or unsubstituted arylene, or $R^{45}$-substituted or unsubstituted heteroarylene.

$R^{45}$ is independently halogen, —CN, —OH, —$NH_2$, —COOH, —$CONH_2$, —$NO_2$, —SH, —$SO_2Cl$, —$SO_3H$, —$SO_4H$, —$SO_2NH_2$, $R^{46}$-substituted or unsubstituted alkyl, $R^{46}$-substituted or unsubstituted heteroalkyl, $R^{46}$-substituted or unsubstituted cycloalkyl, $R^{46}$-substituted or unsubstituted heterocycloalkyl, $R^{46}$-substituted or unsubstituted aryl, or $R^{46}$-substituted or unsubstituted heteroaryl.

$R^{46}$ is independently halogen, —CN, —OH, —$NH_2$, —COOH, —$CONH_2$, —$NO_2$, —SH, —$SO_2Cl$, —$SO_3H$, —$SO_4H$, —$SO_2NH_2$, $R^{47}$-substituted or unsubstituted alkyl, $R^{47}$-substituted or unsubstituted heteroalkyl, $R^{47}$-substituted or unsubstituted cycloalkyl, $R^{47}$-substituted or unsubstituted heterocycloalkyl, $R^{47}$-substituted or unsubstituted aryl, or $R^{47}$-substituted or unsubstituted heteroaryl.

In some embodiments, $L^6$ is in each instance, independently selected from a bond, —C(O)—, —C(O)N($R^7$)—, —C(O)O—, —S(O)$_g$— (i.e. —S—, —S(O)— or —S(O)$_2$), —S(O)$_2$N($R^7$)—, —O—, —N($R^7$)—, —N($R^7$)C(O)N ($R^8$)—, $R^{48}$-substituted or unsubstituted alkylene, $R^{48}$-substituted or unsubstituted heteroalkylene, $R^{48}$-substituted or unsubstituted cycloalkylene, $R^{48}$-substituted or unsubstituted heterocycloalkylene, $R^{48}$-substituted or unsubstituted arylene, or $R^{48}$-substituted or unsubstituted heteroarylene.

$R^{48}$ is independently halogen, —CN, —OH, —$NH_2$, —COOH, —$CONH_2$, —$NO_2$, —SH, —$SO_2Cl$, —$SO_3H$, —$SO_4H$, —$SO_2NH_2$, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl.

$R^{49}$ is independently halogen, —CN, —OH, —$NH_2$, —COOH, —$CONH_2$, —$NO_2$, —SH, —$SO_2Cl$, —$SO_3H$, —$SO_4H$, —$SO_2NH_2$, $R^{50}$-substituted or unsubstituted alkyl, $R^{50}$-substituted or unsubstituted heteroalkyl, $R^{50}$-substituted or unsubstituted cycloalkyl, $R^{50}$-substituted or unsubstituted heterocycloalkyl, $R^{50}$-substituted or unsubstituted aryl, or $R^{50}$-substituted or unsubstituted heteroaryl.

In some embodiments, $R^{35}$, $R^{38}$, $R^{41}$, $R^{44}$, $R^{47}$ and $R^{50}$ are independently hydrogen, unsubstituted alkyl, unsubstituted heteroalkyl, unsubstituted cycloalkyl, unsubstituted heterocycloalkyl, unsubstituted aryl, or unsubstituted heteroaryl.

In some other embodiments, the compounds have the formula (where the variables are as described above):

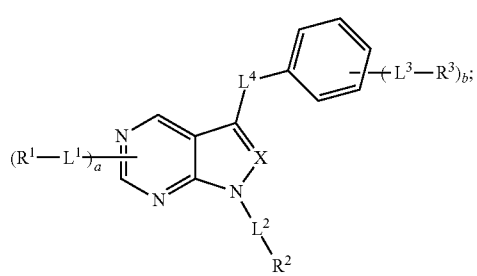

(IV)

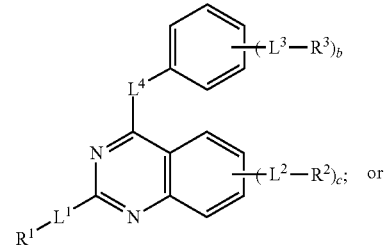

(V)

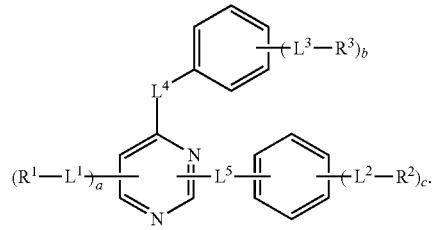

(VI)

In certain embodiments, $L^1$, $L^2$, $L^3$, $L^4$, $L^5$, and $L^6$ are, in each instance, independently a bond, —NH—, or substituted or unsubstituted $C_1$-$C_5$ alkylene. In certain other embodiments, $L^6$ is a bond, —NH—, or unsubstituted $C_1$-$C_5$ alkylene.

In some other embodiments, the compounds have the formula (where the variables are as described above):

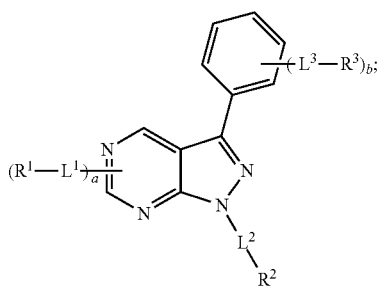

(VII)

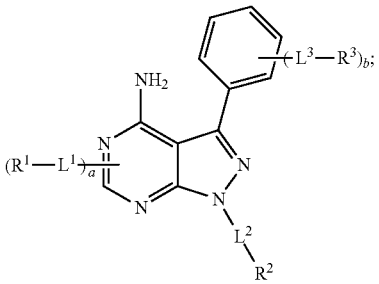

(VIII)

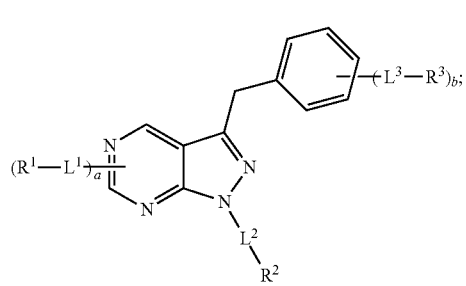

(IX)

(X)
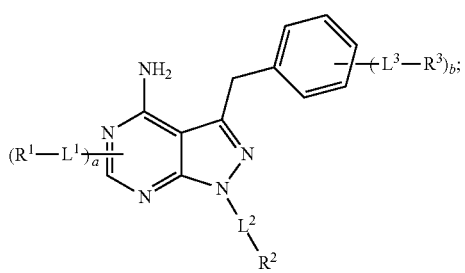

(XI)
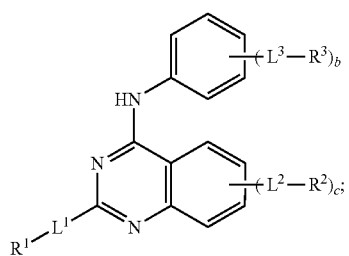

(XII)
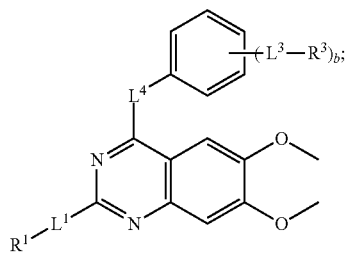

(XIII)
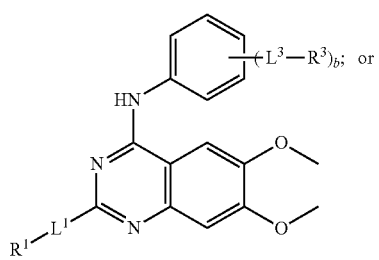

(XIV)
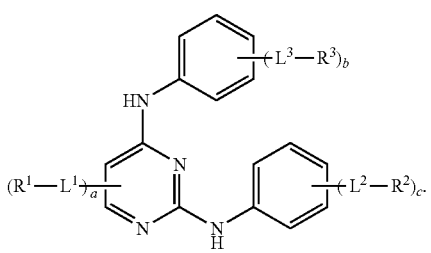

In certain embodiments, at least one -$L^3$-$R^3$ is an electrophilic moiety (e.g. -$L^3$-$R^3$ is or includes an electrophilic moiety). For example, in some embodiments, -$L^3$-$R^3$ forms an electrophilic moiety. In other embodiments, one of $L^3$ or $R^3$ is an electrophilic moiety (e.g. one of $L^3$ or $R^3$ is or includes an electrophilic moiety). In some embodiments, $L^3$ forms an electrophilic moiety. In other embodiments, $R^3$ forms an electrophilic moiety. In certain other embodiments, $L^3$ is a bond, —NH—, substituted or unsubstituted alkylene, or substituted or unsubstituted heteroalkylene; and $R^3$ is a substituted or unsubstituted alkyl, substituted or unsubstituted heteroalkyl, or halogen. In some of the embodiments, $L^3$ is —C(O)—, —S(O)$_2$—, —NHC(O)—, or —NHS(O)$_2$—. $R^3$ may be a substituted or unsubstituted alkyl (e.g. substituted or unsubstituted $C_1$ to $C_5$ alkyl). For example, $R^3$ may be an unsubstituted alkyl or alkyl substituted with chloro, fluoro, methyl, difluoromethyl, or trifluoromethyl. In other embodiments, $R^3$ is ethenyl, ethyl, 2,2,2-trichloroethyl, 2,2-dichloroethyl, 2-chloroethyl, 2,2,2-trifluoroethyl, 2,2-difluoroethyl, or 2-fluoroethyl, propyl, isopropyl, 1-propenyl, or 2-propenyl.

In some embodiments, the compounds suitable for use with the present invention have the structure of one of the formula cited herein wherein -$L^3$-$R^3$ is:

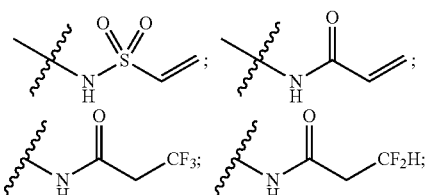

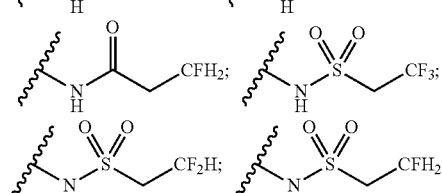

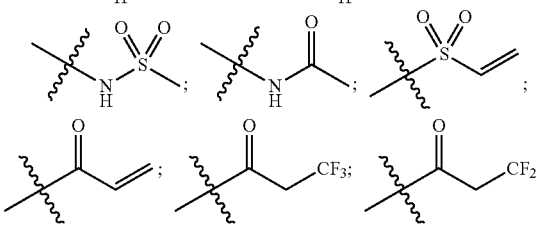

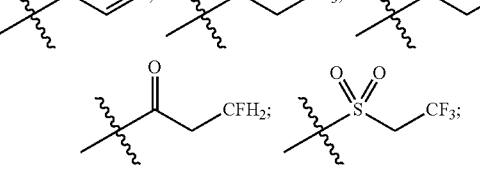

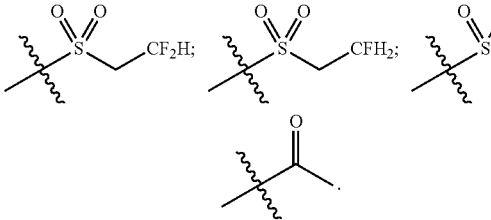

In some other embodiments, the compounds suitable for use with the present invention include those wherein $L^1$ is a bond. $R^1$ may be hydrogen or $NH_2$. In certain embodiments, $L^1$ is a bond; and $R^1$ is hydrogen. In certain other embodiments, $L^1$ is a bond; and $R^1$ is $NH_2$. In some embodiments, the present invention provides a compound where $L^2$ is a bond; and $R^2$ is methyl, ethyl, propyl, isopropyl, butyl, tert-butyl, pentyl, cyclopentyl, hexyl, cyclohexyl, methoxy, ethoxy, propoxy, or butoxy. In certain embodiments, $R^2$ is isopropyl or cyclopentyl. In certain embodiments, $R^2$ is isopropyl. In other embodiments, $R^2$ is cyclopentyl. In some other embodiments, $R^2$ is methoxy. In certain embodiments, c is 2; $L^2$ is a bond, and $R^2$ is methoxy, ethoxy, propoxy, or butoxy. In other embodiments, $R^2$ is methoxy.

In some embodiments, the present invention provides compounds that have:
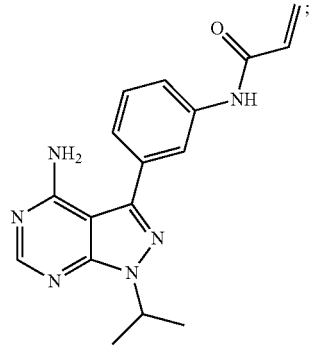
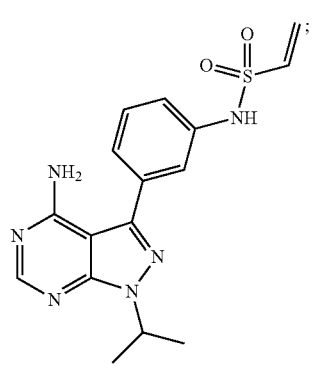
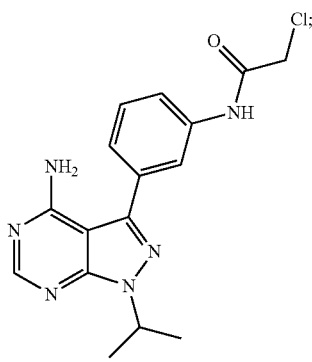
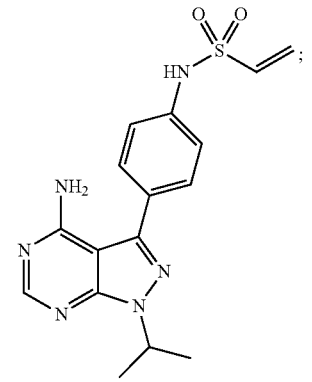
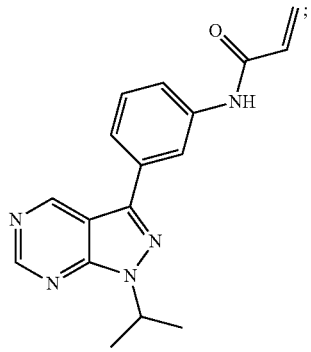
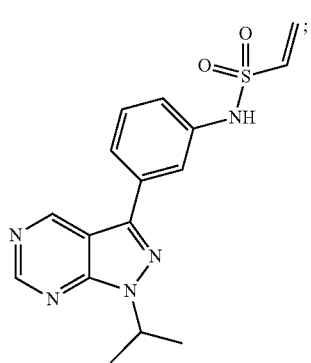
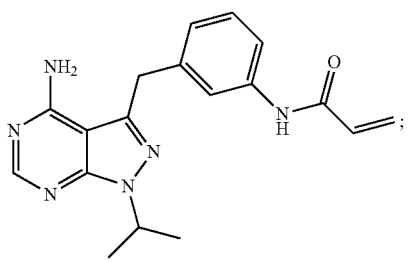
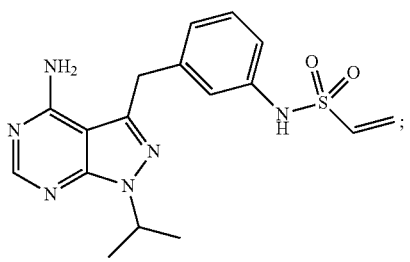
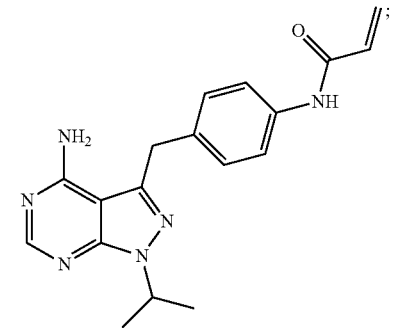

-continued
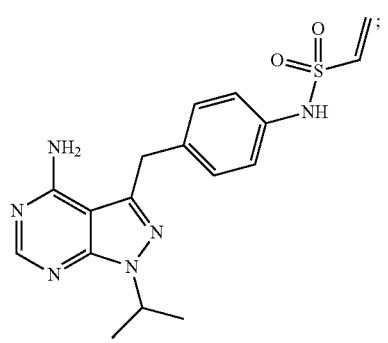
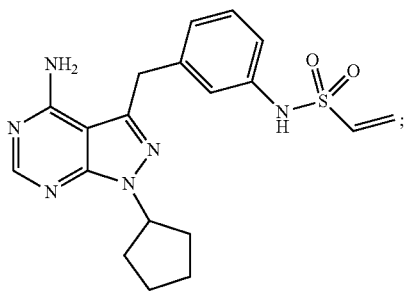
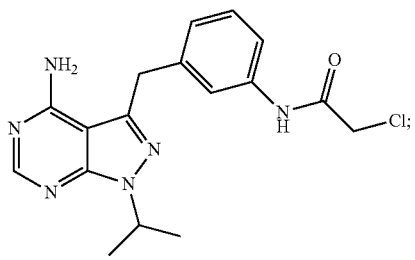
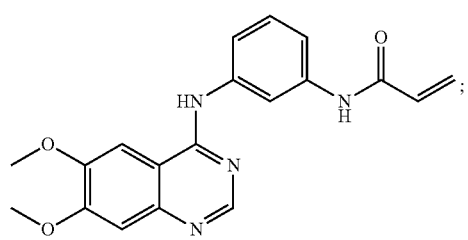
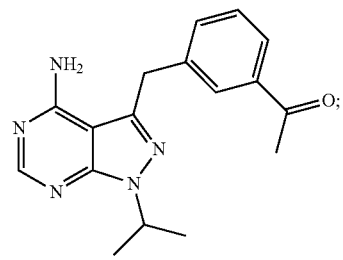
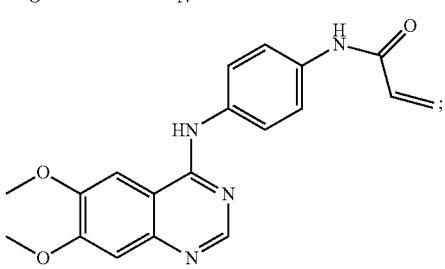
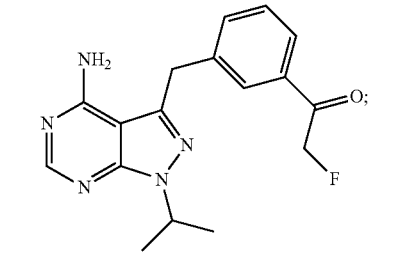
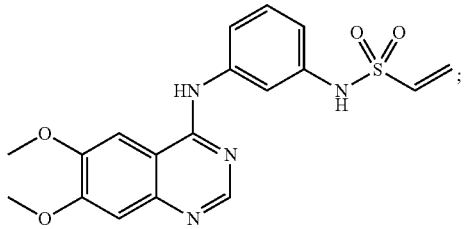
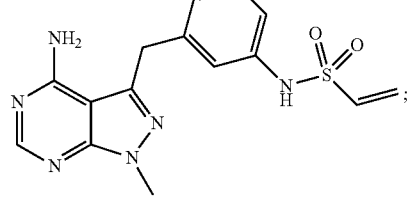
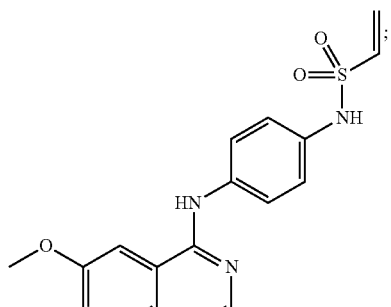
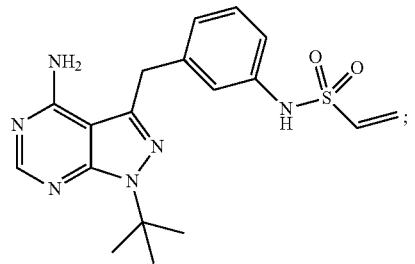
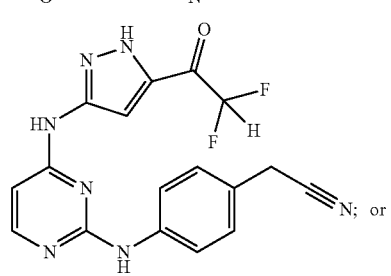

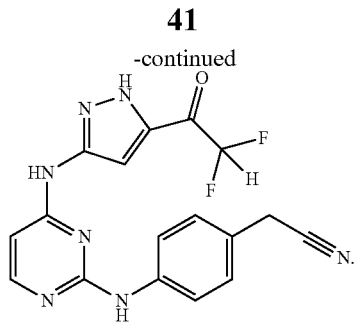

In some other embodiments, the present invention provides a compound having the below formula (which are useful inter alia, as inhibitors of Lrrk-2 kinases):

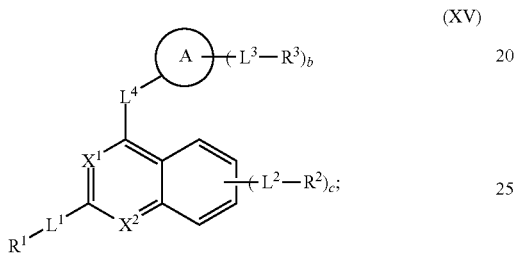
(XV)

$X^1$ and $X^2$ are, in each instance, independently =N— or =C(-$L^6$-$R^6$)—. Ring A is, in each instance, independently selected from cycloalkyl, heterocycloalkyl, aryl, or heteroaryl. $L^1$, $L^2$, $L^3$, and $L^4$ are as defined above (e.g., in each instance, independently selected from a bond, —C(O)—, —C(O)N($R^7$)—, —C(O)O—, —S(O)$_g$—, —S(O)$_2$N($R^7$)—, —O—, —N($R^7$)—, —N($R^7$)C(O)N($R^8$)—), substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, wherein g is an integer from 0 to 2). $R^1$, $R^2$, $R^3$, $R^6$, $R^7$, and $R^8$ are as defined above (e.g., in each instance, independently selected from hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl). The variable b is as defined above (e.g. an integer from 0 to 5; and c is as defined above (e.g. an integer from 0 to 4).

In some embodiments, the present invention provides a compound having the formula:

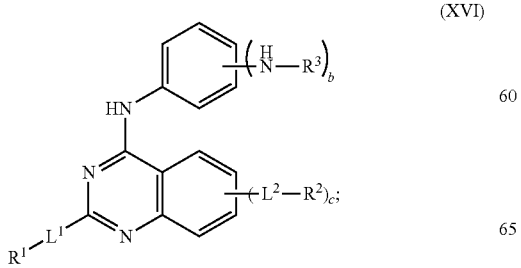
(XVI)

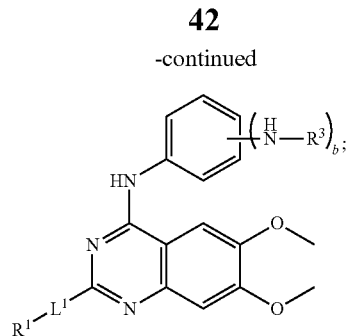
(XVII)

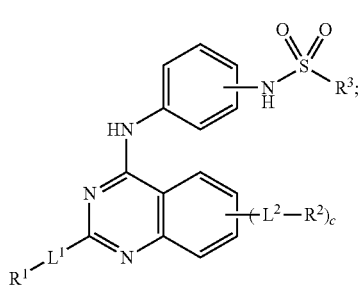
(XVIII)

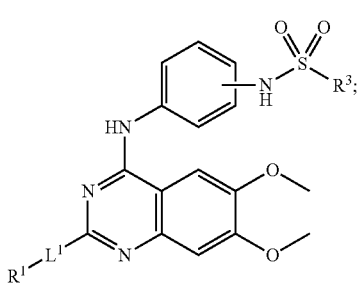
(XIX)

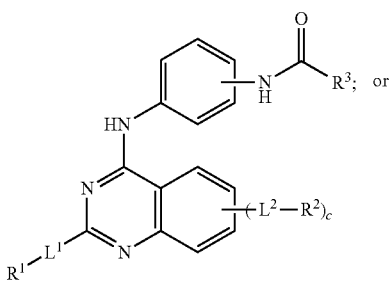
(XX)

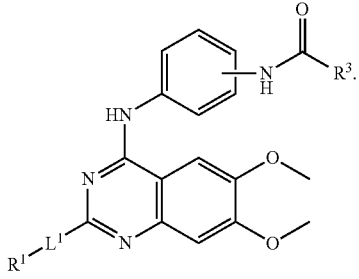
(XXI)

In some other embodiments, the compound provided herein has the formula (with the variables as defined above):

(XXII)
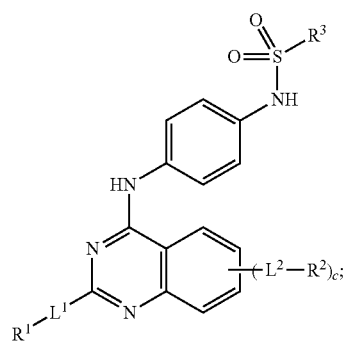
(XXVII)
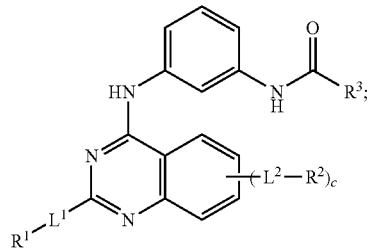
(XXIII)
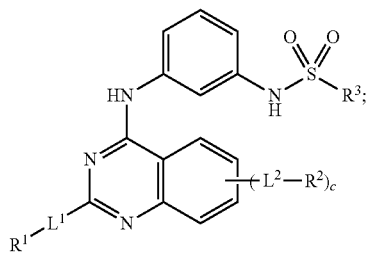
(XXVIII)
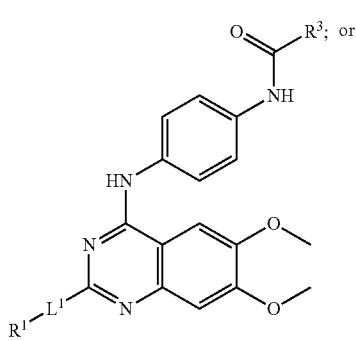
(XXIV)
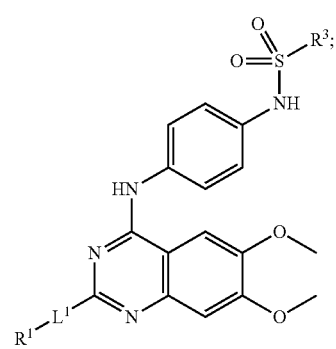
(XXIX)
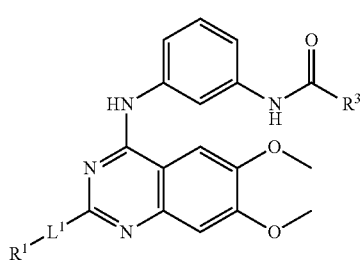
(XXV)
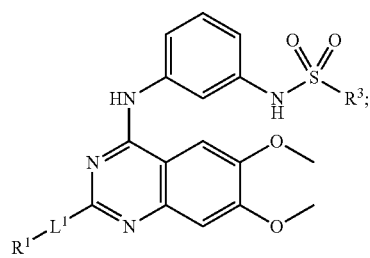
In other embodiments, the present invention provides compounds having the formula in the table below ("Table 1"):
(XXVI)
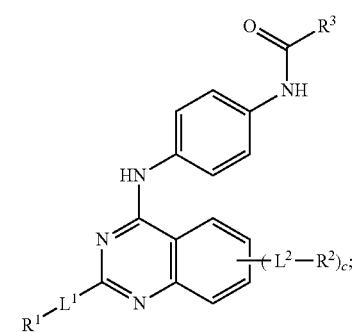
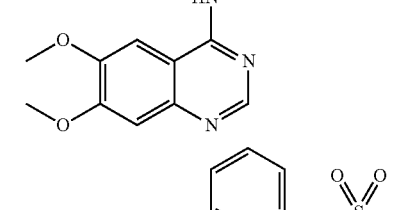
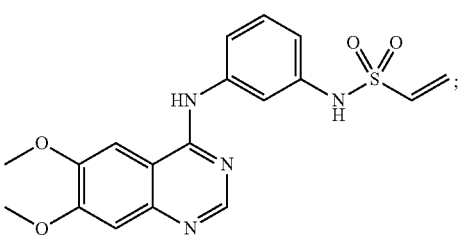

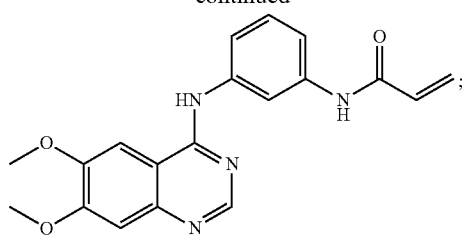
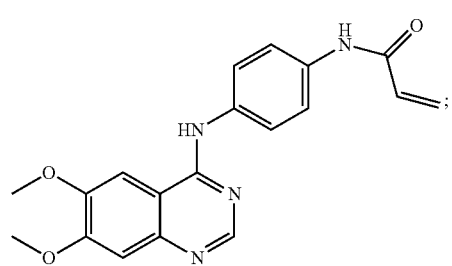
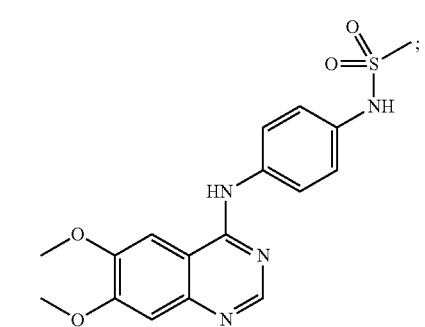
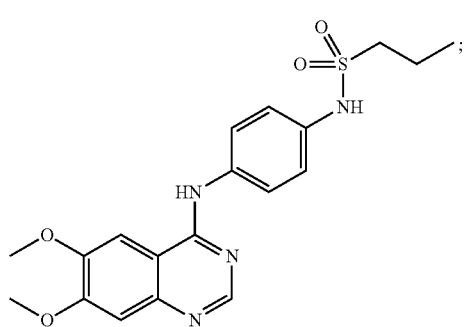
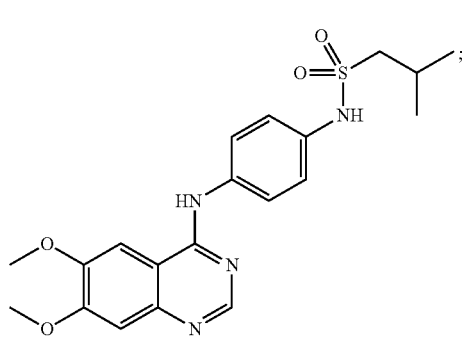
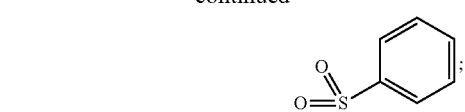
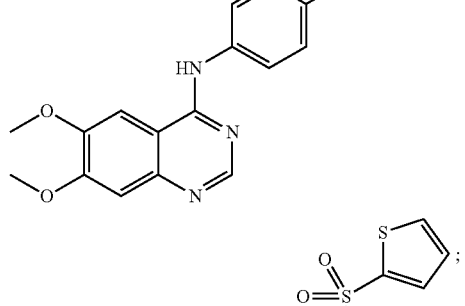
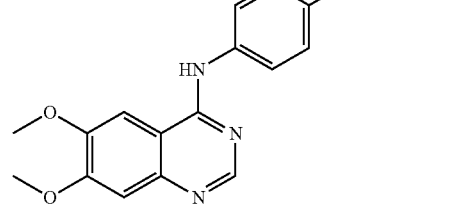
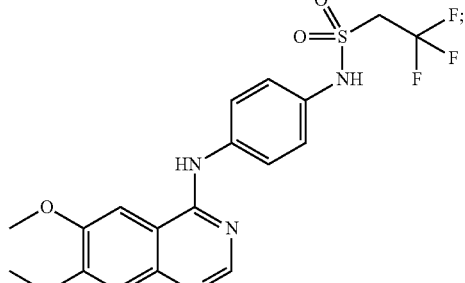
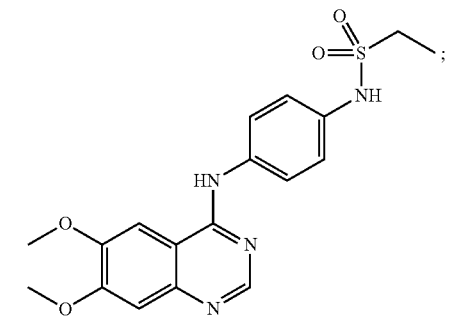
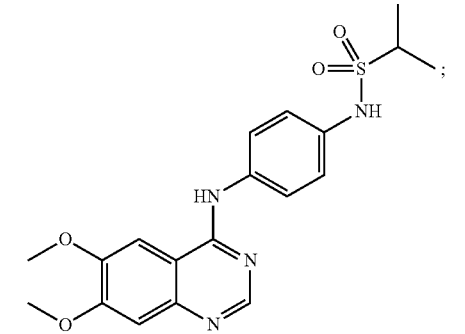

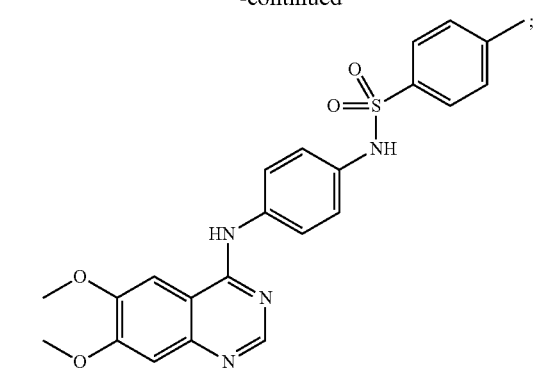

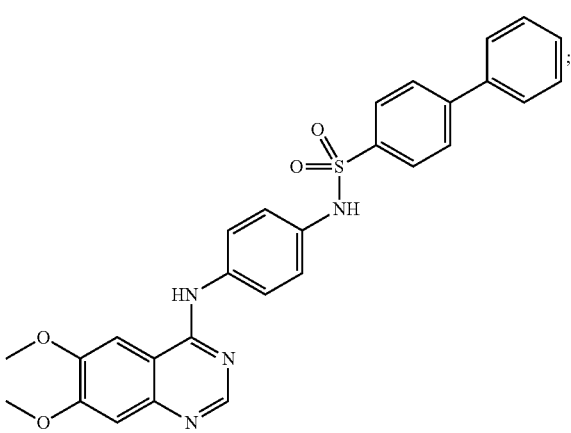

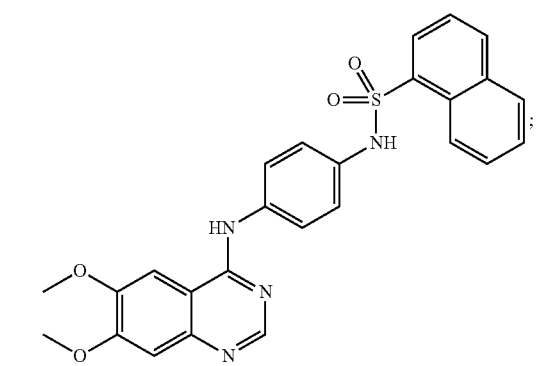

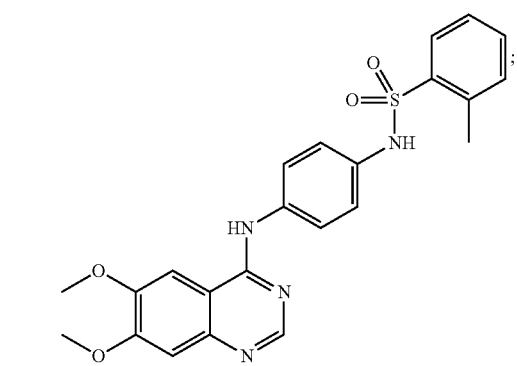

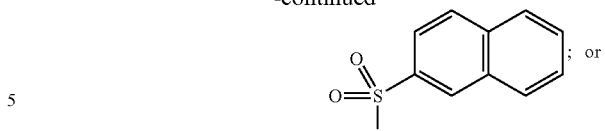

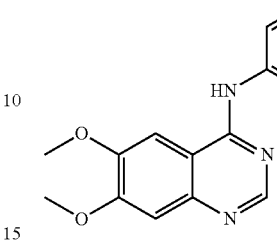

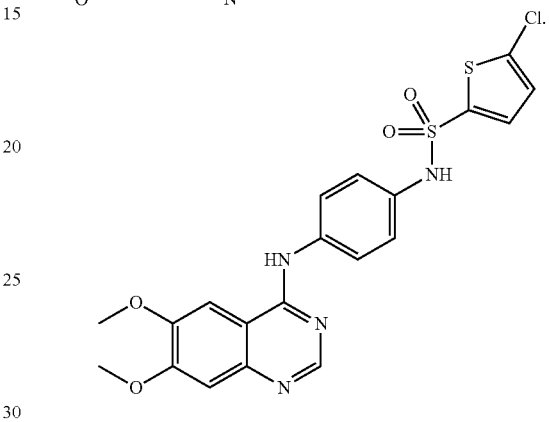

In certain embodiments, L³ is selected from a bond, —NH—, —C(O)—, —S(O₂)—, substituted or unsubstituted alkylene, or substituted or unsubstituted heteroalkylene. R³ may be selected from substituted or unsubstituted alkyl, substituted or unsubstituted heteroalkyl, or halogen. In other embodiments, R³ is methyl; difluoromethyl; trifluoromethyl; ethenyl; ethyl; 2,2,2-trichloroethyl; 2,2-dichloroethyl; 2-chloroethyl; 2,2,2-trifluoroethyl; 2,2-difluoroethyl; or 2-fluoroethyl; propyl; isopropyl; 1-propenyl; 2-propenyl; butyl; tert-butyl; napthyl; thiophene; 2-chloro-thiophene; phenyl; 2-methyl-phenyl; 3-methyl-phenyl; 4-methyl-phenyl; 2-phenyl-phenyl; 3-phenyl-phenyl; 4-phenyl-phenyl 2-chloro-thiophene; or 3-chloro-thiophene.

As described above, the term "inhibitor" may refer to an inhibitor of a recombinant kinase comprising a cysteine substitution at a gatekeeper amino acid position (i.e. a cysteine gatekeeper kinase inhibitor) and includes a compound described herein such as the compound of Formulae (I) to (XIV). In some embodiments, the inhibitors are able to covalently bind to cysteine. In some other embodiments, the inhibitors inhibit the kinase by bonding to the sulfylhydryl group of the cysteine residue at the gatekeeper amino acid position. In some embodiments, a compound provided herein may be a Lrrk-2 kinase inhibitor. In some embodiments, the Lrrk-2 kinase inhibitor is one or more of the compounds set forth in Table Z and/or a compound of Formula (XV) to (XXIX).

A person having ordinary skill in the art would immediately take into account the widely known principles of chemical when considering the description of compounds provided herein. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, or neutral conditions.

It will be apparent to one skilled in the art that certain compounds of this invention may exist in tautomeric forms, all such tautomeric forms of the compounds being within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, the replacement of a carbon by $^{13}$C- or $^{14}$C-enriched carbon, or the replacement of an iodine by $^{125}$I, are within the scope of this invention. All isotopic variations of the compounds of the present invention, whether radioactive or not, are encompassed within the scope of the present invention.

The compounds of the present invention also include the salts, hydrates, solvates and prodrug forms. The compounds of the present invention also include the isomers and metabolites of those described in Formula (I)-(XXIX).

Salts include, but are not limited, to sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases including alkali metal salts such as sodium salts, and potassium salts; alkaline earth metal salts such as calcium salts, and magnesium salts; aluminum salts; and ammonium salts. Other salts with organic bases include salts with diethylamine, diethanolamine, meglumine, and N,N'-dibenzylethylenediamine.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

The present invention also provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

In some embodiments, each substituted group described above for the compounds of the present invention is substituted with at least one substituent group. More specifically, in some embodiments, each substituted alkyl, substituted heteroalkyl, substituted cycloalkyl, substituted heterocycloalkyl, substituted aryl, substituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene described above is substituted with at least one substituent group. In other embodiments, at least one or all of these groups are substituted with at least one size-limited substituent group. Alternatively, at least one or all of these groups are substituted with at least one lower substituent group.

In other embodiments of the compounds described above, each substituted or unsubstituted alkyl is a substituted or unsubstituted $C_1$-$C_{20}$ alkyl, each substituted or unsubstituted alkylene is a substituted or unsubstituted $C_1$-$C_{20}$ alkylene, each substituted or unsubstituted heteroalkyl is a substituted or unsubstituted 2 to 20 membered heteroalkyl, each substituted or unsubstituted heteroalkylene is a substituted or unsubstituted 2 to 20 membered heteroalkylene, each substituted or unsubstituted cycloalkyl is a substituted or unsubstituted $C_3$-$C_8$ cycloalkyl, each substituted or unsubstituted cycloalkylene is a substituted or unsubstituted $C_3$-$C_8$ cycloalkylene, each substituted or unsubstituted heterocycloalkyl is a substituted or unsubstituted 4 to 8 membered heterocycloalkyl, each substituted or unsubstituted heterocycloalkylene is a substituted or unsubstituted 4 to 8 membered heterocycloalkylene, each substituted or unsubstituted aryl is a substituted or unsubstituted $C_6$ or $C_8$ aryl, each substituted or unsubstituted arylene is a substituted or unsubstituted $C_6$ or $C_8$ arylene, each substituted or unsubstituted heteroaryl is a substituted or unsubstituted $C_5$ or $C_6$ heteroaryl, and each substituted or unsubstituted heteroarylene is a substituted or unsubstituted $C_5$ or $C_6$ heteroarylene.

Alternatively, each substituted or unsubstituted alkyl is a substituted or unsubstituted $C_1$-$C_8$ alkyl, each substituted or unsubstituted alkylene is a substituted or unsubstituted $C_1$-$C_8$ alkylene, each substituted or unsubstituted heteroalkyl is a substituted or unsubstituted 2 to 8 membered heteroalkyl, each substituted or unsubstituted heteroalkylene is a substituted or unsubstituted 2 to 8 membered heteroalkylene, each substituted or unsubstituted cycloalkyl is a substituted or unsubstituted $C_3$-$C_6$ cycloalkyl, each substituted or unsubstituted cycloalkyl is a substituted or unsubstituted $C_3$-$C_6$ cycloalkylene, each substituted or unsubstituted heterocycloalkyl is a substituted or unsubstituted 3 to 6 membered heterocycloalkyl, and each substituted or unsubstituted heterocycloalkylene is a substituted or unsubstituted 3 to 6 membered heterocycloalkylene.

V. Kinases

In some embodiments, the present invention provides a recombinant kinase comprising a cysteine substitution at a gatekeeper amino acid position (also referred to as a "cysteine gatekeeper kinase", a "recombinant kinase of the present invention" or a "recombinant kinase set forth herein"). For example, the recombinant kinase can comprise a sequence having a cysteine substitution at the position corresponding to Thr338 of c-Src, such as the positions shown for SEQ ID NOs:58-77, and sequences having substantial identity thereto. That is, the recombinant kinase can comprise a sequence having at least about 85, 90, 92, 93, 94, 95, 96, 97, 98, or 99% identity to a sequence of any one of SEQ ID NOs:58-77, with a cysteine substitution at the position corresponding to Thr338 of c-Src.

In some embodiments, the recombinant kinase can have a sequence of SEQ ID NO:2 (T338C c-Src), or a sequence having substantial identity thereto. In some embodiments the recombinant kinase can comprise a sequence having at least about 85, 90, 92, 93, 94, 95, 96, 97, 98, or 99% identity to the sequence of SEQ ID NO:2 with a cysteine at the position corresponding to 338 (with reference to the full length sequence of SEQ ID NO:3). In some embodiments, the recombinant kinase comprises less than the full length of SEQ ID NO:2 or 3 (and substantially identical variants thereof), but retains the cysteine substitution at the position corresponding to amino acid 338 of SEQ ID NO:3. In some embodiments, the recombinant kinase comprises at least 8, 10, 12, 20, 25, 30, 35, 40, 50, 60, 70, 80, 90, 100, 120, 150, 175, 200 or more contiguous amino acids of SEQ ID NO:2 or a substantially identical sequence over that span retaining a cysteine at the amino acid position corresponding to 338 of SEQ ID NO:3.

In some embodiments, the recombinant kinase can have a sequence of any one of SEQ ID NOs:24-45 or a sequence having substantial identity thereto. These kinase sequences have a naturally occurring gatekeeper cysteine, i.e. a cysteine at the position corresponding to amino acid 338 in c-Src (SEQ ID NO:2 shows the T338C c-Src, while SEQ ID NO:4 shows the wild type T338 c-Src sequence). In some embodiments the recombinant kinase can comprise a sequence having at least about 85, 90, 92, 93, 94, 95, 96, 97, 98, or 99% identity to the sequence of any one of SEQ ID NOs:24-45 with a cysteine at the position corresponding to amino acid 338 of c-Src. In some embodiments, the recombinant kinase comprises less than the full length of any one of SEQ ID NOs:24-45 (and substantially identical variants thereof), but retains the cysteine at the position corresponding to amino acid 338 of c-Src. In some embodiments, the recombinant kinase comprises at least 8, 10, 12, 20, 25, 30, 35, 40, 50, 60, 70, 80, 90, 100, 120, 150, 175, 200 or more contiguous amino acids of any one of SEQ ID NOs:24-45 or a substantially identical sequence over that span retaining a cysteine at the position corresponding to 338 of SEQ ID NO:2.

In some other embodiments, the recombinant kinase has a $k_{cat}$ activity that is not substantially lower than the $k_{cat}$ activity of the corresponding wild-type kinase. In some embodiments, the $k_{cat}$ activity that is not substantially lower than the $k_{cat}$ activity of the corresponding wild-type kinase. In some embodiments, the recombinant kinase has a $K_m$ binding affinity for ATP of the recombinant kinase is not substantially lower than the $K_m$ binding affinity for ATP of the corresponding wild type kinase. In some embodiments, the $K_m$ binding affinity for ATP of the recombinant kinase is not substantially lower than the $K_m$ binding affinity for ATP of the corresponding wild type kinase. The activity is considered "not substantially lower" when the activity is not less than 5-fold less, e.g., 4-fold, 3-fold, or 2-fold less than the reference kinase. In some cases, the term "not substantially lower" is determined in terms of percentage, and a not substantially lower activity is at least 50% of the reference kinase, e.g. higher than 50% of the activity of a wild type kinase. In some embodiments, the activity is 60, 70, 75, 80, 85, 90, 95% or higher of the activity of the reference kinase.

The present invention provides methods for evaluating the use of a cysteine gatekeeper kinase.

In some embodiments, the recombinant kinase includes a recombinant kinase is selected from Src (e.g., c-Src (SEQ ID NOs:2-23 or 59) or v-Src (SEQ ID NO: 46-50 or 58); MOK; Sgk494; Yak/Yrk; SRPK1; CDK; DICTY-I; PAK/STE20; or Ctrl/DPYK1 with a cysteine at the gatekeeper position (at the amino acid position corresponding to 338 of the c-Src protein of SEQ ID NO:3. In some embodiments, the recombinant kinase is a recombinant Src and the gatekeeper amino acid position is T338.

In some embodiments, the recombinant kinase has a greater catalytic efficiency than the corresponding wild type kinase. For example, the kinase activity is greater than 100% of the reference kinase (e.g., wild type c-Src of SEQ ID NO:3). In some embodiments, the activity is 1.2-fold, 1.5-fold, 1.8-fold, 2-fold, 2.5-fold, 3-fold, 4-fold, 5-fold, 10-fold or higher than the reference. In some embodiments, the catalytic efficiency is measured as the ratio of $k_{cat}/K_m$.

In some embodiments, the recombinant kinase further comprises an additional amino acid substitution corresponding to position V323 of c-Src (see, e.g., SEQ ID NOs:10-23). That is, the recombinant kinase can be a cysteine gatekeeper kinase, i.e., comprising a sequence having substantial identity to any one of SEQ ID NOs:2-77 with a cysteine at the position corresponding to amino acid 338 of SEQ ID NO:3, and additionally include a substitution at the position corresponding to amino acid 323 of SEQ ID NO:3. One of skill will understand that the positions corresponding to those of SEQ ID NO:3 can be ascertained for other kinase sequences.

In some embodiments, the recombinant kinase further comprises an additional amino acid substitution corresponding to the position M314 of c-Src, e.g. to gly (G) or ala (A). For example, the recombinant kinase can be a cysteine gatekeeper kinase, i.e., comprising a sequence having substantial identity to any one of SEQ ID NOs:2-77 with a cysteine at the position corresponding to amino acid 338 of SEQ ID NO:3, and additionally include a substitution at the position corresponding to amino acid 314 of SEQ ID NO:3. One of skill will understand that the positions corresponding to those of SEQ ID NO:3 can be ascertained for other kinase sequences.

In some embodiments, the recombinant kinase includes substitutions at two or all three positions corresponding to positions 338, 314 and 323 of c-Src (SEQ ID NO:3). In some embodiments, the recombinant kinase comprises a sequence having substantial identity to SEQ ID NO:2 with a C at the position corresponding to amino acid 338 of c-Src (the full length sequence of SEQ ID NO:3), and also has a substitution at the position corresponding to amino acid 314 of c-Src. In some embodiments, the recombinant kinase comprises a sequence having substantial identity to SEQ ID NO:2 with a C at the position corresponding to amino acid 338 (of the full length sequence of SEQ ID NO:3), and also has a substitution at the position corresponding to amino acid 323 of c-Src. In some embodiments, the recombinant kinase comprises a sequence having substantial identity to SEQ ID NO:2 with a C at the position corresponding to amino acid 338 of c-Src (the full length sequence of SEQ ID NO:3), and also has a substitution at the positions corresponding to amino acids 314 and 323 of c-Src. Again, one of skill will be able to determine the corresponding amino acid positions for kinases with sequences that are not perfectly aligned with c-Src.

In some embodiments, the cysteine gatekeeper kinase has an additional amino acid substitution of alanine (A) or serine (S) at the position corresponding to V323 of c-Src (V323A (c-Src-ES2)] or V323S (c-Src-ES3). In some other embodiments, the recombinant kinase having an additional amino acid substitution at VAL323 has a greater catalytic efficiency of the corresponding recombinant kinase that does not have an additional amino acid substitution at VAL323. In some embodiments, the catalytic efficiency is measured as the ratio of $k_{cat}/K_m$.

In some embodiments, the corresponding substitutions can be performed in other kinases. A person having ordinary skill in the art would understand which amino acids correspond to VAL 323 in other kinases.

In some embodiments, the present invention provides methods and compositions for modifying the microenvironment around the cysteine gatekeeper by alteration of one nearby residue (e.g. Val323) in order to impact inhibitor potency. For example, liberating additional space with a V323A mutation resulted in a 5-fold increase in potency for 13, while the V3232S mutation had a 12-fold effect. In some embodiments, the present invention provides methods of boosting potency which may allow dosing levels sufficient to substantially minimize off-target effects with MOK kinase (the effects due to MOK inhibition can be taken into account by comparing effects in WT vs. ES expressing cells).

A. Forming a Kinase

In some other embodiments, the present invention provides a method of forming a recombinant kinase described herein, wherein the method includes transforming a cell with a nucleic acid encoding a recombinant kinase described herein, thereby forming a recombinant kinase described herein. In some embodiments, the recombinant kinase is selected from Src; MOK; Sgk494; Lrrk-2; Yak/Yrk; SRPK1; CDK; DICTY-I; PAK/STE20; or Ctrl/DPYK1 as described herein.

B. Structure Activity Relationship Studies—Inhibition of Src

In some embodiment, the present invention provides a series of 3-phenyl-substituted pyrazolopyrimidines with electrophilic groups at positions expected to be in close proximity to the gatekeeper residue and as set forth in Table 1. In some other embodiments, the electrophiles include meta and para substituents of the 3-phenyl ring and vinylsulfonamides as well as acrylamides and chloroacetamides. A meta-substituted vinylsulfonamide, 3 inhibited T338C relative to WT c-Src (>9-fold increase), while a para-substituted version, 5, elicited a ~6-fold improvement (Table 1). Acrylamides (1) and chloroacetamides (6) were also shown to be inhibitors. Under the assay conditions used (10 min preincubation with inhibitor prior to addition of ATP) $IC_{50}$ values under 5 µM for either 2 or 4 for WT or T338C c-Src were not shown.

TABLE 1

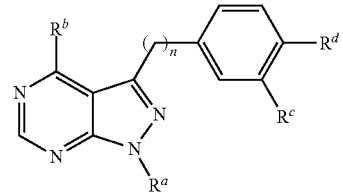

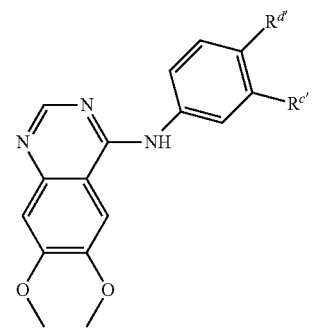

| Compound | n | $R^a$ | $R^b$ | $R^c$ | $R^d$ | WT c-Src $IC_{50}$ (nM) | T338C c-Src $IC_{50}$ (nM) |
|---|---|---|---|---|---|---|---|
| 1 | 0 | iPr | $NH_2$ | $NHCOCHCH_2$ | H | 2319 | 419 |
| 2 | 0 | iPr | H | $NHCOCHCH_2$ | H | >5000 | >5000 |
| 3 | 0 | iPr | $NH_2$ | $NHSO_2CHCH_2$ | H | 1004 | 111 |
| 4 | 0 | iPr | H | $NHSO_2CHCH_2$ | H | >5000 | >5000 |
| 5 | 0 | iPr | $NH_2$ | H | $NHSO_2CHCH_2$ | 899 | 145 |
| 6 | 0 | iPr | $NH_2$ | $NHCOCH_2Cl$ | H | >5000 | 817 |
| 7 | 1 | iPr | $NH_2$ | $NHCOCHCH_2$ | H | >5000 | 2762 |
| 8 | 1 | iPr | $NH_2$ | H | $NHCOCHCH_2$ | >5000 | >5000 |
| 9 | 1 | iPr | $NH_2$ | $NHSO_2CHCH_2$ | H | >5000 | 150 |
| 10 | 1 | iPr | $NH_2$ | H | $NHSO_2CHCH_2$ | 3083 | 1759 |
| 11 | 1 | iPr | $NH_2$ | $NHSO_2CH_2CH_3$ | H | >5000 | 3497 |
| 12 | 1 | iPr | $NH_2$ | $NHCOCH_2Cl$ | H | >5000 | >5000 |
| 13 | 1 | iPr | $NH_2$ | $COCH_2F$ | H | >5000 | 338 |
| 14 | 1 | iPr | $NH_2$ | $COCH_3$ | H | >5000 | 4520 |
| 15 | 1 | Me | $NH_2$ | $NHSO_2CHCH_2$ | H | >5000 | 3161 |
| 16 | 1 | tBu | $NH_2$ | $NHSO_2CHCH_2$ | H | >5000 | 618 |
| 17 | 1 | Cp | $NH_2$ | $NHSO_2CHCH_2$ | H | >5000 | 196 |

| Compound | $R^{c'}$ | $R^{d'}$ | | |
|---|---|---|---|---|
| 18 | $NHCOCHCH_2$ | H | >5000 | 1661 |
| 19 | $NHSO_2CHCH_2$ | H | >5000 | 1004 |
| 20 | H | $NHSO_2CHCH_2$ | 2170 | 560 |

$IC_{50}$ values for electrophile derivatized pyrazolopyrimidines and 4-anilinoquinazolines against WT c-Src and T338C c-Src. Scaffolds are depicted such that the hinge-binding element is located on the left. Note that for covalent inhibitors $IC_{50}$ values are time-dependent. In these assays, the inhibitors were preincubated with the Src for ten minutes prior to assay initialization by addition of ATP.

An array of 3-benzyl-substituted pyrazolopyrimidines modified with electrophiles or isosteric and unreactive negative control groups at the meta and para positions were synthesized and screened against WT and T338C c-Src (compounds 7-17, Table 1). The benzyl functionalized compounds inhibitored wild type c-Src ($IC_{50}$ values >5 µM). Compound, 9, which is functionalized with a vinylsulfonamide, exhibited an $IC_{50}$ value of 150 nM. An unreactive control compound 11 resulted in a 23-fold drop in potency. A fluoromethylketone bearing compound, 13, yielded an $IC_{50}$ value of 338 nM, which was >13-fold more potent than the corresponding ketone, 14.

The present invention also provides methods of determining the activity effects of modifying the N1 position of pyrazolopyrimidines by a structure activity relationship (SAR). In some embodiments, this includes using the pyrazolopyrimidine scaffold with a benzyl-linked m-vinylsulfonamide, see compounds 9, 15-17; Table 1 This analysis revealed that secondary alkyl groups such as isopropyl (9) and cyclopentyl (17) moieties inhibit T338C c-Src. These results indicate that substitution at N1 can be used to modulate potency against T338C c-Src. Accordingly, the present invention provides methods of modulating the potency against kinases, such as c-Src.

The present invention provides methods and compositions that are suitable for use with a variety of kinases, e.g. recombinant, wild type, natural, mutant, and unmutated. In some embodiments, these kinases include c-Src, Src: Src; MOK; Sgk494; Yak/Yrk; SRPK1; CDK; DICTY-I; PAK/STE20; or Ctrl/DPYK1.

In some embodiments, the recombinant kinases described herein include an approximate 15 residue His tag in addition to the sequence for the actual protein, e.g. linker and heptamer for specific TEV protein cutting. In some instances TEV may be cut at residue 248, 249, or 250. It is understood by those in the art that the DNA sequence can be optimized with respect to the code or sequence without affecting the primary protein encoded thereby.

The following sets forth gatekeeper residues. In some embodiments, the gatekeeper residue is cysteine. In some embodiments the kinase is natural, wild type, or recombinant.

As described herein, a Cys gatekeeper is an attractive target for the inhibitory compounds described herein. Representative kinases having a naturally occurring Cys at the gatekeeper position include the entries of Table 2 following. As customary in the art, the terms "GI: number," "GI: No." and the like refer to a unique sequence identifier (i.e., "GenBank Identifier") for a sequence.

TABLE 2

| SEQ ID NO: | GI: No. | Species |
| --- | --- | --- |
| 24 | 4587987 | Arabidopsis thaliana |
| 25 | 19424095 | Arabidopsis thaliana |
| 26 | 1785621 | Arabidopsis thaliana |
| 27 | 4678270 | Arabidopsis thaliana |
| 28 | 4678272 | Arabidopsis thaliana |
| 29 | 4678273 | Arabidopsis thaliana |
| 30 | 4678277 | Arabidopsis thaliana |
| 31 | 4886274 | Arabidopsis thaliana |
| 32 | 3047095 | Arabidopsis thaliana |
| 33 | 334188021 | Arabidopsis thaliana |
| 34 | 9294588 | Arabidopsis thaliana |
| 35 | 11120792 | Arabidopsis thaliana |
| 36 | 11120796 | Arabidopsis thaliana |
| 37 | 8777331 | Arabidopsis thaliana |
| 38 | 7106391 | Mus musculus |
| 39 | 1705720 | Carassius auratus |
| 40 | 6648996 | Capsicum annuum |
| 41 | 7630151 | Leishmania major |
| 42 | 5139689 | Homo sapiens |
| 43 | 486948 | Trichomonas vaginalis |
| 44 | 254688446 | Plasmodium falciparum |
| 45 | 13509297 | Dictyostelium discoideum |

VI. Co-Crystals of Kinase and a Compound

The present invention provides co-crystals of a kinase and a compound, e.g. co-crystal structure of T338C c-Src with a vinylsulfonamide-derivatized pyrazolopyrimidine inhibitor is provided, see Example 34.

In the 9-c-Src-ES1 co-crystal structure, the pyrazolopyrimidine pharmacophore interacts with the backbone amides of Glu339 and Met341 of the hinge region (FIG. 2A). The oxygen atoms of the sulfonamide hydrogen bond directly to the backbone amide of Asp404 and to that of Phe405 via a water molecule (FIG. 2B, C). Additionally, the nitrogen of the sulfonamide makes a direct hydrogen bond to the side chain Glu310 (FIGS. 2A, C). In crystal structures of wild type Src, the hydroxyl of the gatekeeper threonine is often directed towards the C4-exocyclic amine of the adenine portion of ATP mimetics.

In the 9 c-Src-ES1 co-crystal structure, the sulfhydryl of Cys338 adopts a distinct rotamer to accommodate the bulky C-3 benzyl group and facilitate a covalent bond (FIG. 2C).

The flexible ethylsulfonamide moiety is situated to allow the covalent linkage with Cys338 (FIG. 2B). The side chain of Met314, a critical component of the hydrophobic spine, is dramatically shifted relative to its position in other c-Src structures (FIGS. 2B, C). Movement of Met314 may prevent a steric clash with the ethylsulfonamide moiety of 9.

VII. Pharmaceutical Compositions

In some embodiments, the present invention provides a pharmaceutical composition comprising a compound as set forth herein (e.g. a compound of Formula (I)-(XXIX)) and a pharmaceutically acceptable excipient.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

The compounds and compositions of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds and compositions of the present invention can be administered transdermally. The GR modulators of this invention can also be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995). Accordingly, the present invention also provides pharmaceutical compositions including a pharmaceutically acceptable carrier or excipient and either a compound of Formula I, or a pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a GR modulator in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

VIII. Administration

The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The compounds described herein can be used in combination with one another, with other active agents known to be useful in modulating a protein kinase, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

IX. Nucleic Acids

In some embodiments, the present invention provides an isolated nucleic acid comprising a nucleic acid sequence encoding a recombinant kinase provided herein (i.e. a recombinant kinase comprising a cysteine substitution at a gatekeeper amino acid position). This is also referred to herein as a "nucleic acid of the present invention." Thus, provided herein are nucleic acids that encode the cysteine gatekeeper kinases described herein, e.g., recombinant kinases having a cysteine in the position corresponding to amino acid 338 of c-Src (SEQ ID NO:3).

In some embodiments, the nucleic acid sequence encodes a sequence or an enzymatically functional fragment thereof, set forth in SEQ ID NOs 2-77. The enzymatically functional fragment may be 50, 100, 150, or 200 bases in length. In some embodiments, the nucleic acid encodes a polypeptide having substantial identity to any one of SEQ ID NOs:2-77 wherein the polypeptide has a cysteine at the position corresponding to amino acid 338 of c-Src. One of skill will understand that a number of nucleic acid sequences will encode the some polypeptide, due to the degeneracy of the nucleic acid code. In some embodiments, the nucleic acid encodes a polypeptide encoding any one of SEQ ID NOs:2-77, wherein the polypeptide has a cysteine at the position corresponding to 338 of c-Src, or a sequence having at least 75, 80, 85, 90, 91, 92, 93, 94, 95, 96, 97, 98, or 99% identity thereto. In some embodiments, the polypeptide is shorter than the full length of any one of SEQ ID NOs:2-77, but retains enzymatic (kinase) activity. In some embodiments, the polypeptide is at least 25, 30, 40, 50, 75, 80, 100, 120, 150, 200 or more amino acids in length, and has substantial identity over the corresponding length of the selected sequence (selected from the sequences consisting of SEQ ID NOs:2-77, having a C at the position corresponding to 338 of c-Src). For the non-identical amino acids, one of skill will understand that conservative amino acid substitutions can be included.

In some embodiments, the nucleic acid encodes a polypeptide having substantial identity to any one of SEQ ID NOs:2-77 wherein the polypeptide has a cysteine at the position corresponding to amino acid 338 of c-Src, and an additional amino acid substitution at the position corresponding to amino acid 323 of c-Src and/or the position corresponding to amino acid 314 of c-Src. One of skill will understand that a number of nucleic acid sequences will encode the same polypeptide, due to the degeneracy of the nucleic acid code. In some embodiments, the nucleic acid encodes a polypeptide encoding any one of SEQ ID NOs:2-77, wherein the polypeptide has a cysteine at the position corresponding to 338 of c-Src, and optionally one or both of the substitutions at positions corresponding to amino acids 314 or 323 of c-Src, or a sequence having at least 75, 80, 85, 90, 91, 92, 93, 94, 95, 96, 97, 98, or 99% identity thereto. In some embodiments, the polypeptide is shorter than the full length of any one of SEQ ID NOs:2-77, but retains enzymatic (kinase) activity. In some embodiments, the polypeptide is at least 25, 30, 40, 50, 75, 80, 100, 120, 150, 200 or more amino acids in length, and has substantial identity over the corresponding length of the selected sequence (selected from the sequences consisting of SEQ ID NOs:2-77, having a C at the position corresponding to 338 of c-Src, and optionally one or both of the substitutions at positions corresponding to amino acids 314 or 323 of c-Src).

In some other embodiments, the present invention provides an expression cassette comprising a nucleic acid of the present invention. In yet other embodiments, the expression cassette is a recombinant viral vector. In some other embodiments, the expression cassette of is inside of a host cell. In other embodiments, the expression cassette is selected from mammalian, non-mammalian, mouse, rat, or human. In some embodiments, the recombinant kinase is inside a cell. In some other embodiments, the cell is selected from mammalian, non-mammalian, mouse, rat, or human. Thus, in some embodiments, a transgenic mouse or rat is provided, wherein the transgenic mouse or rat expresses a recombinant kinase comprising a cysteine substitution at a gatekeeper amino acid position as described above. Methods of producing a transgenic mouse or rat that expresses recombinant proteins and enzymes are well-known in the art. A detailed description for such procedures may be found elsewhere, for example at U.S. Pat. No. 4,736,866, the contents of which are incorporated by reference in their entirety for all purposes.

A. Descriptions of SEQ ID NOs (1-51) Follows.

The following sets forth SEQ ID NOs: 1-51 that are suitable for use with the compositions, methods, and kits herein:

| SEQ ID NO: | Description |
| --- | --- |
| 1 | DNA construct for T338C c-src (251-533) |
| 2 | Protein encoded by SEQ ID NO: 1 |
| 3 | *Gallus gallus* proto-oncogene (c = -Src) |
| 4 | c-Src (251-533) |
| 5 | c-Src (251-533) with GHM at N-terminal |
| 6 | [T338X]c-Src (251-533) |
| 7 | GHM-[T338X]c-Src (251-533) (GHM at N-terminal) |
| 8 | [T338C]c-Src (251-533) (c-Src "ES1") |
| 9 | GHM-[T338C]c-Src (251-533) (GHM at N-terminal) (c-Src "ES1") |
| 10 | [T338X, V323X]c-Src (251-533) |
| 11 | GHM-[T338X, V323X]c-Src (251-533) (GHM at N-terminal) |
| 12 | [T338C, V323X]c-Src (251-533) |
| 13 | GHM-[T338C, V323X]c-Src (251-533) (GHM at N-terminal) |
| 14 | [T338C, V323A]c-Src (251-533) (c-Src "ES2") |
| 15 | GHM-[T338C, V323A]c-Src (251-533) (GHM at N-terminal) (c-Src "ES2") |
| 16 | [T338C, V323S]c-Src (251-533) (c-Src "ES3") |
| 17 | GHM-[T338C, V323S]c-Src (251-533) (GHM at N-terminal) (c-Src "ES3") |
| 18 | [T338C, V323D]c-Src (251-533) (c-Src "ES4") |
| 19 | GHM-[T338C, V323D]c-Src (251-533) (GHM at N-terminal) (c-Src "ES4") |
| 20 | [T338C, V323E]c-Src (251-533) (c-Src "ES5") |
| 21 | GHM-[T338C, V323E]c-Src (251-533) (GHM at N-terminal) (c-Src "ES5") |
| 22 | [T338C, V323H]c-Src (251-533) (c-Src "ES6") |
| 23 | GHM-[T338C, V323H]c-Src (251-533) (GHM at N-terminal) (c-Src "ES6") |
| 24 | Kinases with gatekeeper Cys (*Arabidopsis thaliana*) 4587987 |
| 25 | Kinases with gatekeeper Cys (*Arabidopsis thaliana*) 19424095 |
| 26 | Kinases with gatekeeper Cys (*Arabidopsis thaliana*) 1785621 |
| 27 | Kinases with gatekeeper Cys (*Arabidopsis thaliana*) 4678270 |
| 28 | Kinases with gatekeeper Cys (*Arabidopsis thaliana*) 4678272 |
| 29 | Kinases with gatekeeper Cys (*Arabidopsis thaliana*) 4678273 |
| 30 | Kinases with gatekeeper Cys (*Arabidopsis thaliana*) 4678277 |
| 31 | Kinases with gatekeeper Cys (*Arabidopsis thaliana*) 4886274 |
| 32 | Kinases with gatekeeper Cys (*Arabidopsis thaliana*) 3047095 |
| 33 | Kinases with gatekeeper Cys (*Arabidopsis thaliana*) 334188021/15238494 |
| 34 | Kinases with gatekeeper Cys (*Arabidopsis thaliana*) 9294588 |
| 35 | Kinases with gatekeeper Cys (*Arabidopsis thaliana*) 11120792 |
| 36 | Kinases with gatekeeper Cys (*Arabidopsis thaliana*) 11120796 |
| 37 | Kinases with gatekeeper Cys (*Arabidopsis thaliana*) 8777331 |
| 38 | Kinases with gatekeeper Cys (*Mus musculus*) 7106391 |
| 39 | Kinases with gatekeeper Cys (*Carassius auratus*) 1705720 |
| 40 | Kinases with gatekeeper Cys (*Capsicum annuum*) 6648996 |
| 41 | Kinases with gatekeeper Cys (*Leishmania major*) 7630151 |
| 42 | Kinases with gatekeeper Cys (*Homo sapiens*) 5139689 |
| 43 | Kinases with gatekeeper Cys (*Trichomonas vaginalis*) 486948 |
| 44 | Kinases with gatekeeper Cys (*Plasmodium falciparum*) 254688446/3845109 |
| 45 | Kinases with gatekeeper Cys (*Dictyostelium discoideum*) 13509297 |
| 46 | v-Src (Rous sarcoma virus) |
| 47 | [I338X]v-Src |
| 48 | [I338C]v-Src |
| 49 | [I338T]v-Src |
| 50 | [I338G]v-Src |
| 51 | Artificial sequence (substrate for methods of testing) |

An exemplary DNA construct useful for the methods described herein was synthesized (SEQ ID NO: 1). This construct encodes the expressed protein set forth in SEQ ID NO:2. The expressed protein includes a His$_6$ (SEQ ID NO:78) tag sequence at the N-terminal, useful for purification of recombinantly expressed protein as known in the art. The expressed protein further includes a spacer sequence (i.e., DYDIPTT, (SEQ ID NO:79), SEQ ID NO:2 residues 7-13) and a tobacco etch viral (TEV) protease site (i.e., ENLYFQG, (SEQ ID NO: 80), SEQ ID NO:2, residues 14-20) as known in the art. An additional spacer (e.g., SEQ ID NO:2, residues 21-22) may be present in expressed proteins, which spacers residues may occupy the N-terminal position(s) of the expressed protein after protease cleavage (e.g., TEV protease cleavage). Thus, it is understood that reference to "c-Src (251-533)" and variants thereof herein contemplates expressed proteins having one or more amino acids at the N-terminal which may result from the process of recombinant protein production. For example, after the action of the TEV protease on the protein of SEQ ID NO:2, the expressed c-Src (251-533) protein may include the N-terminal tripeptide "GHM." It is understood that absent indication otherwise, the numbering of c-Src proteins and variants as discussed herein follows the numbering of the full c-Src protein (SEQ ID NO:3). For example, full length c-Src (SEQ ID NO:3) contains 533 residues. Accordingly, residues 23-305 of SEQ ID NO:2 correspond to residues 251-533 of SEQ ID NO:3. c-Src (251-533) is expressly set forth in SEQ ID NO:4. A recombinantly expressed and processed protein of c-Src (251-533), as described above, having the N-terminal tripeptide "GHM" is set forth in SEQ ID NO:5.

In some embodiments, a c-Src variant is provided wherein the residue at the position equivalent to $Thr^{338}$ of c-Src (SEQ ID NO:3) is substituted with another amino acid. In some embodiments, the substituted amino acid is a naturally occurring amino acid, as known in the art. Exemplary recombinantly expressed proteins having this substitution are set forth in SEQ ID NO:6 and SEQ ID NO:7, wherein SEQ ID NO:7 further includes the N-terminal tripeptide "GHM" as described above. Similarly, in some embodiments, a v-Src variant is provided wherein the residue at the position equivalent to $Thr^{338}$ of v-Src (SEQ ID NO:46) is substituted with another amino acid. An exemplary recombinantly expressed protein having this substitution is set forth in SEQ ID NO:47. Specific exemplary recombinantly expressed proteins having a C, T or G substitution at position 338 of v-Src (i.e., [I338C] v-Src, [I338T]v-Src, [I338G]v-Src), are set forth in SEQ ID NO: 48, SEQ ID NO:49 and SEQ ID NO:50, respectively.

In some embodiments, a protein kinase is provided having a Thr to Cys substitution at the position corresponding to residue 338 of c-Src (i.e., T338C substitution). The protein may be a fragment of full length c-Src. Recombinantly expressed protein variants of c-Src (251-533) having a T338C substitution (i.e., [T338C]c-Src(251-533)) are set forth in SEQ ID NO:8 and SEQ ID NO:9. It is understood that within the context of protein descriptive names, bracketed (i.e., "[ ]") entries denote substitution(s), and that parenthetic entries after the protein name denote the corresponding residues of the fragment. For example, "[T338C]c-Src(251-533)" refers to the fragment of c-Src from residue 251 to residue 533, additionally having a Thr to Cys substitution at position 338 (c-Src numbering). These proteins are also known as "c-Src ES1" proteins. It is further understood that, as customary in the art, the term "XNNNY" refers to substitution of residue "X" at position "NNN" with residue "Y."

In some embodiments, a plurality of substitutions of c-Src, or fragment thereof, are provided. For example, in some embodiments, a protein having double substitutions at residues $T^{338}$ and $V^{323}$ of c-Src is provided. In some embodiments, a protein having double substitutions at residues $T^{338}$ and $V^{323}$ of a fragment of c-Src (e.g., c-Src(251-533)) is provided. See SEQ ID NO:10. In some embodiments, the fragment of c-Src includes an N-terminal oligopeptide sequence resulting from processing of the recombinant protein as described above. See SEQ ID NO:11.

In some embodiments, there is provided a T338C substitution of c-Src, or fragment thereof (e.g., c-Src(251-533), in combination with a substitution at position 323. See SEQ ID NO:12. In some embodiments, such doubly substituted fragment of c-Src includes an N-terminal oligopeptide sequence resulting from processing of the recombinant protein as described above. See SEQ ID NO:13.

In some embodiments, a T338C substitution of c-Src, or fragment thereof (e.g., c-Src(251-533), in combination with a specific substitution at position 323 is provided. For example, $[T^{338}C, V^{323}A]$c-Src(251-533) is set forth in SEQ ID NO:14, and the corresponding protein having an N-terminal oligopeptide sequence resulting from processing of the recombinant protein is set forth in SEQ ID NO:15. These doubly substituted proteins are also known as the so-called c-Src "ES2" variant.

Further exemplary of this embodiment, there is provided $[T^{338}C, V^{323}S]$c-Src(251-533) (SEQ ID NO:16), and the corresponding protein having an N-terminal oligopeptide sequence resulting from processing of the recombinant protein (SEQ ID NO:17). These doubly substituted proteins are also known as the so-called c-Src "ES3" variant.

Further exemplary of this embodiment, there is provided $[T^{338}C, V^{323}D]$c-Src(251-533) (SEQ ID NO:18), and the corresponding protein having an N-terminal oligopeptide sequence resulting from processing of the recombinant protein (SEQ ID NO:19). These doubly substituted proteins are also known as the so-called c-Src "E54" variant.

Further exemplary of this embodiment, there is provided $[T^{338}C, V^{323}E]$c-Src(251-533) (SEQ ID NO:20), and the corresponding protein having an N-terminal oligopeptide sequence resulting from processing of the recombinant protein (SEQ ID NO:21). These doubly substituted proteins are also known as the so-called c-Src "ES5" variant.

Further exemplary of this embodiment, there is provided $[T^{338}C, V^{323}H]$c-Src(251-533) (SEQ ID NO:22), and the corresponding protein having an N-terminal oligopeptide sequence resulting from processing of the recombinant protein (SEQ ID NO:23). These doubly substituted proteins are also known as the so-called c-Src "ES6" variant.

X. Methods

A. General

In some embodiments, the present invention provides methods of determining the role of a kinase in a cell. In certain embodiments, the methods include determining the dependence of transformed cells on aberrant oncogenic signaling by the EGFR kinase. In other embodiments, the determining includes assaying inhibitor-induced conformational changes of kinases. In other embodiments, the methods include elucidating the mechanisms of inhibitor-induced Akt hyperphosphorylation. In some embodiments, the methods include transactivation of RAF dimmers.

In some other embodiments, the present invention provides a chemical genetic approach based on engineered shape complementarity between the kinase active site and a small molecule inhibitor, which allows systematic discovery of an inhibitor for a particular kinase. In some embodiments, a conserved hydrophobic residue in the kinase active site known as the "gatekeeper" is mutated to a small residue such as glycine or alanine to generate a uniquely targetable mutant kinase termed an analog-sensitive (AS) allele.

In certain other embodiments, the present invention provides methods of making engineered kinase which can be targeted with sterically bulky analogs of natural kinase inhibitors, which are capable of occupying the enlarged engineered kinase pocket (FIG. 1). In some embodiments, the methods include wild type kinases which may be resistant to inhibition by the bulky analog as the result of a steric clash with naturally occurring gatekeeper residues (e.g. Met, Leu, Phe, Thr, Gln and others). In yet other instances, the wild type kinases may not be resistant to inhibition by the bulky analog as the result of a steric clash with naturally occurring gatekeeper residues (e.g. Met, Leu, Phe, Thr, Gln and others).

B. Structure Activity Relationship (SAR) Analysis

In order to determine the effects of modifying the group at this position, a structure activity relationship (SAR) analysis was performed on the pyrazolopyrimidine scaffold with a benzyl-linked m-vinylsulfonamide (compounds 9, 15-17; Table 2). This analysis revealed that secondary alkyl groups such as isopropyl (9) and cyclopentyl (17) moieties elicited optimal activity against T338C c-Src. Relative to isopropyl substitution, tert-butyl (16) and methyl (15) derivatization resulted in 4- and 21-fold drops in potency, respectively.

Collectively, these results indicate that substitution at N1 can be used to modulate potency against T338C c-Src. IN some instances, Michael acceptor-derivatized 4-anilino-quinazolines were synthesized and evaluated as inhibitors (compounds 18-20; Table 2).

In some embodiments, the ES kinase alleles should be useful for a host of other applications. For example, fluorescently labeled versions of the inhibitors could be used to quantitatively probe the occupancy of kinase active sites to determine the percent activity required for signaling events. In some other embodiments, the present invention provides a method for determining the properties of pseudokinases, for which there is no good readout of active site occupancy. In certain embodiments, the present invention sets forth the use of irreversible inhibitors and allows for the validation of target specificity.

In some embodiments, the present invention provides methods of evaluating the reversibility of inhibition of a kinase as set forth herein. In some embodiments, an electrophilic inhibitors covalently interact with the cysteine gatekeeper. In one instance, two compounds, 9 and 13, were assayed accordingly. Both compounds inhibited T338C c-Src in a time-dependent manner (Table 3).

Figure 2:
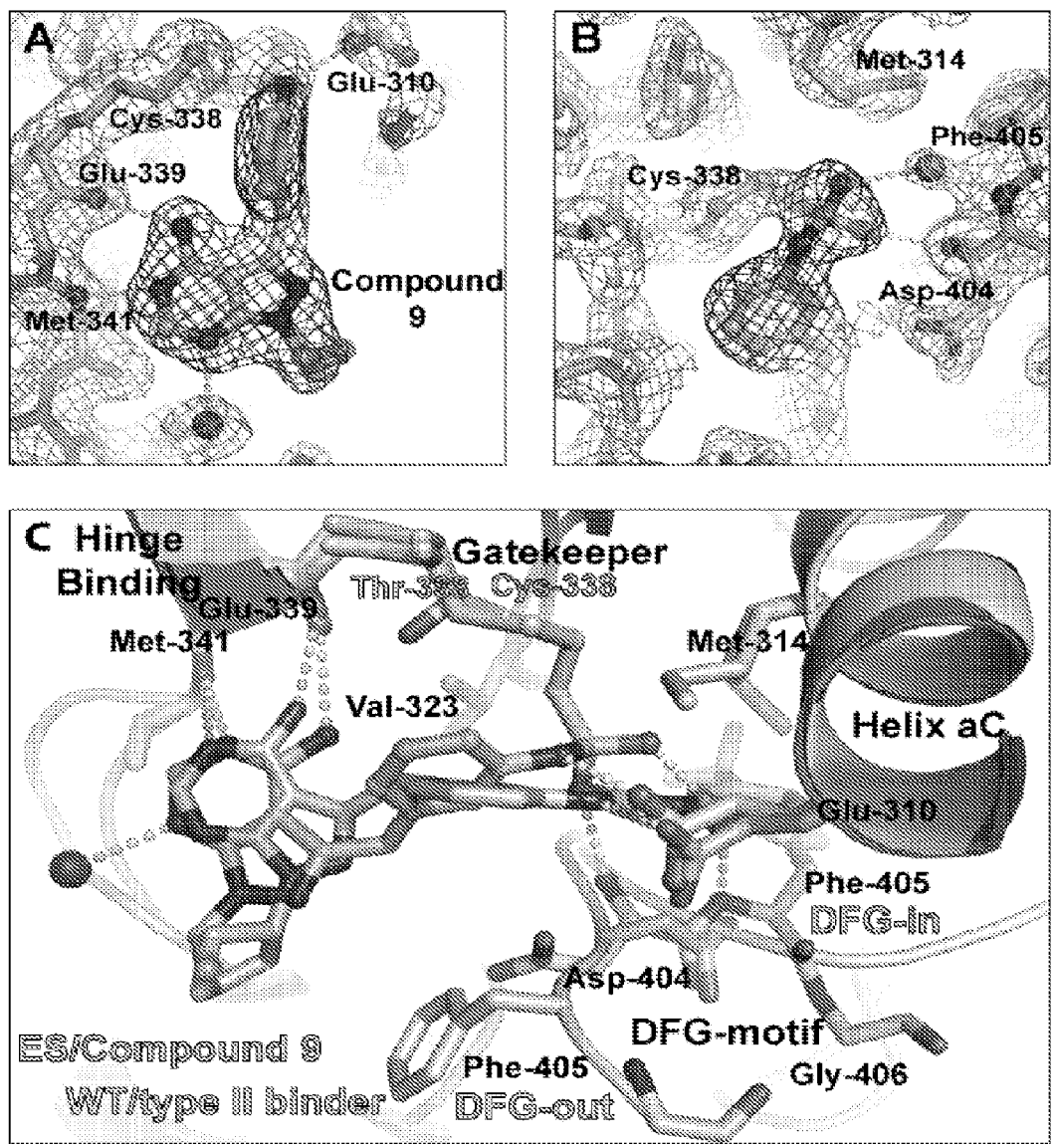
FIG. 2 shows the crystal structure of compound 9 bound covalently to c-Src-ES1. The experimental electron density of c-Src-ES1 at 2.20 Å resolution is shown ($2F_0$-$F_c$ map at 1σ). (A) The pyrazolopyrimidine portion of compound 9 (green) interacts with the hinge region of c-Src (Met-341 and Glu-339), while the sulfonamide group makes a hydrogen bonds with Glu-310 of the αC helix (B) Electron density reveals a covalent linkage between Cys-338 and compound 9. The oxygen atoms of the sulfonamide interact with the backbone of Asp-404 and via a water molecule with Phe-405, both of which are part of the DFG-motif of the kinase (C) Comparison of structural features of compound 9 bound to c-Src-ES1 and a known pyrazolopyrimidine compound bound to WT c-Src. Both compounds engage the hinge region in a similar fashion and bind the αC helix in the "in" conformation. Furthermore, both compounds participate in hydrogen bonding interactions with Glu-310 and backbone amides of the DFG-motif. However while the known pyrazolopyrimidine compound binds in the "DFG-out" conformation, compound 9 engages the "DFG-in" orientation. The sulfhydryl of the Cys-338 points in the opposite direction relative to the hydroxyl group of Thr-338 in order to facilitate a covalent bond with compound 9.
Figure 3:
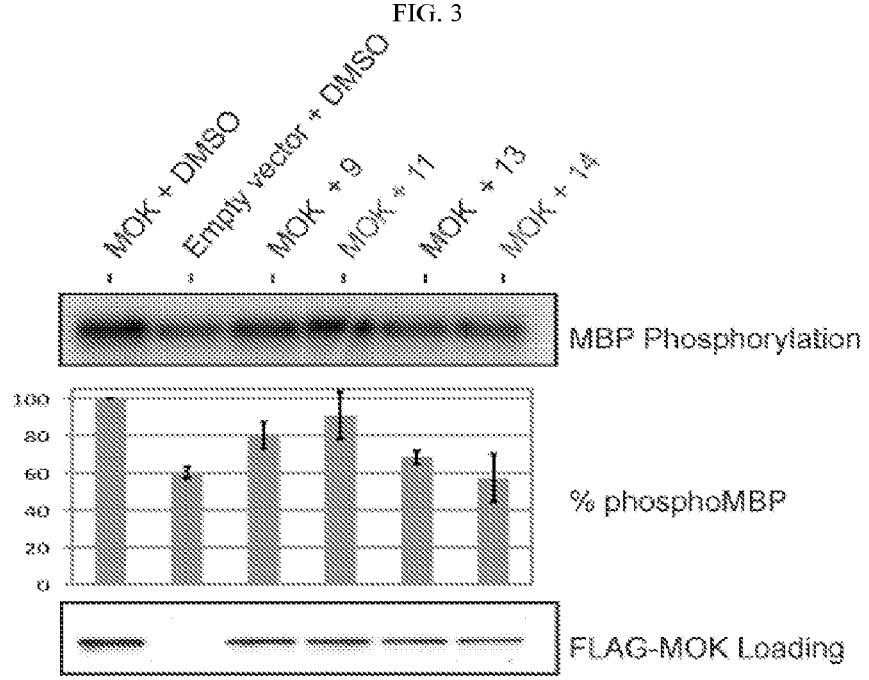
FIG. 3 shows an assay for MOK inhibition by cysteine gatekeeper-targeting compounds. (top) FLAG-MOK expressed in COST cells was immunoprecipitated and assayed in vitro with a myelin basic protein (MBP) substrate and inhibitors at a concentration of 1 μM. Autoradiography is shown. (center) Quantification of the percent MBP phosphorylated from three independent experiments with associated standard errors. All values are normalized relative to the MOK+DMSO lane. (bottom) Western blot of loading controls for FLAG-MOK are shown.
Figure 5:
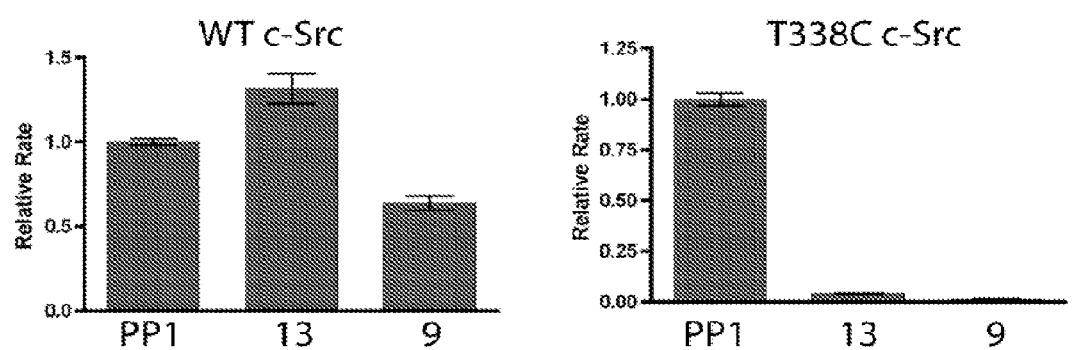
FIG. 5 shows relative rates of wild type c-Src and T338C c-Src following treatment with PP1, 13 or 9 and purification by gel filtration. Assay was done in triplicate, and average values with standard errors are given.
Figure 6:
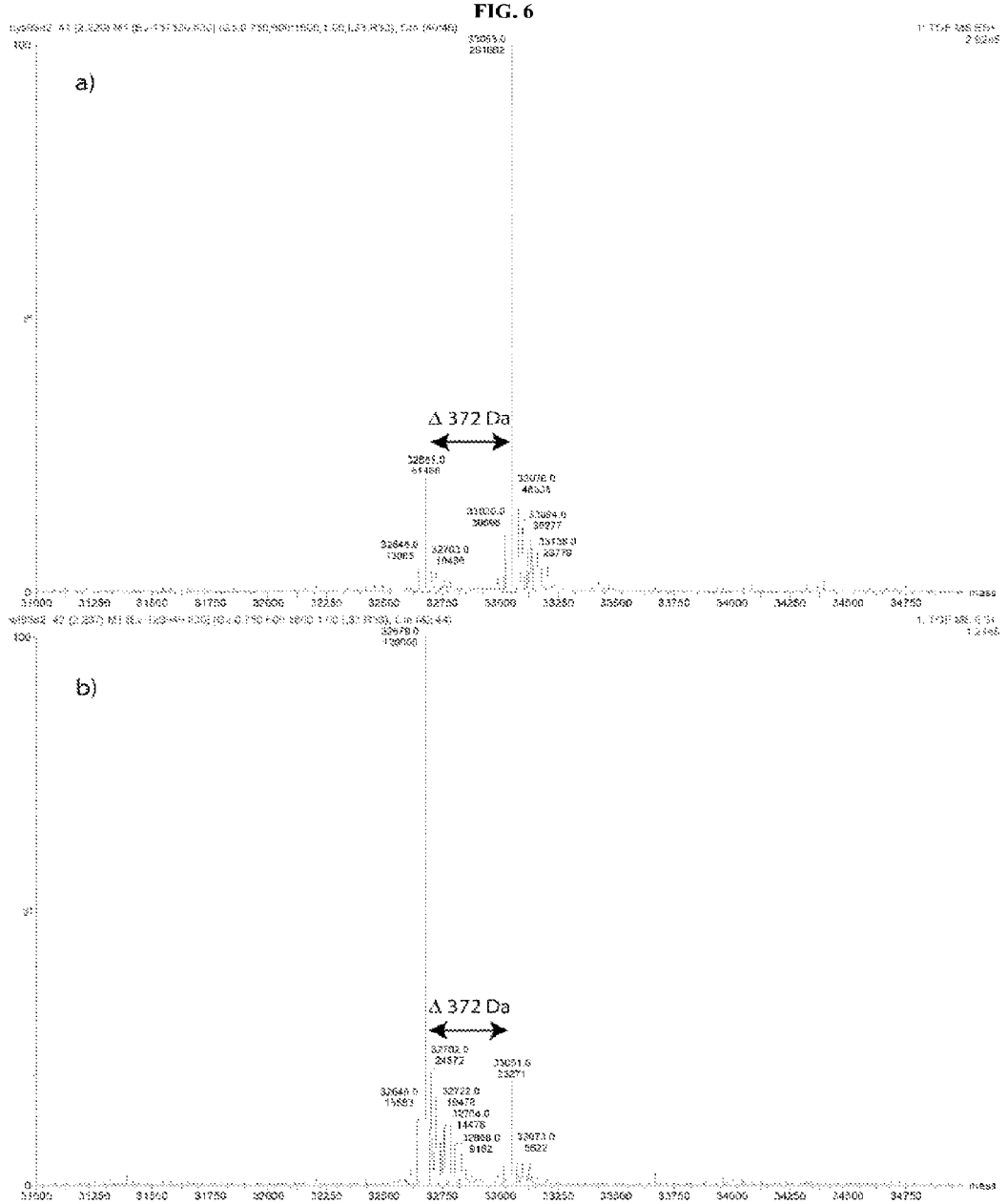
FIG. 6 shows ESI-oa-TOF mass spectral analysis of covalent labeling of T338C c-Src and WT c-Src with compound 9. T338C c-Src (a) or WT c-Src (b) (15 μM) was incubated with two equivalents of compound 9 and analyzed by full-protein mass spectrometry after 5 minutes of reaction. A 372 Da mass change occurs upon covalent labeling. Deconvoluted mass spectra are shown.

In addition, when T338C c-Src was treated with either inhibitor and purified by gel filtration and the inhibitory activity against the kinase was retained. See FIG. 5. In contrast, in the case of WT c-Src, inhibitory activity was lost after gel filtration. Importantly, inhibition by PP1, a reversible Src inhibitor, was abrogated in the cases of both WT and T338C c-Src following gel filtration (FIG. 5). Full protein mass spectrometry suggested specific labeling of T338C relative to WT c-Src for 9 (FIG. 2). However, under similar conditions, an adduct formation with 13 was not observed, possibly due to a reversible covalent interaction. The results suggest that covalent binding of the electrophilic inhibitors depend on the presence of a cysteine gatekeeper, i.e. T338C c-Src as electrophile-sensitive c-Src1 (c-Src-ES1).

TABLE 3

Compounds 9 and 13 exhibit time-dependent inhibition against T338C c-Src. Compounds were preincubated with the enzyme prior to initializing the reaction with ATP.

| Compound | Preincubation Time (min) | | |
|---|---|---|---|
| | 2 | 20 | 40 |
| | T338C c-Src IC$_{50}$ (nM) | | |
| 9 | 981 | 309 | 138 |
| 13 | 1281 | 318 | 136 |

Table 3 shows compounds 9 and 13 exhibit time-dependent inhibition against T338C c-Src. Compounds were preincubated with the enzyme prior to initializing the reaction with ATP.

XI. Methods of Inhibiting a Kinase

In some other embodiments, the present invention provides a method of imparting to a kinase the capability of being inhibited by a heterocyclic compound, comprising replacing a gatekeeper amino acid residue within an ATP binding site of a kinase with a cysteine residue thereby forming a cysteine substituted kinase.

In some embodiments, the present invention provides a method of inhibiting a recombinant kinase as set forth herein, comprising contacting the recombinant kinase with an effective amount of an inhibitor, thereby inhibiting the recombinant kinase. In some embodiments, the inhibitor is capable of forming a covalent bond to the cysteine at the gatekeeper amino acid position of the recombinant kinase. In some embodiments, the inhibitor is a compound as set forth herein, e.g. a compound of formulas I-XXIX. In some other embodiments, the method further comprises determining a level of inhibition for the recombinant kinase. In some embodiments, the determining of said level of inhibition for the recombinant kinase comprises: determining an amount of enzymatic activity of the recombinant kinase in the presence of the inhibitor; determining an amount of enzymatic activity of the recombinant kinase in the absence of the inhibitor; and comparing the amount of enzymatic activity of the recombinant kinase in the presence of the inhibitor with the amount of enzymatic activity of the recombinant kinase in the absence of the inhibitor, thereby determining a level of inhibition for the recombinant kinase. In some embodiments, the enzymatic activity is selected from phosphorylation of a non-specific protein target, phosphorylation of a specific protein target, consumption of ATP, or cell growth.

In other embodiments, the present invention provides a method as set forth herein wherein the recombinant kinase is in a cell. In some embodiments, the methods set forth herein further comprise determining a function of the recombinant kinase in the cell, by: determining an amount of enzymatic activity of the recombinant kinase in the presence of the inhibitor in the cell; determining an amount of enzymatic activity of the recombinant kinase in the absence of the inhibitor in the cell; and comparing the amount of enzymatic activity of the recombinant kinase in the presence of the inhibitor with the amount of enzymatic activity of the recombinant kinase in the absence of the inhibitor, thereby determining a function of the recombinant kinase in the cell. In some embodiments, the enzymatic activity is selected from phosphorylation of a specific protein target.

In other embodiments, the methods as set forth herein include a recombinant kinase is selected from Src; MOK; Sgk494; Lrrk-2; Yak/Yrk; SRPK1; CDK; DICTY-I; PAK/STE20; or Ctrl/DPYK1. In some embodiments, the recombinant kinase is Src.

In some embodiments, the present invention provides a method of inhibiting a Lrrk-2 kinase, comprising contacting the Lrrk-2 kinase with an effective amount of a Lrrk-2 inhibitor, thereby inhibiting the recombinant Lrrk-2 kinase. A Lrrk-2 inhibitor is compound of Formula (XV) to (XXIX) including embodiments thereof.

XII. Methods of Treating

In some embodiments, the present invention provides a method of treating a kinase-associated disease or condition, in a patient in need thereof. The method includes administering to the patient a therapeutically effective amount of a compound provided herein, thereby treating a kinase-associated disease or condition. In some embodiments, the compound is a kinase inhibitor capable of forming a covalent bond to the cysteine at the gatekeeper amino acid position of the recombinant kinase. In some embodiments, the compound is a compound as set forth herein, e.g. a compound of formulas (I)-(XXIX) including embodiments thereof. In certain embodiments, the kinase-associated disease or condition is selective from cancer, immunological disorders, neurological disorders, neurodegenerative disorders, infections, metabolic diseases, Leishmania major, zoonotic cutaneous leishmaniasis, Plasmodium falciparum, malaria, Trichomonas vaginalis, and trichomiasis. In certain other embodiments, the cancer is selected from neoplasm or malignant tumors found in mammals; leukemia; carcinomas and sarcomas; cancer of the brain, breast, cervix, colon, head and neck, liver, kidney, lung, non-small cell lung, ovary, testicle, stomach, uterus; melanoma; mesothelioma; Medulloblastoma; Hodgkin's Disease, Non-Hodgkin's Lymphoma; multiple myeloma; neuroblastoma; rhabdomyosarcoma; primary thrombocytosis; primary macroglobulinemia; primary brain tumors; malignant pancreatic insulanoma; malignant carcinoid; urinary bladder cancer; premalignant skin lesions; lymphomas; thyroid cancer; neuroblastoma; esophageal cancer; genitourinary tract cancer; malignant hypercalcemia; endometrial cancer; adrenal cortical cancer; neoplasms of the endocrine and exocrine pancreas; or prostate cancer. In yet other embodiments, the disease or condition is a neurodegenerative disease selective from Parkinson's disease.

In some other embodiments, the present invention also provides a method of treating a Lrrk-2-associated disease or condition, in a patient in need thereof, said method comprising administering to said patient a therapeutically effective amount of a Lrrk-2 inhibitor, thereby treating a Lrrk-2-associated disease or condition. In some embodiments, the disease or condition is a neurodegenerative disease selected from Parkinson's Disease.

In some embodiments, the methods further include the step of allowing the cell to express the recombinant kinase.

XIII. Tables Relevant to the Methods and Assays Herein

TABLE 4

| Relative $k_{cat}/K_m$ for a series of c-Src variants | |
|---|---|
| c-Src Variant | rel. $k_{cat}/K_m$ |
| ES1 | 1.00 ± 0.09 |
| ES2 | 0.39 ± 0.03 |
| ES3 | 0.21 ± 0.04 |
| ES4 | N.D. |
| ES5 | N.D. |
| ES6 | N.D. |

Table 5a-5c show relative catalytic efficiency for T338C c-Src with second-site mutations (ES1=T338C; ES2=T338C/V323A; ES3=T338C/V323S; ES4=T338C/V323D; ES5=T338C/V323E; ES6=T338C/V323H). Data were fitted to the Michaelis-Menten equation and standard errors of the fits are reported. Data are unitless.

Table 5 shows kinome-wide screening of a panel of inhibitors. Compounds were screened using the SelectScreen™ platform developed by Life Technologies. Z'lyte (a, measures kinase activity), Adapta (b, measures kinase activity) and Lantha assays (c, measures ATP binding) were performed. Inhibition data are represented in a heat map format.

Table 6 shows comparison of selectivity of 13, 1NA-PP1 and 1NM-PP1. All kinases for which >40% inhibition was observed in a kinome wide Z'lyte screen (Life Technologies) are shown. Legend for Tables 5-6: <40% inhibition (gray); 40%-80% inhibition (white); ≥80% inhibition (diagonal stripes).

TABLE 5a

| Compound | Conc | | 1000 nM 3 | 1000 nM 4 | 1000 nM 9 | 1000 nM 13 | 1000 nM 20 |
|---|---|---|---|---|---|---|---|
| ABL1 | Activity | Km app | 7 | 5 | 4 | 2 | 1 |
| ABL1 E255K | Activity | Km app | 14 | 8 | 5 | 3 | 8 |
| ABL1 G250E | Activity | Km app | 3 | 1 | 0 | 3 | 1 |
| ABL1 T315I | Activity | Km app | -1 | 3 | 4 | -2 | 4 |
| ABL1 Y253F | Activity | Km app | 17 | 16 | 12 | 10 | 12 |
| ABL2 (Arg) | Activity | Km app | 17 | 15 | 11 | 5 | 8 |
| ACVR1B (ALK4) | Activity | Km app | 13 | 8 | 5 | 2 | -1 |
| ADRBK1 (GRK2) | Activity | Km app | 23 | 22 | 21 | 18 | 13 |
| ADRBK2 (GRK3) | Activity | Km app | 0 | 0 | 1 | -1 | 0 |
| AKT1 (PKB alpha) | Activity | Km app | -4 | -1 | 0 | 0 | -4 |
| AKT2 (PKB beta) | Activity | Km app | 5 | 3 | 4 | 5 | 3 |
| AKT3 (PKB gamma) | Activity | Km app | -1 | 2 | 3 | 5 | 1 |
| ALK | Activity | Km app | 5 | 7 | 2 | 0 | 1 |
| AMPK A1/B1/G1 | Activity | Km app | 14 | 20 | 29 | 28 | 14 |
| AMPK A2/B1/G1 | Activity | Km app | 12 | 14 | 20 | 19 | 7 |
| AURKA (Aurora A) | Activity | Km app | 7 | 4 | 9 | 3 | 12 |

TABLE 5a-continued

| | | | | | | | |
|---|---|---|---|---|---|---|---|
| AURKB (Aurora B) | Activity | Km app | 9 | 9 | 9 | 5 | 27 |
| AURKC (Aurora C) | Activity | Km app | 8 | 8 | 7 | 6 | 25 |
| AXL | Activity | Km app | 9 | 6 | 1 | 1 | 9 |
| BLK | Activity | Km app | 48 | 34 | 20 | 10 | 42 |
| BMX | Activity | Km app | /// | /// | 68 | 9 | 20 |
| BRAF | Activity | 100 | 35 | 5 | 7 | 4 | 6 |
| BRAF V599E | Activity | 100 | /// | 13 | 17 | 21 | 9 |
| BRSK1 (SAD 1) | Activity | Km app | 11 | 14 | 13 | 9 | 17 |
| BTK | Activity | Km app | 44 | 36 | 42 | 1 | 17 |
| CAMK1D (CaMKI delta) | Activity | Km app | 21 | 22 | 18 | 20 | 16 |
| CAMK2A (CaMKII alpha) | Activity | Km app | -2 | 1 | 2 | 5 | 1 |
| CAMK2B (CaMKII beta) | Activity | Km app | 6 | 6 | 11 | 1 | 8 |
| CAMK2D (CaMKII delta) | Activity | Km app | 16 | 15 | 8 | 10 | 8 |
| CAMK4 (CaMKIV) | Activity | Km app | 9 | 8 | 10 | 11 | 7 |
| CDC42 BPA (MRCKA) | Activity | Km app | 12 | 16 | 22 | 24 | 20 |
| CDC42 BPB (MRCKB) | Activity | Km app | 1 | -1 | -3 | -7 | -1 |
| CDK1/cyclin B | Activity | Km app | 10 | 2 | 7 | 4 | 1 |
| CDK2/cyclin A | Activity | Km app | 9 | 5 | 16 | 11 | 0 |
| CDK5/p25 | Activity | Km app | 13 | 9 | 21 | 12 | 9 |
| CDK5/p35 | Activity | Km app | 18 | 8 | 24 | 7 | 5 |
| CHEK1 (CHK1) | Activity | Km app | 11 | -3 | -5 | -7 | -11 |
| CHEK2 (CHK2) | Activity | Km app | 0 | -3 | 2 | 2 | 17 |
| CLK1 | Activity | Km app | 8 | 7 | 12 | 7 | 7 |
| CLK2 | Activity | Km app | 0 | -1 | 0 | 1 | -3 |
| CLK3 | Activity | Km app | 6 | 8 | 7 | 6 | 7 |
| CSF1R (FMS) | Activity | Km app | 7 | 10 | 7 | 4 | 5 |
| CSK | Activity | Km app | 22 | 9 | 9 | 8 | 12 |
| CSNK1A1 (CK1 alpha 1) | Activity | Km app | 20 | 12 | 6 | 14 | 0 |
| CSNK1D (CK1 delta) | Activity | Km app | 9 | 5 | 8 | 15 | 4 |
| CSNK1E (CK1 epsilon) | Activity | Km app | 18 | 6 | 10 | 40 | 7 |
| CSNK1G1 (CK1 gamma 1) | Activity | Km app | 3 | 4 | 4 | 1 | 15 |
| CSNK1G2 (CK1 gamma 2) | Activity | Km app | 7 | 7 | 8 | 3 | 36 |
| CSNK1G3 (CK1 gamma 3) | Activity | Km app | 6 | 11 | 10 | 9 | 31 |
| CSNK2A1 (CK2 alpha 1) | Activity | Km app | 17 | 18 | 5 | 14 | 12 |
| CSNK2A2 (CK2 alpha 2) | Activity | Km app | 6 | -2 | -1 | 1 | -5 |
| DAPK3 (ZIPK) | Activity | Km app | 1 | 2 | 3 | 0 | 3 |
| DCAMKL2 (DCK2) | Activity | Km app | 7 | 5 | 6 | 2 | 8 |
| DNA-PK | Activity | Km app | 68 | 27 | 15 | 12 | 12 |

TABLE 5a-continued

| | | | | | | | |
|---|---|---|---|---|---|---|---|
| DYRK1A | Activity | Km app | -1 | -1 | 1 | -5 | -3 |
| DYRK1B | Activity | Km app | -1 | 2 | 2 | -1 | 2 |
| DYRK3 | Activity | Km app | 3 | 2 | 23 | 0 | 4 |
| DYRK4 | Activity | Km app | 1 | 3 | 3 | 3 | 2 |
| EEF2K | Activity | Km app | 5 | 7 | 8 | 7 | 5 |
| EGFR (ErbB1) | Activity | Km app | 50 | 26 | 8 | -5 | /// |
| EGFR (ErbB1) L858R | Activity | Km app | 61 | 36 | 23 | 1 | 71 |
| EGFR (ErbB1) L861Q | Activity | Km app | /// | 46 | 18 | 1 | /// |
| EGFR (ErbB1) T790M | Activity | Km app | 36 | 27 | 12 | 4 | 12 |
| EGFR (ErbB1) T790M L858R | Activity | Km app | 64 | 39 | 19 | 10 | 23 |
| EPHA1 | Activity | Km app | 33 | 14 | 14 | 15 | 11 |
| EPHA2 | Activity | Km app | 7 | 5 | 6 | 4 | 5 |
| EPHA4 | Activity | Km app | 19 | 8 | 8 | 7 | 9 |
| EPHA5 | Activity | Km app | 22 | 11 | 11 | 5 | 7 |
| EPHA8 | Activity | Km app | 23 | 7 | 9 | 9 | 6 |
| EPHB1 | Activity | Km app | 12 | 6 | 6 | 5 | 7 |
| EPHB2 | Activity | Km app | 21 | 12 | 15 | 14 | 12 |
| EPHB3 | Activity | Km app | 40 | 10 | 18 | 6 | 8 |
| EPHB4 | Activity | Km app | 14 | 11 | 11 | 6 | 9 |
| ERBB2 (HER2) | Activity | Km app | 40 | 23 | 19 | 16 | 55 |
| ERBB4 (HER4) | Activity | Km app | 70 | /// | 15 | 5 | /// |
| FER | Activity | Km app | 13 | 9 | 7 | 7 | 10 |
| FES (FPS) | Activity | Km app | 8 | 10 | 2 | 12 | 11 |
| FGFR1 | Activity | Km app | 24 | 53 | 22 | 15 | 1 |
| FGFR2 | Activity | Km app | 18 | 3 | 4 | 3 | 8 |
| FGFR3 | Activity | Km app | 20 | 10 | 4 | 6 | 9 |
| FGFR3 K650E | Activity | Km app | 28 | 2 | 6 | -2 | 9 |
| FGFR4 | Activity | Km app | 17 | 8 | 5 | 6 | 4 |
| FGR | Activity | Km app | 79 | 16 | 20 | 6 | 30 |
| FLT1 (VEGFR1) | Activity | Km app | 3 | 1 | 2 | -2 | 2 |
| FLT3 | Activity | Km app | 29 | 0 | 6 | -7 | 31 |
| FLT3 D835Y | Activity | Km app | 34 | 16 | 42 | 8 | 15 |
| FLT4 (VEGFR3) | Activity | Km app | 28 | 33 | 13 | 9 | 41 |
| FRAP1 (mTOR) | Activity | Km app | 24 | -2 | 8 | 8 | 10 |
| FRK (PTK5) | Activity | Km app | 25 | 9 | 8 | 5 | 9 |
| FYN | Activity | Km app | 17 | 9 | 10 | 6 | 3 |
| GRK4 | Activity | Km app | 10 | 10 | 5 | -2 | 0 |
| GRK5 | Activity | Km app | 1 | 3 | 3 | 3 | 2 |
| GRK6 | Activity | Km app | 15 | 16 | 10 | 7 | 5 |

TABLE 5a-continued

| | | | | | | | |
|---|---|---|---|---|---|---|---|
| GRK7 | Activity | Km app | -1 | 0 | -1 | -3 | 0 |
| GSK3A (GSK3 alpha) | Activity | Km app | 3 | 5 | 5 | -3 | 3 |
| GSK3B (GSK3 beta) | Activity | Km app | 3 | 0 | 3 | -5 | -3 |
| HCK | Activity | Km app | 17 | 4 | 6 | 5 | 11 |
| HIPK1 (Myak) | Activity | Km app | 8 | 5 | 4 | 4 | 4 |
| HIPK2 | Activity | Km app | 11 | 6 | 4 | 4 | 4 |
| HIPK3 (YAK1) | Activity | Km app | 5 | 6 | 4 | 3 | 5 |
| HIPK4 | Activity | Km app | 6 | 6 | 9 | 4 | 7 |
| IGF1R | Activity | Km app | 5 | 4 | 0 | -7 | 2 |
| IKBKB (IKK beta) | Activity | Km app | 16 | 17 | 18 | 16 | 12 |
| IKBKE (IKK epsilon) | Activity | Km app | 16 | 20 | 15 | 14 | 10 |
| INSR | Activity | Km app | -2 | 2 | 3 | 2 | 0 |
| INSRR (IRR) | Activity | Km app | 9 | 10 | 9 | 9 | 11 |
| IRAK4 | Activity | Km app | 4 | 1 | 2 | -6 | -2 |
| ITK | Activity | Km app | 3 | -6 | -4 | -4 | -7 |
| JAK1 | Activity | Km app | 4 | 8 | 14 | 16 | 11 |

| | | | | | | | |
|---|---|---|---|---|---|---|---|
| JAK2 | Activity | Km app | 7 | 5 | 5 | 4 | 2 |
| JAK2 JH1 JH2 | Activity | Km app | 1 | -1 | -6 | -4 | -1 |
| JAK2 JH1 JH2 V617F | Activity | Km app | 2 | 1 | -3 | -4 | 2 |
| JAK3 | Activity | Km app | 23 | 72 | 14 | 10 | 12 |
| KDR (VEGFR2) | Activity | Km app | 6 | -14 | -17 | -18 | 16 |
| KIT | Activity | Km app | 17 | 19 | 12 | 7 | 6 |
| KIT T670I | Activity | Km app | 10 | 7 | 8 | 7 | 3 |
| LCK | Activity | Km app | 48 | -1 | -13 | -18 | 11 |
| LTK (TYK1) | Activity | Km app | 1 | 0 | -4 | -5 | 1 |
| LYN A | Activity | Km app | 34 | 9 | 12 | 8 | 28 |
| LYN B | Activity | Km app | 39 | 16 | 15 | 14 | 30 |
| MAP2K1 (MEK1) | Activity | 100 | 31 | 7 | 3 | 5 | 0 |
| MAP2K2 (MEK2) | Activity | 100 | 49 | 12 | 11 | 10 | 7 |
| MAP2K6 (MKK6) | Activity | 100 | 5 | 8 | 11 | 13 | 16 |
| MAP3K8 (COT) | Activity | 100 | 33 | 2 | 0 | 0 | 0 |
| MAP3K9 (MLK1) | Activity | Km app | 8 | 5 | 4 | 1 | 21 |
| MAP4K2 (GCK) | Activity | Km app | 16 | 2 | 7 | 11 | 3 |
| MAP4K4 (HGK) | Activity | Km app | 15 | 14 | 16 | 18 | 21 |
| MAP4K5 (KHS1) | Activity | Km app | 22 | 17 | 48 | 20 | 36 |

TABLE 5a-continued

| | | | | | | | |
|---|---|---|---|---|---|---|---|
| MAPK1 (ERK2) | Activity | Km app | 3 | 6 | 3 | 2 | 2 |
| MAPK10 (JNK3) | Activity | 100 | 6 | 13 | 2 | 7 | 10 |
| MAPK11 (p38 beta) | Activity | Km app | 9 | 11 | 9 | 10 | 9 |
| MAPK12 (p38 gamma) | Activity | Km app | 9 | 13 | 10 | 9 | 14 |
| MAPK13 (p38 delta) | Activity | Km app | 2 | 6 | 6 | 5 | 6 |
| MAPK14 (p38 alpha) | Activity | 100 | 21 | 20 | 22 | 24 | 22 |
| MAPK14 (p38 alpha) Direct | Activity | Km app | -1 | 4 | 9 | 12 | 10 |
| MAPK3 (ERK1) | Activity | Km app | 15 | 31 | 13 | 10 | 14 |
| MAPK8 (JNK1) | Activity | 100 | 17 | 21 | 24 | 21 | 19 |
| MAPK9 (JNK2) | Activity | 100 | 5 | 7 | 8 | 8 | 7 |
| MAPKAPK2 | Activity | Km app | 1 | 2 | 4 | 6 | 5 |
| MAPKAPK3 | Activity | Km app | 5 | 6 | 5 | 3 | 5 |
| MAPKAPK5 (PRAK) | Activity | Km app | -4 | -1 | 4 | 7 | 7 |
| MARK1 (MARK) | Activity | Km app | -1 | 0 | 2 | 2 | -4 |
| MARK2 | Activity | Km app | 1 | 2 | 4 | 5 | 1 |
| MARK3 | Activity | Km app | 6 | 8 | 6 | 2 | 5 |
| MARK4 | Activity | Km app | 2 | 4 | 3 | -1 | -1 |
| MATK (HYL) | Activity | Km app | 3 | 5 | 6 | 5 | 4 |
| MELK | Activity | Km app | 16 | 28 | 29 | 15 | 32 |

| | | | | | | | |
|---|---|---|---|---|---|---|---|
| MERTK (cMER) | Activity | Km app | 9 | 4 | 8 | 17 | 48 |
| MET (cMet) | Activity | Km app | -4 | 27 | 10 | 8 | 0 |
| MET M1250T | Activity | Km app | 7 | 7 | 4 | 2 | 6 |

| | | | | | | | |
|---|---|---|---|---|---|---|---|
| MINK1 | Activity | Km app | 31 | 17 | 23 | 19 | 22 |
| MKNK1 (MNK1) | Activity | Km app | 5 | 0 | -4 | -5 | 16 |
| MST1R (RON) | Activity | Km app | 13 | 11 | 9 | 5 | 9 |
| MST4 | Activity | Km app | 8 | 13 | 21 | 7 | 30 |
| MUSK | Activity | Km app | 15 | 12 | 11 | 18 | 1 |
| MYLK2 (skMLCK) | Activity | Km app | 2 | 2 | 5 | 0 | 2 |
| NEK1 | Activity | Km app | 14 | -5 | 7 | 4 | 10 |
| NEK2 | Activity | Km app | -1 | 4 | 10 | 0 | 8 |
| NEK4 | Activity | Km app | 8 | 10 | 17 | 19 | 15 |
| NEK6 | Activity | Km app | 4 | 5 | 10 | 12 | 4 |
| NEK7 | Activity | Km app | 7 | 8 | 8 | 8 | 6 |
| NEK9 | Activity | Km app | 15 | 12 | 13 | 12 | 12 |
| NTRK1 (TRKA) | Activity | Km app | 37 | 3 | 21 | 17 | 48 |
| NTRK2 (TRKB) | Activity | Km app | 16 | 4 | 23 | 12 | -1 |
| NTRK3 (TRKC) | Activity | Km app | 16 | -5 | 18 | -6 | -8 |
| PAK1 | Activity | Km app | 12 | 12 | 10 | 13 | 16 |

TABLE 5a-continued

| | | | | | | | |
|---|---|---|---|---|---|---|---|
| PAK2 (PAK65) | Activity | Km app | 18 | 12 | 12 | 13 | 10 |
| PAK3 | Activity | Km app | 4 | 3 | 6 | 6 | 2 |
| PAK4 | Activity | Km app | 5 | 8 | 7 | 6 | 5 |
| PAK6 | Activity | Km app | 7 | 10 | 10 | 8 | 5 |
| PAK7 (KIAA1264) | Activity | Km app | 9 | 13 | 13 | 0 | 11 |
| PASK | Activity | Km app | 11 | 9 | 8 | 7 | 7 |
| PDGFRA (PDGFR alpha) | Activity | Km app | 13 | 6 | 5 | 4 | 16 |
| PDGFRA D842V | Activity | Km app | 5 | 3 | 0 | 3 | 9 |
| PDGFRA T674I | Activity | Km app | 11 | 11 | -2 | 4 | 11 |
| PDGFRA V561D | Activity | Km app | 19 | 12 | 5 | 1 | 27 |
| PDGFRB (PDGFR beta) | Activity | Km app | 16 | 10 | 5 | 5 | 11 |
| PDK1 | Activity | 100 | 5 | 11 | 11 | 11 | 11 |
| PDK1 Direct | Activity | Km app | 1 | -1 | 3 | 0 | -5 |
| PHKG1 | Activity | Km app | 8 | 8 | 8 | 10 | 5 |
| PHKG2 | Activity | Km app | 1 | 6 | 4 | 1 | 7 |

| | | | | | | | |
|---|---|---|---|---|---|---|---|
| PIM1 | Activity | Km app | 16 | 12 | 11 | 12 | 10 |
| PIM2 | Activity | Km app | 3 | 1 | 2 | 1 | 3 |
| PKN1 (PRK1) | Activity | Km app | 15 | 17 | 18 | 12 | 9 |
| PLK1 | Activity | Km app | 7 | 3 | 6 | 3 | 4 |
| PLK2 | Activity | Km app | 13 | 8 | 7 | 1 | 7 |
| PLK3 | Activity | Km app | 2 | 4 | 0 | -2 | 3 |
| PRKACA (PKA) | Activity | Km app | 1 | 0 | 1 | 4 | 2 |
| PRKCA (PKC alpha) | Activity | Km app | 8 | 15 | 19 | 17 | 18 |
| PRKCB1 (PKC beta I) | Activity | Km app | 1 | 11 | 10 | 8 | 5 |
| PRKCB2 (PKC beta II) | Activity | Km app | 9 | 13 | 7 | 4 | 4 |
| PRKCD (PKC delta) | Activity | Km app | 14 | 18 | 20 | 16 | 17 |
| PRKCE (PKC epsilon) | Activity | Km app | 12 | 16 | 21 | 19 | 10 |
| PRKCG (PKC gamma) | Activity | Km app | 18 | 13 | 22 | 19 | 14 |
| PRKCH (PKC eta) | Activity | Km app | 28 | 6 | 25 | 24 | 10 |
| PRKCI (PKC iota) | Activity | Km app | 10 | 13 | 13 | 13 | 10 |
| PRKCN (PKD3) | Activity | Km app | 8 | 7 | 12 | 16 | 11 |
| PRKCQ (PKC theta) | Activity | Km app | 9 | 11 | 13 | 13 | 12 |
| PRKCZ (PKC zeta) | Activity | Km app | 0 | 5 | 5 | 8 | 7 |
| PRKD1 (PKC mu) | Activity | Km app | 8 | 10 | 17 | 18 | 10 |

| | | | | | | | |
|---|---|---|---|---|---|---|---|
| PRKD2 (PKD2) | Activity | Km app | 11 | 11 | 12 | 19 | 16 |
| PRKG1 | Activity | Km app | 1 | 2 | 3 | 1 | 4 |
| PRKG2 (PKG2) | Activity | Km app | 0 | 0 | 1 | 0 | 0 |
| PRKX | Activity | Km app | 3 | 5 | 3 | 1 | 5 |
| PTK2 (FAK) | Activity | Km app | 7 | 7 | 8 | 7 | 6 |
| PTK2B (FAK2) | Activity | Km app | 5 | 3 | 2 | 1 | 1 |
| PTK6 (Brk) | Activity | Km app | 68 | 3 | 30 | 27 | 74 |

TABLE 5a-continued

| | | | | | | | |
|---|---|---|---|---|---|---|---|
| RAF1 (cRAF) Y340D Y341D | Activity | 100 | 39 | 7 | 7 | 7 | 18 |
| RET | Activity | Km app | 41 | 11 | 12 | 8 | 40 |
| RET V804L | Activity | Km app | 4 | 3 | 6 | 2 | 13 |
| RET Y791F | Activity | Km app | 44 | 9 | 10 | 8 | 41 |
| ROCK1 | Activity | Km app | 2 | 0 | 0 | -3 | -1 |
| ROCK2 | Activity | Km app | 18 | 21 | 19 | 14 | 24 |
| ROS1 | Activity | Km app | 7 | 23 | 5 | 2 | 5 |
| RPS6KA1 (RSK1) | Activity | Km app | 1 | 1 | 1 | -2 | 5 |
| RPS6KA2 (RSK3) | Activity | Km app | 2 | 8 | 3 | 0 | 12 |
| RPS6KA3 (RSK2) | Activity | Km app | 4 | 4 | 4 | 4 | 4 |
| RPS6KA4 (MSK2) | Activity | Km app | 11 | 7 | 8 | 6 | 6 |
| RPS6KA5 (MSK1) | Activity | Km app | 7 | 8 | 6 | 3 | 7 |
| RPS6KA6 (RSK4) | Activity | Km app | 24 | 21 | 19 | 5 | 53 |
| RPS6KB1 (p70S6K) | Activity | Km app | 8 | 8 | 14 | 13 | 10 |
| SGK (SGK1) | Activity | Km app | 10 | 4 | 6 | -1 | 2 |
| SGK2 | Activity | Km app | 9 | 10 | 7 | 5 | 11 |
| SGKL (SGK3) | Activity | Km app | 5 | 5 | 5 | 3 | 6 |
| SNF1LK2 | Activity | Km app | 3 | 5 | 2 | 1 | 3 |
| SRC | Activity | Km app | 40 | 3 | 1 | -6 | 20 |

| | | | | | | | |
|---|---|---|---|---|---|---|---|
| SRC N1 | Activity | Km app | 53 | 8 | 13 | 4 | 19 |
| SRMS (Srm) | Activity | Km app | /// | 19 | 11 | 10 | 13 |
| SRPK1 | Activity | Km app | 2 | 3 | 4 | 4 | 2 |
| SRPK2 | Activity | Km app | 13 | 13 | 11 | 12 | 9 |
| STK22B (TSSK2) | Activity | Km app | 5 | 3 | 0 | 0 | 6 |
| STK22D (TSSK1) | Activity | Km app | 3 | 6 | 10 | 12 | 11 |
| STK23 (MSSK1) | Activity | Km app | 7 | 7 | 9 | 6 | 8 |
| STK24 (MST3) | Activity | Km app | 13 | 13 | 9 | 10 | 13 |
| STK25 (YSK1) | Activity | Km app | 10 | 8 | 10 | 0 | 9 |
| STK3 (MST2) | Activity | Km app | -7 | -9 | -8 | -9 | -13 |
| STK4 (MST1) | Activity | Km app | 12 | 5 | 3 | 2 | 3 |
| SYK | Activity | Km app | 7 | 6 | 6 | 8 | 2 |
| TAOK2 (TAO1) | Activity | Km app | 6 | 4 | 6 | 2 | 2 |
| TBK1 | Activity | Km app | 5 | 2 | 0 | 11 | 5 |
| TEK (Tie2) | Activity | Km app | -3 | -9 | -8 | -7 | -10 |
| TXK | Activity | Km app | 80 | 66 | /// | 7 | 62 |
| TYK2 | Activity | Km app | -2 | -2 | -2 | -5 | -5 |
| TYRO3 (RSE) | Activity | Km app | 20 | 13 | 10 | 8 | 14 |
| YES1 | Activity | Km app | 64 | 15 | 17 | 8 | 43 |
| ZAP70 | Activity | Km app | 12 | 13 | 10 | 11 | 10 |

TABLE 5b

| Compound | Conc | | 1000 nM 3 | 1000 nM 4 | 1000 nM 9 | 1000 nM 13 | 1000 nM 20 |
|---|---|---|---|---|---|---|---|
| CAMK1 (CaMK1) | Activity | 100 | 6 | 11 | 4 | 8 | 20 |
| CDK7/cyclin H/MNAT1 | Activity | Km app | -7 | -1 | 20 | -10 | 10 |
| CDK9/cyclin T1 | Activity | Km app | 23 | 14 | 2 | 9 | 13 |
| CHUK (IKK alpha) | Activity | Km app | 1 | 5 | 12 | 6 | 2 |
| DAPK1 | Activity | Km app | -1 | 5 | 9 | 5 | 5 |
| GSG2 (Haspin) | Activity | Km app | 21 | 6 | 13 | 12 | 9 |
| IRAK1 | Activity | Km app | 0 | 8 | 15 | 14 | 13 |
| LRRK2 | Activity | Km app | 7 | 7 | 0 | -2 | 21 |
| LRRK2 G2019S | Activity | Km app | -4 | -13 | -17 | -7 | -5 |
| NUAK1 (ARK5) | Activity | Km app | 9 | 15 | 22 | 14 | 12 |
| PI4KA (PI4K alpha) | Activity | 10 | -12 | -6 | 0 | 2 | 9 |
| PI4KB (PI4K beta) | Activity | Km app | 37 | 13 | 29 | 13 | 9 |
| PIK3C2A (PI3K-C2 alpha) | Activity | Km app | -3 | 9 | 3 | -4 | 8 |
| PIK3C2B (PI3K-C2 beta) | Activity | 100 | 26 | 2 | 3 | -1 | 13 |
| PIK3C3 (hVPS34) | Activity | Km app | -6 | 3 | 1 | -5 | 0 |
| PIK3CA/PIK3R1 (p110 alpha/p85 alpha) | Activity | Km app | 51 | -1 | 7 | 2 | 9 |
| PIK3CD/PIK3R1 (p110 delta/p85 alpha) | Activity | Km app | 66 | 7 | 18 | -1 | 4 |
| PIK3CG (p110 gamma) | Activity | Km app | 48 | 11 | -3 | -2 | 5 |
| SPHK1 | Activity | Km app | -16 | 2 | 3 | 8 | 7 |
| SPHK2 | Activity | 100 | 9 | -4 | -7 | -14 | 4 |

TABLE 5c

| Compound | Conc | 1000 nM 3 | 1000 nM 4 | 1000 nM 9 | 1000 nM 13 | 1000 nM 20 |
|---|---|---|---|---|---|---|
| ACVR1 (ALK2) | Binding | ///// | 10 | 12 | 3 | 5 |
| ACVR2B | Binding | 20 | 19 | 4 | 8 | -11 |
| BMPR1A (ALK3) | Binding | 37 | 5 | 4 | 4 | 12 |
| CAMKK1 (CAMKKA) | Binding | 1 | 2 | 1 | -10 | 0 |
| CAMKK2 (CaMKK beta) | Binding | 8 | 8 | 5 | -1 | 5 |
| CDK8/cyclin C | Binding | 23 | 27 | 20 | 9 | 4 |
| CDK9/cyclin K | Binding | 11 | 3 | 10 | 6 | 6 |
| CLK4 | Binding | 35 | 7 | 19 | 7 | 5 |
| DDR1 | Binding | 1 | 1 | 3 | 0 | 2 |
| DDR2 | Binding | 7 | 2 | 1 | 4 | 5 |
| DMPK | Binding | 5 | 3 | 3 | 1 | 10 |
| EPHA3 | Binding | 2 | 8 | -3 | 5 | -3 |

TABLE 5c-continued

| | | | | | | |
|---|---|---|---|---|---|---|
| EPHA7 | Binding | -3 | -5 | -1 | 1 | 10 |
| KIT V654A | Binding | 12 | 5 | 1 | 1 | 8 |
| LIMK1 | Binding | 21 | 4 | 2 | -6 | -4 |
| LIMK2 | Binding | 14 | 12 | 8 | 9 | 10 |
| MAP2K1 (MEK1) S218D S222D | Binding | //// | 4 | 5 | 1 | 2 |
| MAP2K3 (MEK3) | Binding | 12 | 18 | 9 | 0 | 24 |
| MAP2K6 (MKK6) S207E T211E | Binding | 64 | 3 | 4 | 6 | 1 |
| MAP3K10 (MLK2) | Binding | 20 | 3 | 1 | 2 | 9 |
| MAP3K11 (MLK3) | Binding | 5 | 2 | 4 | -2 | 9 |
| MAP3K14 (NIK) | Binding | 6 | 13 | 9 | 12 | 9 |
| MAP3K2 (MEKK2) | Binding | 13 | 0 | 8 | 1 | 6 |
| MAP3K3 (MEKK3) | Binding | 13 | 7 | 10 | 8 | 10 |
| MAP3K5 (ASK1) | Binding | 15 | -11 | 4 | -8 | 4 |
| MAP3K7/MAP3K7IP1 (TAK1-TAB1) | Binding | 2 | 2 | 2 | 2 | 6 |
| MKNK2 (MNK2) | Binding | 19 | 2 | 2 | 2 | 13 |

| | | | | | | |
|---|---|---|---|---|---|---|
| MLCK (MLCK2) | Binding | 1 | 9 | 10 | 6 | 14 |
| MYLK (MLCK) | Binding | 3 | 1 | 0 | 0 | 0 |
| NLK | Binding | 56 | 3 | 1 | -4 | 10 |
| RIPK2 | Binding | 77 | 6 | 4 | 2 | 8 |
| SLK | Binding | 4 | 4 | 4 | 5 | 5 |
| STK16 (PKL12) | Binding | 2 | 3 | 6 | 1 | 3 |
| STK17A (DRAK1) | Binding | 1 | 0 | -2 | 7 | 2 |
| STK33 | Binding | 3 | 7 | 5 | -6 | 5 |
| TAOK3 (JIK) | Binding | 1 | -5 | -2 | -3 | 4 |
| TEC | Binding | 15 | 3 | 14 | 14 | 5 |
| TGFBR1 (ALK5) | Binding | 65 | 7 | 10 | 7 | 3 |
| TNK2 (ACK) | Binding | 11 | 3 | 5 | 4 | 10 |
| TTK | Binding | 30 | 12 | 22 | 16 | 25 |
| WEE1 | Binding | 20 | 1 | 1 | -2 | -14 |
| WNK2 | Binding | 55 | 9 | 7 | 9 | 15 |
| ZAK | Binding | 75 | 27 | 33 | 4 | 8 |

Table 6 Comparison of selectivity of 13, 1NA-PP1 and 1NM-PP1. All kinases for which >40% inhibition was observed in a kinome wide Z'lyte screen (Life Technologies) are shown.

TABLE 6

| Kinase tested | 13 | 1NA-PP1 | 1NM-PP1 |
|---|---|---|---|
| BMX | 9 | 26 | 52 |
| BTK | 1 | 49 | 61 |
| CSF1R (FMS) | 4 | 40 | 28 |
| CSNK1E (CK1 epsilon) | 40 | | |
| EGFR (ErbB1) L858R | 1 | 40 | 29 |
| EGFR (ErbB1) T790M | 4 | 48 | 38 |
| EGFR (ErbB1) T790M L858R | 10 | 65 | 53 |
| EPHA1 | 15 | | |
| EPHA2 | 4 | 75 | 43 |
| EPHA4 | 7 | | 43 |
| EPHA5 | 5 | | 56 |
| EPHA8 | 9 | 67 | 51 |
| EPHB1 | 5 | 63 | 44 |
| EPHB2 | 14 | 78 | 58 |
| EPHB3 | 6 | 48 | 35 |
| EPHB4 | 6 | 73 | 62 |
| FGR | 6 | 71 | 42 |
| FRK (PTK5) | 5 | | 47 |
| FYN | 6 | 45 | 37 |
| HCK | 5 | 59 | 31 |
| LCK | 18 | 52 | 35 |
| LYN A | 8 | | 55 |
| LYN B | 14 | | 55 |
| MAP4K4 (HGK) | 18 | | 56 |
| MAP4K5 (KHS1) | 20 | 69 | 31 |
| MINK1 | 19 | | 52 |
| PRKACA (PKA) | -4 | 12 | 41 |
| PRKCN (PKD3) | 16 | 69 | 65 |
| PRKD1 (PKC mu) | 18 | 1 | 56 |
| PRKD2 (PKD2) | 19 | 59 | |
| PRKGI | -1 | 75 | 0 |
| PTK6 (Brk) | 27 | | 55 |
| RET | 8 | 79 | 65 |
| RET Y791F | 8 | | 70 |
| SRC | 6 | 65 | 27 |
| SRMS (Srm) | 10 | 61 | 7 |
| YES1 | 8 | 54 | 42 |

TABLE 7

| Compound | c-Src variant IC$_{50}$ (nM) | | |
|---|---|---|---|
| | ES1 | ES2 | ES3 |

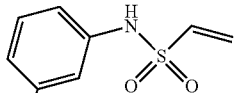

3

111 63 131

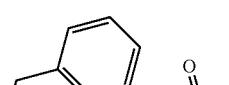

9

150 207 424

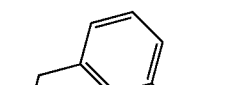

13

338 67 29

IC$_{50}$ values of a panel of electrophilic inhibitors against c-Src-ES variants with second-site mutations (ES1 = T338C; ES2 = T338C/V323A; ES3 = T338C/V323S).

XIV. Kit

In some other embodiments, the present invention provides a kit comprising, a recombinant kinase described herein (see section (V) above) or a nucleic acid described herein (See section IX) and instructions for using the kit. The instructions for using the kit describe the steps set forth in a method provided herein (see section X, XI and XII).

In some embodiments, the present invention provides a kit for testing for inhibition of kinase activity comprising a heterocyclic compound, wherein the heterocyclic compound comprises two or more fused rings and an electrophilic substituent, wherein at least one of the two or more fused rings comprises a nitrogen atom, and a cysteine substituted kinase wherein a gatekeeper amino acid residue within an ATP binding site of the kinase is replaced with a cysteine residue.

XV. Examples

Chemical Synthesis. Reactions were performed in flame dried flasks under argon with magnetic stirring. All $^1$H and $^{13}$C NMR spectra were recorded on a Varian Innova 400 spectrometer and referenced to solvent peaks. $^1$H chemical shifts are reported in δ (ppm) as s (singlet), d (doublet), t (triplet), q (quartet), m (multiplet) or br (broad). Low resolution mass spectra (LC/ESI-MS) were recorded on a Waters Micromass ZQ equipped with a Waters 2695 Separations Module and a XTerra MS C18 3.5 mm column (Waters). RP-HPLC was performed on a Varian ProStar solvent delivery system equipped with a Zorbax 300-SS C18 column using $CH_3CN/H_2O/0.1\%$ TFA (1-100% gradient) and monitoring at 260 nm.

EXAMPLE 1

Preparation of 3-(3-aminophenyl)-1-isopropyl-1H-pyrazolo[3,4-d]pyrimidin-4-amine (22)

This compound was prepared in a similar procedure to that used for (18).

EXAMPLE 2

Preparation of 3-(4-aminophenyl)-1-isopropyl-1H-pyrazolo[3,4-d]pyrimidin-4-amine (23)

This compound was prepared in a similar procedure to that used for (18).

EXAMPLE 3

Preparation of N-(3-(4-amino-1-isopropyl-1H-pyrazolo[3,4-d]pyrimidin-3-yl)phenyl)acrylamide (1)

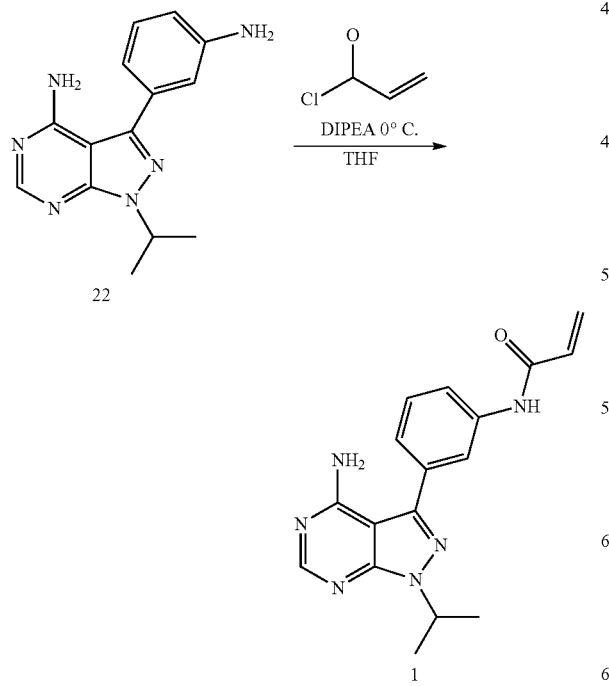

A solution of tetrahydrofuran (20 mL), compound 22 (219 mg, 0.817 mmol) and diisoproylethylamine (156 µL, 0.895 mmol) was cooled to 0° C. Acryloyl chloride (67 µL, 0.828 mmol) was added and the reaction was allowed to proceed for 1 hour and afterwards concentrated in vacuo. The residue was dissolved in dichloromethane (20 mL) and washed with saturated sodium bicarbonate (20 mL). The aqueous layer was extracted with dichloromethane (2×20 mL). The combined organic layers were dried with $MgSO_4$, filtered and concentrated in vacuo. The product was purified by preparative RP-HPLC and lyophilized (70 mg, 26% yield): $^1H$ NMR (400 MHz, DMSO) δ 10.40 (s, 1H), 8.38 (s, 1H), 8.04 (s, 1H), 7.73 (d, J=8.0, 1H), 7.52 (t, J=7.9, 1H), 7.39 (d, J=7.7, 1H), 6.47 (dd, J=17.0, 10.1, 1H), 6.29 (dd, J=17.0, 2.0, 1H), 5.80 (dd, J=10.1, 2.0, 1H), 5.11 (hept, J=6.6, 1H), 1.51 (d, J=6.7, 6H); $^{13}C$ NMR (100 MHz, DMSO) δ 163.47, 154.87, 151.90, 150.94, 144.73, 139.53, 132.54, 131.68, 129.88, 127.31, 123.42, 119.96, 119.22, 96.91, 48.80, 21.74; [M+H]$^+$ calculated for $C_{17}H_{18}N_6O$ 323.1, found 323.5.

EXAMPLE 4

Preparation of N-(3-(4-amino-1-isopropyl-1H-pyrazolo[3,4-d]pyrimidin-3-yl)phenyl)ethenesulfonamide (3)

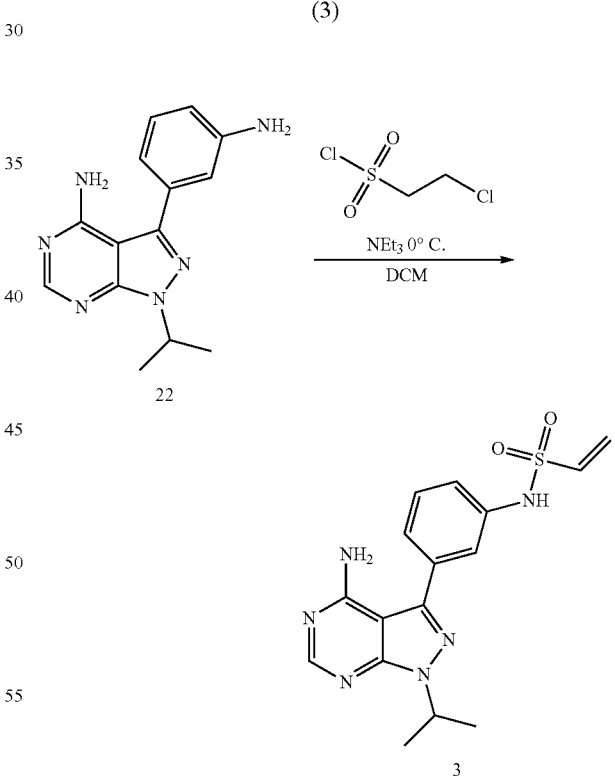

A solution of dichloromethane (2 mL), compound 22 (20 mg, 0.075 mmol) and triethylamine (11 µL, 0.079 mmol) was cooled to 0° C. 2-chloro-1-ethane sulfonyl chloride (7 µL, 0.067 mmol) was added and the reaction was allowed to proceed for 1 hour prior to addition of saturated sodium bicarbonate (10 mL) and extraction with dichloromethane (3×10 mL). The combined organic layers were dried with MgSO₄, filtered and concentrated in vacuo. The product was purified by preparative RP-HPLC and lyophilized (5.6 mg, 23% yield): ¹H NMR (400 MHz, DMSO) δ 10.22 (s, 1H), 8.31 (s, 1H), 7.49 (t, J=7.9, 1H), 7.45 (s, 1H), 7.38 (d, J=7.8, 1H), 7.27 (d, J=7.3, 1H), 6.86 (dd, J=16.4, 10.0, 1H), 6.17 (d, J=16.4, 1H), 6.08 (d, J=9.9, 1H), 5.08 (hept, J=6.7, 1H), 1.50 (d, J=6.7, 6H). ¹³C NMR (100 MHz, DMSO) δ 155.01, 151.96, 151.19, 144.29, 138.50, 136.32, 133.09, 130.22, 127.79, 123.73, 120.09, 119.20, 96.94, 48.85, 21.73; [M+H]⁺ calculated for $C_{16}H_{18}N_6O_2S$ 359.1, found 359.4.

δ 10.57 (s, 1H), 8.41 (s, 1H), 7.95 (s, 1H), 7.67 (d, J=7.6, 1H), 7.53 (t, J=7.9, 1H), 7.41 (d, J=7.7, 1H), 5.11 (hept, J=6.7, 1H), 4.30 (s, 2H), 1.51 (d, J=6.7, 6H); ¹³C NMR (100 MHz, DMSO) δ 165.06, 154.82, 151.89, 150.90, 144.68, 139.03, 132.62, 128.28, 123.81, 120.02, 119.24, 96.92, 48.84, 43.55, 21.77; [M+H]⁺ calculated for $C_{16}H_{17}ClN_6O$ 345.1, found 345.4.

EXAMPLE 5

Preparation of N-(3-(4-amino-1-isopropyl-1H-pyrazolo[3,4-d]pyrimidin-3-yl)phenyl)-2-chloroacetamide (6)

EXAMPLE 6

Preparation of N-(4-(4-amino-1-isopropyl-1H-pyrazolo[3,4-d]pyrimidin-3-yl)phenyl)ethenesulfonamide (5)

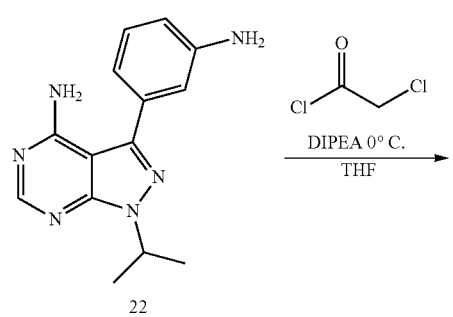

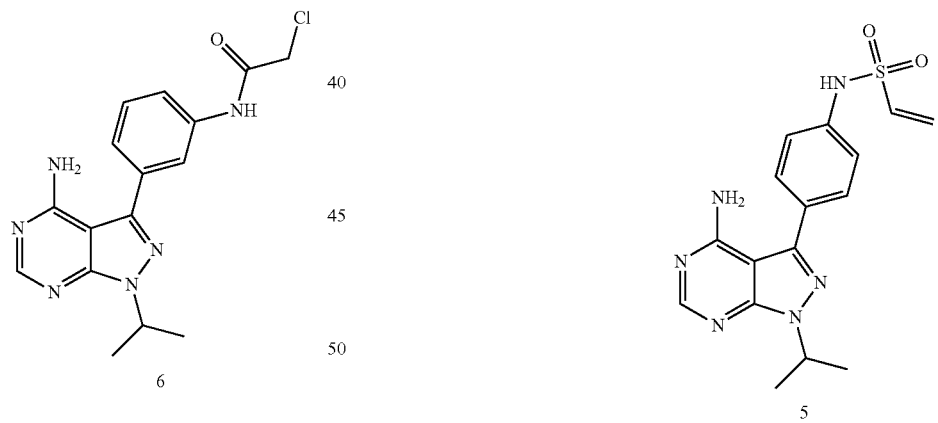

A solution of THF (20 mL), compound 22 (200 mg, 0.75 mmol) and DIPEA (143 μL, 0.821 mmol) was cooled to 0° C. Chloroacetylchloride (54 μL, 0.67 mmol) was added and the reaction was allowed to proceed for 1 hour and afterwards concentrated in vacuo. The residue was dissolved in dichloromethane (20 mL) and washed with saturated sodium bicarbonate (20 mL). The aqueous layer was extracted with dichloromethane (2×20 mL). The combined organic layers were dried with MgSO₄, filtered and concentrated in vacuo. The product was purified by preparative RP-HPLC and lyophilized (30.4 mg, 13% yield): ¹H NMR (400 MHz, DMSO)

A solution of dichloromethane (5 mL), compound 23 (45 mg, 0.168 mmol) and triethylamine (71 μL, 0.509 mmol) was cooled to 0° C. 2-chloro-1-ethane sulfonyl chloride (16 μL, 0.148 mmol) was added and the reaction was allowed to proceed for 1 hour prior to addition of saturated sodium bicarbonate (10 mL) and extraction with dichloromethane (2×10 mL). The combined organic layers were dried with MgSO₄, filtered and concentrated in vacuo. The product was purified by preparative RP-HPLC and lyophilized (8.7 mg, 16% yield): $^1$H NMR (400 MHz, DMSO) δ 10.30 (s, 1H), 8.36 (s, 1H), 7.60 (d, J=8.5, 2H), 7.31 (d, J=8.6, 2H), 6.86 (dd, J=16.4, 9.9, 1H), 6.21 (d, J=16.4, 1H), 6.09 (d, J=9.9, 1H), 5.08 (hept, J=6.7, 2H), 1.49 (d, J=6.7, 6H); $^{13}$C NMR (100 MHz, DMSO) δ 155.44, 152.03, 151.64, 144.22, 138.54, 136.17, 129.25, 127.98, 127.41, 119.52, 96.95, 48.66, 21.75; [M+H]$^+$ calculated for $C_{16}H_{18}N_6O_2S$ 359.1, found 359.5.

EXAMPLE 7

Preparation of 2-(methoxy(3-nitrophenyl)methylene)malononitrile (25)

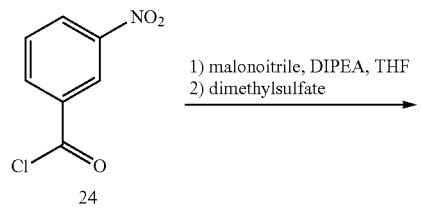

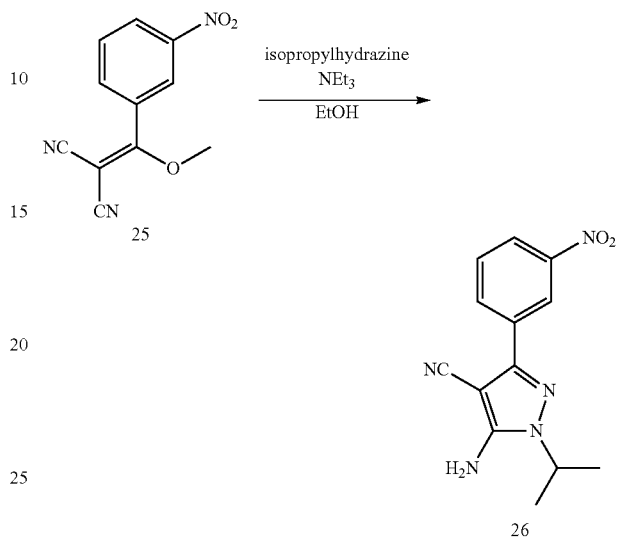

A solution of 3-nitrobenzoylchloride (25 g, 134 mmol), malononitrile (9.74 g, 147 mmol) and THF (140 mL) was cooled to 0° C. DIPEA (59 mL, 335 mmol) was added dropwise and the reaction was allowed to warm to room temperature and proceed for 2 hours. Afterwards, dimethylsulfate (38 mL, 399 mmol) was added and the temperature was raised to 70° C. for 4 hours. Next, the reaction mixture was brought to room temperature and allowed to proceed for an additional 12 hours. EtOAc (200 mL) was added to the reaction mixture in addition to brine (200 mL). The organic and aqueous layers were separated and the aqueous layer was extracted with EtOAc (4×25 mL). The combined organic layers were dried with MgSO$_4$ and concentrated in vacuo. The material was purified over a silica column using chloroform:hexane (90:10) initially and eluted with pure chloroform. After concentrating the fractions containing the product, a yellow oil was triturated with diethyl ether to yield a solid (11.3 g, 37% yield): $^1$H NMR (400 MHz, DMSO) δ 8.63 (s, 1H), 8.51 (d, J=7.7, 1H), 8.16 (d, J=7.7, 1H), 7.94 (t, J=7.8, 1H), 3.93 (s, 3H); $^{13}$C NMR (100 MHz, DMSO) δ 183.66, 147.82, 135.23, 131.00, 129.55, 127.15, 124.08, 113.31, 111.87, 66.71, 61.87; [M+H]$^-$ calculated for $C_{11}H_7N_3O_3$ 228.0, found 214.10 (product appears to hydrolyze during LC/MS analysis).

EXAMPLE 8

5-amino-1-isopropyl-3-(3-nitrophenyl)-1H-pyrazole-4-carbonitrile (26)

Compound 25 (5 g, 21.8 mmol), isopropylhydrazine hydrochloride (2.41 g, 21.8 mmol) (purchased from Ryan Scientific) and triethylamine (6.40 mL, 46.0 mmol) were allowed to react in ethanol (145 mL) at room temperature for 1 hr. After concentrating the reaction mixture, it was purified by silica chromatography using a chloroform/methanol solvent system (methanol gradient increased with time from 0-10%). The relevant fractions were concentrated in vacuo to yield a yellow powder (4.65 g, 79% yield): $^1$H NMR (400 MHz, DMSO) δ 8.59 (s, 1H), 8.24 (m, 2H), 7.78 (t, J=8.2, 1H), 6.82 (br, 2H), 4.53 (hept, J=6.5, 1H), 1.36 (d, J=6.5, 6H). $^{13}$C NMR (100 MHz, DMSO) δ 153.04, 148.76, 146.98, 133.97, 132.22, 131.19, 123.80, 120.37, 116.28, 70.74, 48.64, 22.02; [M+H]$^+$ calculated for $C_{13}H_{11}N_5O_2$ 272.1, found 272.3.

EXAMPLE 9

Preparation of 5-amino-1-isopropyl-3-(3-nitrophenyl)-1H-pyrazole-4-carboxamide (27)

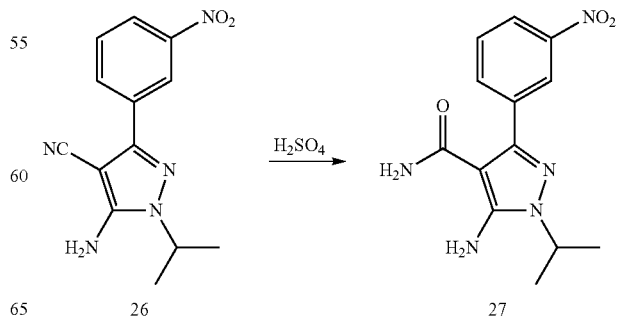

Compound 26 (100 mg, 0.369 mmol) was added to concentrated sulfuric acid (1 mL) and heated to 65° C. for 3 hours. Afterwards, the reaction mixture was poured into ice water and the pH was brought to 14 with 10 M NaOH. The aqueous material was extracted several times with dichloromethane. The combined organic layers were dried over MgSO$_4$, filtered and concentrated to a solid (91 mg, 85% yield): $^1$H NMR (400 MHz, DMSO) δ 8.32 (s, 1H), 8.21 (d, J=8.2, 1H), 7.98 (d, J=7.7, 1H), 7.69 (t, J=8.0, 1H), 6.20 (br, 2H), 4.51 (hept, 1H), 1.35 (d, J=6.5, 6H); $^{13}$C NMR (100 MHz, DMSO) δ 166.17, 149.37, 147.65, 145.50, 135.63, 134.92, 129.69, 122.79, 122.43, 95.43, 47.11, 21.50; [M+H]$^+$ calculated for C$_{13}$H$_{15}$N$_5$O$_3$ 290.1, found 290.0.

EXAMPLE 10

Preparation of 1-isopropyl-3-(3-nitrophenyl)-1H-pyrazolo[3,4-d]pyrimidin-4(5H)-one (28)

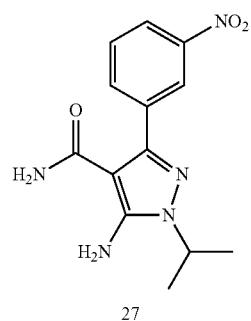

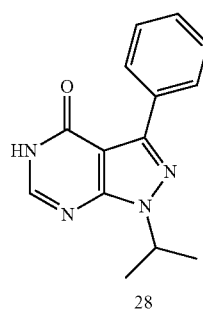

Compound 27 (1 g, 3.46 mmol) was added to formamide (1.167 mL, 29.3 mmol) and heated to 160° C. for 40 hours. Afterwards, the reaction mixture was allowed to cool to room temperature and diluted into ice cold water. The mixture was filtered and a solid was collected (943 mg, 91% yield): $^1$H NMR (400 MHz, DMSO) δ 12.37 (s, 1H), 9.32 (s, 1H), 8.81 (d, J=7.8, 1H), 8.23 (d, J=8.1, 1H), 8.13 (s, 1H), 7.75 (t, J=8.0, 1H), 5.06 (hept, J=6.6, 1H), 1.52 (d, J=6.7, 6H); $^{13}$C NMR (100 MHz, DMSO) δ 157.77, 152.48, 148.16, 148.06, 143.85, 133.58, 129.95, 123.05, 122.07, 103.02, 49.07, 21.74; [M+H]$^+$ calculated for C$_{14}$H$_{13}$N$_5$O$_3$ 300.1, found 300.0.

EXAMPLE 11

Preparation of 3-(1-isopropyl-1H-pyrazolo[3,4-d]pyrimidin-3-yl)aniline (28)

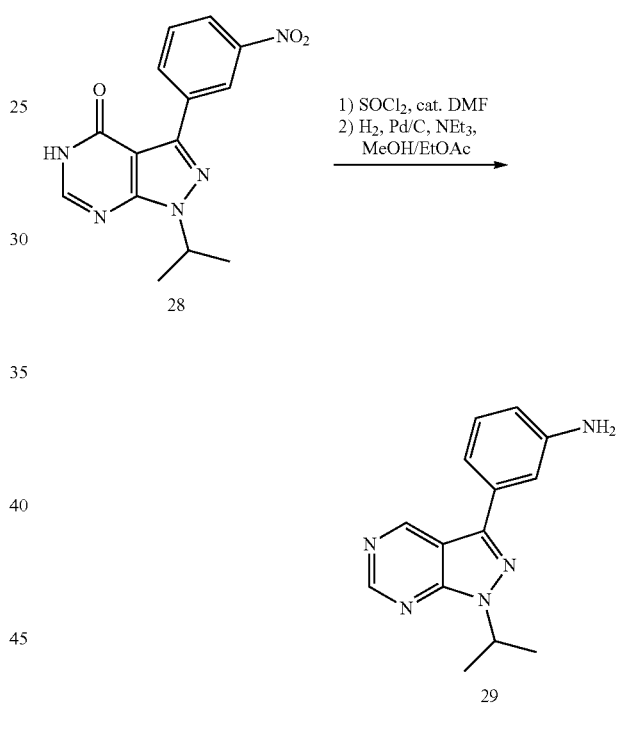

Compound 28 (2 g, 6.68 mmol) was mixed with thionyl chloride (12.5 mL, 171 mmol) and ten drops of DMF and heated to 80° C. for forty minutes. Afterwards, the reaction mixture was poured onto 300 mL of ice and the pH was adjusted to 8 with saturated sodium carbonate. The solution was extracted with dichloromethane (3×150 mL). The combined organic layers were dried over MgSO$_4$ and concentrated in vacuo (2.04 g, yield 96%). The resulting solid (1 g, 3.34 mmol) was dissolved in MeOH/EtOAc (30 mL/20 mL) and reacted with 10% Pd/C (540 mg) and triethylamine (466 μL, 3.34 mmol) under a H$_2$ atmosphere for 24 hours. The reaction mixture was filtered over celite and concentrated. The material was resuspended in dichloromethane (100 mL), which was washed with saturated sodium bicarbonate (2×100 mL) prior to drying with MgSO₄ and concentrating in vacuo. The resulting solid was purified over silica using a dichloromethane/methanol (0-5%) solvent system (487 mg, 58% yield): $^1$H NMR (400 MHz, DMSO) δ 9.59 (s, 1H), 9.02 (s, 1H), 7.34 (s, 1H), 7.23 (d, J=7.6, 1H), 7.18 (t, J=7.7, 1H), 6.66 (d, J=7.7, 1H), 5.30 (br, 2H), 5.21 (kept, J=6.7, 1H), 1.56 (d, J=6.7, 6H); $^{13}$C NMR (100 MHz, DMSO) δ 154.60, 153.03, 151.87, 149.28, 143.17, 132.14, 129.59, 114.65, 114.32, 112.06, 111.85, 48.53, 21.72; [M+H]$^+$ calculated for $C_{14}H_{15}N_5$ 254.1, found 254.0.

EXAMPLE 12

Preparation of N-(3-(1-isopropyl-1H-pyrazolo[3,4-d]pyrimidin-3-yl)phenyl)acrylamide (2)

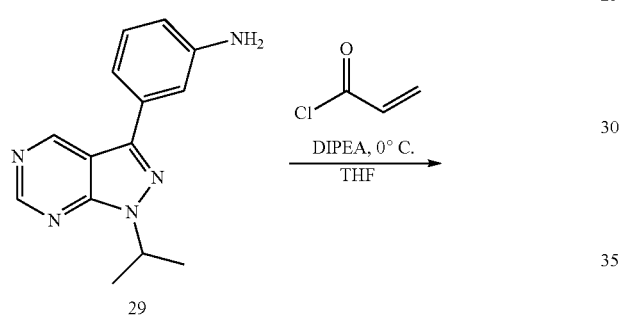

Compound 2 was prepared by the same procedure that was used for compound 1 (49% yield): $^1$H NMR (400 MHz, DMSO) δ 10.36 (s, 1H), 9.66 (s, 1H), 9.08 (s, 1H), 8.41 (t, J=1.8, 1H), 7.84 (m, 2H), 7.52 (t, J=7.9, 1H), 6.48 (dd, J=17.0, 10.0, 1H), 6.32 (dd, J=17.0, 2.0, 1H), 5.81 (dd, J=10.0, 2.0, 1H), 5.24 (kept, J=6.6, 1H), 1.58 (d, J=6.7, 6H); $^{13}$C NMR (100 MHz, DMSO) δ 163.39, 154.53, 152.74, 151.97, 142.36, 139.75, 132.03, 131.77, 129.75, 127.24, 121.84, 119.79, 117.31, 111.98, 48.81, 21.73; [M+H]$^+$ calculated for $C_{17}H_{17}N_5O$ 308.1, found 308.6.

EXAMPLE 13

Preparation of N-(3-(1-isopropyl-1H-pyrazolo[3,4-d]pyrimidin-3-yl)phenyl)ethenesulfonamide (4)

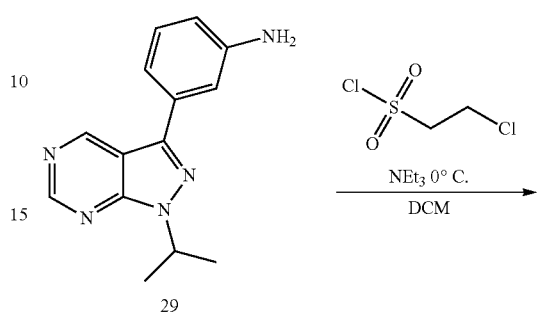

Compound 4 was prepared by the same procedure that was used for compound 3 (18% yield): $^1$H NMR (400 MHz, DMSO) δ 10.17 (s, 1H), 9.61 (s, 1H), 9.08 (s, 1H), 7.90 (t, J=1.9, 1H), 7.82 (d, J=7.7, 1H), 7.49 (t, J=7.9, 1H), 7.29 (ddd, J=8.2, 2.2, 0.9, 1H), 6.87 (dd, J=16.4, 9.9, 1H), 6.17 (d, J=16.4, 1H), 6.07 (d, J=9.9, 1H), 5.23 (hept, J=6.7, 1H), 1.57 (d, J=6.7, 6H); $^{13}$C NMR (100 MHz, DMSO) δ 154.56, 152.69, 151.97, 141.98, 138.59, 136.20, 132.46, 130.16, 127.98, 122.09, 119.78, 117.64, 111.94, 48.89, 21.71; [M+H]$^+$ calculated for $C_{16}H_{17}N_5O_2S$ 344.11, found 344.2.

EXAMPLE 14

Preparation of N-(3-((4-amino-1-isopropyl-1H-pyrazolo[3,4-d]pyrimidin-3-yl)methyl)phenyl)acrylamide (7)

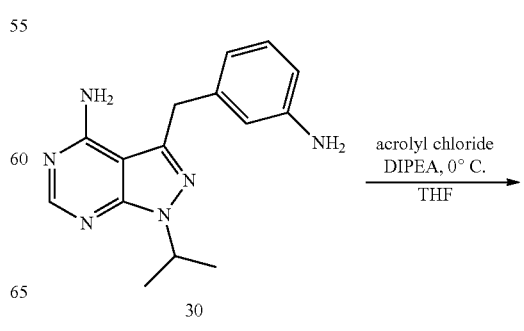

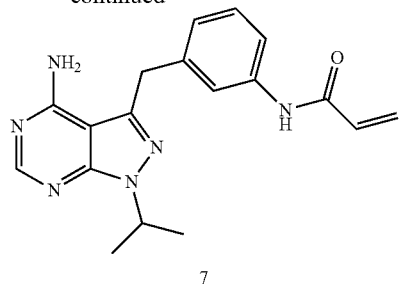

7

A solution of THF (20 mL), compound 30 (200 mg, 0.708 mmol) (prepared as in Dar et al. {Dar, 2008 #18}) and N,N-diisopropylethylamine (136 µL, 0.781 mmol) was cooled 0° C., at which point freshly distilled acryloyl chloride (52 µL, 0.642 mmol) was added. After one hour, the reaction mixture was concentrated in vacuo. The material was resuspended in dichloromethane (20 mL), which was washed with saturated sodium bicarbonate (20 mL). The aqueous layer was extracted with dichloromethane (3×20 mL) and the organic layers were subsequently combined, dried over MgSO$_4$, filtered and concentrated to a solid. The material was purified by RP-HPLC and lyophilized to a white powder (113 mg, 47% yield): $^1$H NMR (400 MHz, DMSO) 10.06 (s, 1H), 8.33 (s, 1H), 7.54 (s, 1H), 7.50 (d, J=8.1, 1H), 7.24 (t, J=7.9, 1H), 6.96 (d, J=7.7, 1H), 6.40 (dd, J=17.0, 10.1, 1H), 6.22 (dd, J=17.0, 2.0, 1H), 5.72 (dd, J=10.1, 1.9, 1H), 4.99 (hept, J=6.5, 1H), 4.40 (s, 2H), 1.46 (d, J=6.7, 6 H); $^{13}$C NMR (100 MHz, DMSO) δ 163.06, 153.94, 151.30, 149.68, 144.69, 139.16, 139.08, 131.86, 128.82, 126.78, 123.59, 119.34, 117.51, 97.90, 48.74, 33.03, 21.70; [M+H]$^+$ calculated for C$_{18}$H$_{20}$N$_6$O 337.2, found 337.4.

EXAMPLE 15

Preparation of N-(3-((4-amino-1-isopropyl-1H-pyrazolo[3,4-d]pyrimidin-3-yl)methyl)phenyl)ethenesulfonamide (9)

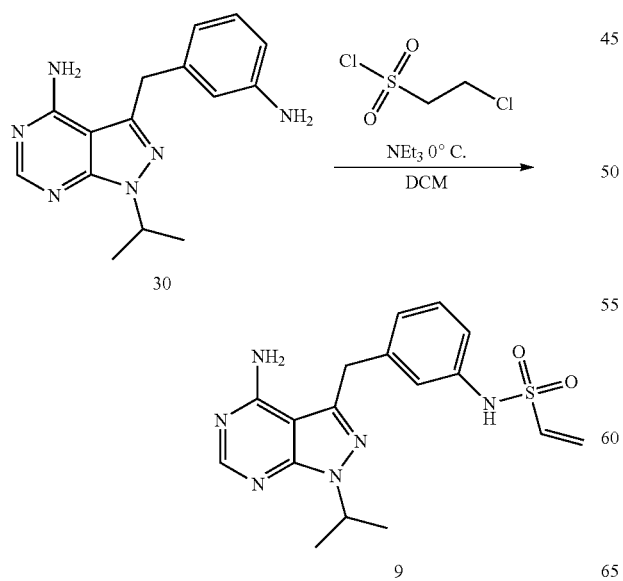

A solution of dichloromethane (20 mL), compound 30 (190 mg, 0.673 mmol) and triethylamine (188 µL, 1.35 mmol) was cooled to 0° C. 2-chloro-1-ethane sulfonyl chloride (70 µL, 0.670 mmol) was added and the reaction was allowed to proceed for 1 hour prior to addition of saturated sodium bicarbonate (20 mL) and extraction with dichloromethane (3×20 mL). The combined organic layers were dried with MgSO$_4$, filtered and concentrated in vacuo. The product was purified by preparative RP-HPLC and lyophilized (14 mg, 6% yield): $^1$H NMR (400 MHz, DMSO) δ 9.95 (s, 1H), 8.31 (s, 1H), 7.21 (t, J=8.1, 1H), 6.97 (m, 3H), 6.69 (dd, J=16.4, 9.9, 1H), 5.97 (d, J=16.5, 1H), 5.93 (d, J=9.9, 1H), 5.00 (hept, J=6.7, 1H), 4.38 (s, 2H), 1.46 (d, J=6.7, 6H); $^{13}$C NMR (100 MHz, DMSO) δ 154.31, 151.46, 150.23, 144.31, 137.91, 136.26, 136.16, 129.25, 127.42, 123.79, 119.26, 117.52, 97.91, 48.59, 32.81, 21.70; [M+H]$^+$ calculated for C$_{17}$H$_{20}$N$_6$O$_2$S 373.1, found 373.4.

EXAMPLE 16

Preparation of N-(4-((4-amino-1-isopropyl-1H-pyrazolo[3,4-d]pyrimidin-3-yl)methyl)phenyl)acrylamide (8)

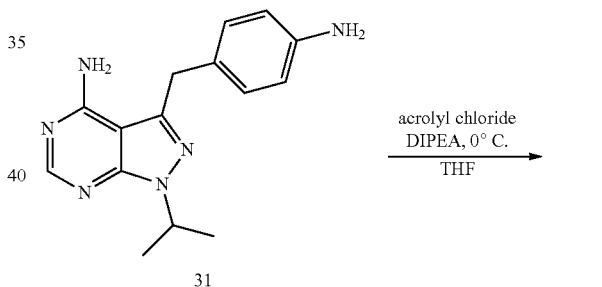

8

A solution of THF (20 mL), compound 31 (200 mg, 0.708 mmol) (prepared as in Dar et al. {Dar, 2008 #18}) and N,N-diisopropylethylamine (136 µL, 0.781 mmol) was cooled 0° C., at which point freshly distilled acryloyl chloride (52 µL, 0.642 mmol) was added. After one hour, the reaction mixture was concentrated in vacuo. The material was resuspended in dichloromethane (20 mL), which was washed with saturated sodium bicarbonate (20 mL). The aqueous layer was extracted with dichloromethane (3×20 mL) and the organic layers were subsequently combined, dried over MgSO$_4$, filtered and concentrated to a solid. The material was purified by RP-HPLC and lyophilized to a white powder (78 mg, 30% yield): $^1$H NMR (400 MHz, DMSO) δ 10.09 (s, 1H), 8.31 (s, 1H), 7.57 (d, J=8.5, 2H), 7.18 (d, J=8.5, 2H), 6.41 (dd, J=17.0, 10.1, 1H), 6.22 (dd, J=17.0, 2.1, 1H), 5.73 (dd, J=10.1, 2.1, 1H), 5.00 (hept, J=6.7, 1H), 4.36 (s, 3H), 1.44 (d, J=6.7, 6H); $^{13}$C NMR (100 MHz, DMSO) δ 163.0, 153.9, 151.3, 149.6, 145.1, 137.4, 133.4, 131.9, 128.7, 126.7, 119.5, 97.8, 48.7, 32.5, 21.6; [M+H]$^+$ calculated for $C_{18}H_{20}N_6O$ 337.2, found 337.4.

dried with MgSO$_4$, filtered and concentrated in vacuo. The product was purified by preparative RP-HPLC and lyophilized (14 mg, 6% yield): $^1$H NMR (400 MHz, DMSO) δ 9.91 (s, 1H), 8.30 (s, 1H), 7.16 (d, J=8.3, 2H), 7.05 (d, J=8.4, 2H), 6.74 (dd, J=16.4, 9.9, 1H), 6.07 (d, J=16.4, 1H), 6.00 (d, J=10.0, 1H), 5.03-4.94 (m, 1H), 4.34 (s, 2H), 1.44 (d, J=6.6, 6H); $^{13}$C NMR (100 MHz, DMSO) δ 154.0, 151.4, 149.8, 144.7, 136.3, 136.0, 133.9, 129.3, 127.5, 120.0, 97.9, 48.6, 32.3, 21.7; [M+H]$^+$ calculated for $C_{17}H_{20}N_6O_2S$ 373.1, found 373.4.

EXAMPLE 18

Preparation of N-(3-((4-amino-1-isopropyl-1H-pyrazolo[3,4-d]pyrimidin-3-yl)methyl)phenyl)ethanesulfonamide (11)

EXAMPLE 17

Preparation of N-(4-((4-amino-1-isopropyl-1H-pyrazolo[3,4-d]pyrimidin-3-yl)methyl)phenyl)ethenesulfonamide (10)

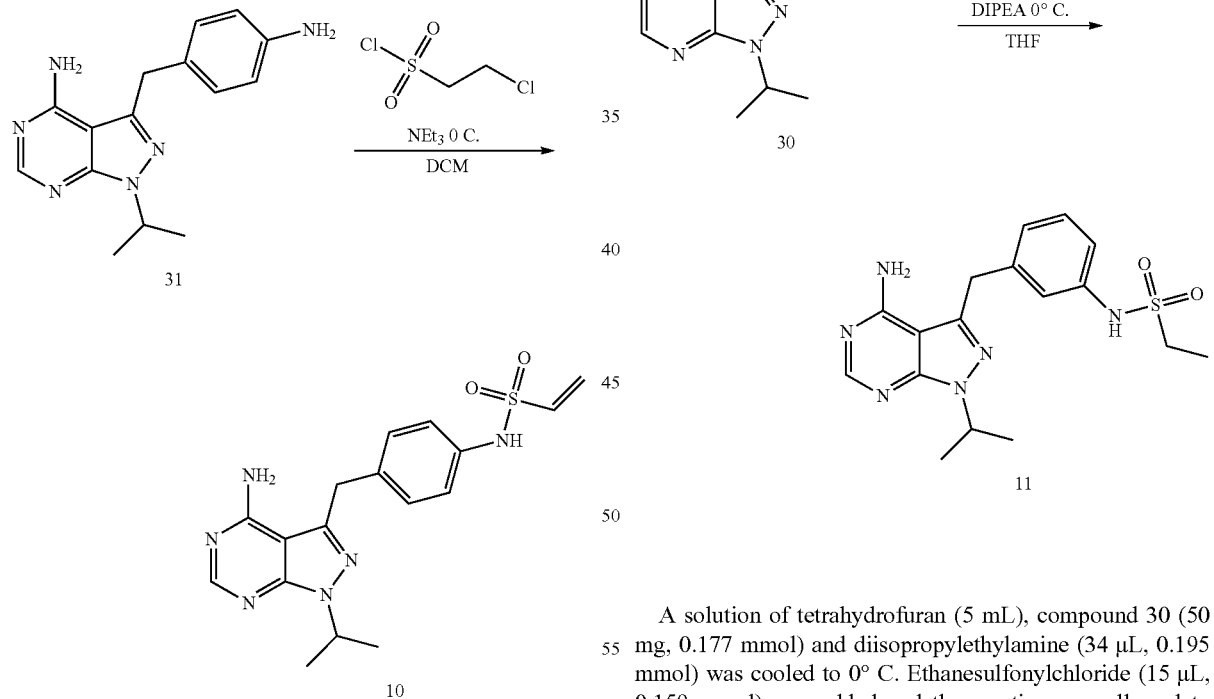

A solution of dichloromethane (20 mL), compound 31 (200 mg, 0.708 mmol) and triethylamine (200 µL, 1.43 mmol) was cooled to 0° C. 2-chloro-1-ethane sulfonyl chloride (70 µL, 0.670 mmol) was added and the reaction was allowed to proceed for 1 hour prior to addition of saturated sodium bicarbonate (20 mL) and extraction with dichloromethane (3×20 mL). The combined organic layers were A solution of tetrahydrofuran (5 mL), compound 30 (50 mg, 0.177 mmol) and diisopropylethylamine (34 µL, 0.195 mmol) was cooled to 0° C. Ethanesulfonylchloride (15 µL, 0.159 mmol) was added and the reaction was allowed to proceed for one hour. After one hour, the reaction mixture was concentrated in vacuo. The material was resuspended in dichloromethane (10 mL), which was washed with saturated sodium bicarbonate (10 mL). The aqueous layer was extracted with dichloromethane (3×10 mL) and the organic layers were subsequently combined, dried over MgSO$_4$, filtered and concentrated to a solid. The combined organic layers were dried with MgSO$_4$, filtered and concentrated in vacuo. The product was purified by preparative RP-HPLC and lyophilized (25 mg, 38% yield): $^1$H NMR (400 MHz, DMSO) δ 9.72 (s, 1H), 8.34 (s, 1H), 7.23 (t, J=7.8, 1H), 7.09 (s, 1H), 7.03 (d, J =7.9, 1H), 6.98 (d, J=7.6, 1H), 5.01 (hept, J=6.7, 1H), 4.40 (s, 2H), 3.01 (q, J=7.3, 2H), 1.46 (d, J=6.7, 6H), 1.13 (t, J=7.3, 3H); $^{13}$C NMR (100 MHz, DMSO) δ 154.11, 151.38, 150.04, 144.45, 139.67, 138.54, 129.28, 123.66, 119.19, 117.45, 97.89, 48.57, 44.89, 32.84, 21.68, 7.90; [M+H]$^+$ calculated for $C_{17}H_{22}N_6O_2S$ 375.1, found 375.6.

EXAMPLE 19

Preparation of N-(3-((4-amino-1-isopropyl-1H-pyrazolo[3,4-d]pyrimidin-3-yl)methyl)phenyl)-2-chloroacetamide (12)

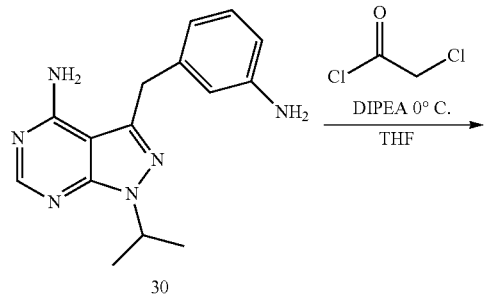

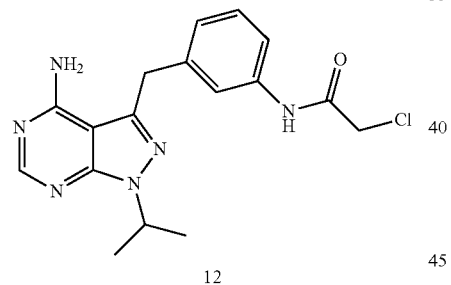

A solution of tetrahydrofuran (10 mL), compound 30 (100 mg, 0.354 mmol) and diisopropylethylamine (68 µL, 0.390 mmol) was cooled to 0° C. Chloroacetylchloride (25.4 µL, 0.313 mmol) was added and the reaction was allowed to proceed for one hour. After one hour, the reaction mixture was concentrated in vacuo. The material was resuspended in dichloromethane (10 mL), which was washed with saturated sodium bicarbonate (10 mL). The aqueous layer was extracted with dichloromethane (3×10 mL) and the organic layers were subsequently combined, dried over MgSO$_4$, filtered and concentrated to a solid. The combined organic layers were dried with MgSO$_4$, filtered and concentrated in vacuo. The product was purified by preparative RP-HPLC and lyophilized (35 mg, 31% yield): $^1$H NMR (400 MHz, DMSO) δ 10.22 (s, 1H), 8.32 (s, 1H), 7.46 (s, 1H), 7.41 (d, J=8.2, 1H), 7.25 (t, J =7.8, 1H), 6.99 (d, J=7.6, 1H), 5.00 (hept, J=6.7, 1H), 4.40 (s, 2H), 4.20 (s, 2H), 1.46 (d, J =6.7, 6H); $^{13}$C NMR (100 MHz, DMSO) δ 164.5, 154.0, 151.3, 150.0, 144.6, 139.2, 138.6, 128.9, 124.0, 119.3, 117.5, 97.9, 48.7, 43.6, 33.0, 21.7; [M+H]$^+$ calculated for $C_{17}H_{19}ClN_6O$ 359.1, found 359.2.

EXAMPLE 20

Preparation of 2-(methoxy(3-bromobenzyl)methylene)malononitrile (33)

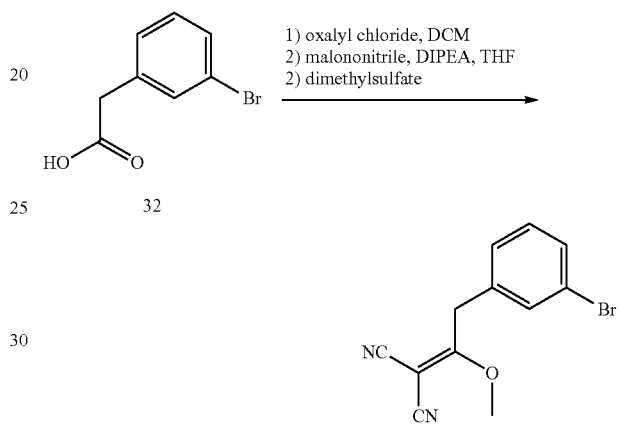

A solution of 3-bromoacetyl acetic acid (5 g, 23.3 mmol) was mixed with oxalyl chloride (10 mL, 121 mmol) in dichloromethane (75 mL) at room temperature for 30 minutes and then concentrated in vacuo. To the resulting solid was added malononitrile (1.69 g, 25.6 mmol) and THF (25 mL). After cooling to 0° C., DIPEA (10.1 mL, 58.1 mmol) was added dropwise and the reaction was allowed to warm to room temperature and proceed for 2 hours. Afterwards, dimethylsulfate (6.60 mL, 69.3 mmol) was added and the temperature was raised to 70° C. for 4 hours. Next, the reaction mixture was brought to room temperature and allowed to proceed for an additional 12 hours. EtOAc (50 mL) was added to the reaction mixture in addition to brine (50 mL). The organic and aqueous layers were separated and the aqueous layer was extracted with EtOAc (4×25 mL). The combined organic layers were dried with MgSO$_4$ and concentrated in vacuo. The material was purified over a silica column using chloroform:hexane (90:10) initially and eluted with pure chloroform. After concentrating the fractions containing the product, an amber oil was triturated with diethyl ether to yield a solid (2.057 g, 32% yield): $^1$H NMR (400 MHz, DMSO) δ 7.56 (m, 2H), 7.38 (t, J=7.7, 1H), 7.31 (d, J=7.7, 1H), 4.19 (s, 2H), 4.01 (s, 3H); $^{13}$C NMR (100 MHz, DMSO) δ 187.96, 135.22, 131.33, 131.18, 130.77, 127.18, 122.32, 113.75, 112.03, 65.62, 60.00, 35.60; [M+H]$^-$ calculated for $C_{12}H_9BrN_2O$ 274.9, 276.9 (50:50), found 274.8, 276.5.

103

EXAMPLE 21

Preparation of 5-amino-3-(3-bromobenzyl)-1-isopropyl-1H-pyrazole-4-carbonitrile (34)

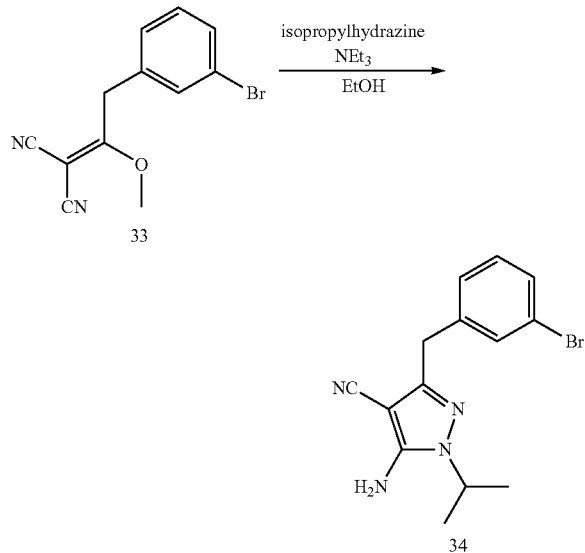

Compound 33 (3.124 g, 11.3 mmol), isopropylhydrazine hydrochloride (1.27 g, 11.5 mmol) (purchased from Ryan Scientific) and triethylamine (6.40 mL, 46.0 mmol) were allowed to react in ethanol (75 mL) at room temperature for 1 hr. After concentrating the reaction mixture, it was purified by silica chromatography using a chloroform/methanol solvent system (methanol gradient increased with time from 0-10%). The relevant fractions were concentrated in vacuo to yield a yellow powder (3.15 g, 87% yield): $^1$H NMR (400 MHz, DMSO) δ 7.41 (m, 2H), 7.26 (td, J=7.7, 1.2, 1H), 7.21 (dt, J=7.7, 1.3, 1H), 6.50 (s, 2H), 4.38 (hept, J=6.5, 1H), 3.81 (s, 2H), 1.27 (d, J=6.5, 6H); $^{13}$C NMR (100 MHz, DMSO) δ 151.01, 150.15, 141.24, 131.05, 130.53, 129.16, 127.45, 121.55, 115.16, 71.77, 47.24, 32.88, 21.35; [M+H]$^+$ calculated for C$_{14}$H$_{15}$BrN$_4$ 319.0, 321.0 found 318.9: 321.0.

EXAMPLE 22

Preparation of 3-(3-bromobenzyl)-1-isopropyl-1H-pyrazolo[3,4-d]pyrimidin-4-amine

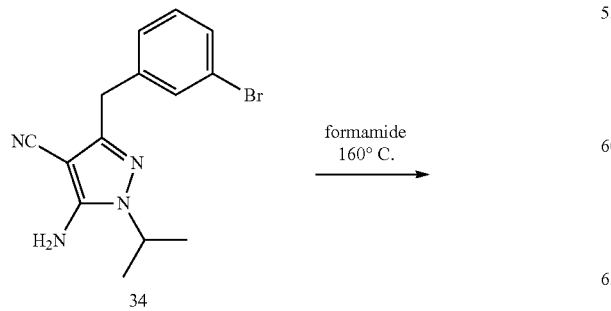

104

-continued

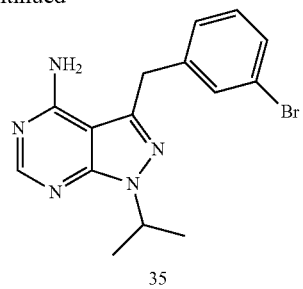

Compound 34 (6.09 g, 19.1 mmol) was added to formamide (26.6 mL, 668 mmol) and heated to 160° C. for 27 hours. Afterwards, the reaction mixture was allowed to cool to room temperature and diluted into ice cold water (50 mL). A viscous material was filtered and dissolved in EtOAc. This solution was washed with brine and concentrated in vacuo (6.23 g, 91% yield): $^1$H NMR (400 MHz, DMSO) δ 8.13 (s, 1H), 7.49 (s, 1H), 7.37 (dt, J=7.5, 1.7, 1H), 7.22 (m, 2H), 4.95 (hept, J=6.6, 1H), 4.38 (s, 2H), 1.43 (d, J=6.7, 6H); $^{13}$C NMR (100 MHz, DMSO) δ 157.90, 155.39, 153.22, 142.01, 141.86, 131.16, 130.52, 129.00, 127.40, 121.56, 98.39, 47.76, 32.66, 21.71; [M+H]$^+$ calculated for C$_{15}$H$_{16}$BrN$_5$ 346.0, 348.0 found 346.0: 348.0.

EXAMPLE 23

Preparation of 3-(3-acetylbenzyl)-1-isopropyl-1H-pyrazolo[3,4-d]pyrimidin-4-amine (14)

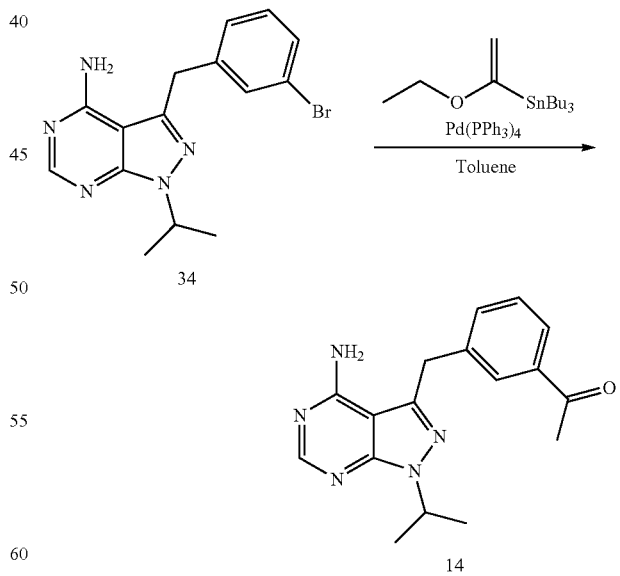

Anhydrous toluene (10 mL) was degassed prior to addition of 34 (3.5 g, 10.1 mmol) Tributyl(1-ethoxyvinyl)tin (4.081 mL, 12.1 mmol), tetrakis(triphenylphosphine) palladium (1.169 g, 10 mol %) and heating to 120° C. After 16 hours, the reaction mixture was concentrated in vacuo. Next, a THF/1M HCl solution (33 mL/10 mL) was added to the brownish material and the reaction was allowed to proceed at room temperature for 12 hours. Afterwards, EtOAc (175 mL) was added to the mixture, which was washed with saturated sodium bicarbonate (700 mL) and extracted with 1 M HCl (2×525 mL). The pH was adjusted to a value of 13 and the mixture was extracted with EtOAc (2×525 mL). The organic layers were dried with sodium sulfate and concentrated in vacuo. The material was purified by silica chromatography using a chloroform/methanol solvent system (methanol gradient increased with time from 0-8%). The relevant fractions were concentrated in vacuo to yield a solid (2.035 g, 65% yield): $^1$H NMR (400 MHz, DMSO) δ 8.13 (s, 1H), 7.91 (s, 1H), 7.79 (d, J=7.5, 1H), 7.48 (d, J=7.7, 1H), 7.43 (t, J=7.6, 1H), 4.97 (hept, J=6.7, 1H), 4.46 (s, 2H), 2.53 (s, 3H), 1.44 (d, J=6.7, 6H); $^{13}$C NMR (100 MHz, DMSO) δ 197.80, 157.96, 155.40, 153.24, 142.22, 139.80, 136.84, 133.15, 128.75, 128.10, 126.32, 98.40, 47.71, 32.94, 26.70, 21.77; [M+H]$^+$ calculated for $C_{17}H_{19}N_5O$ 310.1, found 310.0.

EXAMPLE 24

Preparation of 3-(3-acetylbenzyl)-1-isopropyl-1H-pyrazolo[3,4-d]pyrimidin-4-di-t-butoxycarbonyl amine (14)

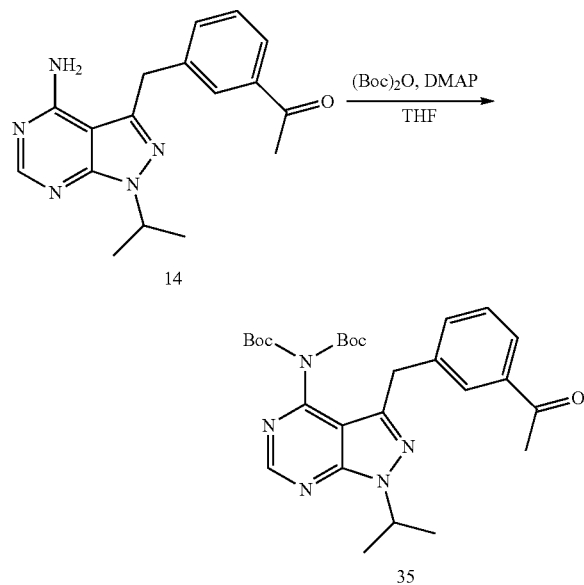

Compound 14, di-tert-butyldicarbonate and dimethylaminopyridine were mixed and allowed to react for 3 hours at room temperature. Afterwards, the reaction mixture was diluted with EtOAc and washed with 1 M HCl and brine. The organic solution was dried with MgSO$_4$ and concentrated in vacuo. The material was purified over a silica column using a hexane/ethyl acetate solvent system (1.834 g, 55% yield): $^1$H NMR (400 MHz, DMSO) δ 8.92 (s, 1H), 7.81 (d, J=7.9, 1H), 7.77 (s, 1H), 7.41 (t, J=7.7, 1H), 7.29 (d, J=7.7, 1H), 5.20 (hept, J=6.7, 1H), 4.25 (s, 2H), 2.53 (s, 3H), 1.55 (d, J=6.7, 6H), 1.28 (s, 18H). $^{13}$C NMR (100 MHz, DMSO) δ 197.42, 154.90, 154.28, 153.19, 149.83, 141.77, 138.25, 136.88, 132.65, 128.85, 127.74, 126.52, 109.01, 83.67, 49.08, 33.51, 27.19, 26.58, 21.63; [M+H]$^+$ calculated for $C_{27}H_{35}N_5O_5$ 510.2, found 510.1.

EXAMPLE 25

Preparation of 1-(3-((4-amino-1-isopropyl-1H-pyrazolo[3,4-d]pyrimidin-3-yl)methyl)phenyl)-2-fluoro-ethanone (13)

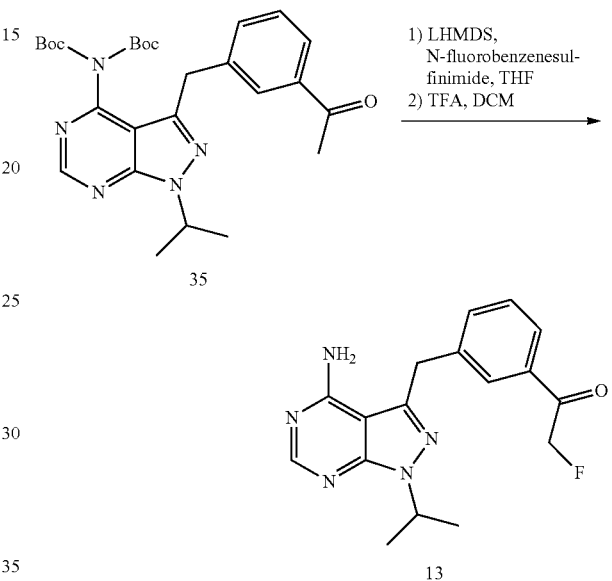

Compound 35 (253 mg, 0.496 mmol) was mixed with anhydrous THF (2 mL) and cooled to −78° C., whereupon 1.0 M LHMDS in THF (0.645 mL, 0.645 mmol) was added dropwise via syringe and allowed to react for 15 minutes. N-fluorobenzenesulfinimide (250 mg, 0.794 mmol) in THF (2 mL) was then added dropwise and the reaction mixture was allowed to come to room temperature over 30 minutes. The reaction mixture was cooled to −78° C. and saturated ammonium chloride (100 mL) was added dropwise. The reaction mixture was extracted with EtOAc (70 mL), and the resulting organic layer was washed with saturated sodium bicarbonate (1×70 mL) and brine (1×70 mL). The organic layer was concentrated in vacuo to give a yellow oil. The resulting product was purified over a silica column (hexane/ethyl acetate solvent system) and fractions containing the monofluorinated product and unreacted material (35) were pooled (they were inseparable). This combined mixture (93 mg) was reacted with TFA (1.5 mL) in DCM for 5 hours at room temperature and then concentrated in vacuo. The Boc-deprotected material was then resuspended in EtOAc (30 mL) and washed with saturated sodium bicarbonate (1×30 mL) and brine (1×30 mL). After concentrating the organic layer, the monofluorinated product was purified by preparative TLC using a 8% MeOH/CHCl$_3$ solvent system (22 mg, 14% yield): $^1$H NMR (400 MHz, DMSO) δ 9.91 (s, 1H), 8.30 (s, 1H), 7.16 (d, J=8.3, 2H), 7.05 (d, J=8.4, 2H), 6.74 (dd, J=16.4, 9.9, 1H), 6.07 (d, J=16.4, 1H), 6.00 (d, J=10.0, 1H), 5.03-4.94 (m, 1H), 4.34 (s, 2H), 1.44 (d, J=6.6, 6H); $^{13}$C NMR (100 MHz, DMSO) δ 154.0, 151.4, 149.8, 144.7, 136.3, 136.0, 133.9, 129.3, 127.5, 120.0, 97.9, 48.6, 32.3, 21.7; [M+H]+ calculated for $C_{17}H_{18}FN_5O$ 328.1, found 328.1.

EXAMPLE 26

Preparation of N-(3-((4-amino-1-methyl-1H-pyrazolo[3,4-d]pyrimidin-3-yl)methyl)phenyl)ethenesulfonamide (15)

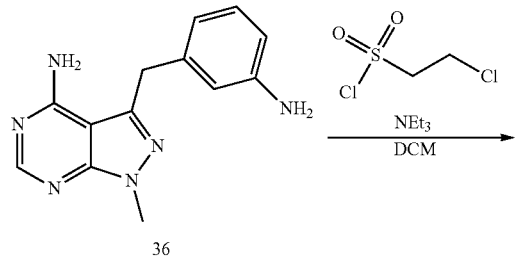

Compound 36 was prepared by the method of Dar et al. {Dar, 2008 #18}. Compound 15 was prepared by the same method used for compound 9 (22% yield): $^1$H NMR (400 MHz, DMSO) δ 9.94 (s, 1H), 8.36 (s, 1H), 7.21 (t, J=7.8, 1H), 6.98 (m, 3H), 6.71 (dd, J=16.4, 9.9, 1H), 6.03 (d, J=16.4, 1H), 5.97 (d, J=9.9, 1H), 4.36 (s, 2H), 3.91 (s, 3H); $^{13}$C NMR (100 MHz, DMSO) δ 154.2, 152.3, 150.4, 144.6, 139.4, 137.9, 136.2, 129.2, 127.6, 124.0, 119.4, 117.5, 97.8, 33.7, 32.8; [M+H]+ calculated for $C_{15}H_{16}N_6O_2S$ 345.1, found 345.4.

EXAMPLE 27

Preparation of N-(3-((4-amino-1-tert-butyl-1H-pyrazolo[3,4-d]pyrimidin-3-yl)methyl)phenyl)ethenesulfonamide (16)

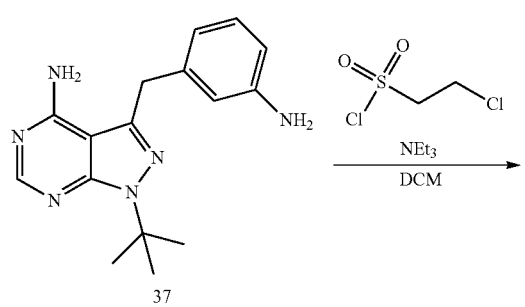

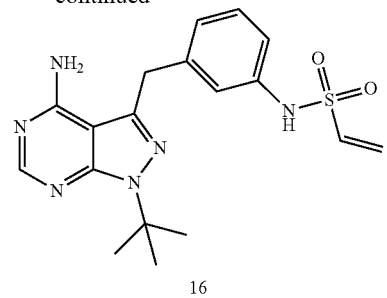

Compound 37 was prepared by the method of Dar et al. {Dar, 2008 #18}. Compound 16 was prepared by the same method used for compound 9 (10% yield): $^1$H NMR (400 MHz, DMSO) δ 9.95 (s, 1H), 8.30 (s, 1H), 7.21 (t, J=8.1, 1H), 6.97 (m, 3H), 6.69 (dd, J=16.4, 9.9, 1H), 5.94 (m, 2H), 4.36 (s, 2H), 1.71 (s, 9H); $^{13}$C NMR (100 MHz, DMSO) δ 154.5, 152.3, 149.6, 142.5, 139.6, 137.9, 136.2, 129.1, 127.4, 123.8, 119.1, 117.4, 99.1, 60.2, 32.8, 28.8; [M+H]+ calculated for $C_{18}H_{22}N_6O_2S$ 387.2, found 387.5.

EXAMPLE 28

Preparation of N-(3-((4-amino-1-cyclopentyl-1H-pyrazolo[3,4-d]pyrimidin-3-yl)methyl)phenyl)ethenesulfonamide (17)

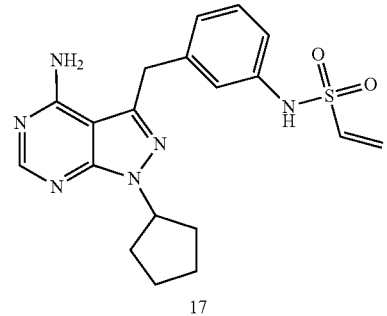

Compound 38 was prepared by the method of Dar et al. {Dar, 2008 #18}. Compound 17 was prepared by the same method used for compound 9 (18% yield): $^1$H NMR (400 MHz, DMSO) δ 9.95 (s, 1H), 8.37 (d, J=6.8, 1H), 7.21 (t, J=8.0, 1H), 6.98 (m, 3H), 6.69 (dd, J=16.4, 9.9, 1H), 5.98 (d, J=16.4, 1H), 5.93 (d, J=9.9, 1H), 5.18 (t, J=7.2, 1H), 4.38 (s, 2H), 2.08 (m, 2H), 1.98 (m, 2H), 1.88 (m, 2H), 1.68 (m, 2H); $^{13}$C NMR (100 MHz, DMSO) δ 153.7, 151.7, 149.6, 144.7, 139.5, 137.9, 136.2, 129.1, 127.4, 123.8, 119.2, 117.5, 97.9, 57.2, 32.8, 31.9, 24.3; [M+H]$^+$ calculated for $C_{19}H_{22}N_6O_2S$ 399.2, found 399.4.

EXAMPLE 29

Preparation of N1-(6,7-dimethoxyquinazolin-4-yl)benzene-1,3-diamine

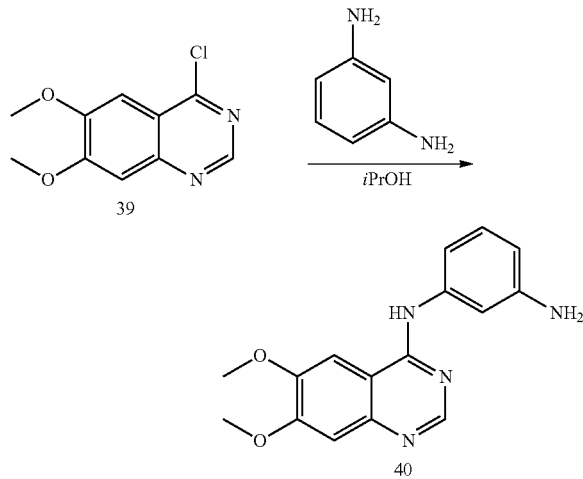

Compound 39 was prepared by a previously described method {Perera, 2008 #110}. Compound 39 (300 mg, 1.34 mmol) and 1,3-phenylenediamine (1.78 g, 16.5 mmol) were heated to 90° C. in isopropanol and allowed to react for 1.5 hours, after which the reaction was brought to room temperature. The resulting green, solid product was collected by filtration and washed with cold isopropanol (173 mg, 44% yield): $^1$H NMR (400 MHz, DMSO) δ 11.01 (br, 1H), 8.72 (s, 1H), 8.24 (s, 1H), 7.36 (s, 1H), 7.15 (t, J=8.0, 1H), 7.00 (s, 1H), 6.93 (d, J=7.9, 1H), 6.62 (d, J=8.0, 1H), 3.99 (s, 3H), 3.97 (s, 3H); $^{13}$C NMR (100 MHz, DMSO) δ 157.85, 155.85, 149.92, 149.21, 137.73, 129.08, 113.52, 112.92, 110.99, 107.35, 103.60, 100.86, 56.73, 56.33; [M+H]$^+$ calculated for $C_{16}H_{16}N_4O_2$ 297.1, found 297.4.

EXAMPLE 30

Preparation of N-(3-(6,7-dimethoxyquinazolin-4-ylamino)phenyl)acrylamide (18)

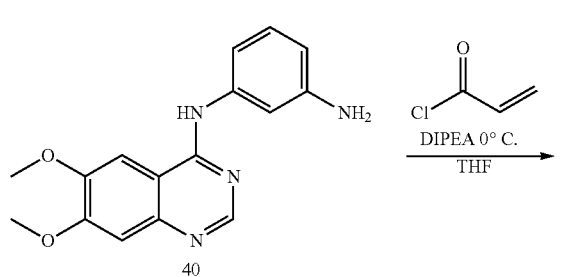

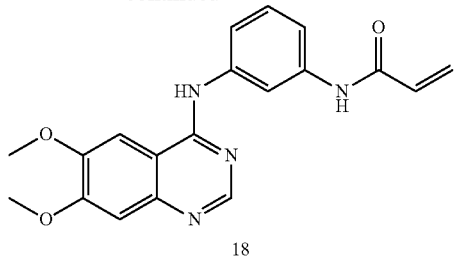

A solution of THF (7 mL), compound 40 (75 mg, 0.253 mmol) and 1N,N-diisopropylethylamine (96 µL, 0.551 mmol) was cooled 0° C., at which point freshly distilled acryloyl chloride (19 µL, 0.230 mmol) was added. After one hour, the reaction mixture was concentrated in vacuo. The material was resuspended in dichloromethane (10 mL), which was washed with saturated sodium bicarbonate (10 mL). The aqueous layer was extracted with dichloromethane (2×10 mL) and the organic layers were subsequently combined, dried over MgSO$_4$, filtered and concentrated to a solid. The material was purified by RP-HPLC and lyophilized to a powder (40 mg, 50% yield): $^1$H NMR (400 MHz, DMSO) δ 10.81 (br, 1H), 10.31 (s, 1H), 8.78 (s, 1H), 8.17 (s, 1H), 8.06 (s, 1H), 7.41 (m, 3H), 7.25 (s, 1H), 6.47 (dd, J=17.0, 10.1, 1H), 6.28 (dd, J=17.0, 1.9, 1H), 5.79 (dd, J=10.1, 1.9, 1H), 4.00 (s, 6H); $^{13}$C NMR (100 MHz, DMSO) δ 163.32, 158.05, 156.18, 150.11, 149.32, 139.48, 137.32, 131.73, 129.02, 127.18, 119.88, 117.10, 115.49, 107.30, 103.23, 100.68, 56.57, 56.45; [M+H]$^+$ calculated for $C_{19}H_{18}N_4O_3$ 351.1, found 351.4.

EXAMPLE 31

Preparation of N-(3-(6,7-dimethoxyquinazolin-4-ylamino)phenyl)ethenesulfonamide (19)

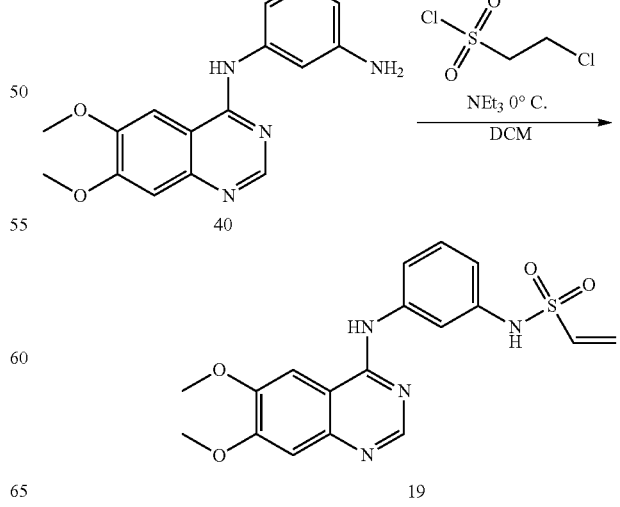

A solution of dichloromethane (10 mL), compound 40 (97 mg, 0.327 mmol) and triethylamine (138 μL, 0.989 mmol) was cooled to 0° C. 2-chloro-1-ethane sulfonyl chloride (30 μL, 0.287 mmol) was added and the reaction was allowed to proceed for 1 hour prior to removal of a greenish precipitate and addition of saturated sodium bicarbonate (10 mL) and extraction with dichloromethane (2×10 mL). The combined organic layers were dried with MgSO$_4$, filtered and concentrated in vacuo. The product (organic layers and green precipitate combined) was purified by preparative RP-HPLC and lyophilized (40 mg, 36% yield): $^1$H NMR (400 MHz, DMSO) δ 10.71 (br, 1H), 10.20 (s, 1H), 8.76 (s, 1H), 8.02 (s, 1H), 7.52 (s, 1H), 7.39 (m, 2H), 7.25 (s, 1H), 7.06 (m, 1H), 6.82 (dd, J=16.4, 9.9, 1H), 6.18 (d, J=16.4, 1H), 6.10 (d, J=9.9, 1H), 3.99 (s, 6H); $^{13}$C NMR (100 MHz, DMSO) δ 157.94, 156.12, 150.06, 149.43, 138.29, 137.85, 136.06, 129.40, 128.11, 119.92, 117.13, 115.32, 107.41, 103.15, 100.96, 56.55, 56.42; [M+H]$^+$ calculated for C$_{18}$H$_{18}$N$_4$O$_4$S 387.1, found 387.5.

EXAMPLE 32

Preparation of N1-(6,7-dimethoxyquinazolin-4-yl)benzene-1,4-diamine (41)

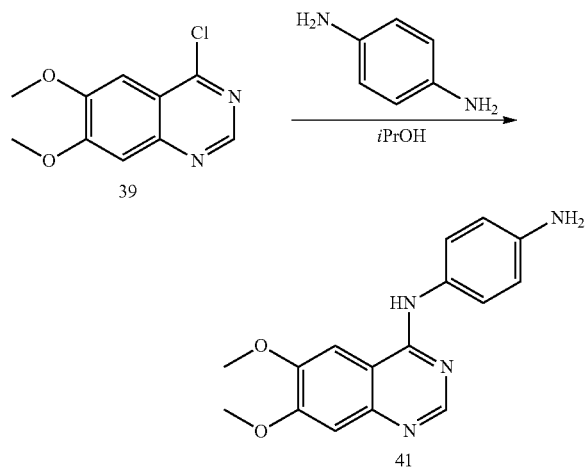

Compound 39 was prepared by a previously described method {Perera, 2008 #110}. Compound 39 (600 mg, 2.68 mmol) and 1,3-phenylenediamine (3.57 g, 33 mmol) were heated to 90° C. in isopropanol and allowed to react for 1.5 hours, after which the reaction was brought to room temperature. The resulting solid product was collected by filtration and washed with cold isopropanol (775 mg, 98% yield): $^1$H NMR (400 MHz, DMSO) δ 10.38 (br, 1H), 8.59 (s, 1H), 8.00 (s, 1H), 7.28 (d, J=8.6, 2H), 7.20 (s, 1H), 6.79 (s, 1H), 6.66 (d, J=8.6, 2H), 3.96 (s, 6H); $^{13}$C NMR (100 MHz, DMSO) δ 157.31, 155.07, 150.47, 149.39, 145.88, 126.53, 125.38, 113.97, 107.62, 103.05, 102.79, 56.49, 56.10; [M+H]$^+$ calculated for C$_{16}$H$_{16}$N$_4$O$_2$ 297.1, found 297.4.

EXAMPLE 33

Preparation of N-(4-(6,7-dimethoxyquinazolin-4-ylamino)phenyl)ethenesulfonamide (20)

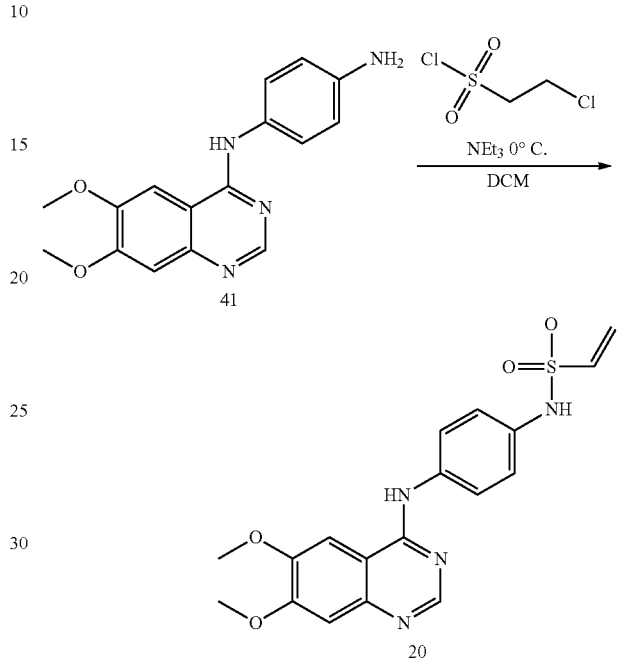

A solution of dichloromethane (10 mL), compound 41 (100 mg, 0.337 mmol) and triethylamine (141 μL, 1.02 mmol) was cooled to 0° C. 2-chloro-1-ethane sulfonyl chloride (32 μL, 0.304 mmol) was added and the reaction was allowed to proceed for 1 hour prior to removal of a precipitate and addition of saturated sodium bicarbonate (10 mL) and extraction with dichloromethane (2×10 mL). The combined organic layers were dried with MgSO$_4$, filtered and concentrated in vacuo. The product was purified by preparative RP-HPLC and lyophilized (24 mg, 20% yield): $^1$H NMR (400 MHz, DMSO) δ 10.81 (br, 1H), 10.13 (s, 1H), 8.75 (s, 1H), 8.02 (s, 1H), 7.58 (d, J=8.9, 2H), 7.25 (m, 3H), 6.83 (dd, J=16.4, 10.0, 1H), 6.15 (d, J=16.5, 1H), 6.07 (d, J=10.0, 1H), 3.99 (s, 3H), 3.98 (s, 3H); $^{13}$C NMR (100 MHz, DMSO) δ 157.93, 156.16, 150.10, 149.26, 136.23, 135.75, 132.76, 127.82, 125.54, 120.00, 107.16, 103.16, 100.51, 56.55, 56.45; [M+H]$^+$ calculated for C$_{18}$H$_{18}$N$_4$O$_4$S 387.1, found 387.4.

EXAMPLE 34

Gel Filtration and Kinetic Assays

Inhibitors (final concentration 23 μM) were incubated with c-Src variants (final concentration 11.5 μM) in kinase reaction buffer (50 mM Tris pH 8, 100 mM NaCl, 1 mM DTT, 5% glycerol, 5% DMSO) for 25 minutes at room temperature. The solutions (2.6 mL total) were then passed over PD10 desalting columns (GE Healthcare) using the kinase reaction buffer for elution. Src concentrations were calculated using the extinction coefficient for c-Src (51.140 mM$^{-1}$cm$^{-1}$)

{Seeliger, 2005 #100}. Kinase assays were performed as described in the experimental section at a final enzyme concentration of 10 mM.

Protein labeling conditions: Kinase labeling reactions were performed by incubating 30 µL quantities of c-Src variants (in 50 mM Tris pH 8, 100 mM NaCl, 1 mM DTT, 5% glycerol) with two equivalents of inhibitor in DMSO (final DMSO concentration=2.4%). The covalent labeling reaction was quenched by removing 4 µL and adding it to 31 µL of 0.1% formic acid. The sample was then analyzed by ESI-oa-TOF mass spectrometry.

EXAMPLE 35

Crystallization and Data Collection for c-Src-ES-9

The c-Src-ES variant was prepared and purified as described above, run over a 0.22 µm PVDF centrifugal filter and diluted to 1.5-3 mg/ml in 50 mM Tris (pH 8.0), 100 mM NaCl, 5% (v/v) glycerol, 1 mM DTT. Compound 9 was freshly dissolved in DMSO and added to the protein solutions (1.5-3 equivalents). After 1.5 hours of incubation at room temperature, the reaction mixtures were spun at 10,000 rpm and the supernatants were collected. Hanging drop crystallization conditions were set up by mixing 1:1 protein and precipitation solutions (100 mM MES (pH 6.5), 50 mM NaOAc, 4-8% PEG 4000). After 24-48 hours at room temperature, thin plate-like crystals were observed. Crystals were cryoprotected in the crystallization solution supplemented with 25% glycerol and stored in liquid nitrogen prior to obtaining diffraction data at beamline 8.2.2 (wavelength of 1.0088 nm, nitrogen gas stream at 100 K) at the Berkeley Lab Advanced Light Source. Data was processed with HKL2000 (HKL Research, Inc.) and Phenix software {Adams, #108}.

Crystal structure of c-Src-ES1 with 9—In order to elucidate the binding mode for a kinase with a cysteine gatekeeper and an irreversible inhibitor, an X-ray crystal structure of the catalytic domain of c-Src-ES1 (residues 251-533) bound to 9 was solved (FIG. 2). Co-crystallization through incubation of c-Src-ES1 with 9 was performed using hanging-drop vapor diffusion. The complex was solved by molecular replacement and, contained two molecules in the crystallographic asymmetric unit of the P1 space group. The structure was refined to 2.2 Å and exhibited electron density for 9 covalently bound to Cys338. Poor electron density was observed near the N-terminus (residues 251-256) and in flexible regions of the kinase such as the glycine-rich loop (residues 275-278) and the activation segment (residues 407-424). However, the DFG motif at the beginning of the activation segment (residues 404-406) was clearly resolved and was in the conformation associated with an active kinase (DFG-in).

The binding mode of 9 (a vinylsulfonamide functionalized compound) with c-Src-ES1 is related to Type I½ kinase inhibition. Like Type I inhibitors, Type I½ inhibitors bind the active conformation of the kinase (DFG-in) and engage in a series of hydrogen bonds in the hinge region. Type I½ are similar to Type II inhibitors in that they occupy the pocket situated behind the gatekeeper and hydrogen bond to the carboxylate of the conserved glutamate on the αC-helix and backbone amide of the DFG aspartate (FIG. 2C). The hydrogen bonds afforded by the tetrahedral arrangement of the sulfone may contribute to the increased potency of 9 relative to 7, which contains an acrylamide.

EXAMPLE 36

Kinome-Wide Profiling of Inhibitors

The percent inhibition results in FIG. were generated with biochemical enzymatic kinase assays using the SelectScreen® Kinase Profiling Service (Life Technologies Corporation, Madison, Wis.). Compounds were assayed at 1 µM at an ATP concentration equal to the ATP Km,app for the assay following the detailed procedures described in the SelectScreen® Customer Protocol and Assay Conditions documents located at www.invitrogen.com/kinaseprofiling.

In order to identify potential off-targets, a panel of the electrophilic inhibitors that showed inhibition of c-Src-ES1 against 307 kinases was screened (Table 5). Compounds that were profiled include, but are not limited to, 3, 4, 9, 13, and 20. Excluding 3, all of the compounds had relatively few off-target effects. The exocyclic amine mimics N6 of ATP and plays an important role in a hydrogen bonding interaction with the hinge region of kinases. Several of the kinases for which >80% inhibition was achieved with vinylsulfonamide-based inhibitors was observed are those with exposed cysteines near the active site (e.g. EGFR, HER4, BTK, BMX, TXK). The fluoromethylketone-type compound, 13, had a clean profile against kinases in the panel. The present invention provides one of the most selective chemical genetic kinase inhibitor reported to date.

EXAMPLE 37

Site Directed Mutagenesis

The T338C mutation was introduced to a pET-28 vector containing a hexahistidine-tagged Src construct using standard site directed mutagenesis methods. The protein was produced in E. coli BL21DE3 cells containing YopH phosphatase and GroEL. The cells were grown in Terrific Broth containing (kanamycin, 50 mg/mL/streptomycin, 50 mg/mL). Cells were grown to an $OD_{600nm}$ of 1.2 at 37° C., and cooled for 1 hour with shaking at 18° C. Afterwards, the cells were induced for 16 h at 18° C. with 0.2 mM IPTG. Cells were harvested and resuspended in 50 mM Tris (pH 8.0), 500 mM NaCl, 5% glycerol, 25 mM imidazole for purification over Ni-NTA resin.

EXAMPLE 38

Expression and Purification of c-Src Variants

Hexahistidine-tagged recombinant chicken c-Src (residues 251-533) was prepared in a similar manner to that described in Seeliger M A, et al. Protein Sci. 14 (12):3135-3139 with the modifications used by Blair J A, et al. (2007) Structure-guided development of affinity probes for tyrosine kinases using chemical genetics. Nat Chem Biol 3(4):229-238. The hexahistidine tag was removed with AcTev protease (Invitrogen) and concentrations were determined spectrophotometrically at 280 nm using an extinction coefficient of 52,370 $M^{-1}cm^{-1}$. All mutations were introduced using the site-directed mutagenesis protocol of Zheng L, Baumann U, Reymond J L (2004) An efficient one-step site-directed and site-saturation mutagenesis protocol. Nucleic Acids Res 32(14): e115. Protein aliquots were stored at −80° C. in 50 mM Tris (pH 8), 100 mM NaCl, 1 mM DTT and 5% glycerol.

EXAMPLE 39

In vitro Kinase Assays

In vitro kinase assays for c-Src variants were performed in 50 mM Tris (pH 8.0), 10 mM $MgCl_2$ and 1 mg/mL BSA. When obtaining kinetic parameters ($k_{cat}$, $K_m$) kinase and peptide substrate (IYGEFKKK) (SEQ ID NO:51) concentrations were 2 nM and 500 μM, respectively, while ATP concentrations ranged from 2000-0.655 μM. Addition of nonradioactive ATP supplemented with $^{32}$P ATP (3,000 Ci/mmol, NEN) was used to initiate kinase reactions. Time points were selected such that product formation never exceeded 10%. Reactions were quenched by spotting 3 μL quantities onto phosphocellulose sheets (P81, Whatman). Afterwards, the sheets were washed 3×5 minutes in 0.5% phosphoric acid and dried. Radioactivity was measured by phosphorimaging and recorded on a Typhoon fluorescence imager (Molecular Dynamics). Data were plotted as rate (min$^{-1}$) versus ATP concentration and fitted to the Michaelis-Menten equation, $v=[(k_{cat})[S]]/(K_m+[S])$, using Kaleidagraph software (Synergy) to extract kinetic parameters. When obtaining IC$_{50}$ values for the inhibitors, 2% (v/v) DMSO was included in kinase reactions. In these cases ATP, peptide, and enzyme concentrations were 15 nM, 100 μM and 5 nM, respectively, while inhibitor concentrations ranged from 10,000-0.610 nM. In all cases, a ten-minute preincubation step between the kinase and the inhibitor preceded addition of ATP and a fifteen-minute reaction. The data was fitted to a sigmoidal dose-response curve using Prism 4.0c (GraphPad Software) to obtain IC$_{50}$ values.

EXAMPLE 40

Crystallization and Data Collection for c-Src-ES1-9

The c-Src-ES1 variant was prepared and purified as described above, run over a 0.22 μm PVDF centrifugal filter and diluted to 1.5-3 mg/ml in 50 mM Tris (pH 8.0), 100 mM NaCl, 5% (v/v) glycerol, 1 mM DTT. Compound 9 was freshly dissolved in DMSO and added to the protein solutions (1.5-3 equivalents). After 1.5 hours of incubation at room temperature, the reaction mixtures were spun at 10,000 rpm and the supernatants were collected. Hanging drop crystallization conditions were set up by mixing 1:1 protein and precipitation solutions (100 mM MES (pH 6.5), 50 mM NaOAc, 4-8% PEG 4000). After 24-48 hours at room temperature, thin plate-like crystals were observed. Crystals were cryoprotected in the crystallization solution supplemented with 25% glycerol and stored in liquid nitrogen prior to obtaining diffraction data at beamline 8.2.2 (wavelength of 1.0088 nm, nitrogen gas stream at 100 K) at the Berkeley Lab Advanced Light Source. Data was processed with HKL2000 (HKL Research, Inc.) and Phenix software.

EXAMPLE 41

Immunoprecipitation and Assay of MOK

A plasmid encoding full-length mouse MOK with a FLAG-tag for expression in mammalian cells was used. Immunoprecipitation from Cos7 cells was performed using a procedure similar to Miyata Y, Akashi M, Nishida E (1999). Molecular cloning and characterization of a novel member of the MAP kinase superfamily. *Genes Cells* 4(5):299-309, with the following modification: MOK was directly immunoprecipitated on ANTI-FLAG M2 magnetic beads (Sigma-Aldrich). Kinase assays were performed directly on-bead for 60 minutes in 30 μL quantities of 50 mM Tris-HCl, 16 mM MOPS, 150 mM NaCl, 10 mM MgCl$_2$, 20 mM β-glycerophosphate, 2 mM EGTA, 0.8 mM sodium orthovanadate, 0.4 mM dithiothreitol, 0.1 mM ATP (supplemented with $^{32}$P ATP (3,000 Ci/mmol, NEN)), and 20 μg of a protein substrate (myelin basic protein) at a pH of 8. Inhibitors were used at a concentration of 1 μM (final DMSO concentration, 2%). Myelin basic protein phosphorylation was analyzed by SDS-PAGE and autoradiography. MOK levels were evaluated by Western blot using HRP conjugated ANTI-FLAG M2 antibody at a 1000:1 dilution.

EXAMPLE 42

Inhibition Assays with v-Src Transformed NIH-3T3 Cells

NIH-3T3 cell lines transformed with v-Src gatekeeper variants were prepared using a procedure similar to that in Bishop A C, et al. (1998) Design of allele-specific inhibitors to probe protein kinase signaling. *Curr Biol* 8(5):257-266. Cells were grown to 60-90% confluence in DMEM supplemented with fetal bovine serum (10%), penicillin 'G' (100 units/ml) and streptomycin sulfate (100 μg/ml) (PenStrep, UCSF Cell Culture Facility) prior to treatment with kinase inhibitors dissolved in DMSO (final DMSO concentration, 0.5%). Following 1 hour of incubation with inhibitors at 37° C., cells were harvested in lysis buffer (50 mM Tris (pH 7.4), 300 mM NaCl, 5 mM EDTA, 1% triton, 0.02% NaN$_3$, 1× complete mini protease inhibitor (Roche), 1 mM PMSF, 1×PHOS-stop (Roche), 0.02 μM microcystin, 2 mM sodium orthovanadate), normalized for concentration and analyzed by Western blot for global phosphotyrosine levels (4G10, Millipore, 1:1000). Levels of β-actin (β-actin Antibody, Cell Signaling, 1:1000) and v-Src (Src 32G6 rabbit mAb, Cell Signaling, 1:1000) were ascertained by Western blot.

EXAMPLE 43

Blockade of v-Src-ES1 Activity in Cells with Electrophilic Inhibitors

Figure 4:
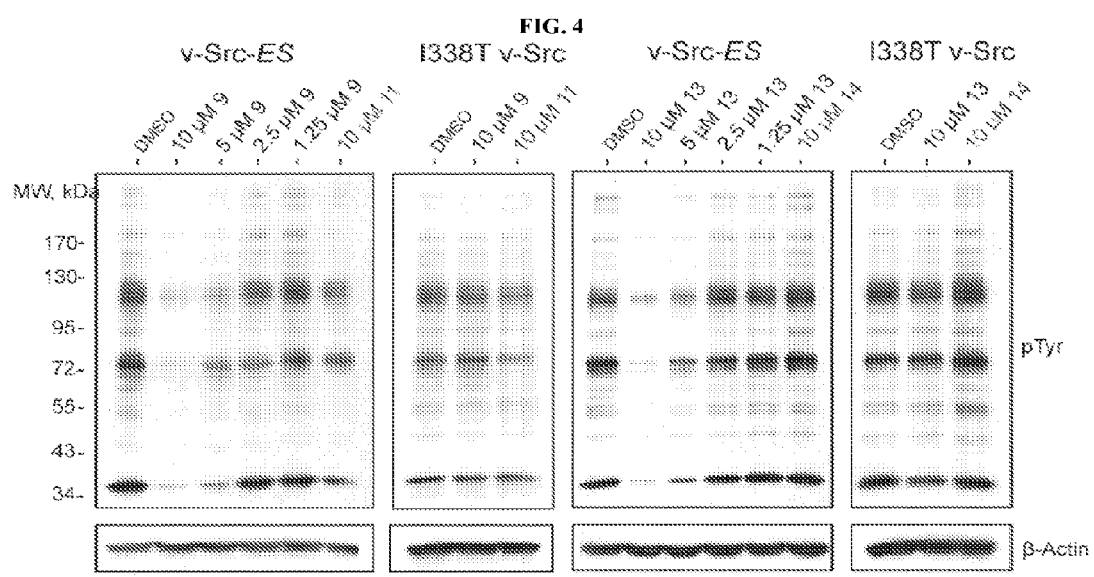
FIG. 4 shows a cellular dose response analysis for inhibition of v-Src-ES1 (I338C) with electrophilic inhibitors. Cells transfected NIH-3T3 with either v-Src-ES1 or I338T v-Src were treated with electrophilic inhibitors or non-reactive analogs for one hour (see the far right column of each run, e.g. 10 μM 11; 10 μM 11; 10 μM 14; 10 μM 14). Kinase activity was monitored by blotting for global phosphotyrosine levels. Actin blots were included to control for protein content.
Figure 7:
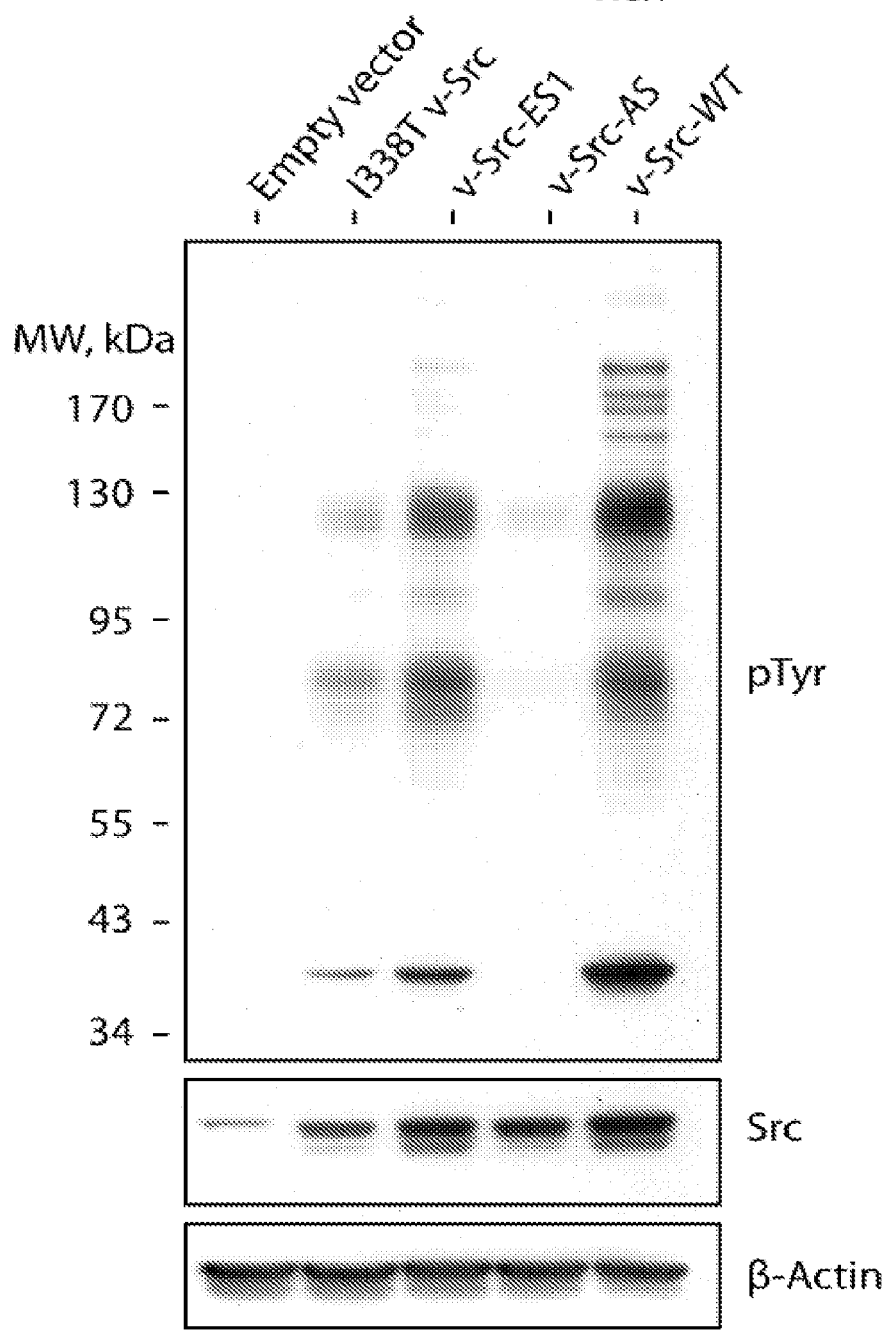
FIG. 7 shows analysis of the activity of v-Src gatekeeper variants in cells by Western blot. NIH-3T3 cells lines were infected with several v-Src gatekeeper variants. The kinase activity of the variants was analyzed by blotting for global phosphotyrosine levels (pTyr). The Src and actin blots account for Src expression levels and total protein content, respectively.
Figure 9:
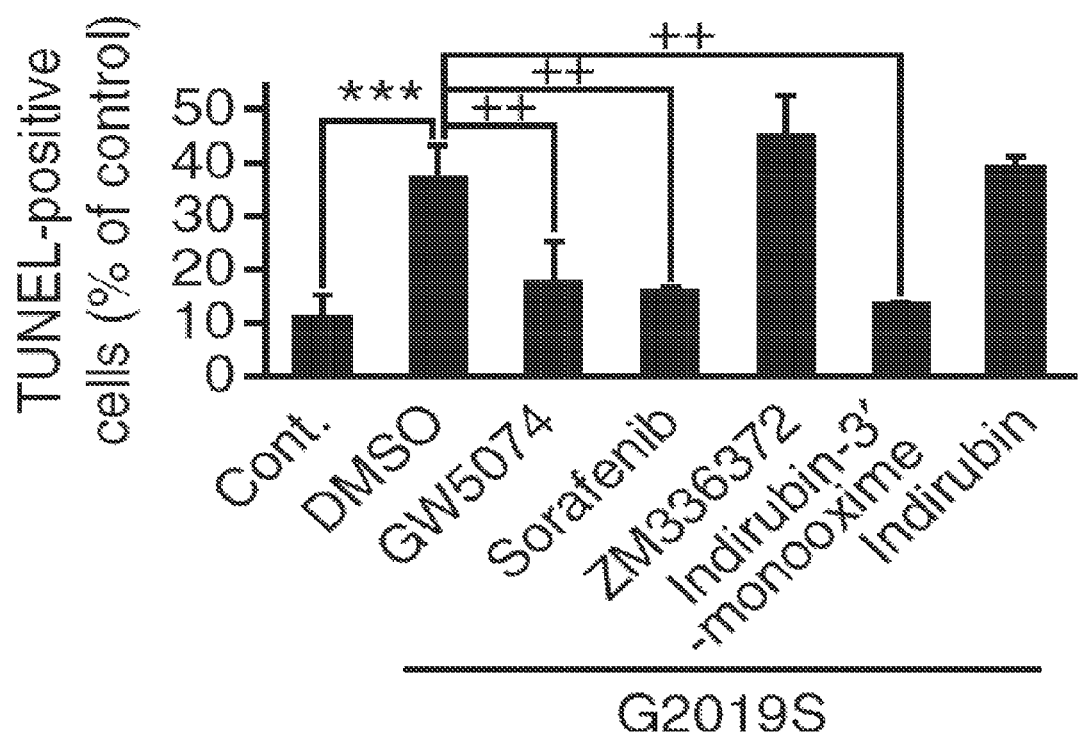
FIG. 9 shows inhibition of Lrrk-2 kinase activity.
Figure 10:
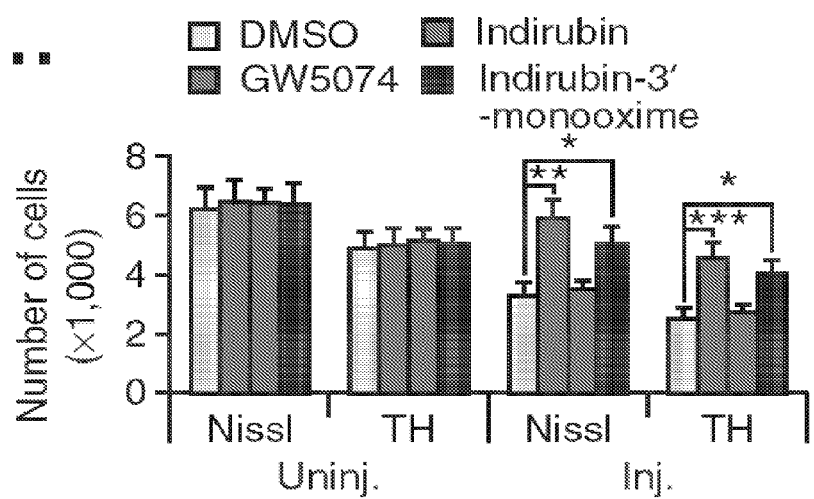
FIG. 10 shows inhibition of Lrrk-2 kinase activity.
Figure 13:
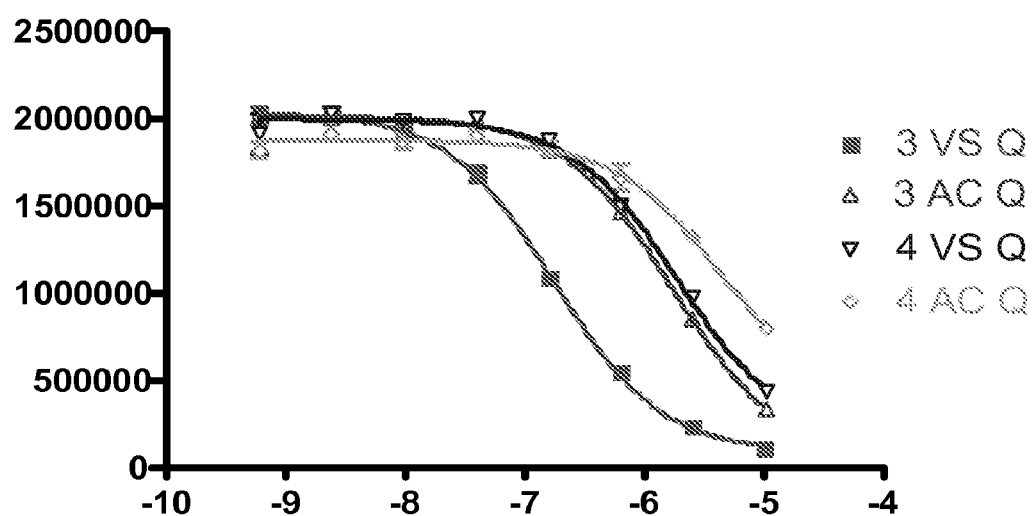
FIG. 13 shows SAR analysis and inhibition as dependent on a vinylsulfonamide in the 3 position.
Figure 14:
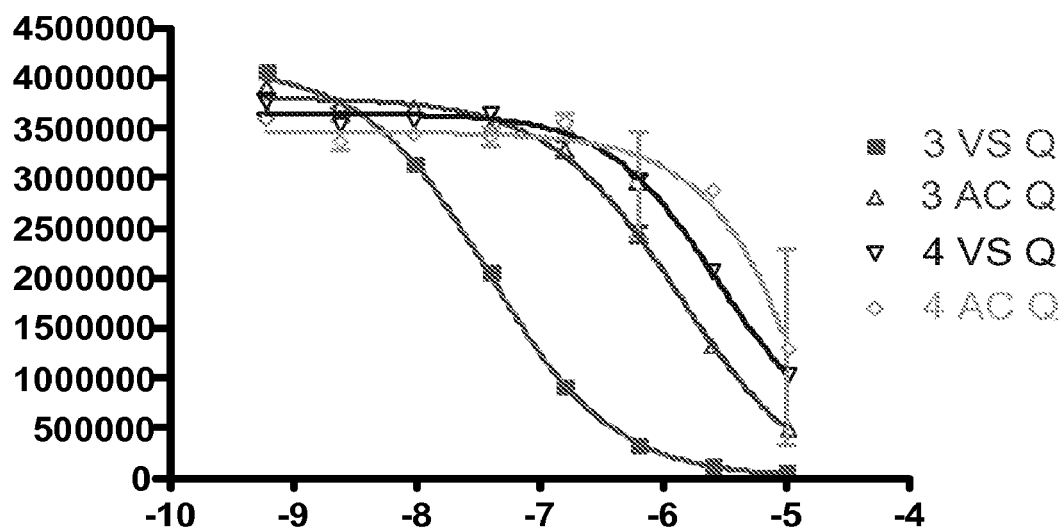
FIG. 14 shows SAR analysis and inhibition as dependent on a vinylsulfonamide in the 3 position.
Figure 15:
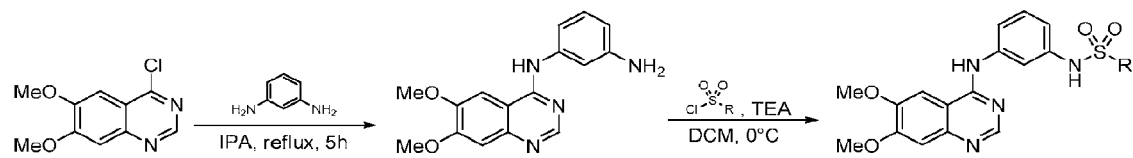
FIG. 15 shows the synthesis of compounds suitable for use with the present invention.
Figure 17:
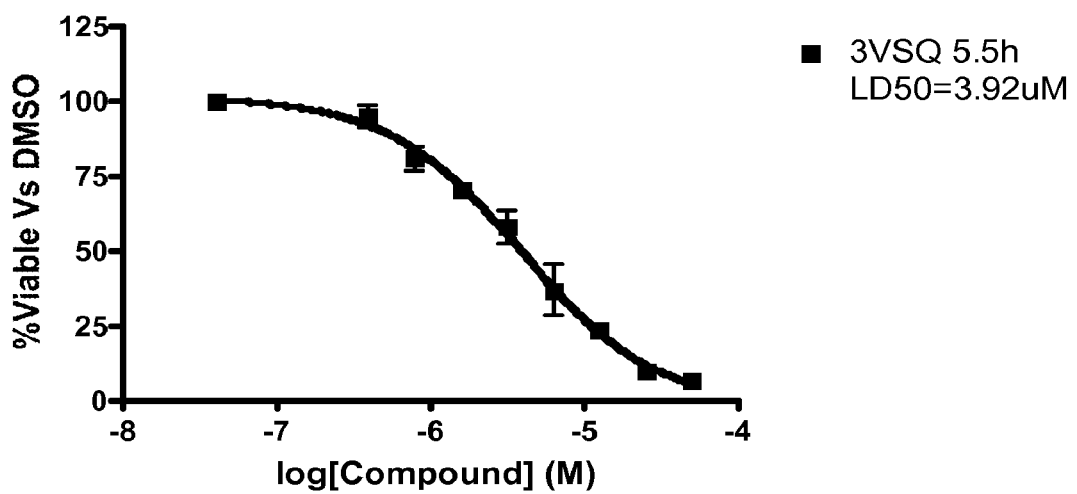
FIG. 17 shows toxicity profiles. LD50 of compound 19 (3-vs-Q) LD50=3.92 µM; All other compounds ≥50 µM.
Figure 18:
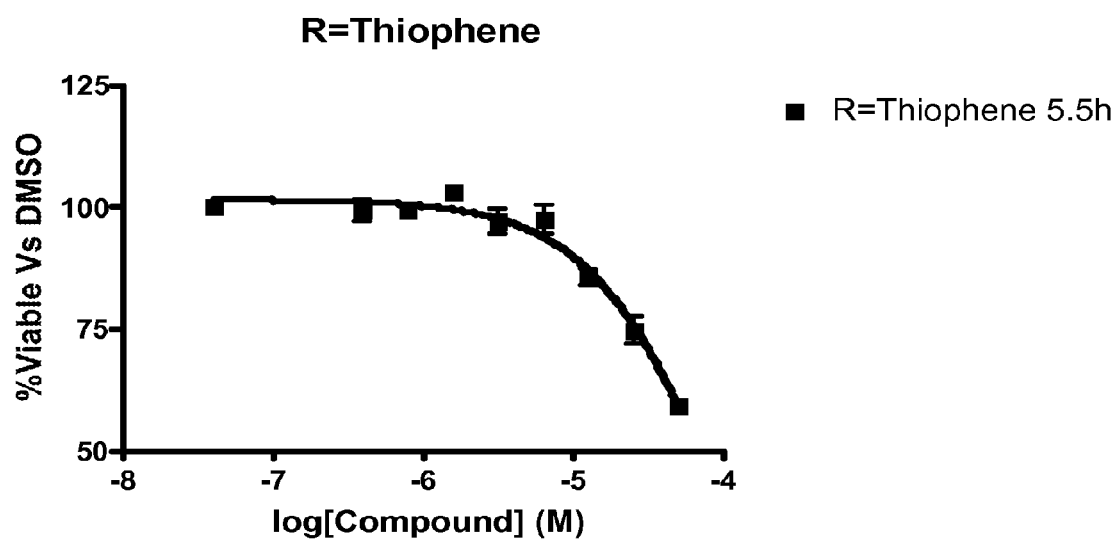
FIG. 18 shows toxicity profiles. LD50 of compound 19 (3-vs-Q) LD50=3.92 µM; All other compounds ≥50 µM.
Figure 19:
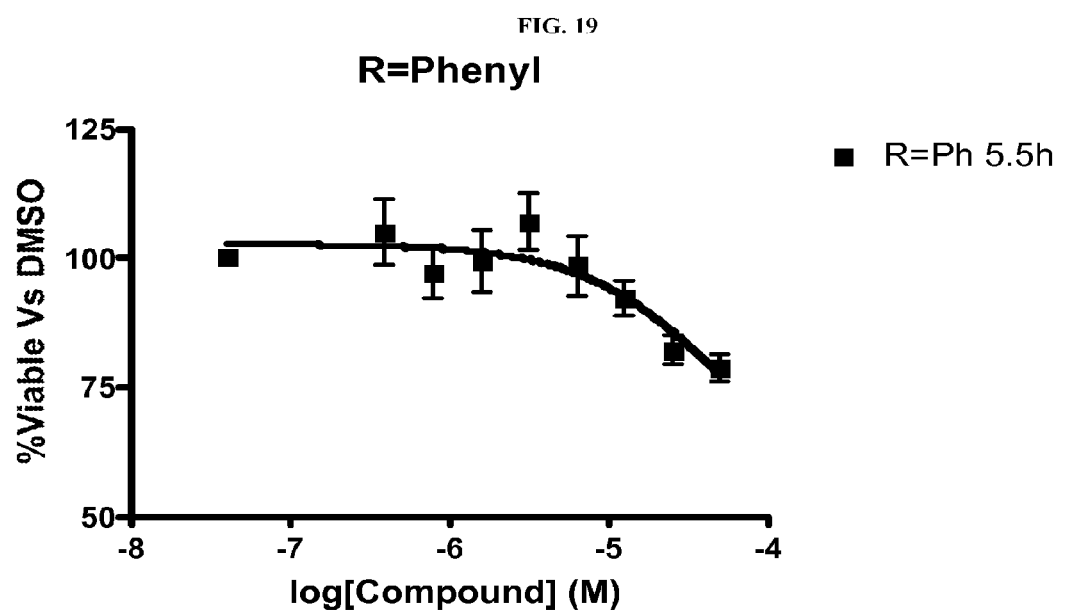
FIG. 19 shows toxicity profiles. LD50 of compound 19 (3-vs-Q) LD50=3.92 µM; All other compounds ≥50 µM.
Figure 21:
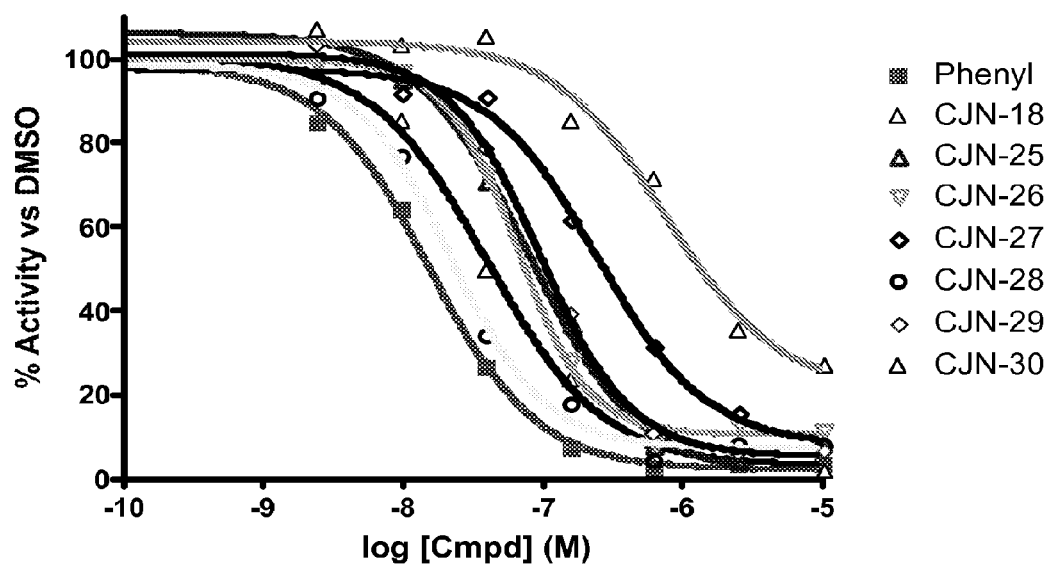
FIG. 21 shows assay data.
Figure 22:
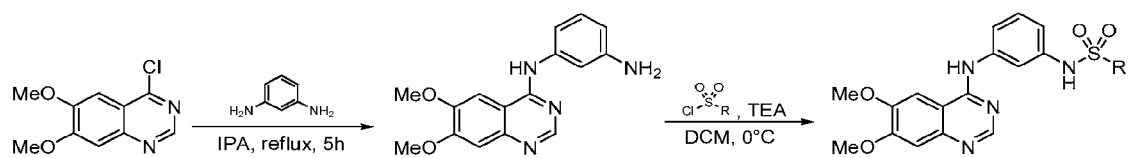
FIG. 22 shows a synthesis of compounds suitable for use with the present invention.

I338C (v-Src-ES1, SEQ ID NO:48), I338T (SEQ ID NO:49), I338G (v-Src-AS1, SEQ ID NO:50) and WT v-Src-transformed NIH-3T3 cell lines were generated. Unlike c-Src, v-Src is constitutively active and harbors an isoleucine gatekeeper. The I338T v-Src variant was generated for consistency with the in vitro c-Src studies. For each cell line, global levels of phosphotyrosine were analyzed (FIG. 7). Importantly, the v-Src-ES1 variant was an excellent mimic of WT v-Src, while the activity of v-Src-AS1 (the mutant used in previous chemical genetic studies) was markedly diminished as judged by whole cell phosphotyrosine levels. To determine whether the electrophilic inhibitors function in cells, the v-Src-ES1 and I338T v-Src-transformed cell lines were treated with 9 and 13. Both 9 and 13 inhibited v-Src-ES1 in a dose-dependent manner, while isosteric control compounds (11 and 14) showed no activity (FIG. 4). Furthermore, neither 9 nor 13 inhibited I338T v-Src even at levels as high as 10 μM. Collectively, these results suggest that a kinase with a cysteine gatekeeper can be selectively targeted in cells.

EXAMPLE 44

Second-site Mutations to Modulate Inhibitor Potency

The design strategy, in order to determine whether further kinase engineering could enhance potency, was to either enhance the reactivity of the cysteine by installing nearby hydrophilic/basic residues or to slightly enlarge the area around the cysteine to allow for additional rotational freedom to facilitate optimized thiol-electrophile attack geometry. Accordingly, mutations at Val323—a residue within 4 Å of the gatekeeper (FIG. 2C) in c-Src—were introduced in combination with T338C. Of the double mutants, V323A/T338C (c-Src-ES2) and V323S/T338C (c-Src-ES3) had substantial activity, while V323D/T338C (c-Src-ES4), V323E/T338C (c-Src-ES5), and V323H/T338C (c-Src-ES6) were inactive (Table 4). Enhanced inhibitor potency was observed for both c-Src-ES2 and c-Src-ES3 when treated with 13 (Table 3). In the latter case, a 12-fold improvement was noted relative to c-Src-ES1. Interestingly, the potencies of 3 and 9 were not modulated appreciably upon introduction of the additional mutations. Taken together, these results indicate that the judicious placement of a secondary mutation can be an effective means for modulating inhibitor potency for an ES allele, but that this strategy needs to be evaluated on a case-by-case basis.

EXAMPLE 45

Evaluating the Use of a Cysteine Gatekeeper Kinase

A recombinant wild type (WT) and T338C c-Src was generated. The recombinant wild type (WT) and the T338C c-Src were assayed for kinase activity, see Table 8. The $k_{cat}$ value for T338C c-Src (183 min$^{-1}$) closely approximated that of WT (159 min$^{-1}$) and was ~3.5-fold greater than that of c-Src-AS1 (51.9 min$^{-1}$). The T338C c-Src variant also recapitulated WT in affinity for ATP as determined by the Michaelis constant ($K_m$) values (21.9 μM vs. 31.9 μM), while c-Src-AS1 (87.5 μM) exhibited ~4-fold loss relative to T338C c-Src. These effects translate to a 14-fold improvement in catalytic efficiency ($k_{cat}/K_m$) for T338C c-Src in relation to c-Src-AS1.

TABLE 8

Kinetic parameters for c-Src variants. Values were determined by fitting data to the Michaelis-Menten equation. Standard errors associated with the fits are reported.

| c-Src Variant | $k_{cat}$ (min$^{-1}$) | $K_{m, ATP}$ (μM) | $k_{cat}/K_m$ (min$^{-1}$ μM$^{-1}$) |
|---|---|---|---|
| WT | 159 ± 4 | 31.9 ± 3.0 | 4.99 ± 0.40 |
| T338C | 183 ± 3 | 21.9 ± 1.7 | 8.34 ± 0.57 |
| AS1 | 51.9 ± 1.9 | 87.5 ± 12.6 | 0.592 ± 0.072 |

Kinetic measurements reveal that in the case of c-Src, the ES1 variant is a mimic of wild type activity. Furthermore, the ES1 variant of v-Src is also a mimic of the wild type, which contains a particularly hydrophobic (isoleucine) gatekeeper. See Tables 9a-9c following. Results on the selectivity of compound 19 in the Invitrogen SelectScreen® Kinase Assay are provided in Tables 9a-9c following. Table 9a is the LanthaScreen™ heat map., Table 9b is the Adapta® heat map, and Table 9c is the Z'-lyte™ heat map. Legend for Tables 9a-9c: <40% inhibition (gray); 40%-80% inhibition (white); 80% inhibition (diagonal stripes). Selected results in the assays are further provided in FIG. 11. In the table below, Cmpd 3-vs-Q refers to compound 19.

TABLE 9a

| Kinase tested | | Cmpd 3-vs-Q 1000 nM |
|---|---|---|
| ACVR1 (ALK2) | Binding | 4 |
| ACVR2B | Binding | 19 |
| BMPR1A (ALK3) | Binding | 10 |
| CAMKK1 (CAMKKA) | Binding | 5 |
| CAMKK2 (CaMKK beta) | Binding | 6 |
| CDK8/cyclin C | Binding | 4 |
| CDK9/cyclin K | Binding | 0 |
| CLK4 | Binding | 24 |
| DDR1 | Binding | 0 |
| DDR2 | Binding | 5 |
| DMPK | Binding | 10 |
| EPHA3 | Binding | 1 |
| EPHA7 | Binding | 2 |
| KIT V654A | Binding | 6 |
| LIMK1 | Binding | 1 |
| LIMK2 | Binding | 6 |
| MAP2K1 (MEK1) S218D S222D | Binding | 20 |
| MAP2K3 (MEK3) | Binding | 6 |
| MAP2K6 (MKK6) S207E T211E | Binding | 3 |
| MAP3K10 (MLK2) | Binding | 6 |
| MAP3K11 (MLK3) | Binding | 1 |
| MAP3K14 (NIK) | Binding | 12 |
| MAP3K2 (MEKK2) | Binding | 2 |
| MAP3K3 (MEKK3) | Binding | 9 |
| MAP3K5 (ASK1) | Binding | 3 |
| MAP3K7/MAP3K7IP1 (TAK1-TAB1) | Binding | 2 |
| MKNK2 (MNK2) | Binding | 36 |
| MLCK (MLCK2) | Binding | 36 |
| MYLK (MLCK) | Binding | 3 |
| NLK | Binding | 5 |
| RIPK2 | Binding | 52 |
| SLK | Binding | 7 |
| STK16 (PKL12) | Binding | 5 |
| STK17A (DRAK1) | Binding | 21 |
| STK33 | Binding | 7 |
| TAOK3 (JIK) | Binding | 3 |
| TEC | Binding | 3 |
| TGFBR1 (ALK5) | Binding | 10 |
| TNK2 (ACK) | Binding | 10 |
| TTK | Binding | 16 |
| WEE1 | Binding | 14 |
| WNK2 | Binding | 10 |
| ZAK | Binding | 6 |

TABLE 9b

| Kinase | | | Cmpd 3-vs-Q 1000 nM |
|---|---|---|---|
| CAMK1 (CaMK1) | Activity | 100 | -21 |
| CDK7/cyclin H/MNAT1 | Activity | Km app | 0 |
| CDK9/cyclin T1 | Activity | Km app | 24 |
| CHUK (IKK alpha) | Activity | Km app | 3 |
| DAPK1 | Activity | Km app | 6 |
| GSG2 (Haspin) | Activity | Km app | 8 |
| IRAK1 | Activity | Km app | 6 |
| LRRK2 | Activity | Km app | 75 |
| LRRK2 G2019S | Activity | Km app | |
| NUAK1 (ARK5) | Activity | Km app | 24 |
| PI4KA (PI4K alpha) | Activity | 10 | 7 |
| PI4KB (PI4K beta) | Activity | Km app | 14 |
| PIK3C2A (PI3K-C2 alpha) | Activity | Km app | -1 |
| PIK3C2B (PI3K-C2 beta) | Activity | 100 | 65 |
| PIK3C3 (hVPS34) | Activity | Km app | 1 |
| PIK3CA/PIK3R1 (p110 alpha/p85 alpha) | Activity | Km app | 13 |
| PIK3CD/PIK3R1 (p110 delta/p85 alpha) | Activity | Km app | 10 |
| PIK3CG (p110 gamma) | Activity | Km app | 27 |
| SPHK1 | Activity | Km app | 3 |
| SPHK2 | Activity | 100 | -11 |

TABLE 9c

| Kinase | | | Cmpd 3-vs-Q 1000 nM |
|---|---|---|---|
| ABL1 | Activity | Km app | 4 |
| ABL1 E255K | Activity | Km app | 7 |
| ABL1 G250E | Activity | Km app | 2 |
| ABL1 T315I | Activity | Km app | 11 |
| ABL1 Y253F | Activity | Km app | 12 |
| ABL2 (Arg) | Activity | Km app | 10 |
| ACVR1B (ALK4) | Activity | Km app | -1 |
| ADRBK1 (GRK2) | Activity | Km app | 13 |
| ADRBK2 (GRK3) | Activity | Km app | 3 |
| AKT1 (PKB alpha) | Activity | Km app | 0 |
| AKT2 (PKB beta) | Activity | Km app | 4 |
| AKT3 (PKB gamma) | Activity | Km app | 4 |
| ALK | Activity | Km app | 3 |
| AMPK A1/B1/G1 | Activity | Km app | 18 |
| AMPK A2/B1/G1 | Activity | Km app | 15 |
| AURKA (Aurora A) | Activity | Km app | 12 |

TABLE 9c-continued

| AURKB (Aurora B) | Activity | Km app | 26 |
|---|---|---|---|
| AURKC (Aurora C) | Activity | Km app | 1 |
| AXL | Activity | Km app | 19 |
| BLK | Activity | Km app | 24 |
| BMX | Activity | Km app | 24 |
| BRAF | Activity | 100 | 4 |
| BRAF V599E | Activity | 100 | 13 |
| BRSK1 (SAD1) | Activity | Km app | 35 |
| BTK | Activity | Km app | 59 |
| CAMK1D (CaMKI delta) | Activity | Km app | 15 |
| CAMK2A (CaMKII alpha) | Activity | Km app | 4 |
| CAMK2B (CaMKII beta) | Activity | Km app | 5 |
| CAMK2D (CaMKII delta) | Activity | Km app | 10 |
| CAMK4 (CaMKIV) | Activity | Km app | 10 |
| CDC42 BPA (MRCKA) | Activity | Km app | 23 |
| CDC42 BPB (MRCKB) | Activity | Km app | -4 |
| CDK1/cyclin B | Activity | Km app | 3 |
| CDK2/cyclin A | Activity | Km app | 4 |
| CDK5/p25 | Activity | Km app | 10 |

| CDK5/p35 | Activity | Km app | 5 |
|---|---|---|---|
| CHEK1 (CHK1) | Activity | Km app | -6 |
| CHEK2 (CHK2) | Activity | Km app | 53 |
| CLK1 | Activity | Km app | 11 |
| CLK2 | Activity | Km app | 3 |

| CLK3 | Activity | Km app | 6 |
|---|---|---|---|
| CSF1R (FMS) | Activity | Km app | 3 |
| CSK | Activity | Km app | 12 |
| CSNK1A1 (CK1 alpha 1) | Activity | Km app | 0 |
| CSNK1D (CK1 delta) | Activity | Km app | 5 |
| CSNK1E (CK1 epsilon) | Activity | Km app | 6 |
| CSNK1G1 (CK1 gamma 1) | Activity | Km app | 12 |
| CSNK1G2 (CK1 gamma 2) | Activity | Km app | 31 |
| CSNK1G3 (CK1 gamma 3) | Activity | Km app | 31 |
| CSNK2A1 (CK2 alpha 1) | Activity | Km app | 13 |
| CSNK2A2 (CK2 alpha 2) | Activity | Km app | -1 |
| DAPK3 (ZIPK) | Activity | Km app | 0 |
| DCAMKL2 (DCK2) | Activity | Km app | 5 |
| DNA-PK | Activity | Km app | 25 |
| DYRK1A | Activity | Km app | -2 |

TABLE 9c-continued

| | | | |
|---|---|---|---|
| DYRK1B | Activity | Km app | 3 |
| DYRK3 | Activity | Km app | 5 |
| DYRK4 | Activity | Km app | 3 |
| EEF2K | Activity | Km app | 5 |
| EGFR (ErbB1) | Activity | Km app | |
| EGFR (ErbB1) L858R | Activity | Km app | 69 |
| EGFR (ErbB1) L861Q | Activity | Km app | 76 |
| EGFR (ErbB1) T790M | Activity | Km app | 27 |
| EGFR (ErbB1) T790M L858R | Activity | Km app | 41 |
| EPHA1 | Activity | Km app | 19 |
| EPHA2 | Activity | Km app | 4 |
| EPHA4 | Activity | Km app | 8 |
| EPHA5 | Activity | Km app | 7 |
| EPHA8 | Activity | Km app | 11 |
| EPHB1 | Activity | Km app | 8 |
| EPHB2 | Activity | Km app | 15 |
| EPHB3 | Activity | Km app | 8 |
| EPHB4 | Activity | Km app | 7 |
| ERBB2 (HER2) | Activity | Km app | 66 |
| ERBB4 (HER4) | Activity | Km app | 80 |
| FER | Activity | Km app | 6 |
| FES (FPS) | Activity | Km app | 16 |
| FGFR1 | Activity | Km app | 8 |
| FGFR2 | Activity | Km app | 14 |
| FGFR3 | Activity | Km app | 11 |
| FGFR3 K650E | Activity | Km app | 18 |
| FGFR4 | Activity | Km app | 14 |
| FGR | Activity | Km app | 33 |
| FLT1 (VEGFR1) | Activity | Km app | 2 |
| FLT3 | Activity | Km app | 32 |
| FLT3 D835Y | Activity | Km app | |
| FLT4 (VEGFR3) | Activity | Km app | 34 |
| FRAP1 (mTOR) | Activity | Km app | 7 |
| FRK (PTK5) | Activity | Km app | 11 |
| FYN | Activity | Km app | 3 |
| GRK4 | Activity | Km app | 15 |
| GRK5 | Activity | Km app | 49 |
| GRK6 | Activity | Km app | 27 |
| GRK7 | Activity | Km app | 2 |
| GSK3A (GSK3 alpha) | Activity | Km app | 2 |
| GSK3B (GSK3 beta) | Activity | Km app | 4 |
| HCK | Activity | Km app | 13 |
| HIPK1 (Myak) | Activity | Km app | 3 |
| HIPK2 | Activity | Km app | 4 |
| HIPK3 (YAK1) | Activity | Km app | 3 |
| HIPK4 | Activity | Km app | 17 |
| IGF1R | Activity | Km app | 5 |
| IKBKB (IKK beta) | Activity | Km app | 13 |
| IKBKE (IKK epsilon) | Activity | Km app | 10 |
| INSR | Activity | Km app | 0 |
| INSRR (IRR) | Activity | Km app | 11 |
| IRAK4 | Activity | Km app | 3 |
| ITK | Activity | Km app | 3 |
| JAK1 | Activity | Km app | 14 |
| JAK2 | Activity | Km app | 0 |
| JAK2 JH1 JH2 | Activity | Km app | -5 |
| JAK2 JH1 JH2 V617F | Activity | Km app | 4 |
| JAK3 | Activity | Km app | 37 |
| KDR (VEGFR2) | Activity | Km app | 6 |
| KIT | Activity | Km app | 7 |
| KIT T670I | Activity | Km app | 5 |
| LCK | Activity | Km app | 0 |
| LTK (TYK1) | Activity | Km app | 4 |
| LYN A | Activity | Km app | 21 |
| LYN B | Activity | Km app | 25 |
| MAP2K1 (MEK1) | Activity | 100 | 3 |
| MAP2K2 (MEK2) | Activity | 100 | 13 |
| MAP2K6 (MKK6) | Activity | 100 | 17 |
| MAP3K8 (COT) | Activity | 100 | -1 |
| MAP3K9 (MLK1) | Activity | Km app | 3 |
| MAP4K2 (GCK) | Activity | Km app | -13 |
| MAP4K4 (HGK) | Activity | Km app | 23 |
| MAP4K5 (KHS1) | Activity | Km app | 23 |
| MAPK1 (ERK2) | Activity | Km app | 2 |
| MAPK10 (JNK3) | Activity | 100 | 2 |
| MAPK11 (p38 beta) | Activity | Km app | 14 |
| MAPK12 (p38 gamma) | Activity | Km app | 10 |
| MAPK13 (p38 delta) | Activity | Km app | 5 |
| MAPK14 (p38 alpha) | Activity | 100 | 24 |
| MAPK14 (p38 alpha) Direct | Activity | Km app | 11 |
| MAPK3 (ERK1) | Activity | Km app | 10 |
| MAPK8 (JNK1) | Activity | 100 | 19 |
| MAPK9 (JNK2) | Activity | 100 | 8 |
| MAPKAPK2 | Activity | Km app | 6 |
| MAPKAPK3 | Activity | Km app | 5 |
| MAPKAPK5 (PRAK) | Activity | Km app | 7 |
| MARK1 (MARK) | Activity | Km app | -1 |
| MARK2 | Activity | Km app | 2 |
| MARK3 | Activity | Km app | 5 |
| MARK4 | Activity | Km app | 1 |

TABLE 9c-continued

| | | | |
|---|---|---|---|
| MATK (HYL) | Activity | Km app | 5 |
| MELK | Activity | Km app | 20 |
| MERTK (cMER) | Activity | Km app | 12 |
| MET (cMet) | Activity | Km app | 3 |
| MET M1250T | Activity | Km app | 8 |
| MINK1 | Activity | Km app | 17 |
| MKNK1 (MNK1) | Activity | Km app | 40 |
| MST1R (RON) | Activity | Km app | 11 |
| MST4 | Activity | Km app | 15 |
| MUSK | Activity | Km app | 14 |
| MYLK2 (skMLCK) | Activity | Km app | 13 |
| NEK1 | Activity | Km app | 2 |
| NEK2 | Activity | Km app | 1 |
| NEK4 | Activity | Km app | 22 |
| NEK6 | Activity | Km app | 6 |

| | | | |
|---|---|---|---|
| NEK7 | Activity | Km app | 6 |
| NEK9 | Activity | Km app | 10 |
| NTRK1 (TRKA) | Activity | Km app | 18 |
| NTRK2 (TRKB) | Activity | Km app | 8 |
| NTRK3 (TRKC) | Activity | Km app | 3 |
| PAK1 | Activity | Km app | 14 |
| PAK2 (PAK65) | Activity | Km app | 12 |
| PAK3 | Activity | Km app | 3 |
| PAK4 | Activity | Km app | 4 |
| PAK6 | Activity | Km app | 8 |
| PAK7 (KIAA1264) | Activity | Km app | 9 |
| PASK | Activity | Km app | 8 |
| PDGFRA (PDGFR alpha) | Activity | Km app | 18 |

| | | | |
|---|---|---|---|
| PDGFRA D842V | Activity | Km app | 22 |
| PDGFRA T674I | Activity | Km app | 25 |
| PDGFRA V561D | Activity | Km app | 45 |
| PDGFRB (PDGFR beta) | Activity | Km app | 8 |
| PDK1 | Activity | 100 | 16 |
| PDK1 Direct | Activity | Km app | 0 |
| PHKG1 | Activity | Km app | 10 |
| PHKG2 | Activity | Km app | 4 |
| PIM1 | Activity | Km app | 12 |
| PIM2 | Activity | Km app | 0 |
| PKN1 (PRK1) | Activity | Km app | 19 |
| PLK1 | Activity | Km app | 1 |
| PLK2 | Activity | Km app | 10 |

TABLE 9c-continued

| | | | |
|---|---|---|---|
| PLK3 | Activity | Km app | 2 |
| PRKACA (PKA) | Activity | Km app | 0 |
| PRKCA (PKC alpha) | Activity | Km app | 14 |
| PRKCB1 (PKC beta I) | Activity | Km app | 10 |
| PRKCB2 (PKC beta II) | Activity | Km app | 5 |
| PRKCD (PKC delta) | Activity | Km app | 15 |
| PRKCE (PKC epsilon) | Activity | Km app | 17 |
| PRKCG (PKC gamma) | Activity | Km app | 14 |
| PRKCH (PKC eta) | Activity | Km app | 15 |
| PRKCI (PKC iota) | Activity | Km app | 10 |
| PRKCN (PKD3) | Activity | Km app | 10 |
| PRKCQ (PKC theta) | Activity | Km app | 13 |
| PRKCZ (PKC zeta) | Activity | Km app | 8 |
| PRKD1 (PKC mu) | Activity | Km app | 12 |

| | | | |
|---|---|---|---|
| PRKD2 (PKD2) | Activity | Km app | 12 |
| PRKG1 | Activity | Km app | 2 |
| PRKG2 (PKG2) | Activity | Km app | 1 |
| PRKX | Activity | Km app | 3 |
| PTK2 (FAK) | Activity | Km app | 9 |
| PTK2B (FAK2) | Activity | Km app | 4 |
| PTK6 (Brk) | Activity | Km app | 9 |
| RAF1 (cRAF) Y340D Y341D | Activity | 100 | 21 |
| RET | Activity | Km app | 19 |
| RET V804L | Activity | Km app | 12 |
| RET Y791F | Activity | Km app | 25 |
| ROCK1 | Activity | Km app | 3 |

| | | | |
|---|---|---|---|
| ROCK2 | Activity | Km app | 13 |
| ROS1 | Activity | Km app | 40 |
| RPS6KA1 (RSK1) | Activity | Km app | 6 |
| RPS6KA2 (RSK3) | Activity | Km app | 26 |
| RPS6KA3 (RSK2) | Activity | Km app | 9 |
| RPS6KA4 (MSK2) | Activity | Km app | 6 |
| RPS6KA5 (MSK1) | Activity | Km app | 0 |
| RPS6KA6 (RSK4) | Activity | Km app | 49 |
| RPS6KB1 (p70S6K) | Activity | Km app | 10 |
| SGK (SGK1) | Activity | Km app | 6 |
| SGK2 | Activity | Km app | 8 |
| SGKL (SGK3) | Activity | Km app | 4 |
| SNF1LK2 | Activity | Km app | 4 |
| SRC | Activity | Km app | 4 |

TABLE 9c-continued

| | | | |
|---|---|---|---|
| SRC N1 | Activity | Km app | 15 |
| SRMS (Srm) | Activity | Km app | 71 |
| SRPK1 | Activity | Km app | 2 |
| SRPK2 | Activity | Km app | 10 |
| STK22B (TSSK2) | Activity | Km app | 2 |
| STK22D (TSSK1) | Activity | Km app | 13 |
| STK23 (MSSK1) | Activity | Km app | 14 |
| STK24 (MST3) | Activity | Km app | 11 |
| STK25 (YSK1) | Activity | Km app | 5 |
| STK3 (MST2) | Activity | Km app | 9 |
| STK4 (MST1) | Activity | Km app | 2 |
| SYK | Activity | Km app | 2 |
| TAOK2 (TAO1) | Activity | Km app | 2 |
| TBK1 | Activity | Km app | 2 |
| TEK (Tie2) | Activity | Km app | 7 |
| TXK | Activity | Km app | 78 |
| TYK2 | Activity | Km app | 4 |
| TYRO3 (RSE) | Activity | Km app | 22 |
| YES1 | Activity | Km app | 30 |
| ZAP70 | Activity | Km app | 10 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having the formula:

(I)

wherein:
- X is =N—;
- Ring A is phenyl;
- $L^1$ is a bond;
- $L^2$ is a bond;
- $L^3$ is —C(O)—, —S(O)$_2$—, or —NHS(O)$_2$—;
- $L^4$ is unsubstituted $C_1$-$C_5$ alkylene;
- $R^1$ is hydrogen or —NH$_2$;
- $R^2$ is substituted or unsubstituted alkyl or substituted or unsubstituted cycloalkyl;
- $R^3$ is substituted or unsubstituted alkyl;
- a is 1;
- b is 1;

and the salts and isomers thereof.

2. The compound of claim 1, wherein
$L^3$ is —C(O)—, —S(O)$_2$—, or —NHS(O)$_2$—; and
$R^3$ is unsubstituted alkyl or alkyl substituted with chloro, fluoro, methyl, difluoromethyl, or trifluoromethyl.

3. The compound of claim 2, wherein $R^3$ is ethenyl, ethyl, 2,2,2-trichloroethyl, 2,2-dichloroethyl, 2-chloroethyl, 2,2,2-trifluoroethyl, 2,2-difluoroethyl, or 2-fluoroethyl, propyl, isopropyl, 1-propenyl, or 2-propenyl.

4. The compound of claim 3, wherein -$L^3$-$R^3$ is:

5. The compound of claim 1, wherein,
$L^1$ is a bond; and
$R^1$ is hydrogen.

6. The compound of claim 1, wherein
$L^1$ is a bond; and
$R^1$ is NH$_2$.

7. The compound of claim 1, wherein
$L^2$ is a bond; and
$R^2$ is methyl, ethyl, propyl, isopropyl, butyl, tert-butyl, pentyl, cyclopentyl, hexyl, or cyclohexyl.

8. The compound of claim 7, wherein $R^2$ is isopropyl or cyclopentyl.

9. The compound of claim 8, wherein $R^2$ is isopropyl.

10. The compound of claim 8, wherein $R^2$ is cyclopentyl.

11. A compound, having the formula:
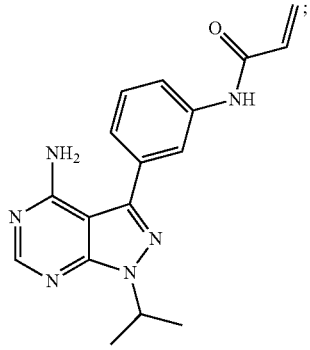
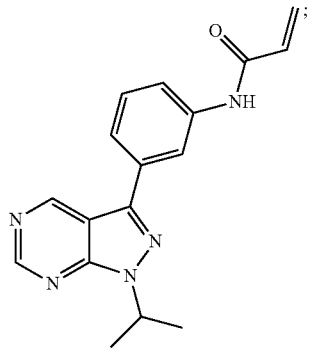
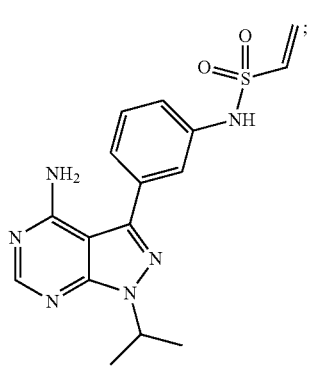
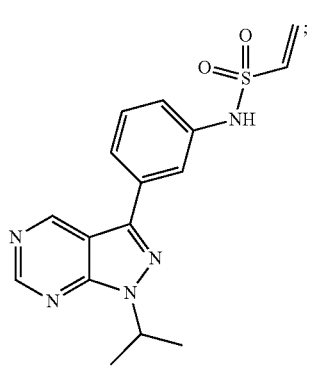
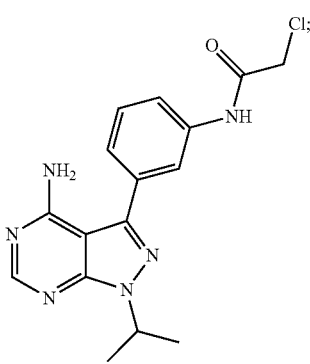
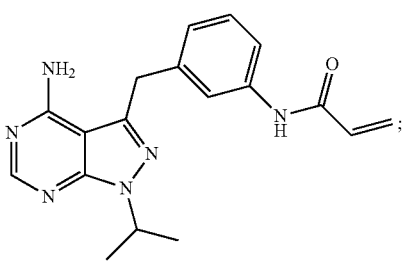
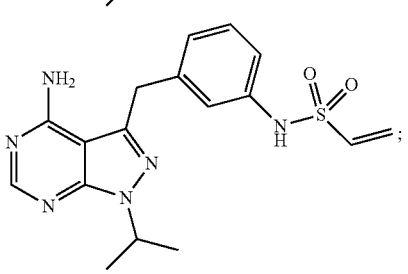
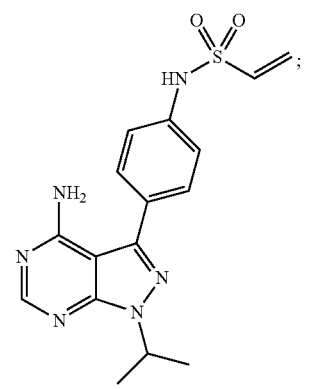
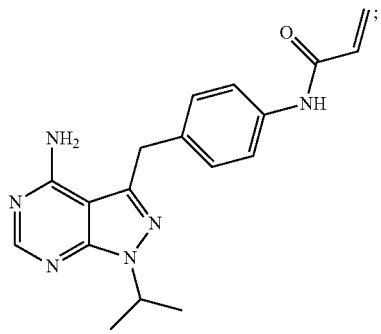

273
-continued
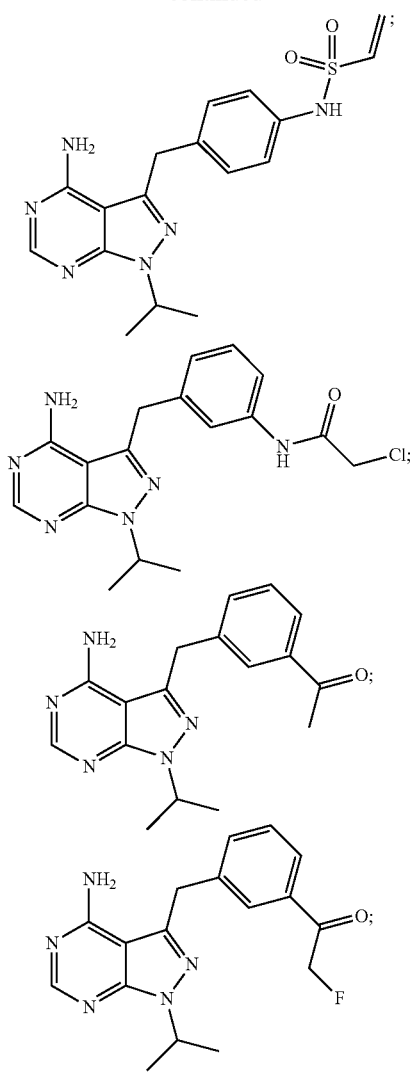
274
-continued
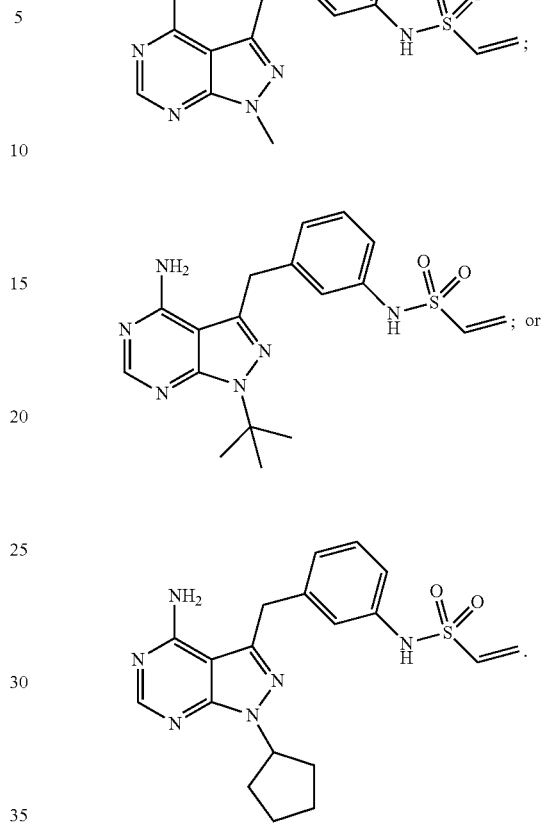
12. A pharmaceutical composition comprising a compound of claim 1 and a pharmaceutically acceptable excipient.
* * * * *